United States Patent
Hoffmann et al.

(10) Patent No.: US 12,180,187 B2
(45) Date of Patent: Dec. 31, 2024

(54) 1-PHENYL-5-AZINYLPYRAZOLYL-3-OXYALKYL ACIDS AND THEIR USE FOR CONTROLLING UNWANTED PLANT GROWTH

(71) Applicant: BAYER AKTIENGESELLSCHAFT, Leverkusen (DE)

(72) Inventors: Michael Gerhard Hoffmann, Constance (DE); Estella Buscato Arsequell, Frankfurt am Main (DE); Harald Jakobi, Frankfurt (DE); Thomas Mueller, Frankfurt (DE); Erin Nicole Smith, Duncraig WA (AU); Elisabeth Asmus, Hoesbach (DE); Anu Bheemaiah Machettira, Frankfurt am Main (DE); Elmar Gatzweiler, Bad Nauheim (DE); Christopher Hugh Rosinger, Hofheim (DE); Dirk Schmutzler, Hattersheim (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 496 days.

(21) Appl. No.: 17/615,786

(22) PCT Filed: May 29, 2020

(86) PCT No.: PCT/EP2020/064977
§ 371 (c)(1),
(2) Date: Dec. 1, 2021

(87) PCT Pub. No.: WO2020/245044
PCT Pub. Date: Dec. 10, 2020

(65) Prior Publication Data
US 2022/0235036 A1   Jul. 28, 2022

(30) Foreign Application Priority Data

Jun. 3, 2019 (EP) .................................. 19177900

(51) Int. Cl.
| | | |
|---|---|---|
| *C07D 403/04* | (2006.01) |
| *A01N 43/54* | (2006.01) |
| *A01N 43/56* | (2006.01) |
| *A01N 43/60* | (2006.01) |
| *A01N 43/78* | (2006.01) |
| *A01P 13/02* | (2006.01) |
| *C07D 401/04* | (2006.01) |
| *C07D 401/14* | (2006.01) |
| *C07D 405/14* | (2006.01) |
| *C07D 417/14* | (2006.01) |

(52) U.S. Cl.
CPC ........... *C07D 403/04* (2013.01); *A01N 43/54* (2013.01); *A01N 43/56* (2013.01); *A01N 43/60* (2013.01); *A01N 43/78* (2013.01); *A01P 13/02* (2021.08); *C07D 401/04* (2013.01); *C07D 401/14* (2013.01); *C07D 405/14* (2013.01); *C07D 417/14* (2013.01)

(58) Field of Classification Search
CPC .. C07D 403/04; C07D 401/04; C07D 401/14; C07D 405/14; C07D 417/14; A01N 43/54; A01N 43/56; A01N 43/60; A01N 43/78; A01N 43/58; A01N 43/66; A01N 43/707; A01P 13/02
See application file for complete search history.

(56) References Cited

U.S. PATENT DOCUMENTS 4,752,324 A  6/1988  Thomas et al.

FOREIGN PATENT DOCUMENTS

| CN | 101284815 B | 4/2011 | |
|---|---|---|---|
| CN | 108503587 A | * 9/2018 | ............. A01N 43/10 |
| DE | 2828529 A1 | 1/1980 | |
| EP | 0007019 A1 | 1/1980 | |
| EP | 0222254 A2 | 5/1987 | |
| JP | H0812654 A | 1/1996 | |
| WO | 2008/083233 A2 | 7/2008 | |
| WO | 2010/015680 A1 | 2/2010 | |

OTHER PUBLICATIONS

CN-108503587-A translated (Year: 2018).*
Liu, Yuanyuan et al., "Synthesis, Crystal Structure, and Fungicidal Activity of Novel 1,5-Diaryl-1H-Pyrazol-3-Oxy Derivatives Containing Oxyacetic Acid or Oxy(2-thioxothiazolidin-3-yl)ethanone Moieties," Journal of Heterocyclic Chemistry, 2012, pp. 1370-1375, vol. 49.
Chemical Abstract Service, Sep. 29, 2006, XP002795159.
International Search Report of International Patent Application No. PCT/EP2020/064977 dated Jul. 15, 2020.

* cited by examiner

*Primary Examiner* — Robert A Wax
*Assistant Examiner* — John Seungjai Kwon
(74) *Attorney, Agent, or Firm* — Gale Wesley Starkey

(57) ABSTRACT

What are described are compounds of the general formula (I) and agrochemically acceptable salts thereof

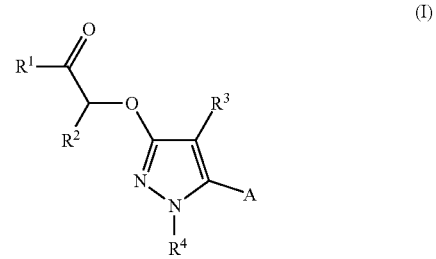

(I)

and their preparation and their use in the crop protection sector.

20 Claims, No Drawings

1-PHENYL-5-AZINYLPYRAZOLYL-3-OXYALKYL ACIDS AND THEIR USE FOR CONTROLLING UNWANTED PLANT GROWTH

CROSS-REFERENCE TO RELATED APPLICATIONS

This application is the National Stage entry of International Application No. PCT/EP2020/064977, filed 29 May 2020, which claims priority to European Patent Application No. 19177900.8, filed 3 Jun. 2019.

BACKGROUND

Field

The invention relates to the technical field of crop protection compositions, particularly to that of herbicides for selective control of broad-leaved weeds and weed grasses in crops of useful plants and in the ornamental garden sector and for general control of broad-leaved weeds and weed grasses in areas of the environment where plant growth is disruptive.

More particularly, the invention relates to substituted 1-phenyl-5-azinylpyrazolyl-3-oxyalkyl acids and their derivatives, to processes for their preparation and to their use for controlling harmful plants.

Description of Related Art

The derivatives of the 1-phenyl-5-azinylpyrazolyl-3-oxyalkyl acids include in particular their esters, salts and/or amides.

The phenyl-5-azinylpyrazolyl-3-oxyalkyl acids according to the invention and their derivatives differ from the already known 1,5-diphenylpyrazolyl-3-oxoacetic acids in that they have a variable azinyl radical (A1-A15) in position 5 of the pyrazole ring.

The prior art also discloses biological effects of substituted 1,5-diphenylpyrazolyl-3-oxoacetic acids and processes for preparing these compounds. DE 2828529 A1 describes the preparation and the lipid-lowering action of 1,5-diphenylpyrazolyl-3-oxoacetic acids.

CN 101284815 discloses 1,5-diphenylpyrazolyl-3-oxoacetic acid derivatives as bactericidally active agrochemicals. Further syntheses and the fungicidal action of 1,5-diphenylpyrazolyl-3-oxoacetic acids are described in Journal of Heterocyclic Chemistry (2012), 49(6), 1370-1375.

In contrast, 1-phenyl-5-azinylpyrazolyl-3-oxyacetic acids or phenyl-5-azinylpyrazolyl-3-oxyalkyl acids and their derivatives have hitherto been unknown.

SUMMARY

It is the object of the present invention to provide novel pyrazole derivatives, namely of 1-phenyl-5-azinylpyrazolyl-3-oxyalkyl acids and their derivatives, which can be used as herbicides or plant growth regulators, having satisfactory herbicidal action and a broad spectrum of activity against harmful plants and/or having high selectivity in crops of useful plants.

The object is achieved by substituted pyrazolyl-3-oxoalkyl acids characterized by an azinyl radical in position 5 of the pyrazole ring, i.e. by substituted 1-phenyl-5-azinylpyrazolyl-3-oxyalkyl acid derivatives, having very good herbicidal action and also very good selectivity.

Surprisingly, these compounds are highly effective against a broad range of economically important weed grasses and broad-leaved weeds. At the same time, the compounds exhibit good crop plant compatibility. Therefore, they can be employed selectively in crop plants, having good activity against harmful plants.

Accordingly, it is an object of the present invention to provide substituted 1-phenyl-5-azinylpyrazolyl-3-oxyalkyl acids of the general formula (I)

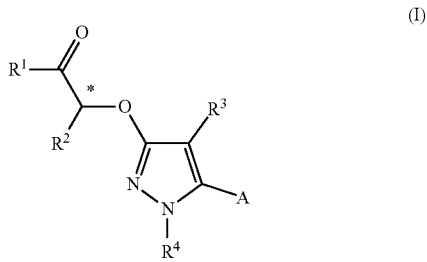

and the agrochemically acceptable salts thereof, where A is selected from the group consisting of A1-A15,

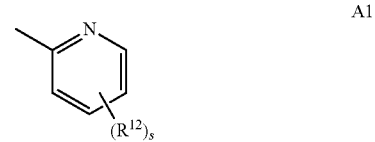

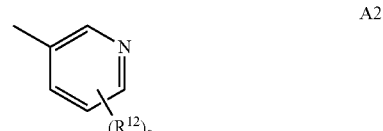

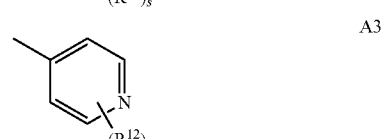

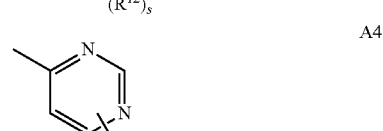

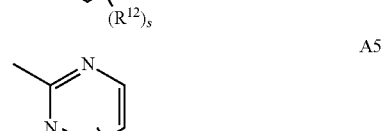

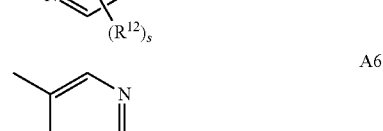

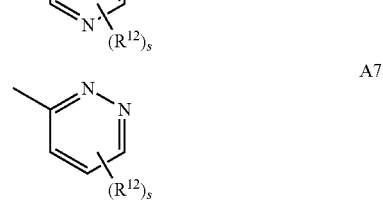

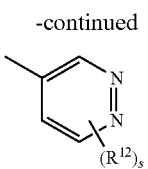
A8

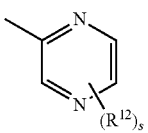
A9

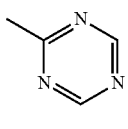
A10

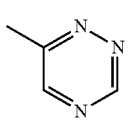
A11

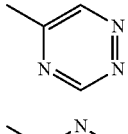
A12

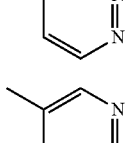
A13

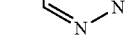
A14

A15

$R^1$ is selected from the group consisting of
  $OR^{1a}$ and
  $NR^9R^{10}$; where
$R^{1a}$ represents hydrogen or
  represents $(C_1-C_6)$-alkyl, $(C_3-C_6)$-cycloalkyl, which is unsubstituted or substituted by one or more substituents selected from the group consisting of halogen, $(C_1-C_6)$-alkyl, $(C_1-C_6)$-haloalkyl, $(C_3-C_6)$-cycloalkyl, $(C_1-C_6)$-alkoxy, cyano and nitro, or $(C_2-C_4)$-alkenyl, $(C_2-C_4)$-alkynyl or
  represents $(C_1-C_4)$-alkyl-SO—$(C_1-C_4)$-alkyl, $(C_1-C_4)$-alkyl-SO$_2$—$(C_1-C_4)$-alkyl- or represents heterocyclyl, heteroaryl, aryl or
  heterocyclyl-$(C_1-C_4)$-alkyl-, heteroaryl-$(C_1-C_4)$-alkyl- and aryl-$(C_1-C_4)$-alkyl-, where aryl, heterocyclyl and heteroaryl are unsubstituted or substituted by halogen, $(C_1-C_6)$-alkyl and/or $(C_1-C_6)$-haloalkyl;
$R^9$ is selected from the group consisting of hydrogen, $(C_1-C_{12})$-alkyl;
$R^{10}$ is selected from the group consisting of
  hydrogen;
  aryl, heteroaryl, heterocyclyl;
  $(C_1-C_2)$-alkyl;
  $(C_3-C_8)$-cycloalkyl, $(C_3-C_7)$-cycloalkyl-$(C_1-C_7)$-alkyl;
  $(C_2-C_{12})$-alkenyl, $(C_5-C_7)$-cycloalkenyl, $(C_2-C_{12})$-alkynyl;
  $S(O)_nR^5$, cyano, nitro, $OR^5$, OH, $SO_2NR^6R^7$, $CO_2R^8$, $COR^8$, $NR^6R^8$, $NR^6COR^8$, $NR^6CO_2R^8$, $NR^6SO_2R^8$;
  where the alkyl, cycloalkyl, alkenyl, cycloalkenyl and alkynyl radicals mentioned above are unsubstituted or in each case independently of one another substituted by m radicals selected from the group consisting of hydrogen, halogen, cyano, nitro, $OR^5$, $S(O)_nR^5$, $SO_2NR^6R^7$, $CO_2R^8$, $CONR^6R^8$, $COR^6$, $NR^6R^8$, $NR^6COR^8$, $NR^6CONR^8R^8$, $NR^6CO_2R^8$, $NR^6SO_2R^8$, $NR^6SO_2NR^6R^8$, $C(R^6)=NOR^8$;
  or
$R^9$ and $R^{10}$ together with the nitrogen atom to which they are attached form a saturated, partially or fully unsaturated five-, six- or seven-membered ring which is optionally mono- to hexasubstituted by radicals from the group consisting of halogen, $(C_1-C_6)$-alkyl, halo-$(C_1-C_6)$-alkyl, $OR^5$, OH, $S(O)_nR^5$, $CO_2R^8$, $CONR^6R^8$, $COR^6$ and $C(R^6)=NOR^8$ and which, in addition to this nitrogen atom, contains r carbon atoms, o oxygen atoms, p sulfur atoms and q elements from the group consisting of $NR^7$, CO and $NCOR^7$ as ring atoms;
$R^5$ represents $(C_1-C_8)$-alkyl, $(C_3-C_6)$-cycloalkyl, $(C_1-C_6)$-haloalkyl or aryl;
$R^6$ represents hydrogen or $R^5$;
$R^7$ represents hydrogen, $(C_1-C_6)$-alkyl, $(C_3-C_6)$-cycloalkyl, $(C_3-C_4)$-alkenyl, $(C_1-C_6)$-alkyl-COO$(C_1-C_2)$-alkyl or $(C_3-C_4)$-alkynyl;
$R^8$ represents hydrogen, $(C_1-C_6)$-alkyl, $(C_3-C_6)$-cycloalkyl, $(C_3-C_4)$-alkenyl or $(C_3-C_4)$-alkynyl;
$R^2$ is selected from the group consisting of
  hydrogen, halogen and cyano;
  $(C_1-C_6)$-alkyl, $(C_1-C_4)$-alkoxy-$(C_1-C_4)$-alkyl, $(C_1-C_6)$-haloalkyl, $(C_1-C_6)$-alkoxy;
  $(C_2-C_6)$-alkenyl, $(C_2-C_6)$-haloalkenyl;
  $(C_2-C_6)$-alkynyl, $(C_2-C_6)$-haloalkynyl;
  $(C_3-C_6)$-cycloalkyl;
$R^3$ is selected from the group consisting of
  hydrogen, $(C_3-C_6)$-cycloalkyl, halogen, cyano, isocyanto, $NO_2$;
  $(C_1-C_6)$-alkyl, $(C_3-C_6)$-cycloalkyl, $(C_1-C_6)$-haloalkyl, $(C_1-C_6)$-alkylcarbonyl, $(C_1-C_6)$-haloalkylcarbonyl, $(C_1-C_4)$-alkyloxycarbonyl;
  $(C_2-C_3)$-alkenyl, $(C_2-C_3)$-haloalkenyl;
  $(C_2-C_3)$-alkynyl, $(C_2-C_3)$-haloalkynyl;
  $(C_1-C_2)$-alkyl-$S(O)_n$ and $(C_1-C_2)$-haloalkyl-$S(O)_n$;
  CHO;
  $NH_2$;
$R^4$ represents phenyl, where the phenyl radical is unsubstituted or mono- or polysubstituted by a radical selected from the group consisting of
  hydrogen, halogen, cyano, isocyanato, nitro;
  $(C_1-C_6)$-alkyl, halo-$(C_1-C_6)$-alkyl, $(C_1-C_3)$-haloalkoxy;
  $(C_2-C_3)$-alkenyl, halo-$(C_2-C_3)$-alkenyl, $(C_1-C_6)$-alkoxy;
  $(C_2-C_3)$-alkynyl, halo-$(C_2-C_3)$-alkynyl, $(C_1-C_4)$-alkyl-$S(O)_n$;
  CHO, $(C_1-C_4)$-alkyloxycarbonyl and $NH_2$;
and where the azinyl substituent or the azinyl substituents $R^{12}$ is selected from the group consisting of
  hydrogen, halogen, cyano, isocyanato, $NO_2$;
  $(C_1-C_6)$-alkyl, $(C_1-C_6)$-haloalkyl, $(C_1-C_6)$-alkylcarbonyl, $(C_1-C_6)$-haloalkylcarbonyl, $(C_1-C_4)$-alkyloxycarbonyl, $(C_1-C_6)$-alkoxy, $(C_1-C_3)$-haloalkoxy, $(C_1-C_4)$-alkyl-$S(O)_n$;
  $(C_2-C_3)$-alkenyl, $(C_2-C_3)$-haloalkenyl;
  $(C_2-C_3)$-alkynyl, $(C_2-C_3)$-haloalkynyl;
  $NH_2$;

and where the running number
m is 0, 1 or 2;
n is 0, 1 or 2;
o is 0, 1 or 2;
p is 0 or 1;
q is 0 or 1;
r is 2, 3, 4, 5 or 6; and
s is 0, 1 or 2.

DETAILED DESCRIPTION OF A PREFERRED EMBODIMENT

There follows a description of preferred, particularly preferred and very particularly preferred definitions of each of the individual substituents. The other substituents of the general formula (I) which are not specified hereinafter have the definition given above.

Accordingly, various embodiments for the compound of the general formula (I) result.

In one embodiment of the invention, the radical A (=azine) is selected from the group consisting of A1-A15

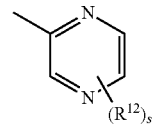 A1

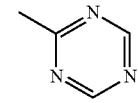 A2

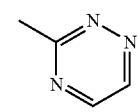 A3

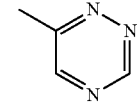 A4

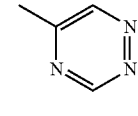 A5

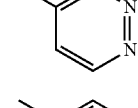 A6

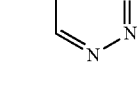 A7

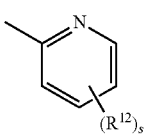 A8

-continued

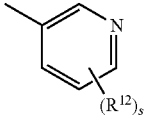 A9

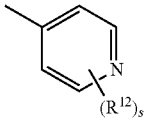 A10

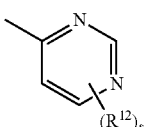 A11

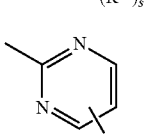 A12

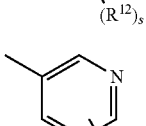 A13

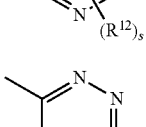 A14

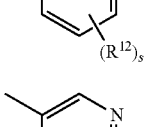 A15

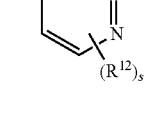 (note: duplicate placement)

Preferably, A is selected from the group consisting of

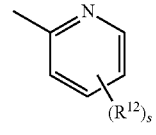 A1

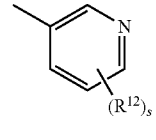 A2

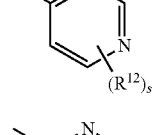 A3

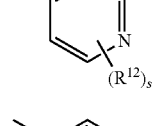 A4

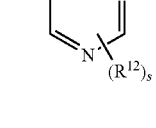 A6

-continued

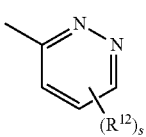
A7

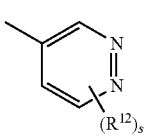
A8

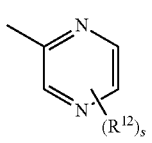
A9

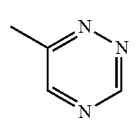
A12

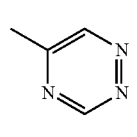
A13

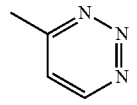
A14

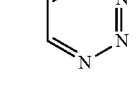
A15

Particularly preferably, A is selected from the group consisting of

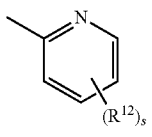
A1

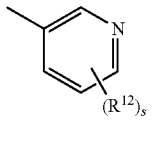
A2

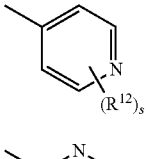
A3

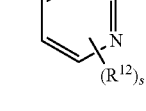
A4

-continued

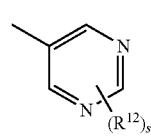
A6

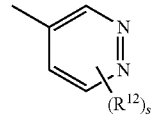
A8

Further embodiments of the invention relate to the radical $R^1$ and the radicals $R^{1a}$ and $R^9$ and $R^{10}$:

$R^1$ is selected from the group consisting of
$OR^{1a}$ and
$NR^9R^{10}$; where
$R^{1a}$ is selected from the group consisting of
hydrogen;
$(C_1-C_6)$-alkyl, $(C_3-C_6)$-cycloalkyl, which is unsubstituted or substituted by one or more substituents selected from the group consisting of halogen, $(C_1-C_6)$-alkyl, $(C_1-C_6)$-haloalkyl, $(C_3-C_6)$-cycloalkyl, $(C_1-C_6)$-alkoxy, cyano and nitro;
$(C_2-C_4)$-alkenyl, $(C_2-C_4)$-alkynyl;
$(C_1-C_4)$-alkyl-SO—$(C_1-C_4)$-alkyl, $(C_1-C_4)$-alkyl-SO$_2$—$(C_1-C_4)$-alkyl-;
heterocyclyl-$(C_1-C_4)$-alkyl, heteroaryl-$(C_1-C_4)$-alkyl and aryl-$(C_1-C_4)$-alkyl, where aryl, heterocyclyl and heteroaryl are unsubstituted or substituted by halogen, $(C_1-C_6)$-alkyl and/or $(C_1-C_6)$-haloalkyl;
$R^9$ is selected from the group consisting of hydrogen, $(C_1-C_{12})$-alkyl;
$R^{10}$ is selected from the group consisting of
hydrogen;
aryl, heteroaryl, heterocyclyl;
$(C_1-C_{12})$-alkyl;
$(C_3-C_8)$-cycloalkyl, $(C_3-C_7)$-cycloalkyl-$(C_1-C_7)$-alkyl;
$(C_2-C_{12})$-alkenyl, $(C_5-C_7)$-cycloalkenyl, $(C_2-C_{12})$-alkynyl;
$S(O)_nR^5$, cyano, nitro, $OR^5$, OH, $SO_2NR^6R^7$, $CO_2R^8$, $COR^8$, $NR^6R^8$, $NR^6COR^8$, $NR^6CO_2R^8$, $NR^6SO_2R^8$;
where the alkyl, cycloalkyl, alkenyl, cycloalkenyl and alkynyl radicals mentioned above are unsubstituted or in each case independently of one another substituted by m radicals selected from the group consisting of
hydrogen, halogen, cyano, nitro, $OR^5$, $S(O)_nR^5$, $SO_2NR^6R^7$, $CO_2R^8$, $CONR^6R^8$, $COR^6$, $NR^6R^8$, $NR^6COR^8$, $NR^6CONR^8R^8$, $NR^6CO_2R^8$, $NR^6SO_2R^8$, $NR^6SO_2NR^6R^8$, $C(R^6)=NOR^8$;
or
$R^9$ and $R^{10}$ together with the nitrogen atom to which they are attached form a saturated, partially or fully unsaturated five-, six- or seven-membered ring which is optionally mono- to hexasubstituted by radicals from the group consisting of halogen, $(C_1-C_6)$-alkyl, halo-$(C_1-C_6)$-alkyl, $OR^5$, $S(O)_nR^5$, $CO_2R^8$, $CONR^6R^8$, $COR^6$ and $C(R^6)=NOR^8$ and which, in addition to this nitrogen atom, contains r carbon atoms, o oxygen atoms, p sulfur atoms and q elements from the group consisting of $NR^7$, CO and $NCOR^7$ as ring atoms.

$R^1$ is preferably selected from the group consisting of
$OR^{1a}$ and
$NR^9R^{10}$; where $R^{1a}$ is preferably selected from the group consisting of
hydrogen;
$(C_1-C_6)$-alkyl, which is unsubstituted or substituted by one or more substituents selected from the group consisting of halogen, $(C_1-C_6)$-alkyl, $(C_1-C_6)$-haloalkyl, $(C_1-C_6)$-alkoxy, cyano and nitro;
$(C_1-C_4)$-alkyl-SO—$(C_1-C_4)$-alkyl, $(C_1-C_4)$-alkyl-SO$_2$—$(C_1-C_4)$-alkyl-;
aryl-$(C_1-C_4)$-alkyl, where the aryl is unsubstituted or substituted by halogen, $(C_1-C_6)$-alkyl and/or $(C_1-C_6)$-haloalkyl;

$R^9$ preferably represents hydrogen or $(C_1-C_4)$-alkyl;
$R^{10}$ is preferably selected from the group consisting of
hydrogen, aryl, $(C_1-C_4)$-alkyl, $(C_3-C_6)$-cycloalkyl, $(C_3-C_6)$-cycloalkyl-$(C_1-C_4)$-alkyl, $(C_2-C_4)$-alkenyl, $S(O)_nR^5$, cyano, nitro, $OR^5$, OH, $SO_2NR^6R^7$, $CO_2R^8$, $COR^8$, $NR^6R^8$, $NR^6COR^8$;
where the alkyl, cycloalkyl and alkenyl radicals mentioned above are unsubstituted or in each case independently of one another substituted by m radicals selected from the group consisting of $S(O)_nR^5$, $SO_2NR^6R^7$, $CO_2R^8$, $NR^6CO_2R^8$;
or
$R^9$ and $R^{10}$ together with the nitrogen atom to which they are attached preferably form a saturated, partially or fully unsaturated five-, six- or seven-membered ring which is optionally mono- to hexasubstituted by radicals from the group consisting of halogen, $(C_1-C_4)$-alkyl, $OR^5$, and which, in addition to this nitrogen atom, contains r carbon atoms, o oxygen atoms, p sulfur atoms and q elements from the group consisting of $NR^7$, CO and $NCOR^7$ as ring atoms.

$R^1$ is particularly preferably selected from the group consisting of
$OR^{1a}$ and
$NR^9R^{10}$; where
$R^{1a}$ is particularly preferably selected from the group consisting of
hydrogen;
$(C_1-C_6)$-alkyl, which is unsubstituted or substituted by one or more substituents selected from the group consisting of halogen, $(C_1-C_6)$-alkyl, $(C_1-C_6)$-haloalkyl, $(C_1-C_6)$-alkoxy;
aryl-$(C_1-C_4)$-alkyl, where the aryl is substituted by $(C_1-C_6)$-alkyl.

$R^9$ particularly preferably represents hydrogen;
$R^{10}$ is particularly preferably selected from the group consisting of aryl, $(C_1-C_4)$-alkyl, $(C_3-C_6)$-cycloalkyl, $(C_3-C_6)$-cycloalkyl-$(C_1-C_7)$-alkyl, $(C_2-C_4)$-alkenyl, $S(O)_nR^5$, $SO_2NR^6R^7$, $CO_2R^8$, $NR^6R^8$,
where the alkyl, cycloalkyl and alkenyl radicals mentioned above are unsubstituted or in each case independently of one another substituted by m radicals selected from the group consisting of $S(O)_nR^5$, $SO_2NR^6R^7$, $CO_2R^8$, $NR^6CO_2R^8$;
or
$R^9$ and $R^{10}$ together with the nitrogen atom to which they are attached particularly preferably form an unsubstituted saturated, partially or fully unsaturated five-, six- or seven-membered ring which, in addition to this nitrogen atom, contains r carbon atoms, o oxygen atoms, p sulfur atoms and q elements from the group consisting of $NR^7$, CO and $NCOR^7$ as ring atoms.

$R^1$ is very particularly preferably selected from the group consisting of
$OR^{1a}$ and
$NR^9R^{10}$; where $R^{1a}$ is very particularly preferably selected from the group consisting of
hydrogen;
methyl and ethyl;
allyl and propargyl;
$PhCH_2$.
$R^9$ very particularly preferably represents hydrogen and
$R^{10}$ is very particularly preferably selected from the group consisting of $(C_1-C_{12})$-alkyl, $S(O)_nR^5$, $SO_2NR^6R^7$, $CO_2R^8$, which are unsubstituted or in each case independently of one another substituted by m radicals selected from the group consisting of $S(O)_nR^5$, $SO_2NR^6R^7$, $CO_2R^8$, $NR^6CO_2R^8$.

Further embodiments of the invention relate to the radical $R^5$.
$R^5$ represents $(C_1-C_4)$-alkyl, $(C_3-C_6)$-cycloalkyl, $(C_1-C_4)$-haloalkyl or aryl.
$R^5$ preferably represents $(C_1-C_4)$-alkyl, $(C_3-C_6)$-cycloalkyl or $(C_1-C_4)$-haloalkyl.
$R^5$ particularly preferably represents $(C_1-C_4)$-alkyl or $(C_1-C_4)$-haloalkyl.
$R^5$ very particularly preferably represents ethyl, methyl, $CF_3$ or $CH_2CF_3$.

Further embodiments of the invention relate to the radical $R^6$.
$R^6$ represents hydrogen or $R^5$.
$R^6$ preferably represents hydrogen.

Further embodiments of the invention relate to the radical $R^7$.
$R^7$ represents hydrogen, $(C_1-C_6)$-alkyl, $(C_3-C_6)$-cycloalkyl, $(C_3-C_4)$-alkenyl, $(C_1-C_6)$-alkyl-COO$(C_1-C_2)$-alkyl or $(C_3-C_4)$-alkynyl.
$R^7$ preferably represents hydrogen or $(C_1-C_6)$-alkyl.
$R^7$ particularly preferably represents hydrogen, methyl or ethyl.

Further embodiments of the invention relate to the radical $R^8$.
$R^8$ represents hydrogen, $(C_1-C_6)$-alkyl, $(C_3-C_6)$-cycloalkyl, $(C_3-C_4)$-alkenyl or $(C_3-C_4)$-alkynyl.
$R^8$ preferably represents hydrogen or $(C_1-C_6)$-alkyl.
$R^8$ particularly preferably represents $(C_1-C_6)$-alkyl.
$R^8$ very particularly preferably represents methyl or ethyl.

Further embodiments of the invention relate to the radical $R^2$.
$R^2$ is selected from the group consisting of
hydrogen, halogen and cyano;
$(C_1-C_6)$-alkyl, $(C_1-C_4)$-alkoxy-$(C_1-C_4)$-alkyl, $(C_1-C_6)$-haloalkyl, $(C_1-C_6)$-alkoxy;
$(C_2-C_6)$-alkenyl, $(C_2-C_6)$-haloalkenyl;
$(C_2-C_6)$-alkynyl, $(C_2-C_6)$-haloalkynyl and
$(C_3-C_6)$-cycloalkyl.
$R^2$ is preferably selected from the group consisting of
hydrogen, halogen, cyano;
$(C_1-C_6)$-alkyl, $(C_1-C_6)$-haloalkyl, $(C_1-C_6)$-alkoxy;
$(C_3-C_6)$-cycloalkyl and $(C_1-C_6)$-alkyl-$(C_1-C_3)$-alkoxy.
$R^2$ is particularly preferably selected from the group consisting of
hydrogen;
$(C_1-C_6)$-alkyl and $(C_1-C_6)$-haloalkyl, $(C_1-C_4)$-alkoxy.
$R^2$ is very particularly preferably selected from the group consisting of
hydrogen;
methyl and ethyl.

Further embodiments of the invention relate to the radical $R^3$.
$R^3$ is selected from the group consisting of
hydrogen, $(C_3-C_6)$-cycloalkyl, halogen, cyano, isocyanato, $NO_2$;
$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_4)$-alkyloxycarbonyl;
$(C_2-C_3)$-alkenyl, $(C_2-C_3)$-haloalkenyl;

$(C_2-C_3)$-alkynyl, $(C_2-C_3)$-haloalkynyl;
$(C_1-C_2)$-alkyl-$S(O)_n$ and $(C_1-C_2)$-haloalkyl-$S(O)_n$;
CHO and
$NH_2$.

$R^3$ is preferably selected from the group consisting of
hydrogen, $(C_3-C_6)$-cycloalkyl, halogen, cyano, isocyanato, $NO_2$;
$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_2)$-alkyloxycarbonyl, $(C_1-C_3)$-alkoxy, $(C_1-C_6)$-haloalkoxy;
$(C_1-C_6)$-alkylthio, $(C_1-C_6)$-haloalkylthio;
$(C_2-C_3)$-alkenyl, $(C_2-C_3)$-haloalkenyl;
$(C_2-C_3)$-alkynyl, $(C_2-C_3)$-haloalkynyl and
$S(O)_n$—$(C_1-C_2)$-alkyl where n=1 or 2.

$R^3$ is particularly preferably selected from the group consisting of
hydrogen, $(C_3-C_6)$-cycloalkyl, halogen, cyano, $NO_2$;
$(C_1-C_6)$-alkyl, $(C_1-C_6)$-haloalkyl, $(C_1-C_6)$-haloalkoxy and
$(C_1-C_6)$-alkylthio.

$R^3$ is very particularly preferably selected from the group consisting of
hydrogen, fluorine, bromine, chlorine, cyano, $NO_2$;
methyl, $CF_3$ and $OCF_3$.

$R^3$ is most preferably selected from the group consisting of
fluorine, chlorine, bromine, iodine, cyano, $NO_2$ and
$CF_3$ (trifluoromethyl).

Further embodiments of the invention relate to the radical $R^4$.

$R^4$ represents phenyl, where the phenyl radical is unsubstituted or mono- or polysubstituted by a radical selected from the group consisting of
hydrogen, halogen, cyano, isocyanato, nitro;
$(C_1-C_6)$-alkyl, halo-$(C_1-C_6)$-alkyl, $(C_1-C_3)$-haloalkoxy;
$(C_2-C_3)$-alkenyl, halo-$(C_2-C_3)$-alkenyl, $(C_1-C_6)$-alkoxy;
$(C_2-C_3)$-alkynyl, halo-$(C_2-C_3)$-alkynyl, $(C_1-C_4)$-alkyl-$S(O)_n$;
CHO, $(C_1-C_4)$-alkyloxycarbonyl and $NH_2$.

$R^4$ preferably represents phenyl, where the phenyl radical is unsubstituted or mono- or polysubstituted by a radical selected from the group consisting of
hydrogen, fluorine, chlorine, bromine;
$(C_1-C_6)$-alkyl, halo-$(C_1-C_6)$-alkyl, $(C_1-C_3)$-haloalkoxy and
$(C_1-C_6)$-alkoxy.

$R^4$ particularly preferably represents phenyl, where the phenyl radical is unsubstituted or mono- or polysubstituted by a radical selected from the group consisting of
hydrogen, fluorine, chlorine, bromine;
methyl, ethyl, $CF_3$ and $OCF_3$.

$R^4$ very particularly preferably represents phenyl, where the phenyl radical is unsubstituted or mono- or polysubstituted by a radical selected from the group consisting of hydrogen, fluorine and chlorine.

$R^4$ most preferably represents phenyl which is mono- or polysubstituted by fluorine and/or chlorine.

Further embodiments of the invention relate to the radical $R^{12}$.

$R^{12}$ is selected from the group consisting of
hydrogen, halogen, cyano, isocyanato, $NO_2$;
$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_4)$-alkyloxycarbonyl, $(C_1-C_6)$-alkoxy, $(C_1-C_3)$-haloalkoxy, $(C_1-C_4)$-alkyl-$S(O)_n$;
$(C_2-C_3)$-alkenyl, $(C_2-C_3)$-haloalkenyl;
$(C_2-C_3)$-alkynyl, $(C_2-C_3)$-haloalkynyl and
$NH_2$.

$R^{12}$ is preferably selected from the group consisting of
hydrogen, halogen, cyano;
$(C_1-C_6)$-alkyl, $(C_1-C_6)$-haloalkyl;
$(C_1-C_6)$-alkoxy and $(C_1-C_3)$-haloalkoxy.

$R^{12}$ is particularly preferably selected from the group consisting of
hydrogen, fluorine, chlorine, cyano;
methyl, ethyl, $CF_3$ and $OCF_3$.

$R^{12}$ is very particularly preferably selected from the group consisting of
hydrogen, fluorine, chlorine, cyano;
methyl, $CF_3$ and $OCF_3$.

$R^{12}$ is most preferably selected from the group consisting of
hydrogen, fluorine, chlorine, cyano and
$CF_3$.

Further embodiments of the invention relate to the running numbers m, n, o, p, q, r and s. The running number
m is 0, 1 or 2;
n is 0, 1 or 2;
o is 0, 1 or 2;
p is 0 or 1;
q is 0 or 1;
r is 2, 3, 4, 5 or 6; and
s is 0, 1 or 2.

Preferably, the running number
m is 0 or 1;
n is 0, 1 or 2;
o is 0 or 1;
p is 0;
r is 6; and
s is 0 or 1.

Particularly preferably, the running number
m is 0 or 1;
n is 0, 1 or 2;
o is 1;
p is 0;
r is 6; and
s is 0 or 1.

In the context of the present invention, it is possible to variably combine the individual definitions, for example the preferred, particularly preferred and very particularly preferred definitions, of the substituents $R^1$, $R^{1a}$, $R^9$, $R^{10}$, $R^5$, $R^6$, $R^7$, $R^8$ and $R^2$, $R^3$, $R^4$ and $R^{12}$ and those of the running numbers m, n, o, p, q, r, s.

This means that the present invention encompasses compounds of the general formula (I) in which, for example, the substituent $R^1$ has a preferred definition and the substituents $R^{1a}$ to $R^{12}$ have the general definition or else the substituent $R^{1a}$ has a preferred definition, the substituent $R^9$ has a particularly preferred or very particularly preferred definition and the remaining substituents have a general definition.

Three of these combinations of the definitions given above for the substituents $R^1$, $R^{1a}$, $R^9$, $R^{10}$, $R^5$, $R^6$, $R^7$, $R^8$ and $R^2$, $R^3$, $R^4$ and $R^{12}$ and the running numbers m, n, o, p, q, r, s are illustrated below in an exemplary manner and thus each specifically disclosed as further embodiments:

combinations of the particularly preferred definitions given respectively above for the substituents $R^1$, $R^{1a}$, $R^9$, $R^{10}$, $R^5$, $R^6$, $R^7$, $R^8$ and $R^2$, $R^3$, $R^4$ and $R^{12}$ and the running numbers m, n, o, p, q, r, s, combinations of the very particularly preferred definitions given respectively above for the substituents $R^1$, $R^{1a}$, $R^9$, $R^{10}$, $R^5$, $R^6$, $R^7$, $R^8$ and $R^2$, $R^3$, $R^4$ and $R^{12}$ and the running numbers m, n, o, p, q, r, s and combinations of the most preferred definitions given respectively above for the substituents $R^1$, $R^{1a}$, $R^9$, $R^{10}$, $R^5$, $R^6$, $R^7$, $R^8$ and $R^2$, $R^3$, $R^4$ and $R^{12}$ and the running numbers m, n, o, p, q, r, s.

Particular preference is given to compounds of the general formula (I) in which

A is selected from the group consisting of

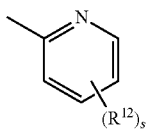
A1

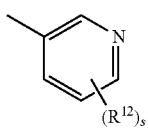
A2

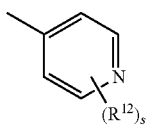
A3

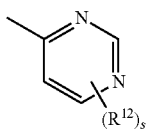
A4

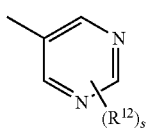
A6

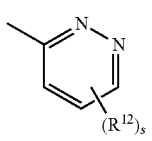
A7

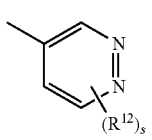
A8

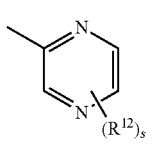
A9

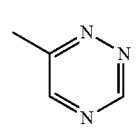
A12

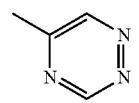
A13

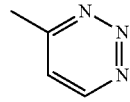
A14

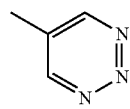
A15

$R^1$ is selected from the group consisting of
OR$^{1a}$ and
NR$^9$R$^{10}$; where
$R^{1a}$ is selected from the group consisting of
hydrogen;
($C_1$-$C_6$)-alkyl, which is unsubstituted or substituted by one or more substituents selected from the group consisting of halogen, ($C_1$-$C_6$)-alkyl, ($C_1$-$C_6$)-haloalkyl, ($C_1$-$C_6$)-alkoxy, cyano and nitro;
($C_1$-$C_4$)-alkyl-SO—($C_1$-$C_4$)—, ($C_1$-$C_4$)-alkyl-SO$_2$—($C_1$-$C_4$)—;
aryl-($C_1$-$C_4$)-alkyl, where the aryl is unsubstituted or substituted by halogen, ($C_1$-$C_6$)-alkyl and/or ($C_1$-$C_6$)-haloalkyl;
$R^9$ represents hydrogen, ($C_1$-$C_4$)-alkyl;
$R^{10}$ is selected from the group consisting of
hydrogen, aryl, ($C_1$-$C_4$)-alkyl, ($C_3$-$C_6$)-cycloalkyl, ($C_3$-$C_6$)-cycloalkyl-($C_1$-$C_4$)-alkyl, ($C_2$-$C_4$)-alkenyl, S(O)$_n$R$^5$, cyano, nitro, OR$^5$, SO$_2$NR$^6$R$^7$, CO$_2$R$^8$, COR$^8$, NR$^6$R$^8$, NR$^6$COR$^8$;
which are unsubstituted or in each case independently of one another substituted by m radicals selected from the group consisting of
S(O)$_n$R$^5$, SO$_2$NR$^6$R$^7$, CO$_2$R$^8$, NR$^6$CO$_2$R$^8$;
or
$R^9$ and $R^{10}$ together with the nitrogen atom to which they are attached form a saturated, partially or fully unsaturated five-, six- or seven-membered ring which is optionally mono- to hexasubstituted by radicals from the group consisting of halogen, ($C_1$-$C_4$)-alkyl, OR$^5$, and which, in addition to this nitrogen atom, contains r carbon atoms, o oxygen atoms, p sulfur atoms and q elements from the group consisting of NR$^7$, CO and NCOR$^7$ as ring atoms;
$R^5$ represents ($C_1$-$C_4$)-alkyl, ($C_3$-$C_6$)-cycloalkyl or ($C_1$-$C_4$)-haloalkyl;
$R^6$ represents hydrogen or R$^5$;
$R^7$ represents hydrogen or ($C_1$-$C_4$)-alkyl;
$R^8$ represents hydrogen or ($C_1$-$C_4$)-alkyl;
$R^2$ is selected from the group consisting of
hydrogen, cyano, halogen;
($C_1$-$C_4$)-alkyl, ($C_1$-$C_4$)-haloalkyl, ($C_1$-$C_6$)-alkoxy;
($C_3$-$C_6$)-cycloalkyl, ($C_1$-$C_6$)-alkyl-($C_1$-$C_3$)-alkoxy;
$R^3$ is selected from the group consisting of
hydrogen, ($C_3$-$C_6$)-cycloalkyl, halogen, cyano, isocyanato, NO$_2$;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_2$)-alkyloxycarbonyl, ($C_1$-$C_3$)-alkoxy, ($C_1$-$C_6$)-haloalkoxy;
($C_1$-$C_6$)-alkylthio, ($C_1$-$C_6$)-haloalkylthio;
($C_2$-$C_3$)-alkenyl, ($C_2$-$C_3$)-haloalkenyl;
($C_2$-$C_3$)-alkynyl, ($C_2$-$C_3$)-haloalkynyl;
S(O)$_n$—($C_1$-$C_2$)-alkyl where n=1 or 2;
$R^4$ represents phenyl, where the phenyl radical is unsubstituted or mono- or polysubstituted by a radical selected from the group consisting of hydrogen, fluorine, chlorine, bromine;
$(C_1-C_6)$-alkyl, halo-$(C_1-C_6)$-alkyl, $(C_1-C_3)$-haloalkoxy;
$(C_1-C_6)$-alkoxy;
$R^{12}$ is selected from the group consisting of
hydrogen, halogen, cyano;
$(C_1-C_6)$-alkyl, $(C_1-C_6)$-haloalkyl;
$(C_1-C_6)$-alkoxy, $(C_1-C_3)$-haloalkoxy;
and where the running number
m is 0 or 1;
n is 0, 1 or 2;
o is 0 or 1;
p is 0;
r is 6; and
s is 0 or 1.

Very particular preference is given to compounds of the general formula (I) in which A is selected from the group consisting of

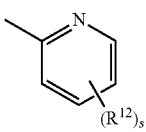

A1

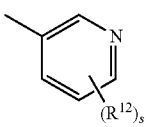

A2

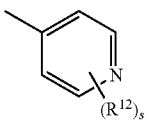

A3

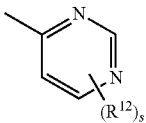

A4

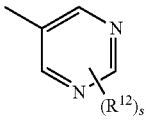

A6

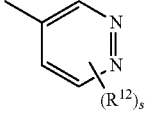

A8

$R^{1a}$ is selected from the group consisting of
hydrogen;
$(C_1-C_6)$-alkyl, which is unsubstituted or substituted by one or more substituents selected from the group consisting of halogen, $(C_1-C_6)$-alkyl, $(C_1-C_6)$-haloalkyl, $(C_1-C_6)$-alkoxy;
aryl-$(C_1-C_4)$-alkyl, where the aryl is substituted by $(C_1-C_6)$-alkyl;
$R^9$ represents hydrogen;
$R^{10}$ is selected from the group consisting of
aryl, $(C_1-C_{12})$-alkyl, $(C_3-C_8)$-cycloalkyl, $(C_3-C_7)$-cycloalkyl-$(C_1-C_7)$-alkyl, $(C_2-C_{12})$-alkenyl, $S(O)_nR^5$, $SO_2NR^6R^7$, $CO_2R^8$, $NR^6R^8$,
which are unsubstituted or where the alkyl, cycloalkyl, alkenyl, cycloalkenyl and alkynyl radicals mentioned above are in each case independently of one another substituted by m radicals selected from the group consisting of $S(O)_nR^5$, $SO_2NR^6R^7$, $CO_2R^8$, $NR^6CO_2R^8$;
or
$R^9$ and $R^{10}$ together with the nitrogen atom to which they are attached form an unsubstituted saturated, partially or fully unsaturated five-, six- or seven-membered ring which, in addition to this nitrogen atom, contains r carbon atoms, o oxygen atoms, p sulfur atoms and q elements from the group consisting of $NR^7$, CO and $NCOR^7$ as ring atoms;
$R^5$ represents $(C_1-C_8)$-alkyl or $(C_1-C_6)$-haloalkyl;
$R^6$ represents hydrogen;
$R^7$ represents hydrogen or $(C_1-C_6)$-alkyl;
$R^8$ represents $(C_1-C_6)$-alkyl;
$R^2$ is selected from the group consisting of
hydrogen;
$(C_1-C_6)$-alkyl, $(C_1-C_6)$-haloalkyl, $(C_1-C_4)$-alkoxy;
$R^3$ is selected from the group consisting of
hydrogen, $(C_3-C_6)$-cycloalkyl, halogen, cyano, $NO_2$;
$(C_1-C_6)$-alkyl, $(C_1-C_6)$-haloalkyl, $(C_1-C_6)$-haloalkoxy;
$(C_1-C_6)$-alkylthio;
$R^4$ represents phenyl, where the phenyl radical is unsubstituted or mono- or polysubstituted by a radical selected from the group consisting of
hydrogen, fluorine, chlorine, bromine;
methyl, ethyl, $CF_3$, $OCF_3$;
$R^{12}$ is selected from the group consisting of
hydrogen, fluorine, chlorine, cyano;
methyl, ethyl, $CF_3$, $OCF_3$;
and where the running number
m is 0 or 1;
n is 0, 1 or 2;
o is 1;
p is 0;
r is 6; and
s is 0 or 1.

Most preference is given to compounds of the general formula (I) in which

A is selected from the group consisting of

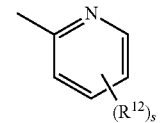

A1

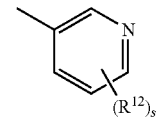

A2

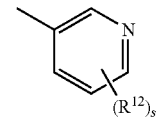

A3

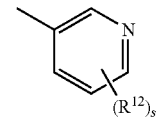

A4

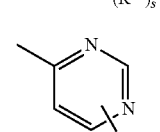

-continued

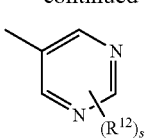

A6

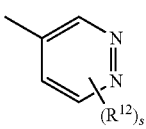

A8

$R^1$ is selected from the group consisting of
  $OR^{1a}$ and
  $NR^9R^{10}$; where
$R^{1a}$ is selected from the group consisting of
  hydrogen;
  methyl and ethyl;
  allyl and propargyl;
  $PhCH_2$;
$R^9$ represents hydrogen and
$R^{10}$ is selected from the group consisting of $(C_1-C_{12})$-alkyl, $S(O)_nR^5$, $SO_2NR^6R^7$, $CO_2R^8$, which are unsubstituted or in each case independently of one another substituted by m radicals selected from the group consisting of $S(O)_nR^5$, $SO_2NR^6R^7$, $CO_2R^8$, $NR^6CO_2R^8$;
$R^5$ represents ethyl, methyl, $CF_3$, $CH_2CF_3$;
$R^6$ represents hydrogen or $R^5$;
$R^7$ represents hydrogen, methyl or ethyl;
$R^8$ represents methyl or ethyl;
$R^2$ is selected from the group consisting of
  hydrogen;
  methyl, ethyl;
$R^3$ is selected from the group consisting of
  hydrogen, fluorine, bromine, chlorine, cyano, $NO_2$;
  methyl, $CF_3$, $OCF_3$;
$R^4$ represents phenyl, where the phenyl radical is unsubstituted or mono- or polysubstituted by a radical selected from the group consisting of hydrogen, fluorine and chlorine;
$R^{12}$ is selected from the group consisting of
  hydrogen, fluorine, chlorine, cyano;
  methyl, $CF_3$, $OCF_3$.

In the context of the compounds of the general formula (I) specifically disclosed herein, for their part the radicals $R^3$, $R^4$ and $R^{12}$ are of particular significance.

$R^3$ is with utmost preference selected from the group consisting of
  fluorine, chlorine, bromine, iodine, cyano, $NO_2$;
  $CF_3$.

$R^4$ with utmost preference represents phenyl which is mono- or polysubstituted by fluorine and/or chlorine.

$R^{12}$ is with utmost preference selected from the group consisting of
  fluorine, chlorine, cyano,
  $CF_3$.

In all the formulae specified hereinafter, the substituents and symbols have the same meaning as described in formula (I), unless defined differently.

Alkyl denotes saturated straight-chain or branched hydrocarbyl radicals having the number of carbon atoms specified in each case, e.g. $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl denotes straight-chain or branched alkyl groups where some or all of the hydrogen atoms in these groups may be replaced by halogen atoms, e.g. $C_1-C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkenyl denotes unsaturated straight-chain or branched hydrocarbyl radicals having the number of carbon atoms stated in each case and one double bond in any position, for example $C_2-C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl denotes straight-chain or branched hydrocarbyl radicals having the number of carbon atoms specified in each case and one triple bond in any position, e.g. $C_2-C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, i-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Cycloalkyl denotes a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene.

In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

Cycloalkenyl denotes a carbocyclic, nonaromatic, partially unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

Alkoxy denotes saturated straight-chain or branched alkoxy radicals having the number of carbon atoms specified in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy denotes straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-1,2-difluoroethoxy, 2,2-dichloro-2-fluoroethoxy, 2,2,2-trichloroethoxy, pentafluoroethoxy and 1,1,1-trifluoroprop-2-oxy.

Heterocyclyl denotes a saturated or partially unsaturated mono-, bi- or tricyclic ring system group of carbon atoms and at least one heteroatom, preferably selected from N, O and/or S.

Heteroaryl, unless defined differently elsewhere: a mono-, bi- or tricyclic heterocyclic group of carbon atoms and at least one heteroatom, where at least one cycle is aromatic. In one embodiment, at least one heteroatom is N, O or S. In one embodiment, all heteroatoms are selected from N, O or S. In one embodiment, the ring system is a 5- to 10- or a 5- to 6-membered ring system. In one embodiment, heteroaryl is an aromatic monocyclic ring system of 5 or 6 ring atoms. In a further embodiment, heteroaryl is an aromatic monocyclic ring system containing 1 to 4 heteroatoms from the group N, O or S. Furthermore, heteroaryl may be a bicyclic ring system consisting of 8 to 14 ring atoms or a tricyclic ring system consisting of 13 to 14 ring atoms. Examples: furyl, thienyl, pyrazolyl, imidazolyl, triazolyl, thiazolyl, indolyl, benzimidazolyl, indazolyl, benzofuranyl, benzothiophenyl, benzothiazolyl, benzoxazolyl, quinolinyl, isoquinolinyl.

The term "aryl" denotes an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl".

Independently of one another, the aryls listed above are preferably mono- to pentasubstituted, for example, by hydrogen, halogen, alkyl, haloalkyl, hydroxyl, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkano, haloalkylthio, alkylthio, hydrothio, hydroxyalkyl, heteroarylalkoxy, arylalkoxy, heterocyclylalkoxy, heterocyclylalkylthio, heterocyclyloxy, heterocyclylthio, heteroaryloxy, bisalkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, bisalkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

When a base structure is substituted "by one or more radicals" from a list of radicals (=group) or a generically defined group of radicals, this in each case includes simultaneous substitution by a plurality of identical and/or structurally different radicals.

The term "halogen" means fluorine, chlorine, bromine or iodine. If the term is used for a radical, "halogen" means a fluorine, chlorine, bromine or iodine atom.

According to the nature of the substituents defined above, the compounds of the formula (I) have acidic properties and can form salts, if appropriate also internal salts or adducts, with inorganic or organic bases or with metal ions. If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl groups, mono-, di- and trialkanolamines of ($C_1$-$C_4$)-alkanols, choline and chlorocholine, and also organic amines such as trialkylamines, morpholine, piperidine or pyridine. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula [NRR'R''R''']$^+$ in which R to R''' each independently of one another represent an organic radical, in particular alkyl, aryl, aralkyl or alkylaryl. Also suitable are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts comprise the conjugate base of the acid as the anion.

Suitable substituents present in deprotonated form, such as, for example, sulfonic acids or carboxylic acids, may form inner salts with groups which for their part can be protonated, such as amino groups. If a group is polysubstituted by radicals, this means that this group is substituted by one or more identical or different radicals from those mentioned.

In all the formulae specified hereinafter, the substituents and symbols have the same meaning as described in formula (I), unless defined differently. Arrows in a chemical formula denote the points at which it is joined to the rest of the molecule.

There follows a description of preferred, particularly preferred and very particularly preferred definitions of each of the individual substituents. The other substituents of the general formula (I) which are not specified hereinafter have the definition given above.

The present compounds of the general formula (I) have, at the second carbon of the alkyl acid structure, a chiral carbon atom which, in the structure shown below, is indicated by the marker (*):

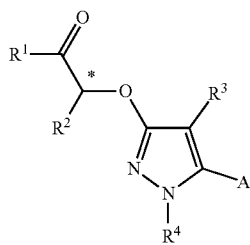

(I)

According to the rules of Cahn, Ingold and Prelog (CIP rules), this carbon atom can have either an (R) configuration or an (S) configuration.

The present invention encompasses compounds of the general formula (I) both with (S) and with (R) configuration, meaning that the present invention encompasses the compounds of the general formula (I) in which the carbon atom in question has (1) an (R) configuration; or
(2) an (S) configuration.

In addition, the scope of the present invention also encompasses (3) any mixtures of compounds of the general formula (I) having an (R) configuration (compounds of the general formula (I-(R)) with compounds of the general formula (I) having an (S) configuration (compounds of the general formula (I-S)), the present invention also encompassing a racemic mixture of the compounds of the general formula (I) having (R) and (S) configuration.

However, within the context of the present invention, preference is given particularly to compounds of the general formula (I) having (R) configuration with a selectivity of 60 to 100%, preferably 80 to 100%, especially 90 to 100%, very particularly 95 to 100%, where the particular (R) compound is present with an enantioselectivity of in each case more than 50% ee, preferably 60 to 100% ee, especially 80 to 100% ee, very particularly 90 to 100% ee, most preferably 95 to 100% ee, based on the total content of (R) compound in question.

Accordingly, the present invention relates especially to compounds of the general formula (I*) in which the stereochemical configuration on the carbon atom marked by (*) is present with a stereochemical purity of 60 to 100% (R), preferably 80 to 100% (R), especially 90 to 100% (R), very particularly 95 to 100% (R).

In addition, depending on the respective radicals chosen, further stereo elements may be present in the compounds of the general formula (I) according to the invention.

Preference is given to the compounds listed in the tables below. The compounds of the general formula (I) having (R) configuration are marked accordingly in the column which lists the radical $R^2$. For example, if $R^2$=alkyl, the preferred stereochemical configuration at the carbon atom marked (*) of the general formula (I) is the (R) configuration.

However, if, for example, $R^2$=alkoxy, the preferred stereochemical configuration at the carbon atom marked (*) of the general formula (I) is the (S) configuration.

TABLE I 2-pyrazyl

| Example number | $R^{1a}$ | $R^2$ | $R^3$ | $R^4$ | $(R^{12})_s$ |
|---|---|---|---|---|---|
| I-001 | Me | (R)-Me | Br | (2-fluorophenyl) | H |
| I-002 | H | (R)-Me | Br | (2-fluorophenyl) | H |
| I-003 | H | H | Br | (2-fluorophenyl) | H |
| I-004 | Et | H | Br | (2-fluorophenyl) | H |

TABLE II 2-pyridyl

| Example number | R¹ | R² | R³ | R⁴ | $(R^{12})_s$ |
|---|---|---|---|---|---|
| II-002 | OMe | H | Br | (2-fluorophenyl) | 6-F |
| II-003 | CH₃O-NH- | H | Br | (2-fluorophenyl) | 5-F |
| II-004 | CH₃O-NH- | H | Br | (2,4-difluorophenyl) | 5-F |
| II-005 | NC-CH₂CH₂-NH- | H | Br | (2-fluorophenyl) | 5-F |
| II-008 | NC-CH₂CH₂-NH- | H | Br | (2,4-difluorophenyl) | 5-F |
| II-011 | CH₃O-NH(CH₃)- | H | Br | (2,4-difluorophenyl) | 5-F |
| II-012 | OEt | H | I | (2-fluorophenyl) | 5-F |
| II-013 | H₃C-O-CH₂-C(O)-NH-* | H | Br | (2-fluorophenyl) | 5-F |
| II-014 | OEt | H | Br | (2-fluorophenyl) | 5-F |
| II-015 | OH | H | Br | (2-fluorophenyl) | 5-F |
| II-016 | CH₃O-NH(CH3)- | H | Br | (2-fluorophenyl) | 5-F |
| II-017 | HO-NH- | H | Br | (2-fluorophenyl) | 5-F |
| II-018 | HO-NH- | H | Br | (2,4-difluorophenyl) | 5-F |

TABLE III 2-pyrimidyl

| Example number | R¹ᵃ | R² | R³ | R⁴ | $(R^{12})_s$ |
|---|---|---|---|---|---|
| III-001 | Me | (R)-Me | Br | (2-fluorophenyl) | 5-F |
| III-002 | Et | H | Br | (2-fluorophenyl) | H |
| III-003 | H | (R)-Me | Br | (2-fluorophenyl) | H |
| III-004 | Et | H | Br | (2-fluorophenyl) | 5-F |
| III-005 | Me | (R)-Me | Br | (2-fluorophenyl) | H |
| III-006 | PhCH₂ | H | Br | (2-fluorophenyl) | 5-F |
| III-007 | H | H | Br | (2-fluorophenyl) | H |
| III-008 | H | H | Br | (2-fluorophenyl) | 5-F |
| III-009 | H | (R)-Me | Br | (2-fluorophenyl) | 5-F |

TABLE IV 4-pyridazyl

| Example number | R¹ᵃ | R² | R³ | R⁴ | $(R^{12})_s$ |
|---|---|---|---|---|---|
| IV-001 | Et | H | Br | (2-fluorophenyl) | H |
| IV-002 | H | H | Br | (2-fluorophenyl) | H |
| IV-003 | Et | H | CN | (2-fluorophenyl) | H |

TABLE V

4-pyrimidyl

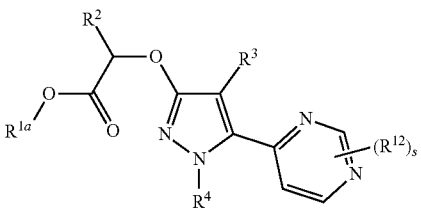

| Example number | R¹ᵃ | R² | R³ | R⁴ | (R¹²)ₛ |
|---|---|---|---|---|---|
| V-001 | Et | H | Br | (2-fluorophenyl) | H |
| V-002 | Et | H | Br | (2-fluorophenyl) | 6-OEt |
| V-003 | Et | H | Br | (2-fluorophenyl) |  |
| V-004 | H | H | Br | (2-fluorophenyl) | H |
| V-005 | Me | (R)-Me | Br | (2-fluorophenyl) | H |
| V-006 | H | (R)-Me | Br | (2-fluorophenyl) | H |
| V-007 | H | H | Br | (2-fluorophenyl) | 6-OEt |

TABLE VI

5-pyrimidyl

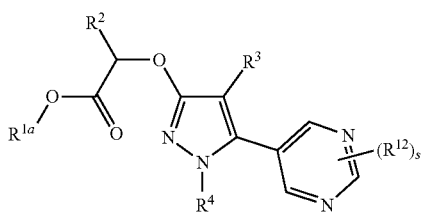

| Example number | R¹ᵃ | R² | R³ | R⁴ | (R¹²)ₛ |
|---|---|---|---|---|---|
| VI-001 | Et | H | Br | (2-fluorophenyl) | H |
| VI-002 | PhCH₂ | H | Br | (2-fluorophenyl) | H |
| VI-003 | Et | H | Cl | (2-fluorophenyl) | H |
| VI-004 | Me | H | Br | (2-fluorophenyl) | H |
| VI-004 | Me | H | Br | (2-fluorophenyl) | H |
| VI-004 | Me | H | Br | (2-fluorophenyl) | H |
| VI-005 | Et | H | NO₂ | (2-fluorophenyl) | H |
| VI-006 | Me | (R)-Me | NO₂ | (2-fluorophenyl) | H |
| VI-007 | H | H | Br | (2-fluorophenyl) | H |
| VI-007 | H | H | Br | (2-fluorophenyl) | H |
| VI-008 | Me | (S)-Me | Br | (2-fluorophenyl) | H |

TABLE VI-continued

5-pyrimidyl

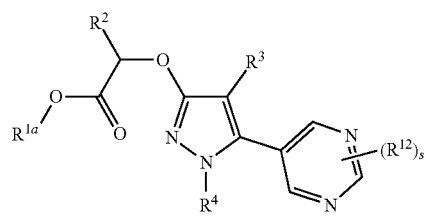

| Example number | R¹ᵃ | R² | R³ | R⁴ | (R¹²)ₛ |
|---|---|---|---|---|---|
| VI-009 | Me | Me | Cl | phenyl | 2-Cl |
| VI-010 | Me | Me | Cl | phenyl | H |
| VI-011 | Me | (R)-Me | Br | (2-fluorophenyl) | H |
| VI-012 | H | (R)-Me | Br | (2-fluorophenyl) | H |
| VI-013 | Me | (R)-Me | Br | phenyl | H |
| VI-014 | H | (R)-Me | Br | (2-fluorophenyl) | H |
| VI-015 | H | Me | Cl | phenyl | H |
| VI-016 | H | (R)-Me | NO₂ | (2-fluorophenyl) | H |
| VI-017 | Me | (R)-Me | Cl | (2-fluorophenyl) | H |
| VI-018 | H | (R)-Me | Cl | (2-fluorophenyl) | H |

TABLE VII

3-pyridyl

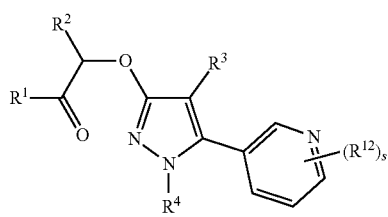

| Example number | R¹ | R² | R³ | R⁴ | (R¹²)ₛ |
|---|---|---|---|---|---|
| VII-001 | OMe | H | Br | (2-fluorophenyl) | 6-F |
| VII-002 | OMe | H | Br | (4-fluorophenyl) | 6-F |

TABLE VII-continued 3-pyridyl

| Example number | R¹ | R² | R³ | R⁴ | (R¹²)ₛ |
|---|---|---|---|---|---|
| VII-003 | OH | H | Br | (2-fluorophenyl) | 6-F |
| VII-004 | OMe | (R)-Me | Br | (2-fluorophenyl) | 6-F |
| VII-005 | OiPr | H | Br | (2-fluorophenyl) | 6-F |
| VII-006 | PhCH₂O- | H | Br | (2-fluorophenyl) | 6-F |
| VII-007 | OEt | H | Br | (2-fluorophenyl) | 6-CF₃ |
| VII-008 | OMe | (R)-Me | Br | phenyl | H |
| VII-009 | OEt | H | Cl | 2,4,5-triF-phenyl | 6-F |
| VII-010 | OEt | H | CF₃ | (2-fluorophenyl) | 6-F |
| VII-011 | OH | H | Br | (2-fluorophenyl) | 6-CF₃ |
| VII-012 | OEt | H | Br | (2-fluorophenyl) | 6-F |
| VII-013 | OMe | Me | Cl | phenyl | 6-Me |
| VII-014 | OMe | Me | Br | phenyl | 6-F |
| VII-015 | OEt | H | Br | (2-fluorophenyl) | 5-F |
| VII-016 | OEt | H | Cl | 2,4-diF-phenyl | 6-F |
| VII-017 | OMe | Me | Cl | phenyl | 6-Cl |
| VII-018 | OMe | H | Br | phenyl | 6-F |
| VII-019 | OEt | Me | Br | (2-fluorophenyl) | 6-F |
| VII-020 | OMe | Me | Br | phenyl | 6-F |
| VII-021 | OEt | H | methylsulfanyl | (2-fluorophenyl) | 6-F |
| VII-022 | OMe | H | Br | (2-fluorophenyl) | 6-MeO |
| VII-023 | OMe | Me | Cl | phenyl | 6-F |
| VII-025 | OH | H | Br | (2-fluorophenyl) | 5-F |
| VII-026 | OMe | Me | Br | phenyl | 6-F |
| VII-027 | OEt | H | F | 2,4-diF-Ph | 6-F |
| VII-028 | OMe | H | Br | (4-fluorophenyl) | H |
| VII-029 | OMe | Et | Br | (2-fluorophenyl) | 6-F |
| VII-030 | OH | H | CF₃ | (2-fluorophenyl) | 6-F |
| VII-031 | OMe | H | CF₃ | (2-fluorophenyl) | 6-F |
| VII-032 | OMe | Me | Cl | phenyl | H |
| VII-033 | OH | H | Cl | 2,4,5-triF-Ph | 6-F |
| VII-034 | OEt | H | F | (2-fluorophenyl) | 6-F |
| VII-035 | OMe | H | Br | (2-fluorophenyl) | 5-F |
| VII-036 | OEt | H | I | (2-fluorophenyl) | 6-F |
| VII-037 | OH | H | I | (2-fluorophenyl) | 6-F |
| VII-038 | OMe | (S)-Me | Cl | (2-fluorophenyl) | 6-F |
| VII-039 | OMe | H | Br | (2-fluorophenyl) | 6-CF₃ |
| VII-040 | OMe | H | F | (2-fluorophenyl) | 6-F |
| VII-041 | OMe | (R)-Me | Cl | phenyl | H |
| VII-042 | OH | (R)-Me | Cl | phenyl | H |
| VII-043 | OH | Me | Cl | phenyl | H |
| VII-044 | OEt | H | Br | (2-fluorophenyl) | 6-SOCH₃ |
| VII-045 | OEt | H | Br | (4-fluorophenyl) | 6-propoxy |
| VII-046 | OEt | H | Br | (2-fluorophenyl) | 6-SO2CH₃ |
| VII-047 | OH | H | Br | (2-fluorophenyl) | 6-S-CH₃ |
| VII-049 | OMe | H | CF₃ | (2-fluorophenyl) | 6-OMe |
| VII-050 | OMe | H | I | (2-fluorophenyl) | 6-OMe |
| VII-051 | OH | H | I | (4-fluorophenyl) | 6-hydroxy |
| VII-052 | -O-CH₂-CH₂-OMe | H | Br | (2-fluorophenyl) | 6-F |
| VII-053 | OEt | H | acetyl | (2-fluorophenyl) | 6-F |
| VII-056-a | OEt | H | Br | (2-methylphenyl) | 6-F |
| VII-056 | OH | H | methylsulfanyl | (2-fluorophenyl) | 6-F |
| VII-057-a | OH | F | Br | (2-fluorophenyl) | 6-F |
| VII-057 | OEt | Me | I | (2-fluorophenyl) | 6-F |
| VII-058 | OEt | H | I | (2-methylphenyl) | 6-F |
| VII-059 | OEt | H | CF₃ | (4-fluorophenyl) | 6-F |
| VII-060 | OMe | Me | Br | (2-fluorophenyl) | 6-F |
| VII-061 | OMe | H | cyano | (2,6-difluorophenyl) | 6-F |
| VII-062 | OMe | (R)-Me | Br | (2,5-difluorophenyl) | 6-F |
| VII-063 | OMe | H | cyano | (2,5-difluorophenyl) | 6-F |

TABLE VII-continued 3-pyridyl

[Structure: pyrazole core with R³ at 4-position, 3-pyridyl (with (R¹²)ₛ) at 5-position, N-R⁴ at 1-position, and O-CHR²-C(=O)R¹ at 3-position]

| Example number | R¹ | R² | R³ | R⁴ | (R¹²)ₛ |
|---|---|---|---|---|---|
| VII-064 | [(S)-tetrahydrothiophen-2-one-3-yl-O-*] | H | Br | (2-fluorophenyl) | 6-F |
| VII-065 | OEt | H | Br | (4-fluorophenyl) | 6-F |
| VII-066 | OEt | Me | CF₃ | (2-fluorophenyl) | 6-F |
| VII-067 | OH | H | Br | (4-methylphenyl) | 6-F |
| VII-068 | -NH-OMe | H | Br | (2-fluorophenyl) | 6-F |
| VII-069 | OH | H | I | (4-fluorophenyl) | 6-F |
| VII-071-a | OEt | F | Br | (2-fluorophenyl) | 6-F |
| VII-071 | OEt | H | methylsulfonyl | (2-fluorophenyl) | 6-F |
| VII-072 | OEt | H | methylsulfinyl | (2-fluorophenyl) | 6-F |
| VII-073 | OH | H | methylsulfonyl | (2-fluorophenyl) | 6-F |
| VII-074 | OH | H | methylsulfinyl | (2-fluorophenyl) | 6-F |
| VII-075-a | OMe | (R)-Me | Cl | (2-fluorophenyl) | 6-F |
| VII-075 | -OCH₂CH₂COOMe | (R)-Me | Br | (2-fluorophenyl) | 6-F |
| VII-076 | OH | H | Br | phenyl | 6-F |
| VII-077 | OH | H | cyclopropyl | (2-fluorophenyl) | 6-F |
| VII-078 | OEt | H | difluoromethyl | (2-fluorophenyl) | 6-F |
| VII-079 | OEt | H | nitro | phenyl | 6-F |
| VII-080 | OEt | H | nitro | (4-nitrophenyl) | 6-F |
| VII-081 | -OCH₂CH₂COOMe | (R)-Me | Cl | (2-fluorophenyl) | 6-F |
| VII-082 | OH | (R)-Me | Cl | (2-fluorophenyl) | 6-F |
| VII-083 | OH | H | cyano | phenyl | 6-F |
| VII-084 | OEt | H | cyano | phenyl | 6-F |
| VII-085 | -OCH₂CH₂COOMe | H | cyclopropyl | (2-fluorophenyl) | 6-F |
| VII-086 | OMe | (R)-Me | Br | (4-nitrophenyl) | 6-F |
| VII-087 | OEt | H | Br | (4-nitrophenyl) | 6-F |
| VII-088 | OEt | H | ethynyl | (2-fluorophenyl) | 6-F |
| VII-089 | OMe | H | Br | (2,5-difluorophenyl) | 6-F |
| VII-090 | [(tetrahydrofuran-2-yl)methyl-O-*] | H | Br | (2-fluorophenyl) | 6-F |
| VII-091 | [(tetrahydrofuran-3-yl)methyl-O-*] | H | Br | (2-fluorophenyl) | 6-F |
| VII-092 | OH | (R)-Me | Br | (2-fluorophenyl) | 6-F |
| VII-095 | OH | H | Br | (4-fluorophenyl) | 6-F |
| VII-096 | OH | Me | Br | (2-fluorophenyl) | 6-F |
| VII-097 | OH | H | I | (2-methylphenyl) | 6-F |
| VII-098 | [(furan-2-yl)methyl-O-*] | H | Br | (2-fluorophenyl) | 6-F |
| VII-099 | OMe | (R)-Me | CN | (2,5-difluorophenyl) | 6-F |
| VII-100 | OH | H | Br | (2,4-difluorophenyl) | 6-F |

TABLE VII-continued 3-pyridyl

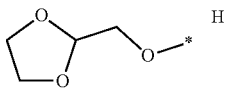

| Example number | $R^1$ | $R^2$ | $R^3$ | $R^4$ | $(R^{12})_s$ |
|---|---|---|---|---|---|
| VII-101 | OEt | H | Br | (2,4-difluorophenyl) | 6-F |
| VII-102 | OEt | H | I | (4-fluorophenyl) | 6-F |
| VII-103 | (1,3-dioxolan-2-yl)methoxy | H | Br | (2-fluorophenyl) | 6-F |
| VII-104 | NC-CH$_2$CH$_2$-O- | H | Br | (2-fluorophenyl) | 6-F |
| VII-105 | OEt | H | CF$_3$ | (2-methylphenyl) | 6-F |
| VII-106 | OH | Me | CF$_3$ | (2-fluorophenyl) | 6-F |
| VII-107 | OMe | (S)-Me | Br | (2,5-difluorophenyl) | 6-F |
| VII-108 | Cl-CH$_2$CH$_2$-O- | H | Br | (2-fluorophenyl) | 6-F |
| VII-109 | OMe | H | Br | (2,6-difluorophenyl) | 6-F |
| VII-110 | NC-CH$_2$CH$_2$-O- | H | Br | (2-fluorophenyl) | 6-F |
| VII-111 | -O-CH$_2$CH$_2$COOMe | H | Br | (2-fluorophenyl) | 6-F |
| VII-113 | OMe | H | I | (2-fluorophenyl) | 6-F |
| VII-114 | OEt | H | formyl | (2-fluorophenyl) | 6-F |
| VII-115 | OH | H | F | (2-fluorophenyl) | 6-F |
| VII-116 | OEt | H | Br | phenyl | 6-F |
| VII-117 | OEt | H | Me | (2-fluorophenyl) | 6-F |
| VII-118 | OH | Me | I | (2-fluorophenyl) | 6-F |
| VII-119 | OEt | H | cyclopropyl | (2-fluorophenyl) | 6-F |
| VII-121 | OEt | (R)-Me | Br | (2-fluorophenyl) | 6-F |
| VII-123-a | OMe | (R)-Me | Br | (2-fluorophenyl) | 6-F |
| VII-123 | OMe | H | methylsulfanyl | (2-fluorophenyl) | 6-F |
| VII-124 | MeS-CH$_2$-CH$_2$-O- | H | Br | (2-fluorophenyl) | 6-F |
| VII-125 | OH | H | CF$_3$ | (4-fluorophenyl) | 6-F |
| VII-127 | OEt | H | Br | (2-fluorophenyl) | 6-OEt |
| VII-128 | OH | (R)-Me | Br | (2-fluorophenyl) | 5-F |
| VII-130 | OEt | (R)-Me | Br | (2-fluorophenyl) | 5-F |
| VII-132 | OMe | (R)-Me | Br | (2,5-difluorophenyl) | 5-F |
| VII-134 | -CH$_2$CH$_2$COOMe | (R)-Me | Br | (2-fluorophenyl) | 5-F |
| VII-135 | OMe | (R)-Me | I | (2,5-difluorophenyl) | 5-F |
| VII-136 | OEt | (R)-Me | Br | (2,5-difluorophenyl) | 5-F |
| VII-137 | OH | (R)-Me | Br | (2,5-difluorophenyl) | 5-F |
| VII-138 | -CH$_2$CH$_2$COOMe | H | Br | (2-fluorophenyl) | 5-F |
| VII-140 | OEt | (R)-Me | cyclopropyl | (2,5-difluorophenyl) | 5-F |
| VII-141 | OH | (R)-Me | cyclopropyl | (2,5-difluorophenyl) | 5-F |
| VII-142 | OH | (R)-Me | CN | (2,5-difluorophenyl) | 5-F |
| VII-143 | OEt | (R)-Me | CN | (2,5-difluorophenyl) | 5-F |
| VII-144 | -CH$_2$CH$_2$COOMe | (R)-Me | Br | (2,5-difluorophenyl) | 5-F |
| VII-145 | MeO-CH$_2$-CH$_2$-O- | (R)-Me | Br | (2,5-difluorophenyl) | 5-F |
| VII-146 | OMe | (R)-Me | cyclopropyl | (2,5-difluorophenyl) | 5-F |
| VII-147 | OMe | (R)-Me | CN | (2,5-difluorophenyl) | 5-F |
| VII-148 | OEt | H | Br | (2-fluorophenyl) | 5,6-diF |
| VII-149 | OMe | (R)-Me | Br | (2-fluorophenyl) | 5,6-diF |

TABLE VIII

4-pyridyl

| Example number | R¹ | R² | R³ | R⁴ | (R¹²)ₛ |
|---|---|---|---|---|---|
| VIII-001 | OMe | Me | Cl | phenyl | 2-Cl |
| VIII-002 | OMe | H | Br | (2-fluorophenyl) | 2-F |
| VIII-003 | OEt | H | Br | (2-fluorophenyl) | 2-F |
| VIII-004 | OH | H | Br | (2-fluorophenyl) | 2-F |
| VIII-005 | OMe | H | Br | (4-fluorophenyl) | 2-F |
| VIII-006 | OMe | (R)-Me | Br | (2-fluorophenyl) | 2-F |
| VIII-007 | OMe | Me | Cl | phenyl | 2-F |
| VIII-008 | OMe | H | CN | (2,5-difluorophenyl) | 2-F |
| VIII-009 | methyl (methylamino)acetate group | H | Br | (2-fluorophenyl) | 2-F |
| VIII-010 | OMe | H | Br | (2,5-difluorophenyl) | 2-F |
| VIII-011 | (tetrahydrofuran-3-yl)methoxy | H | Br | (2-fluorophenyl) | 2-F |
| VIII-012 | MeSO₂-NH- | H | Br | (2-fluorophenyl) | 2-F |

TABLE IX

Amides-5-pyrimidyl

| Example number | R² | R³ | R⁴ | R⁹ | R¹⁰ | (R¹²)ₛ |
|---|---|---|---|---|---|---|
| IX-001 | H | Br | (2-fluorophenyl) | CH₂=CHCH₂- | H | H |
| IX-002 | (R)-Me | NO₂ | (2-fluorophenyl) | CH₂=CHCH₂- | H | H |

TABLE X 3-pyridyl

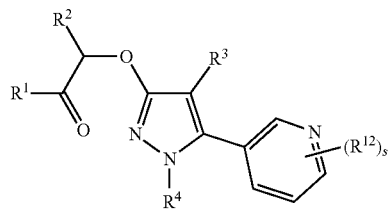

| Example number | R¹ | R² | R³ | R⁴ | $(R^{12})_s$ |
| --- | --- | --- | --- | --- | --- |
| X-001 | CH₂=CHCH₂NH- | H | Br | (2-fluorophenyl) | 6-F |
| X-002 | MeO₂CCH₂NH- | H | Br | (2-fluorophenyl) | 6-F |
| X-003 | CF₃CH₂SO₂NH- | H | Br | (2-fluorophenyl) | 6-F |
| X-004 | MeSO₂NH- | H | Br | (2-fluorophenyl) | 6-F |
| X-005 | Me₂NSO₂NH- | H | Br | (2-fluorophenyl) | 6-F |
| X-006 | CF₃CH₂SO₂NH- | H | CF₃ | (2-fluorophenyl) | 6-F |
| X-007 | MeO₂CCH₂NH- | H | CF₃ | (2-fluorophenyl) | 6-F |
| X-008 | *-N-piperidine-4-COOH | H | Br | (2-fluorophenyl) | 6-F |
| X-009 | *-N-pyrrolidine-2-COOH | H | Br | (2-fluorophenyl) | 6-F |
| X-010 | *-N-pyrrolidine-3-COOH | H | Br | (2-fluorophenyl) | 6-F |
| X-011 | *-N-thiazolidin-2-one | H | Br | (2-fluorophenyl) | 6-F |
| X-012 | HOOC-CH₂-NH-* | F | Br | (2-fluorophenyl) | 6-F |
| X-013 | *-N-pyrrolidine-3-C(O)OMe | H | Br | (2-fluorophenyl) | 6-F |
| X-014 | MeO-C(O)-CH₂-NH-* | F | Br | (2-fluorophenyl) | 6-F |

TABLE X-continued 3-pyridyl

[Structure: R²-CH(R¹C(O))-O-C(=pyrazole with R³, N-R⁴)-pyridyl-(R¹²)ₛ]

| Example number | R¹ | R² | R³ | R⁴ | (R¹²)ₛ |
|---|---|---|---|---|---|
| X-015 | [N-ethyl piperidine-4-carboxylate, N-linked] | H | Br | (2-fluorophenyl) | 6-F |
| X-016 | [methyl pyrrolidine-2-carboxylate, N-linked] | H | Br | (2-fluorophenyl) | 6-F |
| X-018 | [methyl piperidine-3-carboxylate, N-linked] | H | Br | (2-fluorophenyl) | 6-F |
| X-019 | MeO-N(CH₃)- | H | Br | (2-fluorophenyl) | 6-F |
| X-020 | [methyl glycinate, N-linked: MeO-C(O)-CH₂-NH-*] | H | CF₃ | (4-fluorophenyl) | 6-F |
| X-021-a | [HO-C(O)-CH₂-NH-*] | H | Br | (2-fluorophenyl) | 6-F |
| X-021 | [MeO-C(O)-CH₂-NH-*] | (R)-Me | Br | (2-fluorophenyl) | 6-F |
| X-022 | F₃C-CH₂-SO₂-NH- | H | CF₃ | (4-fluorophenyl) | 6-F |
| X-023 | HO-NH- | H | Br | (2-fluorophenyl) | 6-F |
| X-024 | MeO-NH- | H | Br | (2,4-difluorophenyl) | 6-F |
| X-025 | MeO-N(CH₃)- | H | Br | (2,4-difluorophenyl) | 6-F |
| X-026 | [HO-C(O)-CH₂-NH-*] | H | CF₃ | (2-fluorophenyl) | 6-F |
| X-027 | -NMe2 | H | Br | (2-fluorophenyl) | 6-F |
| X-028 | HO-NH- | H | Br | (2,4-difluorophenyl) | 6-F |
| X-029 | NC-CH₂CH₂-NH- | H | Br | (2,4-difluorophenyl) | 6-F |
| X-030 | [MeO-C(O)-CH₂-N(Me)-*] | H | Br | (2-fluorophenyl) | 6-F |

TABLE X-continued 3-pyridyl

[Structure: pyrazole with R¹-C(O)-CH(R²)-O- at 3-position, R³ at 4-position, N-R⁴ at N1, and 3-pyridyl(R¹²)s at 5-position]

| Example number | R¹ | R² | R³ | R⁴ | (R¹²)s |
|---|---|---|---|---|---|
| X-031 | ethyl N-methyl-N-(sulfamoyl*)glycinate [EtO-C(O)-CH₂-N(CH₃)-S(O)₂-NH-*] | H | Br | (2-fluorophenyl) | 6-F |
| X-032 | NC-CH₂CH₂-NH- | H | Br | (2-fluorophenyl) | 6-F |
| X-033 | *-N-piperidin-3-yl-COOH | H | Br | (2-fluorophenyl) | 5-F |
| X-034 | *-N-piperidin-3-yl-C(O)OCH₃ | H | Br | (2-fluorophenyl) | 5-F |
| X-035 | *-N-pyrrolidin-2-yl-C(O)OCH₃ | H | Br | (2-fluorophenyl) | 5-F |
| X-036 | *-N-piperidin-4-yl-C(O)OEt | H | Br | (2-fluorophenyl) | 5-F |
| X-037 | *-N-pyrrolidin-3-yl-C(O)OCH₃ | H | Br | (2-fluorophenyl) | 5-F |
| X-038 | *-N-piperidin-4-yl-COOH | H | Br | (2-fluorophenyl) | 5-F |

TABLE X-continued 3-pyridyl

| Example number | R¹ | R² | R³ | R⁴ | $(R^{12})_s$ |
|---|---|---|---|---|---|
| X-039 | (pyrrolidine-2-carboxylic acid, N-linked) | H | Br | (2-fluorophenyl) | 5-F |
| X-040 | (pyrrolidine-3-carboxylic acid, N-linked) | H | Br | (2-fluorophenyl) | 5-F |
| X-041 | (ethyl 2-(N-methyl-N-sulfamoyl)acetate linked via N) | H | Br | (2-fluorophenyl) | 5-F |

A further aspect of the invention relates to the preparation of the compounds of the general formula (I) according to the invention. The compounds according to the invention can be prepared in various ways.

Compounds according to the invention can be prepared, for example, by the synthesis processes shown in Scheme 1 below from substituted 1-phenyl-5-azinyl-1H-pyrazol-3-ols (II).

The synthesis of the compound of the general formula (I) can be prepared by alkylation of the compound of the general formula (Ia) using a halide of the general formula (III) in the presence of a base, by or analogously to methods known to the person skilled in the art (see Scheme 1). The base may be a carbonate salt of an alkali metal. Preferably, the base is a carbonate salt of an alkali metal selected from the group consisting of lithium, sodium, potassium and caesium, (for example lithium, sodium, potassium or caesium), and the reaction is preferably carried out in the temperature range between room temperature and 150° C. in a suitable solvent, for example dichloromethane, acetonitrile, N,N-dimethylformamide or ethyl acetate. See *J. Med. Chem.* 2011, 54(16), 5820-5835 and WO2010/010154. The radical "X" represents, for example, chlorine, bromine or iodine.

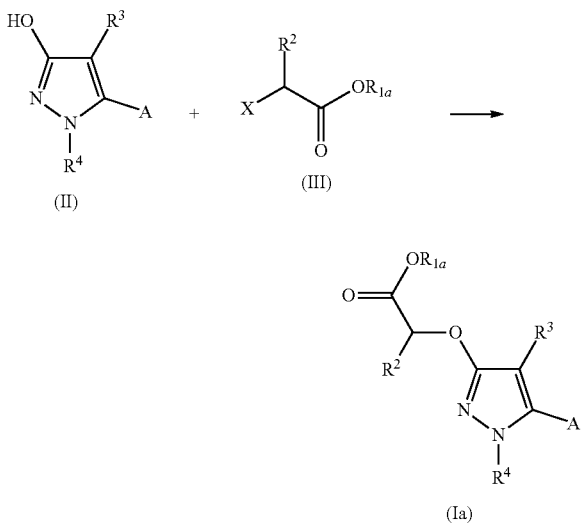

Scheme 1

Scheme 2 describes the synthesis of the compound of the general formula (Ib) by reaction of a pyrazole of the general formula (Ia) with a halosuccinimide of the general formula (IV) in a suitable solvent such as N,N-dimethylformamide.

Scheme 2

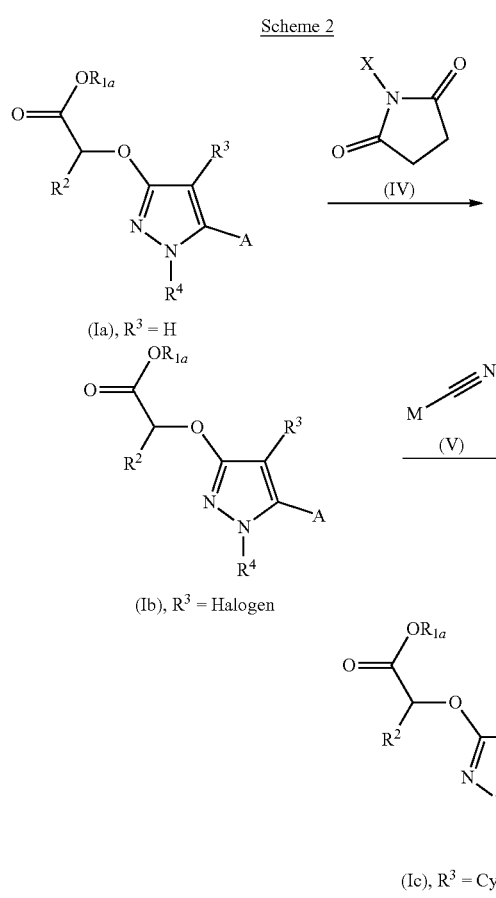

A compound of the general formula (Ic) can be prepared, for example, by reaction of a compound of the formula (Ib) in a suitable solvent with a metal cyanide M-CN (V) with addition of a suitable amount of a transition metal catalyst, in particular palladium catalysts such as palladium(0)tetrakis(triphenylphosphine) or palladium diacetate or bis(triphenylphosphine)palladium(II) dichloride or nickel catalysts such as nickel(II) acetylacetonate or bis(triphenylphosphine)nickel(II) chloride, preferably at elevated temperature in an organic solvent such as, for example, 1,2-dimethoxyethane or N,N-dimethylformamide (Scheme 2). The radical "M" represents, for example, magnesium, zinc, lithium or sodium. Generally suitable are cross-coupling methods described in R. D. Larsen, Organometallics in Process Chemistry 2004 Springer Verlag, in I. Tsuji, *Palladium Reagents and Catalysts* 2004 Wiley, and in M. Belier, C. Bolm, *Transition Metals for Organic Synthesis* 2004 VCH-Wiley. Further suitable synthesis methods are described in *Chem. Rev.* 2006, 106, 2651; *Platinum Metals Review,* 2009, 53, 183; *Platinum Metals Review* 2008, 52, 172 and *Acc. Chem. Res.* 2008, 41, 1486.

The 3-hydroxypyrazoles (II) can be prepared analogously to methods known from the literature from substituted 3-azinylpropynoic acid derivatives and phenylhydrazines (Scheme 3; e.g.: *Adv. Synth. Catal.* 2014, 356, 3135-3147) or from substituted azinylacrylic acid derivatives and phenylhydrazines (Scheme 3; e.g.: *J. Heterocyclic Chem.,* 49, 130 (2012)).

The compounds of the general formula (VIII) are synthesized via an amide coupling of an acid of the general formula (VI) with an arylhydrazine or hetarylhydrazine of the general formula (VII) in the presence of an amide coupling reagent such as, for example, T3P, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide (see Chemistry of Peptide Synthesis, Ed. N. Leo Benoiton, Taylor & Francis, 2006, ISBN-10: 1-57444-454-9). Polymer-bound reagents, for example polymer-bound dicyclohexylcarbodiimide, are also suitable for this coupling reaction. The reaction takes place preferably within the temperature range between 0° C. and 80° C., in a suitable solvent, for example dichloromethane, tetrahydrofuran, acetonitrile, N,N-dimethylformamide or ethyl acetate, and in the presence of a base, for example triethylamine, N,N-diisopropylethylamine or 1,8-diazabicyclo[5.4.0]undec-7-cene (see Scheme 3). For T3P peptide coupling conditions see *Organic Process Research & Development* 2009, 13, 900-906.

Scheme 3

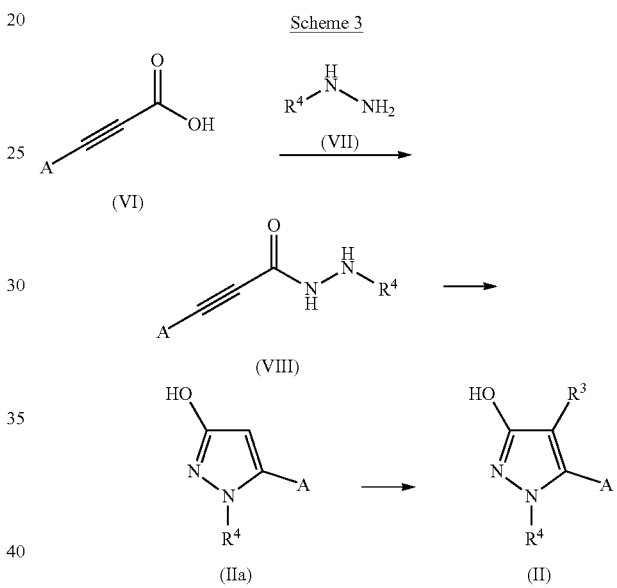

Scheme 3 describes the synthesis of the compound of the general formula (II) by reaction of a pyrazole of the general formula (IIa) with an electrophile such as N-bromosuccinimide. The reaction preferably takes place in the temperature range between 0° C. and 120° C. in a suitable solvent such as N,N-dimethylformamide, 1,2-dichloroethane or acetonitrile.

The synthesis of the 3-hydroxypyrazoles of the general formula (IIa) takes place by reaction of the compounds of the general formula (VIII) in the presence of a copper halide such as copper(I) iodide, copper(I) bromide or an acid such as methanesulfonic acid. The reaction preferably takes place in the temperature range between 0° C. and 120° C. in a suitable solvent such as 1,2-dichloroethane, acetonitrile, N,N-dimethylformamide, n-propanol or ethyl acetate. Preferably, the reaction takes place in N,N-dimethylformamide.

Scheme 4

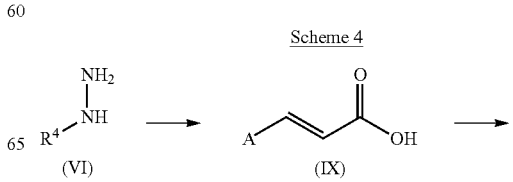

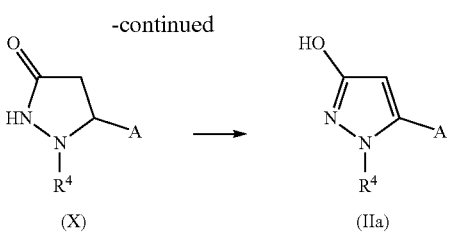

Compounds of the general formula (X) can be synthesized via an amide coupling of an acid of the general formula (IX) with an arylhydrazine or hetarylhydrazine of the general formula (VI) in the presence of an amide coupling reagent such as, for example, T3P, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide. The reaction takes place preferably within the temperature range between 0° C. and 80° C., in a suitable solvent, for example dichloromethane, acetonitrile, N,N-dimethylformamide or ethyl acetate, and in the presence of a base, for example triethylamine, N,N-diisopropylethylamine or 1,8-diazabicyclo[5.4.0]undec-7-ene (see Scheme 4).

The synthesis of the 3-hydroxypyrazoles of the general formula (IIa) takes place by reaction of the compounds of the general formula (X) in the presence of an iron halide such as iron(III) chloride. The reaction preferably takes place in the temperature range between 0° C. and 120° C. in a suitable solvent such as 1,2-dichloroethane, acetonitrile, N,N-dimethylformamide or ethyl acetate.

Compounds of the general formula (XIII) can be synthesized by N-arylation of a 3-hydroxypyrazole of the general formula (XI) with an aryl halide in the presence of a copper halide such as copper(I) iodide. The reaction takes place preferably within the temperature range between 0° C. and 120° C., in a suitable solvent, for example acetonitrile or N,N-dimethylformamide, and in the presence of a base, for example triethylamine or caesium carbonate (see Scheme 5). The compounds of the general formula (XI) can be prepared to methods analogously known to the person skilled in the art (*Chem. Med. Chem.* 2015, 10, 1184-1199). The radical "X" represents, for example, chlorine, bromine or iodine.

Scheme 5

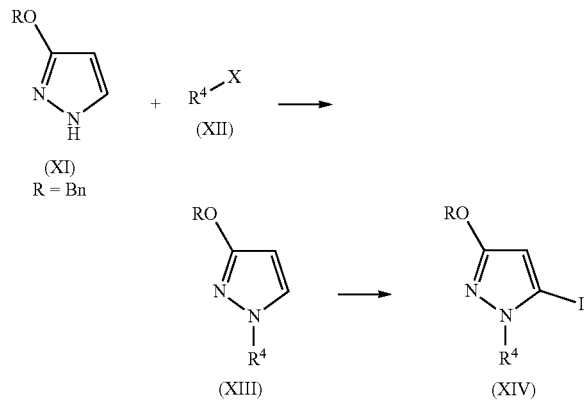

The 5-iodopyrazoles of the general formula (XIV) are synthesized by reaction of the compounds of the general formula (XIII) in the presence of a base such as lithium diisopropylamide and iodine. The reaction (Scheme 5) preferably takes place in the temperature range between −78° C. and −60° C. in a suitable solvent such as diethyl ether and tetrahydrofuran.

A compound of the formula (XVI) can be prepared, for example, by reaction of a compound of the formula (XIV) in a suitable solvent with an A-M (XVI) with addition of a suitable amount of a transition metal catalyst, in particular palladium catalysts such as palladium diacetate or bis(triphenylphosphine)palladium(II) dichloride or nickel catalysts such as nickel(II) acetylacetonate or bis(triphenylphosphine)nickel(II) chloride, preferably at elevated temperature in an organic solvent such as 1,2-dimethoxyethane. The radical "M" represents, for example, $B(OR^b)(OR^c)$, where the radicals $R^b$ and $R^c$ independently of one another represent, for example, hydrogen or $(C_1-C_4)$-alkyl, or, if the radicals $R^b$ and $R^c$ are attached to one another, together represent ethylene or propylene.

Scheme 6

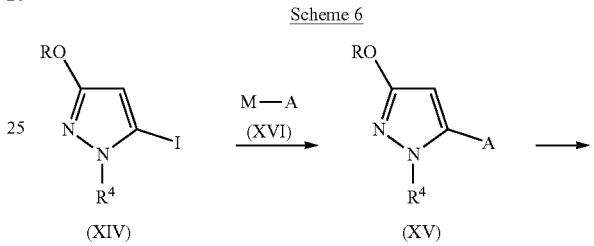

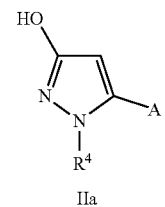

IIa

The compound of the general formula (XVIII) can be synthesized by alkylation of the compound of the general formula (XVII) using a halide of the general formula (III) in the presence of a base, by or analogously to methods known to the person skilled in the art (see Scheme 7). The base can be a carbonate salt of an alkali metal (for example lithium, sodium, potassium or caesium), and the reaction is preferably carried out in the temperature range between room temperature and 150° C. in a suitable solvent, for example dichloromethane, acetonitrile, N,N-dimethylformamide or ethyl acetate. The compounds of the general formulae (XVII) are commercially available.

Compounds of the general formula (XIX) can be prepared by diazotization or Sandmeyer reaction with the compound of the general formula (XVIII) using the customary organic and inorganic nitrites such as 1,1-dimethylethyl nitrite, tert-butyl nitrite or isoamyl nitrite in the presence of usable reagents such as mixtures of copper(I) and copper(II) bromide/chloride or iodine (Scheme 7). The reaction preferably takes place in the temperature range between room temperature and 0° C. and 120° C. in a suitable solvent such as dichloromethane, acetonitrile, N,N-dimethylformamide or diiodomethane. The radical "X" represents, for example, chlorine, bromine or iodine.

Scheme 7

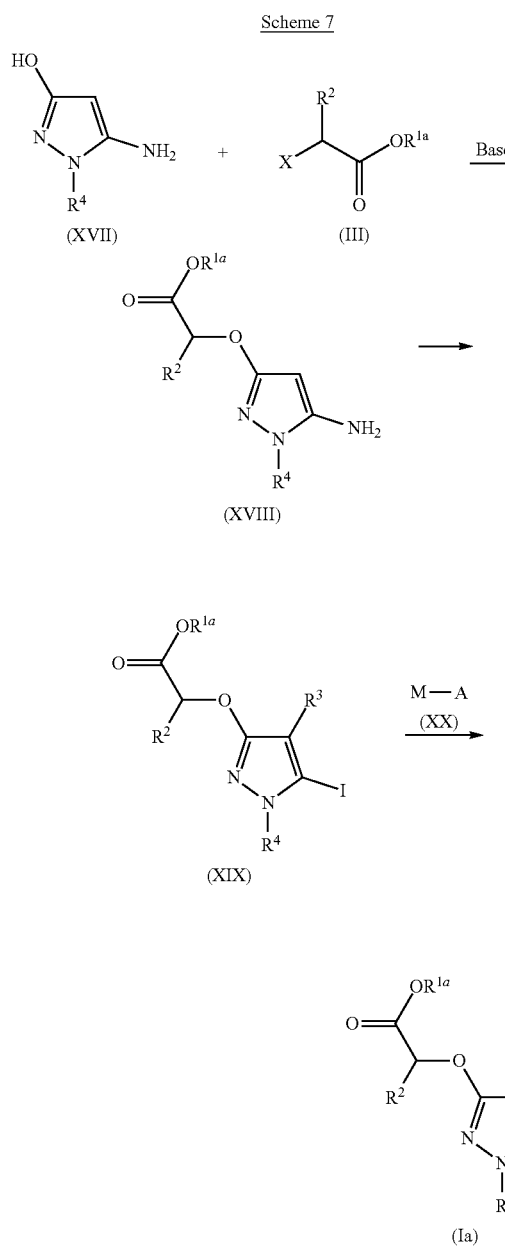

(XVII) (III) (XVIII) (XIX) (Ia)

A compound of the formula (Ia) can be prepared, for example, by reaction of a compound of the formula (XIX) in a suitable solvent with an A-M (XVI) with addition of a suitable amount of a transition metal catalyst, in particular palladium catalysts such as palladium diacetate or bis(triphenylphosphine)palladium(II) dichloride or nickel catalysts such as nickel(II) acetylacetonate or bis(triphenylphosphine)nickel(II) chloride, preferably at elevated temperature in an organic solvent such as 1,2-dimethoxyethane. The radical "M" represents, for example, Mg-Hal, Zn-Hal, $Sn((C_1-C_4)\text{-alkyl})_3$, lithium, copper or $B(OR^b)(OR^c)$, where the radicals $R^b$ and $R^c$ independently of one another represent, for example, hydrogen, $(C_1-C_4)$-alkyl, or, if the radicals $R^b$ and $R^c$ are attached to one another, together represent ethylene or propylene.

A further aspect of the invention relates to compounds of the general formula (II) and their salts

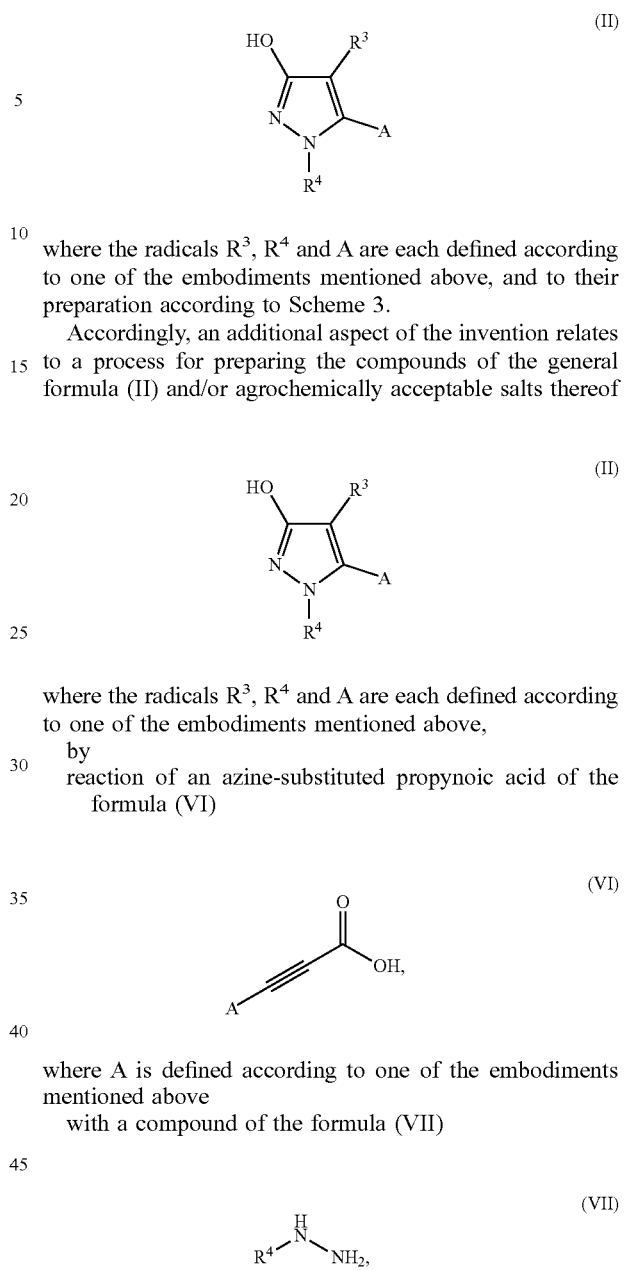

where the radicals $R^3$, $R^4$ and A are each defined according to one of the embodiments mentioned above, and to their preparation according to Scheme 3.

Accordingly, an additional aspect of the invention relates to a process for preparing the compounds of the general formula (II) and/or agrochemically acceptable salts thereof where the radicals $R^3$, $R^4$ and A are each defined according to one of the embodiments mentioned above,
by
reaction of an azine-substituted propynoic acid of the formula (VI)

where A is defined according to one of the embodiments mentioned above
with a compound of the formula (VII)

where $R^4$ is defined according to one of the embodiments mentioned above,
in a solvent
in the presence of a metal halide.

A further aspect relates to the use of a compound of the general formula (II) and of one of their salts as intermediate for the preparation of fine chemicals and active compounds for agriculture.

The compounds of the formula (I) according to the invention (and/or salts thereof), referred to collectively as "compounds of the invention" hereinafter, have excellent herbicidal efficacy against a broad spectrum of economically important monocotyledonous and dicotyledonous annual harmful plants.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds of the invention are applied to the soil surface before germination, either the weed seedlings are prevented completely from emerging or the weeds grow until they have reached the cotyledon stage, but then stop growing.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

The compounds of the invention can be selective in crops of useful plants and can also be employed as non-selective herbicides.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain active compounds used in the agrochemical industry, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further particular properties lie in tolerance or resistance to abiotic stress factors, for example heat, cold, drought, salinity and ultraviolet radiation.

Preference is given to using the inventive compounds of the formula (I) or salts thereof in economically important transgenic crops of useful and ornamental plants.

The compounds of the formula (I) can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). What has been described are, for example, several cases of genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377 A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant), transgenic crop plants, for example cotton, capable of producing *Bacillus thuringiensis* toxins (Bt toxins), which make the plants resistant to particular pests (EP 0142924 A, EP 0193259 A), transgenic crop plants having a modified fatty acid composition (WO 91/013972 A), genetically modified crop plants having novel constituents or secondary metabolites, for example novel phytoalexins, which cause an increase in disease resistance (EP 0309862 A, EP 0464461 A)

genetically modified plants having reduced photorespiration, which have higher yields and higher stress tolerance (EP 0305398 A)

transgenic crop plants which produce pharmaceutically or diagnostically important proteins ("molecular pharming")

transgenic crop plants which feature higher yields or better quality transgenic crop plants which are distinguished by a combination, for example of the abovementioned novel properties ("gene stacking").

Numerous molecular biology techniques which can be used to produce novel transgenic plants with modified properties are known in principle; see, for example, I. Potrykus and G. Spangenberg (eds), Gene Transfer to Plants, Springer Lab Manual (1995), Springer Verlag Berlin, Heidelberg or Christou, "Trends in Plant Science" 1 (1996) 423-431).

For such genetic manipulations, nucleic acid molecules which allow mutagenesis or sequence alteration by recombination of DNA sequences can be introduced into plasmids. With the aid of standard methods, it is possible, for example, to undertake base exchanges, remove part sequences or add natural or synthetic sequences. To join the DNA fragments with one another, adapters or linkers can be placed onto the fragments, see, for example, Sambrook et al., 1989, Molecular Cloning, A Laboratory Manual, 2nd ed. Cold Spring Harbor Laboratory Press, Cold Spring Harbor, NY; or Winnacker "Gene und Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants. Thus, transgenic plants can be obtained whose properties are altered by overexpression, suppression or inhibition of homologous (=natural) genes or gene sequences or expression of heterologous (=foreign) genes or gene sequences.

The compounds (I) of the invention can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds, or to any desired combinations of these active compounds.

The compounds of the invention can be used with particular preference in transgenic crop plants which are resistant to a combination of glyphosates and glufosinates, glyphosates and sulfonylureas or imidazolinones. Most preferably, the compounds of the invention can be used in transgenic crop plants such as corn or soya with the trade name or the designation Optimum™ GAT™ (glyphosate ALS tolerant), for example.

When the active compounds of the invention are employed in transgenic crops, not only do the effects towards harmful plants to be observed in other crops occur, but frequently also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the inventive compounds of the formula (I) as herbicides for controlling harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schanfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Technology], volume 7, C. Hanser Verlag Munich, 4th Ed. 1986.

On the basis of these formulations, it is also possible to produce combinations with other active compounds, for example insecticides, acaricides, herbicides, fungicides, and also with safeners, fertilizers and/or growth regulators, for example in the form of a finished formulation or as a tank mix.

Active compounds which can be employed in combination with the compounds of the invention in mixed formulations or in a tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as described, for example, in Weed Research 26 (1986) 441-445 or "The Pesticide Manual", 16th edition, The British Crop Protection Council and the Royal Soc. of Chemistry, 2006 and the literature cited therein. Known herbicides or plant growth regulators which can be combined with the compounds of the invention are, for example, the following, where said active compounds are designated either with their "common name" in accordance with the International Organization for Standardization (ISO) or with the chemical name or with the code number. They always encompass all the use forms, for example acids, salts, esters and also all isomeric forms such as stereoisomers and optical isomers, even if they are not mentioned explicitly.

Examples of such herbicidal mixing partners are:
acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-5-fluoro-6-(7-fluoro-1H-indol-6-yl)pyridine-2-carboxylic acid, aminocyclopyrachlor, aminocyclopyrachlor-potassium, aminocyclopyrachlor-methyl, aminopyralid, amitrole, ammonium sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bixlozone, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, 1-{2-chloro-3-[(3-cyclopropyl-5-hydroxy-1-methyl-1H-pyrazol-4-yl)carbonyl]-6-(trifluoromethyl) phenyl}piperidin-2-one, 4-{2-chloro-3-[(3,5-dimethyl-1H-pyrazol-1-yl)methyl]-4-(methylsulfonyl)benzoyl}-1,3-dimethyl-1H-pyrazol-5-yl-1,3-dimethyl-1H-pyrazol-4-carboxylate, chlorfenac, chlorfenac-sodium, chlorfenprop, chlorflurenol, chlorflurenol-methyl, chloridazon, chlorimuron, chlorimuron-ethyl, 2-[2-chloro-4-(methylsulfonyl)-3-(morpholin-4-ylmethyl)benzoyl]-3-hydroxycyclohex-2-en-1-one, 4-{2-chloro-4-(methylsulfonyl)-3-[(2,2,2-trifluorethoxy)methyl]benzoyl}-1-ethyl-1H-pyrazol-5-yl-1,3-dimethyl-1H-pyrazol-4-carboxylate, chlorophthalim, chlorotoluron, chlorthal-dimethyl, chlorsulfuron, 3-[5-chloro-4-(trifluoromethyl)pyridin-2-yl]-4-hydroxy-1-methylimidazolidin-2-one, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, 3-(2,6-dimethylphenyl)-6-[(2-hydroxy-6-oxocyclohex-1-en-1-yl)carbonyl]-1-methylquinazolin-2,4(1H,3H)-dione, 1,3-dimethyl-4-[2-(methylsulfonyl)-4-(trifluoromethyl)benzoyl]-1H-pyrazol-5-yl-1,3-dimethyl-1H-pyrazol-4-carboxylate, dimetrasulfuron, dinitramine, dinoterb, diphenamid, diquat, diquat-dibromid, dithiopyr, diuron, DMPA, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, ethyl-[(3-{2-chloro-4-fluoro-5-[3-methyl-2,6-dioxo-4-(trifluoromethyl)-3,6-dihydropyrimidin-1(2H)-yl]phenoxy}pyridin-2-yl)oxy] acetate, F-9960, F-5231, i.e. N-[2-chloro-4-fluoro-5-[4-(3-fluoropropyl)-4,5-dihydro-5-oxo-1H-tetrazol-1-yl]-phenyl] ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, florpyrauxifen, florpyrauxifen-benzyl, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl (2,4-dichlorophenoxy)acetate, 4-hydroxy-1-methoxy-5-methyl-3-[4-(trifluoromethyl)pyridin-2-yl]imidazolidin-2-one, 4-hydroxy-1-methyl-3-[4-(trifluoromethyl)pyridin-2-yl]imidazolidin-2-one, (5-hydroxy-1-methyl-1H-pyrazol-4-yl)(3,3,4-trimethyl-1,1-dioxido-2,3-dihydro-1-benzothiophen-5-yl)methanone, 6-[(2-hydroxy-6-oxocyclohex-1-en-1-yl)carbonyl]-1,5-dimethyl-3-(2-methylphenyl)quinazolin-2,4(1H,3H)-dione, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-ammonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, 2-({2-[(2-methoxyethoxy) methyl]-6-(trifluoromethyl)pyridin-3-yl}carbonyl)cyclohexan-1,3-dione, methyl isothiocyanate, 1-methyl-4-[(3,3,4-trimethyl-1,1-dioxido-2,3-dihydro-1-benzothiophen-5-yl) carbonyl]-1H-pyrazol-5-ylpropan-1-sulfonate, metobromuron, metolachlor, S-metolachlor, metosulam, metoxuron, metribuzin, metsulfuron, metsulfuron-methyl, molinate, monolinuron, monosulfuron, monosulfuron esters, MT-5950, i.e. N-[3-chloro-4-(1-methylethyl)-phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxotrione (lancotrione), oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, QYM-201, QYR-301, rimsulfuron, saflufenacil, sethoxydim, siduron, simazine, simetryn, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, tetflupyrolimet, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline.

Examples of plant growth regulators as possible mixing partners are:
acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4 [(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Safeners which can be used in combination with the inventive compounds of the formula (I) and optionally in combinations with further active compounds such as insecticides, acaricides, herbicides, fungicides as listed above are preferably selected from the group consisting of:

S1) Compounds of the formula (S1)

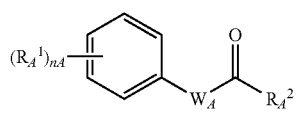

where the symbols and indices are defined as follows:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$,

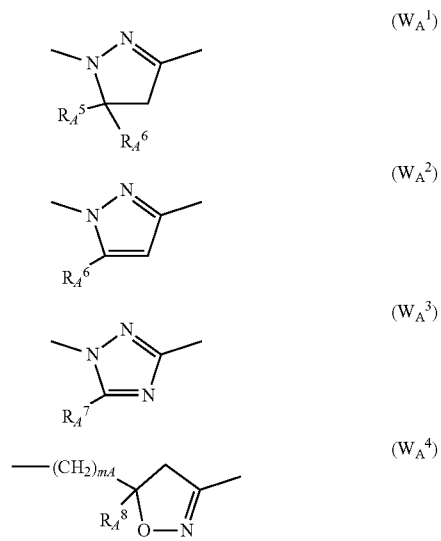

$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;
$R_A^3$ is hydrogen or an unsubstituted or substituted aliphatic hydrocarbon radical, preferably having a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;
preferably:
a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;
b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

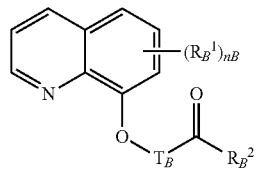

where the symbols and indices have the meanings below:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ is $OR_B^3$, $SR_B^3$ or $NR_B^3R_B^4$ or a saturated
or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;
$R_B^3$ is hydrogen or an unsubstituted or substituted aliphatic hydrocarbon radical, preferably having a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;
preferably:

a) compounds of the 8-quinolinoxyacetic acid type (S2$^a$), preferably 1-methylhexyl (5-chloro-8-quinolinoxy)acetate ("cloquintocet-mexyl") (S2-1), (1,3-dimethylbut-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (52-6), allyl (5-chloro-8-quinolinoxy)acetate (52-7), 2-(2-propylideneiminoxy)-1-ethyl (5-chloro-8-quinolinoxy)acetate (52-8), 2-oxoprop-1-yl (5-chloro-8-quinolinoxy)acetate (52-9) and related compounds, as described in EP-A-86 750, EP-A-94 349 and EP-A-191 736 or EP-A-0 492 366, and also (5-chloro-8-quinolinoxy)acetic acid (52-10), hydrates and salts thereof, for example the lithium, sodium, potassium, calcium, magnesium, aluminium, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

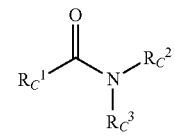

where the symbols and indices are defined as follows:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$cycloalkyl, preferably dichloromethyl;

$R_C^2$, $R_C^3$ are identical or different and are hydrogen, $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_1-C_4)$alkylcarbamoyl-$(C_1-C_4)$alkyl, $(C_2-C_4)$alkenylcarbamoyl-$(C_1-C_4)$alkyl, $(C_1-C_4)$alkoxy-$(C_1-C_4)$alkyl, dioxolanyl-$(C_1-C_4)$alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azasniro[4.5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-acylsulfonamides of the formula (S4) and salts thereof,

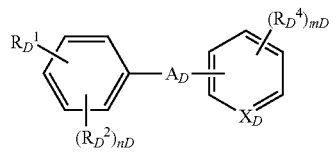
(S4)

in which the symbols and indices are defined as follows:
$A_D$ is $SO_2$—$NR_D^3$—$CO$ or $CO$—$NR_D^3$—$SO_2$
$X_D$ is CH or N;
$R_D^1$ is $CO$—$NR_D^5 R_D^6$ or $NHCO$—$R_D^7$;
$R_D^2$ is halogen, $(C_1$-$C_4)$-haloalkyl, $(C_1$-$C_4)$-haloalkoxy, nitro, $(C_1$-$C_4)$-alkyl, $(C_1$-$C_4)$-alkoxy, $(C_1$-$C_4)$-alkylsulfonyl, $(C_1$-$C_4)$-alkoxycarbonyl or $(C_1$-$C_4)$-alkylcarbonyl;
$R_D^3$ is hydrogen, $(C_1$-$C_4)$-alkyl, $(C_2$-$C_4)$-alkenyl or $(C_2$-$C_4)$-alkynyl;
$R_D^4$ is halogen, nitro, $(C_1$-$C_4)$-alkyl, $(C_1$-$C_4)$-haloalkyl, $(C_1$-$C_4)$-haloalkoxy, $(C_3$-$C_6)$-cycloalkyl, phenyl, $(C_1$-$C_4)$-alkoxy, cyano, $(C_1$-$C_4)$-alkylthio, $(C_1$-$C_4)$-alkylsulfinyl, $(C_1$-$C_4)$-alkylsulfonyl, $(C_1$-$C_4)$-alkoxycarbonyl or $(C_1$-$C_4)$-alkylcarbonyl;
$R_D^5$ is hydrogen, $(C_1$-$C_6)$-alkyl, $(C_3$-$C_6)$-cycloalkyl, $(C_2$-$C_6)$-alkenyl, $(C_2$-$C_6)$-alkynyl, $(C_5$-$C_6)$-cycloalkenyl, phenyl or 3- to 6-membered heterocyclyl containing $v_D$ heteroatoms from the group consisting of nitrogen, oxygen and sulfur, where the seven latter radicals are substituted by $v_D$ substituents from the group consisting of halogen, $(C_1$-$C_6)$-alkoxy, $(C_1$-$C_6)$-haloalkoxy, $(C_1$-$C_2)$-alkylsulfinyl, $(C_1$-$C_2)$-alkylsulfonyl, $(C_3$-$C_6)$-cycloalkyl, $(C_1$-$C_4)$-alkoxycarbonyl, $(C_1$-$C_4)$-alkylcarbonyl and phenyl and, in the case of cyclic radicals, also $(C_1$-$C_4)$-alkyl and $(C_1$-$C_4)$-haloalkyl;
$R_D^6$ is hydrogen, $(C_1$-$C_6)$-alkyl, $(C_2$-$C_6)$-alkenyl or $(C_2$-$C_6)$-alkynyl, where the three latter radicals are substituted by $v_D$ radicals from the group consisting of halogen, hydroxyl, $(C_1$-$C_4)$-alkyl, $(C_1$-$C_4)$-alkoxy and $(C_1$-$C_4)$-alkylthio, or
$R_D^5$ and $R_D^6$ together with the nitrogen atom carrying them form a pyrrolidinyl or piperidinyl radical;
$R_D^7$ is hydrogen, $(C_1$-$C_4)$-alkylamino, di-$(C_1$-$C_4)$-alkylamino, $(C_1$-$C_6)$-alkyl, $(C_3$-$C_6)$-cycloalkyl, where the 2 latter radicals are substituted by $v_D$ substituents from the group consisting of halogen, $(C_1$-$C_4)$-alkoxy, $(C_1$-$C_6)$-haloalkoxy and $(C_1$-$C_4)$-alkylthio and, in the case of cyclic radicals, also $(C_1$-$C_4)$-alkyl and $(C_1$-$C_4)$-haloalkyl;
$n_D$ is 0, 1 or 2;
$m_D$ is 1 or 2;
$v_D$ is 0, 1, 2 or 3;
among these, preference is given to compounds of the N-acylsulfonamide type, for example of the formula (S4a) below, which are known, for example, from WO-A-97/45016

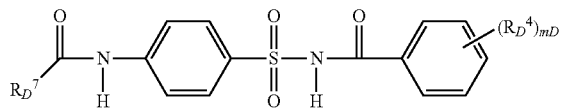
(S4$^a$)

in which
$R_D^7$ is $(C_1$-$C_6)$-alkyl, $(C_3$-$C_6)$-cycloalkyl, where the 2 latter radicals are substituted by $v_D$ substituents from the group consisting of halogen, $(C_1$-$C_4)$-alkoxy, $(C_1$-$C_6)$-haloalkoxy and $(C_1$-$C_4)$-alkylthio and, in the case of cyclic radicals, also $(C_1$-$C_4)$-alkyl and $(C_1$-$C_4)$-haloalkyl;

$R_D^4$ is halogen, $(C_1$-$C_4)$-alkyl, $(C_1$-$C_4)$-alkoxy, $CF_3$;
$m_D$ is 1 or 2;
$v_D$ is 0, 1, 2 or 3;
and also
acylsulfamoylbenzamides, for example of the formula (S4$^b$) below, which are known, for example, from WO-A-99/16744,

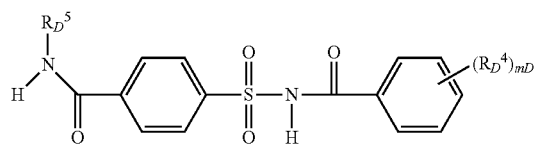
(S4$^b$)

e.g. those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and also
compounds of the N-acylsulfamoylphenylurea type of the formula (S4$^c$), which are known, for example, from EP-A-365484,

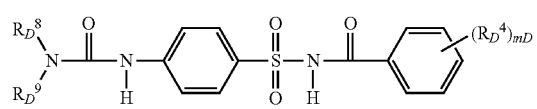
(S4$^c$)

in which
$R_D^8$ and $R_D^9$ independently represent hydrogen, $(C_1$-$C_8)$-alkyl, $(C_3$-$C_8)$-cycloalkyl, $(C_3$-$C_6)$-alkenyl, $(C_3$-$C_6)$-alkynyl,
$R_D^4$ is halogen, $(C_1$-$C_4)$-alkyl, $(C_1$-$C_4)$-alkoxy, $CF_3$,
$m_D$ is 1 or 2,
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
and also
N-phenylsulfonylterephthalamides of the formula (S4$^d$), which are known, for example, from CN 101838227,

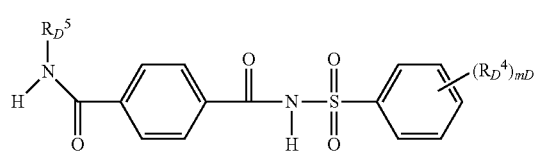
(S4$^d$)

e.g. those in which
$R_D^4$ is halogen, $(C_1$-$C_4)$-alkyl, $(C_1$-$C_4)$-alkoxy, $CF_3$;
$m_D$ is 1 or 2;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl.

S5) Active compounds from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

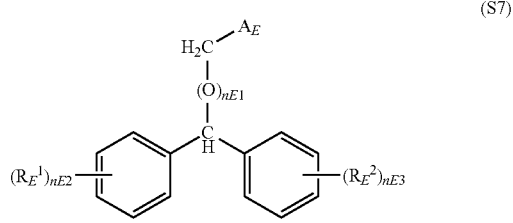

(S7)

in which the symbols and indices are defined as follows:
$R_E^1$, $R_E^2$ are independently halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E^3$ or $COSR_E^4$
$R_E^3$, $R_E^4$ are independently hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium,
$n_E^1$ is 0 or 1
$n_E^2$, $n_E^3$ independently of one another are 0, 1 or 2, preferably:
diphenylmethoxyacetic acid,
ethyl diphenylmethoxyacetate,
methyl diphenylmethoxyacetate (CAS reg. no. 41858-19-9) (57-1).

S8) Compounds of the formula (S8), as described in WO-A-98/27049,

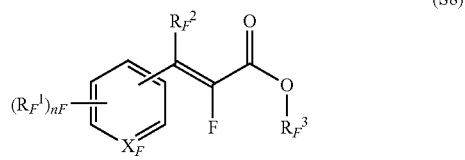

(S8)

in which
$X_F$ is CH or N,
$n_F$ in the case that $X_F$=N is an integer from 0 to 4 and in the case that $X_F$=CH is an integer from 0 to 5,
$R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy; or salts thereof,
preferably compounds in which
$X_F$ is CH,
$n_F$ is an integer from 0 to 2,
$R_F^1$ is halogen, $(C_1-C_4)$-alkyl, $(C_1-C_4)$-haloalkyl, $(C_1-C_4)$-alkoxy, $(C_1-C_4)$-haloalkoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), for example
1,2-dihydro-4-hydroxy-1-ethyl-3-(5-tetrazolylcarbonyl)-2-quinolone (CAS reg. no. 219479-18-2),
1,2-dihydro-4-hydroxy-1-methyl-3-(5-tetrazolylcarbonyl)-2-quinolone (CAS Reg. No. 95855-00-8),
as described in WO-A-1999/000020.

S10) Compounds of the formulae (S10$^a$) or (S10$^b$) as described in WO-A-2007/023719 and WO-A-2007/023764

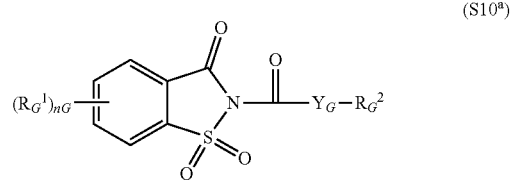

(S10$^a$)

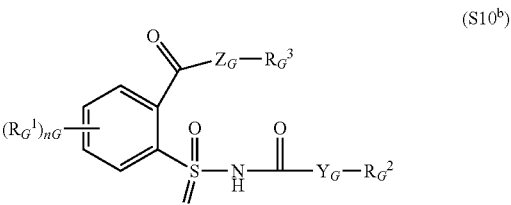

(S10$^b$)

in which
$R_G^1$ is halogen, $(C_1-C_4)$-alkyl, methoxy, nitro, cyano, $CF_3$, $OCF_3$,
$Y_G$, $Z_G$ independently of one another represent O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.

S11) Active compounds of the oxyimino compounds type (S11), which are known as seed-dressing agents, for example
"oxabetrinil" ((Z)-1,3-dioxolan-2-ylmethoxyimino(phenyl)acetonitrile) (S11-1), which is known as a seed-dressing safener for millet/sorghum against metolachlor damage,
"fluxofenim" (1-(4-chlorophenyl)-2,2,2-trifluoro-1-ethanone 0-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino (phenyl)acetonitrile) (S11-3), which is known as a seed-dressing safener for millet/sorghum against metolachlor damage.

S12) Active compounds from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as a seed-dressing safener for corn against thiocarbamate herbicide damage,
"fenclorim" (4,6-dichloro-2-phenylpyrimidine) (S13-2), which is known as a safener for pretilachlor in sown rice,
"flurazole" (benzyl 2-chloro-4-trifluoromethyl-1,3-thiazole-5-carboxylate) (S13-3), which is known as a seed-dressing safener for millet/sorghum against alachlor and metolachlor damage,
"CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones,
"MG 191" (CAS Reg. No. 96420-72-3) (2-dichloromethyl-2-methyl-1,3-dioxolane) (S13-5) from Nitrokemia, which is known as a safener for corn,
"MG 838" (CAS Reg. No. 133993-74-5) (2-propenyl 1-oxa-4-azaspiro[4.5]decane-4-carbodithioate) (S13-6) from Nitrokemia,
"disulfoton" (0,0-diethyl S-2-ethylthioethyl phosphorodithioate) (S13-7),
"dietholate" (0,0-diethyl 0-phenyl phosphorothioate) (S13-8),
"mephenate" (4-chlorophenyl methylcarbamate) (S13-9).

S14) Active compounds which, in addition to herbicidal action against harmful plants, also have safener action on crop plants such as rice, for example
"dimepiperate" or "MY 93" (S-1-methyl 1-phenylethylpiperidine-1-carbothioate), which is known as a safener for rice against damage by the herbicide molinate,
"daimuron" or "SK 23" (1-(1-methyl-1-phenylethyl)-3-p-tolylurea), which is known as a safener for rice against damage by the herbicide imazosulfuron,
"cumyluron"="JC 940" (3-(2-chlorophenylmethyl)-1-(1-methyl-1-phenylethyl)urea, see JP-A-60087254), which is known as safener for rice against damage by some herbicides,
"methoxyphenone" or "NK 049" (3,3'-dimethyl-4-methoxybenzophenone), which is known as a safener for rice against damage by some herbicides,
"CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

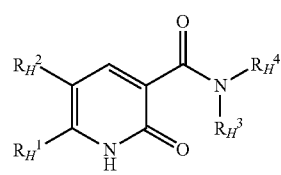

(S15)

as described in WO-A-2008/131861 and WO-A-2008/131860 in which $R_H^1$ is a $(C_1-C_6)$-haloalkyl radical and
$R_H^2$ is hydrogen or halogen and
$R_H^3$, $R_H^4$ independently of one another represent hydrogen, $(C_1-C_{16})$-alkyl, $(C_2-C_{16})$-alkenyl or $(C_2-C_{16})$-alkynyl,
where each of the 3 latter radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted,
or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring,
where each of the 4 latter radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted,
or
$R_H^3$ is $(C_1-C_4)$-alkoxy, $(C_2-C_4)$-alkenyloxy, $(C_2-C_6)$-alkynyloxy or $(C_2-C_4)$-haloalkoxy and
$R_H^4$ is hydrogen or $(C_1-C_4)$-alkyl or
$R_H^3$ and $R_H^4$ together with the directly attached nitrogen atom represent a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Particularly preferred safeners are mefenpyr-diethyl, cyprosulfamide, isoxadifen-ethyl, cloquintocet-mexyl, dichlormid and metcamifen.

Wettable powders are preparations uniformly dispersible in water which, in addition to the active compound and apart from a diluent or inert substance, also comprise surfactants of ionic and/or nonionic type (wetting agent, dispersant), e.g. polyethoxylated alkylphenols, polyethoxylated fatty alcohols, polyethoxylated fatty amines, fatty alcohol polyglycolethersulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidal active compounds are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention. In wettable powders, the active compound concentration is, for example, about 10 to 90% by weight, the remainder to 100% by weight consisting of customary formulation constituents. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) and their salts varies according to the external conditions such as, inter alia, temperature, humidity and the type of herbicide used. It can vary within wide limits, for example between 0.001 and 10.0 kg/ha or more of active substance, but it is preferably between 0.005 and 5 kg/ha, more preferably in the range of from 0.01 to 1.5 kg/ha, particularly preferably in the range of from 0.05 to 1 kg/ha g/ha. This applies both to the pre-emergence and the post-emergence application.

A carrier is a natural or synthetic, organic or inorganic substance with which the active compounds are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. It is likewise possible to use mixtures of such carriers. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Suitable liquefied gaseous extenders or carriers are liquids which are gaseous at standard temperature and under atmospheric pressure, for example aerosol propellants such as halogenated hydrocarbons, or else butane, propane, nitrogen and carbon dioxide.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins, and synthetic phospholipids. Further additives may be mineral and vegetable oils.

When the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The compositions of the invention may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is necessary if one of the active compounds and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active compounds can be combined with any solid or liquid additive commonly used for formulation purposes. In general, the compositions and formulations of the invention contain between 0.05 and 99% by weight, 0.01 and 98% by weight, preferably between 0.1 and 95% by weight, more preferably between 0.5 and 90% active compound, most preferably between 10 and 70 percent by weight. The active compounds or compositions of the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, sprayable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be produced in a manner known per se, for example by mixing the active compounds with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The compositions of the invention include not only formulations which are already ready for use and can be deployed with a suitable apparatus onto the plant or the seed, but also commercial concentrates which have to be diluted with water prior to use.

The active compounds of the invention may be present as such or in their (commercial standard) formulations, or else in the use forms prepared from these formulations as a mixture with other (known) active compounds, such as insecticides, attractants, sterilants, bactericides, acaricides, nematicides, fungicides, growth regulators, herbicides, fertilizers, safeners or semiochemicals.

The inventive treatment of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

As also described below, the treatment of transgenic seed with the active compounds or compositions of the invention is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis.*

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, when treating the seed, it has to be ensured that the amount of the composition of the invention and/or further additives applied to the seed is chosen such that the germination of the seed is not impaired and the plant which arises therefrom is not damaged. This has to be ensured particularly in the case of active compounds which can exhibit phytotoxic effects at certain application rates.

The compositions of the invention can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272, 417 A, 4,245,432 A, 4,808,430, 5,876,739, US 2003/0176428 A1, WO 2002/080675 A1, WO 2002/028186 A2.

The active compounds of the invention can be converted to the customary seed-dressing formulations, such as solutions, emulsions, suspensions, powders, foams, slurries or other coating compositions for seed, and also ULV formulations.

These formulations are produced in a known manner, by mixing the active compounds with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Preference can be given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances usable for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

The seed-dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For the treatment of seed with the seed-dressing formulations usable in accordance with the invention or with the preparations prepared therefrom by addition of water, useful equipment is all mixing units usable customarily for seed dressing. Specifically, the seed dressing procedure is to place the seed into a mixer, to add the particular desired amount of seed-dressing formulations, either as such or after prior dilution with water, and to mix them until the formulation is distributed homogeneously on the seed. If appropriate, this is followed by a drying operation.

The active compounds of the invention, given good plant compatibility, favourable homeotherm toxicity and good environmental compatibility, are suitable for protection of plants and plant organs, for increasing harvest yields, and for improving the quality of the harvested crop. They can preferably be used as crop protection agents. They are active against normally sensitive and resistant species and also against all or specific stages of development.

Plants which can be treated in accordance with the invention include the following main crop plants: maize, soya bean, cotton, *Brassica* oil seeds such as *Brassica napus* (e.g. Canola), *Brassica rapa, B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and Chinese cabbage), Leguminosae sp. (for example peanuts, peas, and beans—for example runner beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and genetically modified varieties of each of these plants.

As mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes and genotypes.

The treatment method of the invention can be used for the treatment of genetically modified organisms (GMOs), e.g. plants or seeds. Genetically modified plants (or transgenic plants) are plants in which a heterologous gene has been stably integrated into the genome. The term "heterologous gene" means essentially a gene which is provided or assembled outside the plant and which, upon introduction into the nuclear genome, the chloroplast genome or the mitochondrial genome, imparts to the transformed plant novel or improved agronomical or other traits because it expresses a protein or polypeptide of interest or another gene which is present in the plant, or other genes which are present in the plant are down-regulated or switched off (for example by means of antisense technology, co-suppression technology or RNAi technology [RNA interference]). A heterologous gene that is located in the genome is also called a transgene. A transgene that is defined by its specific presence in the plant genome is called a transformation or transgenic event.

Depending on the plant species or plant cultivars, their location and growth conditions (soils, climate, vegetation period, diet), the inventive treatment may also result in superadditive ("synergistic") effects. For example, the following effects which exceed the effects actually to be expected are possible: reduced application rates and/or widened spectrum of activity and/or increased efficacy of the active compounds and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf colour, earlier flowering, higher quality and/or a higher nutritional value of the harvested products, higher sugar concentration within the fruits, better storage stability and/or processibility of the harvested products.

Plants and plant cultivars which are preferably treated in accordance with the invention include all plants which have genetic material which imparts particularly advantageous, useful traits to these plants (whether obtained by breeding and/or biotechnological means).

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants that may be treated according to the invention are hybrid plants that already express the characteristics of heterosis, or hybrid effect, which results generally in higher yield, vigour, better health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in maize) be produced by detasselling (i.e. the mechanical removal of the male reproductive organs or male flowers) but, more typically, male sterility is the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science, 221, 370-371), the CP4 gene of the bacterium *Agrobacterium* sp. (Barry et al., 1992, Curr. Topics Plant Physiol. 7, 139-145), the genes encoding a petunia EPSPS (Shah et al., 1986, Science 233, 478-481), a tomato EPSPS (Gasser et al., 1988, J. Biol. Chem. 263, 4280-4289) or an Eleusine EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally-occurring mutations of the abovementioned genes. Plants which express EPSPS genes which impart glyphosate tolerance have been described. Plants which express other genes which impart glyphosate tolerance, for example decarboxylase genes, have been described.

Other herbicide-resistant plants are for example plants made tolerant to herbicides inhibiting the enzyme glutamine synthase, such as bialaphos, phosphinothricin or glufosinate.

Such plants can be obtained by expressing an enzyme detoxifying the herbicide or a mutant of the glutamine synthase enzyme that is resistant to inhibition. One example of such an effective detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyse the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite inhibition of the native HPPD enzyme by the HPPD inhibitor. Such plants are described in WO 99/34008 and WO 02/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyloxy(thio)benzoates, and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulfonylurea-tolerant plants and imidazolinone-tolerant plants has been described. Further sulfonylurea- and imidazolinone-tolerant plants have also been described.

Further plants tolerant to imidazolinones and/or sulfonylureas can be obtained by induced mutagenesis, by selection in cell cultures in the presence of the herbicide or by mutation breeding (cf., for example, for soya beans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific components of the harvested product such as, for example:
1) Transgenic plants which synthesize a modified starch which, in its physicochemical characteristics, in particular the amylose content or the amylose/amylopectin ratio, the degree of branching, the average chain length, the side chain distribution, the viscosity behaviour, the gelling strength, the starch granule size and/or the starch granule morphology, is changed in comparison with the synthesized starch in wild-type plant cells or plants, so that this modified starch is better suited to specific applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.
4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, containing an altered form of cellulose synthase genes;
b) plants, such as cotton plants, which contain an altered form of rsw2 or rsw3 homologous nucleic acids, such as cotton plants with an increased expression of sucrose phosphate synthase;
c) plants, such as cotton plants, with increased expression of sucrose synthase;
d) plants, such as cotton plants, wherein the timing of the plasmodesmatal gating at the basis of the fibre cell is altered, for example through downregulation of fibre-selective β-1,3-glucanase;
e) plants, such as cotton plants, which have fibres with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:
a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, MD 20737, USA), for example via the website http://www.aphis.usda.gov/brs/not_reg.html. At the filing date of this application, the petitions with the following information were either granted or pending at APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which non-regulated status is being requested.

APHIS documents: Various documents which have been published by APHIS with regard to the petition or can be obtained from APHIS on request.

Particularly useful transgenic plants which can be treated in accordance with the invention are plants which comprise one or more genes which code for one or more toxins, for example the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned include maize varieties, cotton varieties and soya bean varieties which are available under the following trade names: Roundup Ready® (tolerance to glyphosates, for example corn, cotton, soya beans), Liberty Link® (tolerance to phosphinothricin, for example oilseed rape), IMI® (tolerance to imidazolinone) and SCS® (tolerance to sulfonylurea), for example corn. Herbicide-resistant plants (plants bred in a conventional manner for herbicide tolerance) which may be mentioned include the varieties sold under the name Clearfield® (for example corn).

The examples which follow illustrate the present invention.

EXAMPLES

The present invention is illustrated in detail by the examples which follow, but these examples do not restrict the invention in any way.

A. Synthesis Examples

Synthesis of methyl {[4-bromo-1-(2-fluorophenyl)-5-(pyrimidin-5-yl)-1H-pyrazol-3-yl]oxy}acetate (VI-004)

3-(Benzyloxy)-1-(2-fluorophenyl)-1H-pyrazole

A mixture of 3 g (17.2 mmol) of 3-benzyloxypyrazole, 3.06 g (13.77 mmol) of 1-fluoro-2-iodobenzene, 0.46 g (2.41 mmol) copper(I) iodide and 7.86 g (311.93 mmol) of caesium carbonate in 25 ml of DMF is stirred at 120° C. for 8 hours and then allowed to stand at room temperature overnight. The mixture is then filtered and the DMF solution is concentrated to dryness. The residue is taken up in $CH_2Cl_2$ and washed with sat. $NH_4Cl$ solution. The organic phase is dried over $Na_2SO_4$ and concentrated. The residue is purified by column chromatography on silica gel using heptane/ethyl acetate (1:1). This gives 2.0 g (43%) of product as a colourless oil.

$^1$H NMR (400 MHz, $CDCl_3$): δ 5.30 (s, 2H), 5.95 (d, 1H), 7.20 (m, 3H), 7.35 (m, 3H), 7.50 (m, 2H), 7.85 (d, 1H), 7.90 (m, 1H).

3-(Benzyloxy)-1-(2-fluorophenyl)-5-iodo-1H-pyrazole

At −78° C., a solution of 11.9 g (44.36 mmol) of 3-(benzyloxy)-1-(2-fluorophenyl)-1H-pyrazole in 250 ml of THF is added dropwise to a solution of 75.7 mmol of LDA in 270 ml of THF and this mixture is stirred at −78° C. for a further 90 minutes. A solution of 18 g (70.97 mmol) of iodine is then added dropwise to the reaction mixture, and the reaction mixture is stirred for a further 60 minutes and subsequently allowed to warm to room temperature and allowed to stand overnight. The reaction mixture is then added to $H_2O$ and extracted repeatedly with $CH_2Cl_2$. The organic phase is dried over $Na_2SO_4$ and then concentrated. The crude product is purified by column chromatography on silica gel using heptane/ethyl acetate (8:2). This gives 10.6 g (60%) of product as a colourless oil.

$^1$H NMR (400 MHz, $CDCl_3$): δ 5.20 (s, 2H), 6.10 (s, 1H), 7.20-7.50 (m, 9H).

3-(Benzyloxy)-1-(2-fluorophenyl)-5-(4,4,5,5-tetramethyl-1,3,2-dioxaborolan-2-yl)-1H-pyrazole A reaction mixture of 1 g (2.54 mmol) of 3-(benzyloxy)-1-(2-fluorophenyl)-5-iodo-1H-pyrazole, 0.49 g (3.80 mmol) of pinacol borane ester, 0.77 g (7.61 mmol) of triethylamine and 17 mg (0.0033 mmol) of bis(tri-t-butylphosphine)palladium(0) in 10 ml of dioxane is stirred under reflux for 24 hours. The solid is then filtered off and washed with methyl t-butyl ether and the combined organic phase is concentrated. Purification of the crude product by column chromatography on silica gel using heptane/ethyl acetate (7:3) gives 0.59 g (59%) of product as a colourless oil.

$^1$H NMR (400 MHz, CDCl$_3$): δ 1.20 (s, 12H), 5.25 (s, 2H), 6.30 (s, 1H), 7.10-7.55 (m, 9H).

5-[3-(Benzyloxy)-1-(2-fluorophenyl)-1H-pyrazol-5-yl]pyrimidine 53 mg (0.075 mmol) of bis(triphenylphosphine)palladium (II) chloride, 0.24 g (1.50 mmol) of 5-bromopyrimidine, 0.62 g (4.49 mmol) of potassium carbonate and 0.6 ml of H$_2$O are added successively to a solution of 0.59 g (1.50 mmol) of 3-(benzyloxy)-1-(2-fluorophenyl)-5-(4,4,5,5-tetramethyl-1,3,2-dioxaborolan-2-yl)-1H-pyrazole in 10 ml of dioxane and the reaction mixture is stirred under reflux for 4 hours. The reaction mixture is then added to H$_2$O and extracted repeatedly with CH$_2$Cl$_2$. The organic phase is dried over Na$_2$SO$_4$ and concentrated. Purification of the crude mixture by column chromatography gives 0.36 g (69%) of product.

$^1$H NMR (400 MHz, CDCl$_3$): δ 5.30 (s, 2H), 6.18 (s, 1H), 7.10-7.55 (5m, 9H), 8.60 (s, 2H), 9.12 (s, 1H).

5-[3-(Benzyloxy)-4-bromo-1-(2-fluorophenyl)-1H-pyrazol-5-yl]pyrimidine

A mixture of 0.36 g (1.04 mmol) of 5-[3-(benzyloxy)-1-(2-fluorophenyl)-1H-pyrazol-5-yl]pyrimidine and 0.185 g (1.04 mmol) of bromosuccinimide in 10 ml of DMF is stirred at 50° C. for 4 hours and then allowed to stand overnight. The reaction mixture is then added to water and extracted repeatedly with CH$_2$Cl$_2$. Drying of the organic phase over Na$_2$SO$_4$ and subsequent concentration gives 0.44 g (100%) of crude product sufficiently pure for further reactions.

$^1$H NMR (400 MHz, CDCl$_3$): δ 5.40 (s, 2H), 7.05-7.50 (4m, 9H), 8.67 (s, 2H), 9.18 (s, 1H).

4-Bromo-1-(2-fluorophenyl)-5-(pyrimidin-5-yl)-1H-pyrazol-3-ol

A solution of 0.48 g (1.13 mmol) of 5-[3-(benzyloxy)-4-bromo-1-(2-fluorophenyl)-1H-pyrazol-5-yl]pyrimidine in 18 ml of toluene and 18 ml of trifluoroacetic acid is stirred under reflux for 6 hours and then allowed to stand overnight. The mixture is then concentrated to dryness and the residue is taken up in CH$_2$Cl$_2$ and washed with a sat. NH$_4$Cl solution. Drying of the organic phase over Na$_2$SO$_4$ and subsequent concentration gives 0.44 g of crude product sufficiently pure for further reactions.

$^1$H NMR (400 MHz, CDCl$_3$): δ 7.10-7.50 (5m, 9H), 8.71 (s, 2H), 9.23 (s, 1H).

Methyl {[4-bromo-1-(2-fluorophenyl)-5-(pyrimidin-5-yl)-1H-pyrazol-3-yl]oxy}acetate (VI-004)

0.43 g (3.13 mmol) of potassium carbonate is added to a solution of 0.35 g (1.04 mmol) of 4-bromo-1-(2-fluorophenyl)-5-(pyrimidin-5-yl)-1H-pyrazol-3-ol in 15 ml of acetonitrile and the mixture is stirred at room temperature for 10 minutes. 0.17 g (1.13 mmol) of methyl bromoacetate is then added and the reaction mixture is stirred under reflux for 5 hours and then allowed to stand at room temperature overnight. After filtration and concentration of the filtrate, the residue is taken up in H$_2$O and extracted repeatedly with CH$_2$Cl$_2$. The organic phase is dried and concentrated. Purification by column chromatography on silica gel using heptane/ethyl acetate (1:1) gives 0.28 g (49%) of product.

$^1$H NMR (400 MHZ, CDCl$_3$): δ 3.70 (s, 3H), 4.95 (s, 1H), 7.05 (m, 1H), 7.20 (m, 1H), 7.38 (m, 1H), 7.45 (m, 1H), 8.70 (s, 2H), 9.20 (s, 1H).

{[4-Bromo-1-(2-fluorophenyl)-5-(pyrimidin-5-yl)-1H-pyrazol-3-yl]oxy}acetic Acid (VI-007)

A reaction mixture of 0.17 g (0.42 mmol) of methyl {[4-bromo-1-(2-fluorophenyl)-5-(pyrimidin-5-yl)-1H-pyrazol-3-yl]oxy}acetate and 14 mg (0.58 mmol) of lithium hydroxide in 3.8 ml of H$_2$O and 1.7 ml of THF is stirred at 65° C. for 5 hours. The THF is then removed on a rotary evaporator and the aqueous phase is adjusted to pH 2 using 2N HCl solution. The resulting solid is filtered off with suction and dried. This gives 0.113 g (65%) of product as a solid.

$^1$H NMR (400 MHz, CDCl$_3$): δ 5.00 (s, 2H), 7.00-7.50 (4m, 4H), 8.79 (s, 2H), 9.20 (s, 1H).

Methyl (2R)-2-{[4-bromo-1-(2-fluorophenyl)-5-(pyrimidin-5-yl)-1H-pyrazol-3-yl]oxy}propanoate (VI-011)

0.61 g (4.47 mmol) of potassium carbonate is added to a solution of 0.50 g (1.49 mmol) of 4-bromo-1-(2-fluorophenyl)-5-(pyrimidin-5-yl)-1H-pyrazol-3-ol in 36 ml of acetonitrile and the mixture is stirred at room temperature for 10 minutes. 0.18 g (1.49 mmol) of methyl (2S)-2-chloropropanoate is then added and the reaction mixture is stirred under reflux for 5 hours and then allowed to stand at room temperature overnight. After filtration and concentration of the filtrate, the residue is taken up in H$_2$O and extracted repeatedly with CH$_2$Cl$_2$. The organic phase is dried and concentrated. Purification by column chromatography on silica gel using heptane/ethyl acetate (1:1) gives 0.31 g (47%) of product.

$^1$H NMR (400 MHz, CDCl$_3$): δ 1.70 (d, 3H), 3.80 (s, 3H), 5.20 (q, 2H), 7.00 (m, 1H), 7.22 (m, 1H), 7.35 (m, 1H), 7.40 (m, 1H), 8.65 (s, 2H), 9.15 (s, 1H).

Ethyl {[4-bromo-1-(2-fluorophenyl)-5-(6-fluoropyridin-3-yl)-1H-pyrazol-3-yl]oxy}acetate (VII-012)

A reaction mixture of 0.6 g (1.52 mmol) of 3-(benzyloxy)-1-(2-fluorophenyl)-5-iodo-1H-pyrazole, 0.21 g (1.52 mmol) of 2-fluoropyridine-5-boronic acid, 53 mg (0.076 mmol) of bis(triphenylphosphine)palladium(II) chloride and 1 ml of H$_2$O in 10 ml of dioxane is stirred under reflux for 6 hours and then allowed to stand overnight. The reaction mixture is added to H$_2$O and extracted repeatedly with CH$_2$Cl$_2$. The organic phase is dried over Na$_2$SO$_4$ and concentrated. Purification by column chromatography on silica gel using heptane/ethyl acetate (1:1) gives 0.43 g (77%) of product.

$^1$H NMR (400 MHz, CDCl$_3$): δ 5.30 (s, 2H), 6.10 (d, 1H), 6.85 (m, 1H), 7.10 (m, 1H), 7.20-7.50 (m, 5H), 7.60 (m, 1H), 8.10 (d, 1H).

Bromination and debenzylation are carried out as described for the preparation of Example VI-004.

Ethyl {[4-bromo-1-(2-fluorophenyl)-5-(6-fluoropyridin-3-yl)-1H-pyrazol-3-yl]oxy}acetate (VII-012)

1.29 g (9.37 mmol) of potassium carbonate are added to a solution of 1.1 g (3.12 mmol) of 4-bromo-1-(2-fluorophenyl)-5-(6-fluoropyridin-5-yl)-1H-pyrazol-3-ol in 36 ml of acetonitrile and the mixture is stirred at room temperature for 10 minutes. 0.52 g (9.37 mmol) of ethyl bromoacetate is then added and the reaction mixture is stirred under reflux for 5 hours and then allowed to stand at room temperature overnight. After filtration and concentration of the filtrate, the residue is taken up in $H_2O$ and extracted repeatedly with $CH_2Cl_2$. The organic phase is dried and concentrated. Purification by column chromatography on silica gel using heptane/ethyl acetate (1:1) gives 0.36 g (26%) of product.

$^1$H NMR (400 MHZ, CDCl$_3$): δ 1.25 (t, 3H), 4.25 (q, 2H), 4.90 (s, 2H), 6.95 (m, 1H), 7.05 (m, 1H), 7.20 (m, 1H), 7.35 (m, 1H), 7.40 (m, 1H), 7.75 (m, 1H), 8.10 (s, 1H).

Methyl (2R)-2-{[4-bromo-1-(2-fluorophenyl)-5-(6-fluoropyridin-3-yl)-1H-pyrazol-3-yl]oxy}propanoate (VII-004)

65 mg (0.47 mmol) of potassium carbonate are added to a solution of 0.55 g (0.156 mmol) of 4-bromo-1-(2-fluorophenyl)-5-(6-fluoropyridin-5-yl)-1H-pyrazol-3-ol in 4 ml of acetonitrile and the mixture is stirred at room temperature for 10 minutes. 19 mg (0.156 mmol) of methyl (2S)-2-chloropropanoate is added and the reaction mixture is stirred under reflux for 5 hours and then allowed to stand at room temperature overnight. After filtration and concentration of the filtrate, the residue is taken up in $H_2O$ and extracted repeatedly with $CH_2Cl_2$. The organic phase is dried and concentrated. Purification by column chromatography on silica gel using heptane/ethyl acetate (1:1) gives 0.02 g (27%) of product.

$^1$H NMR (400 MHZ, CDCl$_3$): δ 1.70 (d, 2H), 3.80 (s, 3H), 5.20 (q, 1H), 6.92 (m, 1H), 7.05 (m, 1H), 7.20 (m, 1H), 7.35 (m, 2H), 7.75 (m, 1H), 8.10 (s, 1H).

Ethyl {[4-bromo-1-(2-fluorophenyl)-5-(2-fluoropyridin-4-yl)-1H-pyrazol-3-yl]oxy}acetate (VIII-002)

58 mg (0.08 mmol) of bis(triphenylphosphine)palladium (II) chloride, 0.29 g (1.64 mmol) of 4-bromo-2-fluoropyridine, 0.68 g (4.94 mmol) of potassium carbonate and 0.7 ml of $H_2O$ are added successively to a solution of 0.65 g (1.64 mmol) of 3-(benzyloxy)-1-(2-fluorophenyl)-5-(4,4,5,5-tetramethyl-1,3,2-dioxaborolan-2-yl)-1H-pyrazole in 10 ml of dioxane and the reaction mixture is stirred under reflux for 4 hours. The reaction mixture is then added to $H_2O$ and extracted repeatedly with $CH_2Cl_2$. The organic phase is dried over $Na_2SO_4$ and concentrated. Purification of the crude mixture by column chromatography gives 0.43 g (72%) of product.

Bromination and debenzylation are carried out as described for the preparation of Example VI-004.

Ethyl {[4-bromo-1-(2-fluorophenyl)-5-(2-fluoropyridin-4-yl)-1H-pyrazol-3-yl]oxy}acetate (VIII-002)

0.14 g (1.02 mmol) of potassium carbonate are added to a solution of 0.12 g (0.34 mmol) of 4-bromo-1-(2-fluorophenyl)-5-(2-fluoropyridin-4-yl)-1H-pyrazol-3-ol in 8 ml of acetonitrile and the mixture is stirred at room temperature for 10 minutes. 0.057 g (0.34 mmol) of ethyl bromoacetate is then added and the reaction mixture is stirred under reflux for 5 hours and then allowed to stand at room temperature overnight. After filtration and concentration of the filtrate, the residue is taken up in $H_2O$ and extracted repeatedly with $CH_2Cl_2$. The organic phase is dried and concentrated. This gives 0.14 g (93%) of product.

Ethyl {[4-bromo-1-(2-fluorophenyl)-5-(pyridazin-4-yl)-1H-pyrazol-3-yl]oxy}acetate (IV-001)

89 mg (0.12 mmol) of bis(triphenylphosphine)palladium (II) chloride, 0.61 g (2.53 mmol) of 5-bromopyridazine hydrobromide, 1.4 g (10.1 mmol) of potassium carbonate and 1.5 ml of $H_2O$ are added successively to a solution of 1.0 g (2.53 mmol) of 3-(benzyloxy)-1-(2-fluorophenyl)-5-(4,4,5,5-tetramethyl-1,3,2-dioxaborolan-2-yl)-1H-pyrazole in 16 ml of dioxane and the reaction mixture is stirred under reflux for 4 hours. The reaction mixture is then added to $H_2O$ and extracted repeatedly with $CH_2Cl_2$. The organic phase is dried over $Na_2SO_4$ and concentrated. Purification of the crude mixture by column chromatography gives 0.51 g (58%) of product.

Bromination and debenzylation are carried out as described for the preparation of Example VI-004.

Ethyl {[4-bromo-1-(2-fluorophenyl)-5-(pyridazin-4-yl)-1H-pyrazol-3-yl]oxy}acetate (IV-001)

0.21 g (1.52 mmol) of potassium carbonate are added to a solution of 0.17 g (0.50 mmol) of 4-bromo-1-(2-fluorophenyl)-5-(pyridazin-4-yl)-1H-pyrazol-3-ol in 5.5 ml of acetonitrile and the mixture is stirred at room temperature for 10 minutes. 0.085 g (0.50 mmol) of ethyl bromoacetate is then added and the reaction mixture is stirred under reflux for 5 hours and then allowed to stand at room temperature overnight. After filtration and concentration of the filtrate, the residue is taken up in $H_2O$ and extracted repeatedly with $CH_2Cl_2$. The organic phase is dried and concentrated. This gives 0.19 g (84%) of product.

Ethyl {[4-cyano-1-(2-fluorophenyl)-5-(pyridazin-4-yl)-1H-pyrazol-3-yl]oxy}acetate (IV-003)

A mixture consisting of 0.25 g (0.58 mmol) of ethyl {[4-bromo-1-(2-fluorophenyl)-5-(pyridazin-4-yl)-1H-pyrazol-3-yl]oxy}acetate, 0.048 g (0.41 mmol) of zinc cyanide and 0.068 g (0.05 mmol) of tetrakis(triphenylphosphine) palladium in 11 ml of dimethylacetamide is heated to 180° C. in a microwave with stirring for 40 minutes. The reaction mixture is then concentrated, taken up in $H_2O$ and extracted repeatedly with $CH_2Cl_2$. The organic phase is dried over $Na_2SO_4$ and concentrated and the crude product thus obtained is purified on silica gel using heptane/ethyl acetate (1:1). This gives 88 mg (40%) of product.

$^1$H NMR (400 MHz, CDCl$_3$): δ 5.40 (s, 2H), 7.15 (m, 1H), 7.30-7.60 (m, 4H), 9.00 (s, 1H), 9.30 (d, 1H).

Methyl (2R)-2-{[4-bromo-1-(2-fluorophenyl)-5-(5-fluoropyrimidin-2-yl)-1H-pyrazol-3-yl]oxy}propanoate (III-001)

89 mg (0.12 mmol) of bis(triphenylphosphine)palladium (II) chloride, 0.45 g (2.53 mmol) of 2-bromo-5-fluoropyrimidine, 1.05 g (7.604 mmol) of potassium carbonate and 1 ml of $H_2O$ are added successively to a solution of 1.00 g (2.53 mmol) of 3-(benzyloxy)-1-(2-fluorophenyl)-5-(4,4,5,5-tetramethyl-1,3,2-dioxaborolan-2-yl)-1H-pyrazole in 16 ml of dioxane and the reaction mixture is stirred under reflux for 4 hours. The reaction mixture is then added to $H_2O$ and extracted repeatedly with $CH_2Cl_2$. The organic phase is dried over Na$_2$SO$_4$ and concentrated. This gives 1 g (91%) of product sufficiently pure for further reactions.

$^1$H NMR (400 MHz, CDCl$_3$): δ 5.30 (s, 2H), 6.63 (s, 1H), 7.30-7.55 (m, 4H), 8.45 (s, 2H).

Bromination and debenzylation are carried out as described for the preparation of Example VI-004.

Methyl (2R)-2-{[4-bromo-1-(2-fluorophenyl)-5-(5-fluoropyrimidin-2-yl)-1H-pyrazol-3-yl]oxy}propanoate (III-001)

124 mg (0.89 mmol) of potassium carbonate are added to a solution of 0.105 g (0.29 mmol) of 4-bromo-1-(2-fluorophenyl)-5-(5-fluoropyrimidin-2-yl)-1H-pyrazol-3-ol in 7 ml of acetonitrile and the mixture is stirred at room temperature for 10 minutes. 55 mg (0.44 mmol) of methyl (2S)-2-chloropropanoate is then added and the reaction mixture is stirred under reflux for 5 hours and then allowed to stand at room temperature overnight. After filtration and concentration of the filtrate, the residue is taken up in H$_2$O and extracted repeatedly with CH$_2$Cl$_2$. The organic phase is dried and concentrated. Purification by column chromatography on silica gel using heptane/ethyl acetate (1:1) gives 45 mg (35%) of product.

$^1$H NMR (400 MHz, CDCl$_3$): δ 1.70 (d, 3H), 3.78 (s, 3H), 5.25 (q, 1H), 7.00 (m, 1H), 7.23 (m, 1H), 7.30 (m, 1H), 7.48 (m, 1H), 8.60 (s, 2H).

Methyl 2-{[4-chloro-5-(6-fluoropyridin-3-yl)-1-phenyl-1H-pyrazol-3-yl]oxy}propanoate (VII-023)

2.65 g (8.13 mmol) of caesium carbonate and 1.2 g (6.51 mmol) of methyl 2-chloropropanoate are added successively to a solution of 1 g (5.42 mmol) of 5-amino-1-phenyl-1H-pyrazol-3-ol in 5 ml of DMF and the mixture is stirred at room temperature for 3 hours. The reaction mixture is concentrated and the residue is taken up in diethyl ether. The solid is filtered off with suction and the filtrate is concentrated. This gives 0.85 g (57%) of product.

$^1$H NMR (400 MHz, CDCl$_3$): δ 1.60 (d, 3H), 3.75 (s, 3H), 3.80 (bs, 2H), 5.15 (q, 1H), 5.20 (s, 1H), 7.35 (m, 1H), 7.45 (m, 2H), 7.50 (m, 2H).

Methyl 2-[(5-amino-4-chloro-1-phenyl-1H-pyrazol-3-yl)oxy]propanoate 0.44 g (3.30 mmol) of N-chlorosuccinimide is added to a solution of 8.8 g (2.75 mmol) of methyl 2-[(5-amino-1-phenyl-1H-pyrazol-3-yl)oxy]propanoate in 5 ml of DMF and the mixture is stirred at room temperature for 30 minutes. The DMF is removed and the residue is taken up in H$_2$O and extracted repeatedly with CH$_2$Cl$_2$. The organic phase is dried over Na$_2$SO$_4$ and concentrated. Subsequent chromatographic purification on silica gel using heptane/ethyl acetate (4:1) gives 0.5 g (58%) of product.

$^1$H NMR (400 MHz, CDCl$_3$): δ 1.70 (d, 3H), 3.70 (s, 3H), 5.25 (q, 1H), 7.15 (m, 1H), 7.40 (m, 2H), 7.80 (m, 2H), 8.20 (bs, 2H).

Methyl 2-[(4-chloro-5-iodo-1-phenyl-1H-pyrazol-3-yl)oxy]propanoate 0.36 g (1.35 mmol) of diiodomethane and 0.79 g (0.67 mmol) of isopentyl nitrite are added successively to a solution of 0.1 g (0.34 mmol) of methyl 2-[(5-amino-4-chloro-1-phenyl-1H-pyrazol-3-yl)oxy]propanoate in 2 ml of acetonitrile and this reaction mixture is stirred at 50° C. for 30 minutes. The reaction mixture is then added to H$_2$O and extracted repeatedly with ethyl acetate. The organic phase is dried over Na$_2$SO$_4$ and concentrated and the crude product is purified by column chromatography on silica gel using heptane/ethyl acetate (4:1). This gives 102 mg (70%) of product.

$^1$H NMR (400 MHz, CDCl$_3$): δ 1.69 (d, 3H), 3.79 (s, 3H), 5.20 (q, 1H), 7.40-7.50 (m, 5H).

Methyl 2-{[4-chloro-5-(6-fluoropyridin-3-yl)-1-phenyl-1H-pyrazol-3-yl]oxy}propanoate (VII-023)

50 mg (0.36 mmol) of (6-fluoropyridin-3-yl)boronic acid, 8.36 mg (0.012 mmol) of bis(triphenylphosphine)palladium (II) chloride and 0.2 ml of a 2.5M aqueous caesium carbonate solution are added successively to a solution of 0.1 g (0.25 mmol) of methyl 2-[(4-chloro-5-iodo-1-phenyl-1H-pyrazol-3-yl)oxy]propanoate in 3 ml of dimethoxyethane and the reaction mixture is stirred at 80° C. for 3 hours. The reaction mixture is then concentrated, the residue is taken up in H$_2$O and the aqueous phase is extracted repeatedly with ethyl acetate. The organic phase is dried over Na$_2$SO$_4$ and concentrated and the residue is purified by column chromatography on silica gel using heptane/ethyl acetate (4:1). This gives 83 mg (83%) of product.

$^1$H NMR (400 MHz, CDCl$_3$): δ 1.70 (d, 3H), 3.70 (s, 3H), 5.25 (q, 1H), 6.90 (dd, 1H), 7.10 (m, 2H), 7.30 (m, 2H), 7.78 (m, 1H), 8.18 (d, 1H).

{[4-Bromo-1-(2-fluorophenyl)-5-(6-fluoropyridin-3-yl)-1H-pyrazol-3-yl]oxy}acetic acid (VI-003)

A solution of 0.6 g (1.37 mmol) of ethyl 3-[4-bromo-1-(2-fluorophenyl)-5-(6-fluoropyridin-3-yl)-1H-pyrazol-3-yl]propanoate, 46 mg (1.92 mmol) of LiGH and 6 ml of THF in 14 ml of H$_2$O is stirred at room temperature for 12 hours. The solution is concentrated and the aqueous phase that remains is adjusted to pH 2 using 2N HCl. The precipitated solid is filtered off with suction and dried. This gives 0.44 g (74%) of product.

$^1$H NMR (400 MHz, CDCl$_3$): δ 5.00 (s, 2H), 6.93 (dd, 1H), 7.02 (m, 1H), 7.20 (m, 1H), 7.35 (m, 1H), 7.41 (m, 1H), 7.75 (m, 1H), 8.12 (s, 1H).

N-Allyl-2-{[4-bromo-1-(2-fluorophenyl)-5-(6-fluoropyridin-3-yl)-1H-pyrazol-3-yl]oxy}acetamide (X-001)

At room temperature, a mixture of 60 mg (0.146 mmol) of {[4-bromo-1-(2-fluorophenyl)-5-(6-fluoropyridin-3-yl)-1H-pyrazol-3-yl]oxy}acetic acid, 9 mg (0.161 mmol) of allylamine and 34 mg (0.176 mmol) of 1-(3-dimethylaminopropyl)-3-ethylcarbodiimide hydrochloride is stirred in a solvent mixture of 3 ml of THF and 6 ml of DMF for 12 hours. A 2N HCl solution is then added to the reaction mixture, and the reaction mixture is extracted repeatedly with CH$_2$C$_2$. The organic phase is dried over Na$_2$SO$_4$ and concentrated and the residue thus obtained is purified by column chromatography on silica gel using heptane/ethyl acetate (7/3). This gives 13 mg (19%) of product.

$^1$H NMR (400 MHz, CDCl$_3$) δ 4.00 (m, 2H), 4.85 (m, 2H9, 5.70 (2m, 2h), 5.90 (m, 1H9, 6.65 (bs, 1H, NH), 6.95 (m, 1H), 7.05 (m, 1H), 7.35 (m, 1H), 7.38 (m, 1H9, 7.45 (m, 1H97.73 (m, 1H9, 8.10 (s, 1H).

NMR Data of Selected Examples

NMR Peak List Method

The 1H NMR data of selected examples are noted in the form of 1H NMR peak lists. For each signal peak, first the $\delta$ value in ppm and then the signal intensity in round brackets are listed. The pairs of $\delta$ value-signal intensity numbers for different signal peaks are listed with separation from one another by semicolons.

The peak list for one example therefore takes the form of: $\delta_1$ (intensity$_1$); $\delta_2$ (intensity$_2$); ...; $\delta_i$ (intensity$_i$); ...; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

---

VII-002: $^1$H-NMR(400.0 MHz, CDCl3):
$\delta$ = 8.1749 (0.8); 8.1730 (1.2); 8.1709 (0.9); 8.1689 (0.9); 8.1667 (1.2); 8.1648 (0.8); 7.7044 (0.7); 7.6981 (0.7); 7.6857 (0.8); 7.6831 (0.8); 7.6794 (0.8); 7.6769 (0.8); 7.6645 (0.7); 7.6582 (0.7); 7.2622 (17.5); 7.1308 (1.4); 7.1250 (0.5); 7.1189 (1.5); 7.1135 (0.9); 7.1079 (2.2); 7.1019 (0.6); 7.0960 (2.2); 7.0309 (2.2); 7.0249 (0.6); 7.0137 (0.7); 7.0108 (2.4); 7.0080 (1.6); 7.0050 (0.6); 6.9938 (0.5); 6.9880 (1.4); 6.9779 (0.9); 6.9763 (0.9); 6.9703 (0.9); 6.9687 (0.8); 6.9566 (0.8); 6.9550 (0.8); 6.9490 (0.8); 6.9475 (0.8); 4.9307 (8.4); 3.8127 (16.0); 2.0076 (9.8); 1.5646 (0.5); −0.0002 (10.5)

VII-002: $^1$H-NMR(400.6 MHz, CDCl3):
$\delta$ = 8.1733 (1.1); 8.1670 (1.2); 7.7036 (0.7); 7.6974 (0.6); 7.6850 (0.7); 7.6825 (0.8); 7.6788 (0.7); 7.6762 (0.8); 7.6638 (0.7); 7.6576 (0.7); 7.2606 (19.7); 7.1300 (1.4); 7.1242 (0.5); 7.1182 (1.5); 7.1128 (0.9); 7.1072 (2.2); 7.1012 (0.6); 7.0954 (2.1); 7.0309 (2.2); 7.0250 (0.6); 7.0137 (0.6); 7.0108 (2.4); 7.0081 (1.6); 7.0050 (0.7); 6.9939 (0.5); 6.9881 (1.5); 6.9775 (0.8); 6.9761 (0.8); 6.9699 (0.8); 6.9685 (0.9); 6.9563 (0.7); 6.9549 (0.8); 6.9488 (0.8); 6.9473 (0.8); 5.3002 (1.2); 4.9309 (8.3); 4.9255 (0.7); 3.9574 (0.9); 3.8131 (16.0); 1.5421 (4.7); 0.0080 (0.7); −0.0002 (26.9); −0.0085 (0.8)

VII-012: $^1$H-NMR(400.0 MHz, CDCl3):
$\delta$ = 8.1075 (2.3); 8.1013 (2.3); 7.7699 (1.1); 7.7636 (1.1); 7.7511 (1.3); 7.7487 (1.4); 7.7449 (1.2); 7.7425 (1.3); 7.7299 (1.1); 7.7237 (1.1); 7.4268 (0.9); 7.4225 (1.0); 7.4075 (1.7); 7.4033 (1.8); 7.3888 (1.0); 7.3843 (1.2); 7.3704 (0.5); 7.3582 (0.5); 7.3515 (0.9); 7.3472 (0.8); 7.3391 (0.9); 7.3348 (0.8); 7.3308 (0.8); 7.3263 (0.6); 7.3186 (0.8); 7.3140 (0.6); 7.2613 (31.1); 7.2246 (1.2); 7.2054 (1.7); 7.1879 (0.7); 7.0479 (1.2); 7.0446 (1.1); 7.0270 (1.1); 7.0232 (1.8); 7.0195 (1.2); 7.0019 (1.0); 6.9986 (1.0); 6.9424 (1.6); 6.9349 (1.6); 6.9212 (1.5); 6.9148 (1.4); 4.9008 (16.0); 4.2971 (2.0); 4.2792 (6.2); 4.2614 (6.3); 4.2436 (2.1); 3.5057 (0.6); 3.4881 (1.8); 3.4706 (1.8); 3.4530 (0.6); 1.5542 (15.5); 1.3088 (7.4); 1.2910 (15.1); 1.2731 (7.3); 1.2262 (1.9); 1.2087 (3.8); 1.1911 (1.8); 0.0080 (0.7); −0.0002 (25.9); −0.0085 (0.8)

VII-012: $^1$H-NMR(400.6 MHz, d$_6$-DMSO):
$\delta$ = 8.2014 (2.1); 8.1951 (2.3); 7.9621 (0.9); 7.9558 (0.9); 7.9426 (1.2); 7.9409 (1.3); 7.9363 (1.2); 7.9346 (1.3); 7.9215 (1.0); 7.9152 (1.0); 7.5783 (0.6); 7.5748 (0.9); 7.5599 (1.4); 7.5554 (1.9); 7.5403 (1.0); 7.5360 (1.1); 7.4994 (0.5); 7.4931 (0.8); 7.4879 (0.9); 7.4804 (0.8); 7.4759 (0.8); 7.4727 (0.8); 7.4680 (0.6); 7.4598 (0.7); 7.4554 (0.6); 7.3380 (1.0); 7.3350 (1.3); 7.3191 (1.7); 7.3156 (3.2); 7.3086 (1.0); 7.2962 (2.6); 7.2934 (1.8); 7.2905 (2.4); 7.2890 (2.5); 7.2850 (1.3); 7.2762 (1.5); 7.2748 (1.6); 7.2677 (2.2); 7.2642 (1.0); 4.9348 (11.0); 4.1956 (1.9); 4.1778 (6.1); 4.1601 (6.2); 4.1424 (1.9); 3.3210 (62.7); 2.5410 (0.8); 2.5242 (1.2); 2.5195 (1.6); 2.5107 (25.1); 2.5062 (55.3); 2.5016 (78.2); 2.4970 (54.7); 2.4924 (25.2); 2.0745 (2.3); 1.2054 (7.4); 1.1983 (0.8); 1.1877 (16.0); 1.1700 (7.2); 0.0080 (2.0); −0.0002 (70.4); −0.0085 (2.3)

VII-127: $^1$H-NMR(400.0 MHz, CDCl3):
$\delta$ = 8.0580 (3.4); 8.0531 (3.3); 7.4762 (2.4); 7.4701 (2.4); 7.4546 (2.6); 7.4485 (2.5); 7.3869 (1.0); 7.3826 (1.1); 7.3676 (1.9); 7.3636 (2.2); 7.3488 (1.2); 7.3443 (1.8); 7.3316 (0.7); 7.3245 (1.1); 7.3124 (1.1); 7.3044 (1.1); 7.2997 (0.8); 7.2920 (0.8); 7.2876 (0.7); 7.2613 (10.8); 7.1896 (1.4); 7.1704 (2.2); 7.1527 (0.9); 7.0516 (1.3); 7.0485 (1.3); 7.0306 (1.3); 7.0271 (2.1); 7.0236 (1.5); 7.0059 (1.1); 7.0029 (1.1); 6.6762 (3.4); 6.6546 (3.3); 4.8925 (16.0); 4.3593 (2.0); 4.3416 (6.4); 4.3239 (6.6); 4.3062 (2.1); 4.2920 (2.1); 4.2742 (6.3); 4.2563 (6.4); 4.2385 (2.1); 1.5625 (8.8); 1.3902 (6.5); 1.3725 (13.3); 1.3548 (6.4); 1.3039 (7.2); 1.2861 (14.6); 1.2682 (7.2); −0.0002 (13.1)

VII-012: $^1$H-NMR(400.0 MHz, d$_6$-DMSO):
$\delta$ = 8.2011 (1.0); 8.1948 (1.1); 7.9422 (0.6); 7.9404 (0.6); 7.9359 (0.6); 7.9341 (0.6); 7.5594 (0.7); 7.5550 (0.9); 7.3346 (0.6); 7.3187 (0.8); 7.3151 (1.4); 7.2955 (1.2); 7.2882 (1.2); 7.2843 (0.6); 7.2739 (0.7); 7.2669 (1.1); 4.9346 (5.3); 4.1958 (0.9); 4.1781 (2.9); 4.1603 (3.0); 4.1426 (0.9); 3.3175 (16.0);

2.5240 (0.5); 2.5194 (0.7); 2.5106 (9.6); 2.5061 (20.8); 2.5014 (29.0); 2.4968 (20.2); 2.4922 (8.9); 2.0742 (12.3); 1.2057 (3.5); 1.1879 (7.6); 1.1701 (3.4); 0.0081 (0.8); −0.0002 (28.7); −0.0086 (0.8)

VII-012: $^1$H-NMR(400.6 MHz, CDCl3):
δ = 8.1108 (1.0); 8.1091 (1.4); 8.1070 (1.1); 8.1048 (1.2); 8.1028 (1.5); 8.1008 (1.0); 7.7702 (0.8); 7.7639 (0.8); 7.7514 (0.9); 7.7490 (0.9); 7.7452 (0.9); 7.7427 (0.9); 7.7303 (0.8); 7.7240 (0.8); 7.4282 (0.6); 7.4239 (0.7); 7.4090 (1.0); 7.4046 (1.2); 7.3902 (0.7); 7.3858 (0.8); 7.3520 (0.6); 7.3501 (0.5); 7.3476 (0.5); 7.3398 (0.6); 7.3353 (0.6); 7.3334 (0.5); 7.3313 (0.6); 7.3191 (0.6); 7.2663 (6.2); 7.2284 (0.7); 7.2267 (0.8); 7.2250 (0.8); 7.2235 (0.7); 7.2078 (1.0); 7.2070 (1.1); 7.2054 (1.1); 7.1881 (0.5); 7.0482 (0.8); 7.0450 (0.8); 7.0274 (0.7); 7.0236 (1.2); 7.0198 (0.8); 7.0024 (0.7); 6.9991 (0.7); 6.9450 (1.1); 6.9434 (1.1); 6.9376 (1.1); 6.9360 (1.0); 6.9238 (1.1); 6.9222 (1.1); 6.9163 (1.1); 6.9147 (1.0); 4.9009 (11.4); 4.2962 (1.4); 4.2784 (4.5); 4.2606 (4.6); 4.2428 (1.5); 2.0072 (16.0); 1.3080 (6.0); 1.2902 (12.6); 1.2723 (5.8); −0.0002 (4.6)

VII-019: $^1$H-NMR(400.0 MHz, d$_6$-DMSO):
δ = 8.1923 (0.7); 8.1860 (0.7); 7.5279 (0.5); 7.3088 (1.3); 7.2894 (0.9); 7.2850 (0.8); 7.2639 (0.7); 5.1129 (0.9); 5.0956 (0.9); 4.1785 (0.5); 4.1608 (1.7); 4.1431 (1.8); 4.1254 (0.6); 3.3184 (16.0); 2.5192 (0.6); 2.5105 (7.0); 2.5060 (15.0); 2.5014 (20.5); 2.4968 (14.4); 2.4922 (6.5); 2.0741 (1.4); 1.5748 (2.6); 1.5574 (2.6); 1.1724 (1.9); 1.1548 (4.1); 1.1370 (1.8); −0.0002 (12.2)

VII-005: $^1$H-NMR(400.0 MHz, d$_6$-DMSO):
δ = 7.3119 (0.7); 4.8894 (2.1); 3.3183 (16.0); 2.5191 (0.5); 2.5104 (6.6); 2.5058 (14.2); 2.5012 (19.7); 2.4966 (13.7); 2.4920 (6.1); 2.0739 (1.3); 1.1962 (4.7); 1.1806 (4.7); −0.0002 (13.7)

VII-029: $^1$H-NMR(400.0 MHz, d$_6$-DMSO):
δ = 8.1992 (0.6); 8.1929 (0.6); 7.3093 (0.9); 7.2899 (0.8); 7.2861 (0.7); 7.2648 (0.5); 4.9811 (0.6); 3.6843 (6.3); 3.3196 (16.0); 2.5107 (4.9); 2.5062 (10.6); 2.5015 (14.7); 2.4969 (10.2); 2.4924 (4.5); 1.9343 (0.5); 1.0440 (1.0); 1.0256 (2.4); 1.0070 (1.0); −0.0002 (10.0)

VII-003: $^1$H-NMR(400.0 MHz, d$_6$-DMSO):
δ = 8.2013 (1.4); 8.1950 (1.5); 7.9639 (0.6); 7.9576 (0.6); 7.9445 (0.8); 7.9428 (0.9); 7.9381 (0.8); 7.9364 (0.8); 7.9233 (0.6); 7.9170 (0.6); 7.5898 (0.6); 7.5747 (1.0); 7.5703 (1.2); 7.5551 (0.6); 7.5508 (0.7); 7.4949 (0.5); 7.4821 (0.5); 7.4743 (0.5); 7.3406 (0.6); 7.3377 (0.8); 7.3216 (1.0); 7.3182 (1.4); 7.3106 (0.8); 7.3081 (0.6); 7.3020 (0.6); 7.2979 (1.2); 7.2902 (1.6); 7.2849 (1.0); 7.2816 (0.8); 7.2748 (1.0); 7.2692 (0.9); 7.2679 (1.0); 7.2639 (0.7); 7.2608 (0.6); 4.8400 (7.0); 3.4368 (0.7); 2.5243 (0.6); 2.5197 (0.9); 2.5109 (10.8); 2.5064 (23.1); 2.5017 (32.0); 2.4971 (22.2); 2.4926 (9.9); 2.0744 (16.0); 0.0080 (1.0); 0.0040 (0.6); −0.0002 (29.1); −0.0085 (0.8)

VII-003: $^1$H-NMR(400.0 MHz, d$_6$-DMSO):
δ = 8.2042 (3.5); 8.1979 (3.6); 7.9673 (1.4); 7.9609 (1.4); 7.9461 (2.0); 7.9398 (1.9); 7.9266 (1.5); 7.9203 (1.4); 7.5967 (1.1); 7.5926 (1.4); 7.5775 (2.4); 7.5732 (2.8); 7.5580 (1.5); 7.5537 (1.6); 7.5154 (0.7); 7.5110 (0.7); 7.5026 (0.8); 7.4964 (1.2); 7.4910 (1.2); 7.4836 (1.2); 7.4792 (1.2); 7.4760 (1.3); 7.4712 (0.9); 7.4630 (1.0); 7.4585 (0.8); 7.3430 (1.6); 7.3401 (2.0); 7.3239 (2.6); 7.3206 (3.4); 7.3139 (2.0); 7.3013 (3.8); 7.2940 (3.4); 7.2881 (2.2); 7.2847 (1.8); 7.2799 (3.4); 7.2731 (2.2); 7.2671 (1.5); 7.2640 (1.3); 4.8417 (16.0); 3.0137 (1.0); 2.6721 (0.5); 2.5256 (1.6); 2.5210 (2.3); 2.5121 (28.3); 2.5076 (61.6); 2.5030 (85.4); 2.4984 (59.7); 2.4939 (26.4); 2.4180 (11.6); 2.3299 (0.5); 2.0774 (3.3); 1.9098 (3.2); 1.2198 (0.6); 1.1692 (0.6); 0.0081 (1.7); 0.0057 (0.6); −0.0002 (57.6); −0.0085 (1.6)

VII-003: $^1$H-NMR(400.6 MHz, CDCl3):
δ = 8.1103 (0.5); 7.2620 (13.4); 4.9739 (3.8); 2.1111 (2.3); 2.0087 (16.0); −0.0002 (7.6)

VII-003: $^1$H-NMR(400.2 MHz, d$_6$-DMSO):
δ = 8.2026 (7.9); 8.1966 (8.1); 7.9658 (2.6); 7.9596 (2.5); 7.9449 (4.2); 7.9391 (4.0); 7.9252 (2.8); 7.9189 (2.6); 7.5959 (2.1); 7.5921 (2.4); 7.5766 (4.5); 7.5728 (4.9); 7.5572 (2.7); 7.5533 (2.7); 7.5137 (1.2); 7.5096 (1.3); 7.5009 (1.5); 7.4945 (2.6); 7.4900 (2.6); 7.4814 (2.6); 7.4774 (2.7); 7.4700 (1.9); 7.4614 (1.8); 7.4574 (1.6); 7.3389 (3.8); 7.3194 (6.4); 7.3116 (4.2); 7.3000 (7.7); 7.2923 (6.9); 7.2860 (4.9); 7.2825 (4.3); 7.2787 (5.4); 7.2719 (4.9); 7.2648 (3.1); 7.2622 (2.7); 4.8305 (16.0); 3.6746 (0.4); 3.3398 (3.4); 2.6724 (0.4); 2.5258 (1.4); 2.5210 (2.1); 2.5122 (23.1); 2.5078 (48.1); 2.5033 (65.3); 2.4988 (46.9); 2.4944 (21.8); 2.3303 (0.4); 1.3873 (1.4); 0.0000 (8.3)

VII-019: $^1$H-NMR(400.6 MHz, CDCl3):
δ = 8.1016 (1.2); 8.0998 (1.9); 8.0978 (1.5); 8.0957 (1.5); 8.0936 (2.0); 8.0916 (1.4); 8.0193 (0.6); 7.7611 (1.0); 7.7549 (1.0); 7.7423 (1.2); 7.7399 (1.3); 7.7361 (1.2); 7.7336 (1.2); 7.7212 (1.1); 7.7149 (1.1); 7.3960 (0.8); 7.3916 (0.9); 7.3768 (1.3); 7.3724 (1.7); 7.3576 (1.2); 7.3444 (0.6); 7.3398 (0.6); 7.3376 (0.8); 7.3359 (0.7); 7.3332 (0.7); 7.3314 (0.7); 7.3254 (0.8); 7.3237 (0.7); 7.3209 (0.7); 7.3192 (0.7); 7.3170 (0.8); 7.3125 (0.6); 7.3048 (0.8); 7.3003 (0.6); 7.2621 (16.2); 7.2122 (0.9); 7.2106 (1.0); 7.2088 (1.0); 7.2074 (1.0); 7.1912 (1.4); 7.1892 (1.5); 7.1737 (0.6); 7.1720 (0.6); 7.1703 (0.6); 7.1689 (0.6); 7.0361 (1.0); 7.0328 (1.0); 7.0153 (0.9); 7.0114 (1.6); 7.0077 (1.1); 6.9901 (0.9); 6.9869 (0.9); 6.9368 (1.4); 6.9353 (1.5); 6.9294 (1.4); 6.9278 (1.4); 6.9157 (1.3); 6.9141 (1.4); 6.9082 (1.4); 6.9066 (1.4); 5.3002 (6.0); 5.2152 (0.8); 5.1978 (3.0); 5.1804 (3.0); 5.1630 (0.8); 4.2641 (1.1); 4.2623 (1.2); 4.2463 (3.6); 4.2445 (3.8); 4.2284 (3.8); 4.2268 (3.8); 4.2106 (1.3); 4.2091 (1.3); 2.9641 (5.3); 2.9567 (6.1); 2.8852 (5.2); 2.8838 (5.4); 2.7731 (3.6); 1.6903 (11.6); 1.6729 (11.6); 1.5678 (5.6); 1.2781 (7.7); 1.2603 (16.0); 1.2425 (7.4); 0.0080 (0.6); −0.0002 (21.8); −0.0084 (0.7)

VII-019: $^1$H-NMR(400.6 MHz, CDCl3):
δ = 8.0999 (1.8); 8.0979 (1.4); 8.0956 (1.4); 8.0936 (1.9); 7.7611 (1.0); 7.7548 (0.9); 7.7423 (1.1); 7.7399 (1.2); 7.7361 (1.1); 7.7336 (1.1); 7.7212 (1.0); 7.7149 (1.0); 7.3959 (0.7); 7.3915 (0.8); 7.3767 (1.3); 7.3724 (1.6); 7.3576 (1.0); 7.3534 (1.2); 7.3441 (0.5); 7.3395 (0.5); 7.3373 (0.8); 7.3356 (0.6); 7.3329 (0.6); 7.3311 (0.6); 7.3251 (0.8); 7.3235 (0.6); 7.3206 (0.6); 7.3189 (0.6); 7.3167 (0.8); 7.3122 (0.6); 7.3045 (0.7); 7.3000 (0.6); 7.2617 (11.7); 7.2118 (0.8); 7.2103 (0.9); 7.2085 (1.0); 7.1909 (1.3); 7.1890 (1.4); 7.1733 (0.6); 7.1718 (0.6); 7.1700 (0.6); 7.1687 (0.6); 7.0359 (1.0); 7.0327 (0.9); 7.0151 (0.9); 7.0113 (1.5); 7.0075 (1.0); 6.9900 (0.9); 6.9867 (0.8); 6.9366 (1.3); 6.9352 (1.3); 6.9292 (1.3); 6.9277 (1.3); 6.9154 (1.2); 6.9139 (1.3); 6.9079 (1.3); 6.9064 (1.3); 5.2154 (0.7); 5.1980 (2.8); 5.1806 (2.8); 5.1632 (0.8); 4.2641 (1.0); 4.2623 (1.1); 4.2463 (3.4); 4.2446 (3.4); 4.2284 (3.6); 4.2269 (3.5); 4.2105 (1.2); 4.2093 (1.2); 2.0451 (1.6); 1.6903 (10.7); 1.6729 (10.7); 1.5617 (2.8); 1.2780 (7.5); 1.2603 (16.0); 1.2425 (7.1); 0.8987 (1.1); 0.8818 (3.9); 0.8641 (1.5); −0.0002 (13.6)

VII-034: $^1$H-NMR(400.6 MHz, CDCl3):
δ = 8.0721 (1.7); 8.0692 (1.5); 8.0663 (1.8); 7.7047 (0.7); 7.7035 (0.7); 7.6984 (0.7); 7.6973 (0.7); 7.6841 (1.0); 7.6822 (0.9); 7.6800 (0.8); 7.6779 (1.0); 7.6648 (0.7); 7.6636 (0.7); 7.6586 (0.7); 7.6574

(0.6); 7.4525 (0.8); 7.4482 (0.9); 7.4333 (1.5); 7.4289 (1.7); 7.4144 (1.0); 7.4100 (1.2); 7.3948 (0.5); 7.3827 (0.5); 7.3781 (0.6); 7.3760 (0.8); 7.3742 (0.7); 7.3715 (0.7); 7.3698 (0.7); 7.3638 (0.8); 7.3621 (0.7); 7.3593 (0.8); 7.3575 (0.7); 7.3553 (0.8); 7.3508 (0.7); 7.3432 (0.8); 7.3387 (0.6); 7.2613 (16.8); 7.2544 (1.0); 7.2527 (1.1); 7.2510 (1.1); 7.2497 (1.0); 7.2316 (1.6); 7.2158 (0.7); 7.2142 (0.8); 7.2125 (0.8); 7.2112 (0.7); 7.0836 (1.1); 7.0803 (1.1); 7.0628 (1.0); 7.0589 (1.7); 7.0552 (1.2); 7.0377 (0.9); 7.0344 (0.9); 6.9405 (1.5); 6.9391 (1.5); 6.9330 (1.4); 6.9315 (1.4); 6.9192 (1.4); 6.9177 (1.4); 6.9116 (1.3); 6.9102 (1.3); 4.9025 (0.8); 4.8899 (15.7); 4.3036 (1.9); 4.2858 (6.0); 4.2679 (6.1); 4.2501 (2.0); 1.5683 (1.9); 1.3131 (7.7); 1.2953 (16.0); 1.2775 (7.6); 0.0079 (0.6); −0.0002 (19.6); −0.0085 (0.6)

VII-034: $^1$H-NMR(400.6 MHz, CDCl3):
δ = 7.7945 (3.6); 7.6603 (1.1); 7.6126 (3.6); 7.3291 (1.0); 7.3067 (0.9); 7.2605 (23.3); 5.0760 (2.8); 5.0576 (2.8); 5.0249 (2.4); 2.7476 (16.0); 1.5488 (10.5); 1.2539 (0.6); 0.0079 (0.7); −0.0002 (23.5); −0.0085 (0.7)

VII-024: $^1$H-NMR(400.0 MHz, d$_6$-DMSO):
δ = 8.2791 (1.0); 8.2702 (1.2); 8.2638 (1.2); 8.0366 (0.5); 8.0306 (0.8); 8.0241 (0.5); 8.0111 (0.8); 8.0047 (0.6); 8.0029 (0.6); 7.6852 (0.6); 7.6819 (0.7); 7.5796 (0.7); 7.5622 (0.5); 7.4414 (0.7); 7.4217 (1.1); 7.3302 (0.8); 7.3243 (0.8); 7.3230 (0.8); 7.3153 (0.9); 7.3088 (1.4); 7.3030 (0.8); 7.3016 (0.7); 7.2939 (0.8); 7.2882 (0.7); 5.7573 (2.0); 4.9491 (4.7); 4.1981 (0.9); 4.1804 (3.0); 4.1626 (3.0); 4.1448 (1.0); 3.3209 (16.0); 2.5209 (0.7); 2.5122 (8.6); 2.5076 (18.8); 2.5030 (26.0); 2.4984 (18.2); 2.4938 (8.1); 1.2088 (3.6); 1.1911 (7.9); 1.1733 (3.5); 0.0080 (0.7); −0.0002 (21.7); −0.0085 (0.6)

VII-010: $^1$H-NMR(400.0 MHz, CDCl3):
δ = 8.0567 (1.8); 8.0507 (1.8); 7.7355 (0.6); 7.7292 (0.6); 7.7154 (0.9); 7.7093 (0.9); 7.6957 (0.6); 7.6895 (0.6); 7.3950 (0.6); 7.3911 (1.0); 7.3867 (0.8); 7.3763 (1.2); 7.3737 (2.3); 7.3722 (2.1); 7.3673 (1.4); 7.3616 (0.7); 7.3540 (2.5); 7.3492 (0.7); 7.3471 (0.9); 7.3426 (0.6); 7.3346 (0.8); 7.3302 (0.5); 7.2610 (21.5); 7.2165 (0.9); 7.2149 (1.0); 7.2133 (1.1); 7.2118 (1.0); 7.1956 (1.8); 7.1939 (1.7); 7.1779 (0.7); 7.1762 (0.8); 7.1746 (0.7); 7.1732 (0.6); 7.0435 (1.0); 7.0408 (0.8); 7.0226 (1.0); 7.0193 (1.6); 7.0161 (0.8); 7.0136 (0.5); 6.9973 (1.0); 6.9944 (0.6); 6.9321 (1.4); 6.9306 (1.4); 6.9246 (1.4); 6.9231 (1.4); 6.9109 (1.4); 6.9093 (1.4); 6.9034 (1.4); 6.9018 (1.4); 4.9054 (14.6); 4.2899 (1.9); 4.2720 (6.0); 4.2542 (6.1); 4.2363 (2.0); 2.6154 (1.4); 1.5563 (0.7); 1.3020 (7.7); 1.2842 (16.0); 1.2663 (7.5); 0.0080 (0.6); −0.0002 (19.2)

VII-010: $^1$H-NMR(400.6 MHz, CDCl3):
δ = 8.0570 (1.6); 8.0510 (1.7); 7.7361 (0.5); 7.7299 (0.6); 7.7161 (0.8); 7.7100 (0.8); 7.6965 (0.6); 7.6903 (0.6); 7.3958 (0.6); 7.3919 (0.9); 7.3873 (0.7); 7.3772 (1.0); 7.3744 (2.2); 7.3729 (2.0); 7.3680 (1.2); 7.3622 (0.7); 7.3577 (0.8); 7.3546 (2.3); 7.3498 (0.7); 7.3477 (0.9); 7.3432 (0.7); 7.3353 (0.8); 7.3308 (0.5); 7.2620 (25.1); 7.2578 (0.5); 7.2172 (0.8); 7.2155 (0.9); 7.2139 (1.0); 7.2123 (0.9); 7.1985 (0.8); 7.1963 (1.6); 7.1945 (1.5); 7.1786 (0.6); 7.1769 (0.7); 7.1753 (0.7); 7.1738 (0.6); 7.0439 (0.9); 7.0412 (0.8); 7.0401 (0.7); 7.0230 (0.9); 7.0197 (1.5); 7.0165 (0.8); 7.0141 (0.6); 6.9981 (1.0); 6.9948 (0.6); 6.9331 (1.3); 6.9315 (1.4); 6.9256 (1.4); 6.9240 (1.4); 6.9119 (1.3); 6.9102 (1.4); 6.9044 (1.3); 6.9028 (1.4); 5.3001 (4.4); 4.9058 (13.8); 4.8967 (0.9); 4.2900 (1.8); 4.2722 (5.7); 4.2614 (0.5); 4.2544 (5.8); 4.2366 (1.8); 1.5630 (3.0); 1.3022 (7.6); 1.2936 (0.5); 1.2907 (0.6); 1.2892 (0.5); 1.2844 (16.0); 1.2781 (0.5); 1.2758 (1.0); 1.2666 (7.5); 1.2579 (0.6); 0.0080 (0.5); 0.0023 (0.6); −0.0002 (17.1); −0.0025 (1.0); −0.0084 (0.5)

VII-015: $^1$H-NMR(400.0 MHz, CDCl3):
δ = 8.4470 (2.7); 8.4401 (2.7); 8.2886 (1.7); 8.2850 (2.8); 8.2814 (1.7); 7.4433 (0.9); 7.4389 (1.0); 7.4286 (1.4); 7.4241 (2.8); 7.4214 (2.3); 7.4176 (1.6); 7.4060 (1.9); 7.4015 (2.1); 7.3950 (1.2); 7.3784 (2.6); 7.3673 (2.2); 7.3612 (1.0); 7.3593 (0.8); 7.3568 (0.8); 7.3549 (0.7); 7.3488 (0.9); 7.3445 (0.9); 7.3426 (0.8); 7.3405 (0.9); 7.3360 (0.7); 7.3282 (0.8); 7.3237 (0.7); 7.2632 (18.5); 7.2401 (0.9); 7.2386 (1.1); 7.2368 (1.2); 7.2172 (1.7); 7.2015 (0.8); 7.2000 (0.8); 7.1983 (0.8); 7.0549 (1.1); 7.0517 (1.1); 7.0341 (1.1); 7.0302 (1.8); 7.0265 (1.2); 7.0089 (1.0); 7.0057 (0.8); 5.3016 (4.1); 4.9057 (15.8); 4.7058 (2.9); 4.2992 (2.0); 4.2813 (6.3); 4.2635 (6.3); 4.2456 (2.0); 1.3104 (7.8); 1.2925 (16.0); 1.2747 (7.6); −0.0002 (13.4)

VII-007: $^1$H-NMR(400.0 MHz, CDCl3):
δ = 8.6067 (2.3); 8.6017 (2.2); 7.8649 (1.2); 7.8609 (1.1); 7.8446 (1.5); 7.8404 (1.4); 7.6899 (2.8); 7.6882 (2.8); 7.6694 (2.3); 7.6677 (2.2); 7.4643 (0.9); 7.4600 (1.0); 7.4450 (1.6); 7.4407 (1.8); 7.4261 (1.1); 7.4217 (1.2); 7.3903 (0.5); 7.3780 (0.6); 7.3735 (0.6); 7.3713 (0.9); 7.3669 (0.8); 7.3652 (0.7); 7.3590 (0.9); 7.3546 (0.8); 7.3527 (0.8); 7.3507 (0.8); 7.3462 (0.7); 7.3384 (0.8); 7.3339 (0.6); 7.2629 (27.9); 7.2504 (1.2); 7.2486 (1.2); 7.2289 (1.7); 7.2118 (0.7); 7.2099 (0.7); 7.0559 (1.2); 7.0527 (1.1); 7.0351 (1.1); 7.0312 (1.8); 7.0275 (1.2); 7.0100 (1.0); 7.0066 (1.0); 5.3025 (0.8); 4.9125 (16.0); 4.3021 (2.0); 4.2843 (6.4); 4.2664 (6.5); 4.2486 (2.1); 1.5622 (1.4); 1.3131 (7.8); 1.2953 (15.9); 1.2774 (7.6); 0.0079 (0.6); −0.0002 (20.2); −0.0086 (0.6)

VII-030: $^1$H-NMR(400.0 MHz, d$_6$-DMSO):
δ = 8.2537 (4.7); 8.0545 (1.4); 8.0485 (1.5); 8.0337 (2.6); 8.0141 (1.6); 8.0082 (1.3); 7.6336 (1.8); 7.6142 (3.2); 7.5983 (1.9); 7.5270 (1.0); 7.5113 (2.1); 7.4946 (2.2); 7.4790 (1.3); 7.3241 (5.8); 7.3046 (6.8); 7.2879 (5.4); 7.2669 (3.4); 7.2606 (2.9); 7.2137 (0.5); 4.8785 (16.0); 4.8350 (0.6); 4.4919 (1.1); 2.5069 (55.5); 2.5029 (65.1); 2.4990 (48.8); 2.0748 (7.4); 1.9099 (1.4); 1.3571 (2.2); 1.2367 (1.4); −0.0002 (24.2)

VII-011: $^1$H-NMR(400.0 MHz, d$_6$-DMSO):
δ = 8.7310 (4.0); 8.7276 (4.0); 8.0616 (1.4); 8.0573 (1.4); 8.0417 (3.4); 8.0368 (3.5); 8.0143 (5.9); 8.0125 (5.5); 7.9938 (2.6); 7.9919 (2.3); 7.6256 (1.3); 7.6216 (1.7); 7.6064 (2.7); 7.6021 (2.9); 7.5869 (1.7); 7.5826 (1.7); 7.5272 (0.7); 7.5228 (0.8); 7.5143 (0.9); 7.5082 (1.5); 7.5034 (1.4); 7.4953 (1.5); 7.4909 (1.5); 7.4832 (1.1); 7.4747 (1.1); 7.4705 (0.9); 7.3573 (1.8); 7.3546 (2.1); 7.3381 (2.9); 7.3351 (3.6); 7.3279 (2.3); 7.3191 (1.6); 7.3159 (1.7); 7.3072 (1.9); 7.3020 (2.4); 7.2989 (1.9); 7.2809 (1.6); 7.2779 (1.4); 4.8639 (16.0); 2.5264 (1.6); 2.5217 (2.4); 2.5129 (22.1); 2.5085 (45.5); 2.5039 (61.4); 2.4994 (44.4); 2.4949 (21.6); 2.0778 (15.2); 1.9105 (4.3); 1.3559 (2.4); 1.2347 (0.7); 0.0080 (1.7); −0.0002 (47.2); −0.0085 (2.0)

VII-025: $^1$H-NMR(400.0 MHz, d$_6$-DMSO):
δ = 13.0301 (0.6); 8.6453 (4.6); 8.6383 (4.7); 8.3565 (2.5); 8.3524 (4.6); 8.3485 (2.2); 7.7935 (1.6); 7.7891 (1.7); 7.7865 (1.7); 7.7821 (1.5); 7.7698 (1.7); 7.7654 (1.8); 7.7628 (1.6); 7.7585 (1.5); 7.6079 (1.0); 7.6037 (1.2); 7.5885 (2.1); 7.5842 (2.3); 7.5691 (1.2); 7.5647 (1.3); 7.5190 (0.6); 7.5146 (0.6); 7.5063 (0.6); 7.5002 (1.0); 7.4955 (0.9); 7.4873 (1.0); 7.4829 (1.0); 7.4796 (1.0); 7.4749 (0.8); 7.4667

(0.8); 7.4623 (0.7); 7.3493 (1.3); 7.3465 (1.6); 7.3303 (2.0); 7.3270 (2.5); 7.3204 (0.6); 7.3112 (2.4); 7.3081 (3.5); 7.2905 (1.3); 7.2853 (1.6); 7.2820 (1.3); 7.2643 (1.2); 7.2611 (1.1); 4.8464 (14.0); 3.3201 (1.8); 2.5236 (1.3); 2.5189 (1.9); 2.5102 (25.5); 2.5056 (55.1); 2.5010 (76.8); 2.4964 (53.3); 2.4918 (23.6); 2.0730 (16.0); 1.3559 (0.8); 0.0080 (1.5); −0.0002 (52.1); −0.0086 (1.4)

VII-025: $^1$H-NMR(400.0 MHz, DMSO__5 mm):
δ = 8.6467 (1.4); 8.6397 (1.4); 8.3562 (0.8); 8.3521 (1.4); 8.3484 (0.7); 7.7913 (0.5); 7.7887 (0.5); 7.7720 (0.5); 7.7677 (0.5); 7.5895 (0.6); 7.5852 (0.7); 7.3318 (0.6); 7.3286 (0.8); 7.3122 (0.7); 7.3093 (0.7); 7.2863 (0.5); 4.8449 (4.1); 3.4095 (0.6); 3.3920 (1.2); 3.3745 (1.7); 3.3374 (16.0); 2.5250 (1.0); 2.5204 (1.3); 2.5117 (9.6); 2.5071 (20.0); 2.5025 (27.2); 2.4979 (19.1); 2.4933 (8.5); 1.1083 (0.6); 1.0908 (1.3); 1.0733 (0.6); 0.0079 (0.5); −0.0002 (15.0)

VII-001: $^1$H-NMR(400.0 MHz, d$_6$-DMSO):
δ = 8.2036 (1.5); 8.1973 (1.6); 7.9638 (0.6); 7.9575 (0.6); 7.9442 (0.9); 7.9426 (0.9); 7.9379 (0.9); 7.9363 (0.9); 7.9231 (0.7); 7.9168 (0.7); 7.5832 (0.6); 7.5681 (1.0); 7.5637 (1.3); 7.5485 (0.7); 7.5442 (0.8); 7.4947 (0.6); 7.4896 (0.6); 7.4820 (0.6); 7.4775 (0.6); 7.4743 (0.6); 7.3391 (0.7); 7.3365 (0.9); 7.3203 (1.2); 7.3168 (1.9); 7.2974 (1.8); 7.2892 (1.9); 7.2750 (1.1); 7.2678 (1.6); 5.7567 (1.9); 4.9609 (7.4); 3.7004 (16.0); 3.3183 (5.7); 2.5199 (0.7); 2.5112 (8.6); 2.5066 (18.1); 2.5021 (25.0); 2.4975 (18.2); 2.4930 (9.0); 0.0080 (0.6); −0.0002 (17.6); −0.0085 (0.8)

VII-039: $^1$H-NMR(400.0 MHz, CDCl3):
δ = 8.6065 (1.6); 8.6019 (1.6); 7.8612 (0.8); 7.8566 (0.8); 7.8410 (1.0); 7.8362 (1.0); 7.6852 (1.9); 7.6648 (1.5); 7.4598 (0.5); 7.4555 (0.6); 7.4404 (1.0); 7.4364 (1.2); 7.4217 (0.7); 7.4173 (0.7); 7.3707 (0.6); 7.3663 (0.5); 7.3583 (0.6); 7.3505 (0.6); 7.2608 (9.1); 7.2468 (0.8); 7.2277 (1.2); 7.2095 (0.5); 7.0566 (0.7); 7.0536 (0.7); 7.0358 (0.7); 7.0320 (1.2); 7.0284 (0.8); 7.0107 (0.6); 7.0075 (0.6); 4.9319 (9.3); 3.8108 (16.0); 1.2553 (1.5); −0.0002 (11.7)

VII-040: $^1$H-NMR(400.0 MHz, CDCl3):
δ = 8.0732 (1.0); 8.0703 (0.9); 8.0673 (1.0); 7.6829 (0.6); 7.6810 (0.5); 7.6766 (0.6); 7.4481 (0.6); 7.4333 (0.9); 7.4289 (1.0); 7.4143 (0.6); 7.4099 (0.7); 7.3772 (0.5); 7.3650 (0.6); 7.3565 (0.5); 7.3443 (0.5); 7.2617 (8.0); 7.2554 (0.6); 7.2537 (0.6); 7.2520 (0.6); 7.2505 (0.6); 7.2324 (0.9); 7.0852 (0.6); 7.0819 (0.6); 7.0643 (0.6); 7.0605 (1.0); 7.0567 (0.7); 7.0391 (0.6); 7.0358 (0.6); 6.9400 (1.0); 6.9384 (1.0); 6.9324 (0.9); 6.9308 (0.9); 6.9187 (0.9); 6.9171 (1.0); 6.9111 (0.9); 6.9095 (0.9); 4.9234 (0.6); 4.9116 (8.7); 3.8118 (16.0); 3.8084 (1.2); 3.8018 (1.2); 2.0057 (7.7); 1.5593 (0.7); −0.0002 (8.7)

VII-031: $^1$H-NMR(400.0 MHz, CDCl3):
δ = 8.0591 (1.0); 8.0531 (1.1); 7.7159 (0.6); 7.7098 (0.5); 7.3902 (0.6); 7.3880 (0.5); 7.3743 (1.3); 7.3713 (1.2); 7.3683 (0.9); 7.3547 (1.7); 7.3516 (0.7); 7.3482 (0.6); 7.3358 (0.5); 7.2611 (7.2); 7.2173 (0.6); 7.2156 (0.6); 7.2140 (0.6); 7.2126 (0.6); 7.1964 (1.1); 7.1947 (0.9); 7.0455 (0.6); 7.0247 (0.6); 7.0214 (0.9); 6.9996 (0.6); 6.9321 (0.8); 6.9306 (0.9); 6.9246 (0.9); 6.9231 (0.8); 6.9109 (0.8); 6.9093 (0.8); 6.9034 (0.8); 6.9019 (0.8); 4.9250 (8.3); 3.8009 (16.0); 3.7967 (0.8); 2.0051 (4.0); 1.2560 (0.6); −0.0002 (7.9)

VII-031: $^1$H-NMR(400.6 MHz, CDCl3):
δ = 8.0583 (1.2); 8.0524 (1.3); 7.7167 (0.6); 7.7114 (0.6); 7.3909 (0.7); 7.3749 (1.4); 7.3722 (1.3); 7.3557 (1.8); 7.3493 (0.6); 7.3368 (0.5); 7.2605 (12.3); 7.2150 (0.7); 7.1975 (1.2); 7.0461 (0.6); 7.0430 (0.5); 7.0219 (1.0); 7.0001 (0.6); 6.9331 (1.0); 6.9257 (1.0); 6.9120 (0.9); 6.9045 (1.0); 4.9257 (9.0); 3.8021 (16.0); 1.5410 (3.4); 0.0079 (0.5); −0.0002 (19.7); −0.0084 (0.8)

VII-035: $^1$H-NMR(400.0 MHz, CDCl3):
δ = 8.4474 (1.4); 8.4405 (1.4); 8.2912 (0.9); 8.2876 (1.5); 8.2839 (0.9); 7.4341 (0.6); 7.4246 (0.8); 7.4200 (1.5); 7.4179 (1.3); 7.4146 (1.2); 7.4136 (1.2); 7.4022 (0.9); 7.4004 (0.8); 7.3979 (1.0); 7.3955 (1.4); 7.3909 (0.7); 7.3609 (0.5); 7.3487 (0.5); 7.3402 (0.5); 7.2612 (17.9); 7.2384 (0.6); 7.2367 (0.6); 7.2350 (0.6); 7.2335 (0.6); 7.2154 (0.9); 7.0565 (0.6); 7.0532 (0.6); 7.0357 (0.6); 7.0318 (1.0); 7.0280 (0.6); 7.0105 (0.6); 7.0072 (0.5); 4.9251 (8.6); 3.8075 (16.0); 2.0056 (3.8); −0.0002 (11.5)

X-002: $^1$H-NMR(400.0 MHz, d$_6$-DMSO):
δ = 8.4718 (0.8); 8.1893 (1.3); 8.1830 (1.4); 7.9491 (0.6); 7.9428 (0.5); 7.9297 (0.7); 7.9279 (0.8); 7.9234 (0.7); 7.9216 (0.8); 7.9085 (0.6); 7.9022 (0.6); 7.6294 (0.6); 7.6142 (1.0); 7.6098 (1.1); 7.5947 (0.6); 7.5904 (0.6); 7.3504 (0.6); 7.3475 (0.7); 7.3313 (1.0); 7.3280 (1.2); 7.3091 (1.2); 7.2992 (0.9); 7.2935 (0.9); 7.2922 (0.9); 7.2885 (0.7); 7.2831 (0.8); 7.2794 (1.4); 7.2721 (0.8); 7.2709 (0.8); 7.2621 (0.6); 5.7546 (1.9); 4.7987 (6.1); 3.9249 (2.9); 3.9101 (2.8); 3.6297 (16.0); 3.3132 (9.4); 2.5240 (0.5); 2.5193 (0.7); 2.5106 (8.3); 2.5060 (17.9); 2.5014 (24.9); 2.4967 (17.2); 2.4921 (7.5); 1.9089 (0.8); 0.0081 (0.6); −0.0002 (19.8); −0.0086 (0.5)

VII-036: $^1$H-NMR(400.0 MHz, CDCl3):
δ = 8.1044 (2.3); 8.0981 (2.3); 7.7584 (1.0); 7.7521 (1.0); 7.7395 (1.2); 7.7373 (1.3); 7.7333 (1.2); 7.7311 (1.2); 7.7185 (1.1); 7.7122 (1.1); 7.4086 (0.9); 7.4043 (1.0); 7.3894 (1.6); 7.3851 (1.9); 7.3705 (1.1); 7.3661 (1.2); 7.3556 (0.5); 7.3434 (0.5); 7.3366 (0.9); 7.3322 (0.8); 7.3243 (0.9); 7.3199 (0.8); 7.3180 (0.8); 7.3160 (0.9); 7.3114 (0.7); 7.3037 (0.8); 7.2992 (0.6); 7.2614 (13.2); 7.2125 (1.2); 7.2108 (1.2); 7.1914 (1.8); 7.1739 (0.8); 7.0357 (1.2); 7.0325 (1.1); 7.0149 (1.1); 7.0111 (1.8); 7.0074 (1.2); 6.9898 (1.0); 6.9866 (1.0); 6.9407 (1.6); 6.9394 (1.6); 6.9332 (1.6); 6.9194 (1.5); 6.9182 (1.5); 6.9120 (1.5); 5.2999 (1.3); 4.8940 (16.0); 4.2929 (2.0); 4.2750 (6.3); 4.2572 (6.4); 4.2394 (2.1); 1.5530 (4.5); 1.3072 (7.6); 1.2894 (15.7); 1.2715 (7.5); −0.0002 (18.1); −0.0085 (0.6)

VII-021: $^1$H-NMR(400.6 MHz, CDCl3):
δ = 8.0711 (0.9); 8.0691 (0.7); 8.0670 (0.8); 8.0649 (1.0); 8.0630 (0.7); 7.7508 (0.5); 7.7446 (0.5); 7.7319 (0.6); 7.7297 (0.6); 7.7257 (0.6); 7.7234 (0.6); 7.7108 (0.6); 7.7045 (0.5); 7.4113 (0.7); 7.4070 (0.8); 7.3881 (0.5); 7.2610 (12.3); 7.2173 (0.5); 7.1976 (0.7); 7.0183 (0.8); 7.0144 (0.6); 6.9344 (0.7); 6.9328 (0.7); 6.9269 (0.7); 6.9254 (0.7); 6.9132 (0.6); 6.9116 (0.7); 6.9058 (0.7); 6.9042 (0.7); 4.9401 (7.2); 4.2897 (1.0); 4.2719 (2.9); 4.2540 (3.0); 4.2362 (1.0); 2.3166 (16.0); 1.5496 (2.5); 1.3066 (3.8); 1.2888 (8.0); 1.2709 (3.8); −0.0002 (16.7); −0.0085 (0.5)

X-004: $^1$H-NMR(400.6 MHz, d$_6$-DMSO):
δ = 8.2053 (1.1); 8.1990 (1.2); 7.9459 (0.6); 7.9441 (0.7); 7.9396 (0.6); 7.9378 (0.6); 7.9248 (0.5); 7.5705 (0.7); 7.5669 (0.9); 7.5472 (0.5); 7.3343 (0.7); 7.3183 (1.1); 7.3156 (2.1); 7.2981 (1.2); 7.2961 (1.5); 7.2919 (1.4); 7.2785 (0.7); 7.2771 (0.8); 7.2713 (1.1); 4.9030 (4.8); 3.3275 (2.0); 3.2359 (12.0);

-continued 2.5243 (0.7); 2.5196 (0.8); 2.5109 (10.4); 2.5063 (22.7); 2.5017 (31.8); 2.4971 (22.1); 2.4925 (9.9); 2.0745 (16.0); 0.0079 (0.8); −0.0002 (28.5); −0.0027 (1.3); −0.0085 (0.8)
X-003: $^1$H-NMR(400.6 MHz, CDCl3):
δ = 8.1208 (0.8); 8.1188 (0.6); 8.1164 (0.7); 8.1145 (0.9); 8.1127 (0.6); 7.7553 (0.5); 7.7490 (0.5); 7.4071 (0.8); 7.4041 (0.8); 7.4011 (0.7); 7.3876 (1.1); 7.2621 (5.7); 7.2590 (0.6); 7.2413 (0.8); 7.2395 (0.7); 7.0619 (0.6); 6.9760 (0.6); 6.9745 (0.6); 6.9686 (0.6); 6.9671 (0.6); 6.9547 (0.6); 6.9532 (0.6); 6.9473 (0.6); 6.9457 (0.6); 4.9362 (7.2); 4.3239 (0.7); 4.3025 (2.3); 4.2810 (2.4); 4.2595 (0.8); 2.0083 (16.0); −0.0002 (7.5)
VII-027: $^1$H-NMR(400.6 MHz, CDCl3):
δ = 8.0709 (1.8); 8.0676 (1.6); 8.0650 (1.9); 7.7057 (0.7); 7.6994 (0.7); 7.6851 (1.0); 7.6830 (0.9); 7.6789 (1.0); 7.6659 (0.8); 7.6595 (0.8); 7.4483 (0.8); 7.4340 (0.9); 7.4267 (1.4); 7.4124 (1.4); 7.4052 (1.0); 7.3909 (0.9); 7.2613 (15.9); 6.9979 (0.7); 6.9942 (0.6); 6.9911 (0.6); 6.9874 (0.6); 6.9789 (0.6); 6.9754 (1.1); 6.9720 (1.2); 6.9686 (1.1); 6.9634 (1.7); 6.9618 (1.5); 6.9559 (1.9); 6.9542 (1.7); 6.9498 (0.7); 6.9461 (0.6); 6.9421 (1.5); 6.9406 (1.4); 6.9345 (1.5); 6.9329 (1.3); 6.8532 (0.9); 6.8464 (0.8); 6.8324 (1.0); 6.8283 (1.1); 6.8257 (1.0); 6.8216 (0.9); 6.8077 (1.0); 6.8009 (0.9); 4.8755 (15.8); 4.3013 (1.9); 4.2834 (6.0); 4.2656 (6.1); 4.2478 (2.0); 1.5511 (1.8); 1.3120 (7.7); 1.2942 (16.0); 1.2764 (7.6); 0.0080 (0.6); −0.0002 (21.0); −0.0085 (0.6)
VII-037: $^1$H-NMR(400.6 MHz, d$_6$-DMSO):
δ = 8.1742 (1.5); 8.1680 (1.6); 7.9395 (0.6); 7.9332 (0.6); 7.9184 (0.9); 7.9121 (0.9); 7.8989 (0.7); 7.8926 (0.7); 7.5593 (0.6); 7.5443 (1.0); 7.5399 (1.3); 7.5248 (0.7); 7.5204 (0.7); 7.4710 (0.5); 7.4661 (0.5); 7.4583 (0.6); 7.4538 (0.5); 7.4506 (0.6); 7.3209 (0.6); 7.3179 (0.9); 7.3018 (1.0); 7.2985 (1.5); 7.2913 (0.9); 7.2888 (0.7); 7.2831 (1.5); 7.2777 (1.3); 7.2709 (0.8); 7.2653 (1.1); 7.2621 (1.7); 7.2561 (1.1); 7.2447 (0.7); 7.2416 (0.6); 4.8087 (7.0); 4.0556 (0.5); 4.0378 (1.7); 4.0201 (1.7); 4.0023 (0.6); 2.5240 (0.5); 2.5194 (0.8); 2.5106 (21.7); 2.5060 (49.6); 2.5014 (71.0); 2.4969 (50.4); 2.4923 (23.7); 1.9887 (7.9); 1.9086 (16.0); 1.3553 (3.7); 1.2356 (0.7); 1.1922 (2.3); 1.1744 (4.7); 1.1566 (2.3); 0.0080 (0.8); −0.0002 (31.9); −0.0050 (0.7); −0.0058 (0.6); −0.0085 (1.0)
VII-006: $^1$H-NMR(400.6 MHz, CDCl3):
δ = 8.0896 (2.2); 8.0874 (1.7); 8.0852 (1.8); 8.0833 (2.3); 7.7571 (1.1); 7.7508 (1.1); 7.7384 (1.3); 7.7359 (1.4); 7.7321 (1.3); 7.7296 (1.3); 7.7172 (1.2); 7.7109 (1.1); 7.3684 (0.5); 7.3640 (0.7); 7.3579 (0.9); 7.3564 (1.0); 7.3516 (1.8); 7.3499 (1.9); 7.3453 (2.2); 7.3433 (2.5); 7.3399 (2.2); 7.3355 (3.5); 7.3328 (4.6); 7.3249 (3.6); 7.3218 (2.3); 7.3171 (9.0); 7.3142 (4.3); 7.3104 (4.7); 7.3066 (1.9); 7.3052 (1.8); 7.3005 (3.6); 7.2982 (1.8); 7.2940 (1.1); 7.2597 (34.6); 7.2103 (1.1); 7.2089 (1.2); 7.2071 (1.2); 7.1904 (1.8); 7.1889 (1.7); 7.1873 (1.5); 7.1719 (0.7); 7.1704 (0.7); 7.1686 (0.7); 7.0392 (1.1); 7.0361 (1.0); 7.0184 (1.1); 7.0145 (1.7); 7.0109 (1.0); 6.9933 (1.0); 6.9904 (0.6); 6.9439 (1.6); 6.9423 (1.5); 6.9364 (1.6); 6.9349 (1.4); 6.9227 (1.6); 6.9212 (1.4); 6.9152 (1.6); 6.9137 (1.4); 5.2489 (12.6); 4.9565 (16.0); 1.5404 (5.5); 1.2594 (0.6); 1.2556 (0.6); 0.8819 (0.7); 0.0079 (1.3); −0.0002 (46.7); −0.0085 (1.2)
X-001: $^1$H-NMR(400.6 MHz, CDCl3):
δ = 8.1303 (2.5); 8.1283 (2.0); 8.1261 (2.0); 8.1240 (2.6); 8.1222 (1.8); 7.7599 (1.4); 7.7537 (1.4); 7.7413 (1.5); 7.7387 (1.6); 7.7350 (1.5); 7.7324 (1.6); 7.7201 (1.4); 7.7138 (1.4); 7.4635 (1.0); 7.4591 (1.2); 7.4442 (1.8); 7.4398 (2.1); 7.4254 (1.3); 7.4210 (1.4); 7.3986 (0.6); 7.3942 (0.6); 7.3864 (0.7); 7.3819 (0.7); 7.3798 (1.0); 7.3779 (0.9); 7.3754 (0.9); 7.3735 (0.9); 7.3675 (1.1); 7.3657 (0.9); 7.3631 (1.0); 7.3612 (0.9); 7.3590 (1.1); 7.3545 (0.9); 7.3468 (1.2); 7.3423 (0.8); 7.2628 (14.2); 7.2589 (1.4); 7.2572 (1.4); 7.2554 (1.4); 7.2540 (1.3); 7.2358 (1.9); 7.2203 (0.8); 7.2186 (0.9); 7.2169 (0.8); 7.2154 (0.8); 7.0645 (1.3); 7.0612 (1.3); 7.0436 (1.2); 7.0398 (2.1); 7.0361 (1.4); 7.0185 (1.2); 7.0153 (1.1); 6.9556 (1.8); 6.9540 (1.9); 6.9481 (1.9); 6.9465 (1.9); 6.9344 (1.7); 6.9328 (1.9); 6.9269 (1.8); 6.9252 (1.8); 6.6597 (0.6); 5.9488 (0.6); 5.9351 (1.4); 5.9230 (0.8); 5.9216 (0.8); 5.9094 (1.5); 5.9059 (0.8); 5.8958 (0.7); 5.8923 (1.6); 5.8801 (0.9); 5.8787 (0.9); 5.8666 (1.7); 5.8529 (0.8); 5.2999 (3.8); 5.2790 (0.9); 5.2747 (2.1); 5.2715 (2.2); 5.2672 (1.0); 5.2361 (0.8); 5.2318 (1.9); 5.2286 (1.9); 5.2244 (0.9); 5.1960 (0.9); 5.1924 (2.5); 5.1891 (2.4); 5.1855 (0.9); 5.1703 (0.8); 5.1667 (2.3); 5.1634 (2.2); 5.1598 (0.9); 4.8582 (16.0); 4.0392 (1.1); 4.0352 (2.1); 4.0312 (1.3); 4.0247 (2.1); 4.0209 (3.6); 4.0173 (2.2); 4.0108 (1.3); 4.0067 (2.1); 4.0027 (1.2); 1.5925 (0.7); 1.2543 (0.6); 0.0079 (0.5); −0.0002 (19.1); −0.0085 (0.6)
X-005: $^1$H-NMR(400.0 MHz, d$_6$-DMSO):
δ = 11.7114 (0.7); 8.2113 (0.7); 8.2051 (0.8); 7.5735 (0.6); 7.3182 (1.3); 7.2985 (1.2); 7.2913 (0.8); 7.2769 (0.5); 7.2703 (0.7); 4.8803 (2.7); 3.3207 (16.0); 2.8972 (1.7); 2.7140 (14.7); 2.5193 (0.5); 2.5106 (10.5); 2.5060 (23.6); 2.5014 (33.3); 2.4968 (23.4); 2.4923 (10.6); 2.0742 (7.5); 1.9087 (1.1); −0.0002 (16.9); −0.0085 (0.5)
VII-004: $^1$H-NMR(400.6 MHz, CDCl3):
δ = 8.1029 (0.7); 8.1010 (1.0); 8.0988 (0.7); 8.0968 (0.8); 8.0948 (1.0); 8.0927 (0.7); 7.7592 (0.6); 7.7529 (0.5); 7.7404 (0.6); 7.7380 (0.7); 7.7342 (0.6); 7.7317 (0.6); 7.7192 (0.6); 7.7130 (0.6); 7.3716 (0.7); 7.3672 (0.9); 7.3530 (0.5); 7.3485 (0.7); 7.2612 (7.5); 7.2123 (0.5); 7.2105 (0.6); 7.2091 (0.5); 7.1945 (0.7); 7.1930 (0.8); 7.1910 (0.8); 7.0410 (0.5); 7.0377 (0.5); 7.0162 (0.8); 7.0126 (0.5); 6.9375 (0.8); 6.9359 (0.7); 6.9300 (0.8); 6.9285 (0.7); 6.9163 (0.7); 6.9147 (0.7); 6.9088 (0.7); 6.9072 (0.7); 5.2998 (3.8); 5.2312 (1.5); 5.2138 (1.5); 3.7763 (16.0); 1.6951 (6.3); 1.6777 (6.2); 1.5531 (0.9); −0.0002 (10.8)
VII-005: $^1$H-NMR(400.6 MHz, CDCl3):
δ = 8.1075 (1.0); 8.1054 (0.8); 8.1032 (0.9); 8.1013 (1.1); 7.7702 (0.6); 7.7639 (0.6); 7.7515 (0.6); 7.7490 (0.7); 7.7452 (0.6); 7.7427 (0.6); 7.7303 (0.6); 7.7240 (0.6); 7.4020 (0.8); 7.3977 (0.9); 7.3832 (0.5); 7.3788 (0.6); 7.2615 (6.6); 7.2222 (0.6); 7.2204 (0.6); 7.2192 (0.5); 7.2009 (0.8); 7.0449 (0.6); 7.0416 (0.5); 7.0241 (0.5); 7.0202 (0.9); 7.0165 (0.6); 6.9990 (0.5); 6.9430 (0.8); 6.9415 (0.8); 6.9355 (0.8); 6.9340 (0.7); 6.9218 (0.8); 6.9203 (0.7); 6.9143 (0.8); 6.9128 (0.7); 5.1486 (0.9); 5.1330 (1.2); 5.1173 (0.9); 4.8628 (9.4); 2.0074 (0.7); 1.5577 (1.0); 1.2742 (15.9); 1.2585 (16.0); −0.0002 (8.7)
VII-005: $^1$H-NMR(400.0 MHz, CDCl3):
δ = 8.1082 (1.2); 8.1020 (1.2); 7.7704 (0.6); 7.7642 (0.6); 7.7516 (0.7); 7.7492 (0.7); 7.7454 (0.7); 7.7430 (0.7); 7.7304 (0.6); 7.7242 (0.6); 7.4172 (0.5); 7.4023 (0.9); 7.3980 (1.0); 7.3834 (0.6); 7.3790 (0.7); 7.2629 (8.5); 7.2223 (0.6); 7.2205 (0.6); 7.2012 (0.9); 7.0453 (0.6); 7.0420 (0.6); 7.0244 (0.6); 7.0205 (1.0); 7.0168 (0.6); 6.9992 (0.6); 6.9961 (0.5); 6.9432 (0.8); 6.9420 (0.8); 6.9358 (0.9); 6.9219

(0.8); 6.9207 (0.8); 6.9144 (0.8); 5.2999 (2.4); 5.1486 (1.0); 5.1329 (1.3); 5.1173 (1.0); 4.8630 (9.6); 1.5752 (0.8); 1.2742 (16.0); 1.2585 (15.9); −0.0002 (5.4)

VII-117: $^1$H-NMR(400.6 MHz, CDCl3):

δ = 8.0431 (1.1); 8.0370 (1.2); 7.5899 (0.6); 7.5837 (0.6); 7.5708 (0.7); 7.5688 (0.8); 7.5646 (0.7); 7.5626 (0.7); 7.5498 (0.6); 7.5436 (0.6); 7.3986 (0.5); 7.3837 (0.9); 7.3794 (1.0); 7.3648 (0.6); 7.3603 (0.6); 7.2905 (0.5); 7.2784 (0.5); 7.2700 (0.5); 7.2653 (0.5); 7.2622 (5.8); 7.2579 (0.6); 7.1876 (0.6); 7.1862 (0.6); 7.1841 (0.7); 7.1676 (0.9); 7.1647 (1.0); 7.0145 (0.7); 7.0111 (0.6); 6.9937 (0.6); 6.9896 (1.0); 6.9857 (0.7); 6.9684 (0.6); 6.9650 (0.6); 6.9006 (0.9); 6.8993 (0.8); 6.8932 (0.9); 6.8918 (0.8); 6.8794 (0.8); 6.8781 (0.8); 6.8721 (0.8); 6.8707 (0.8); 5.2995 (0.7); 4.8755 (9.5); 4.2948 (1.2); 4.2770 (3.8); 4.2592 (3.9); 4.2413 (1.2); 2.0518 (16.0); 1.3125 (4.9); 1.2947 (10.1); 1.2769 (4.8); −0.0002 (8.1)

VII-053: $^1$H-NMR(400.0 MHz, CDCl3):

δ = 7.9479 (1.4); 7.9420 (1.5); 7.8614 (0.6); 7.8552 (0.5); 7.8408 (0.8); 7.8348 (0.7); 7.8214 (0.6); 7.8152 (0.6); 7.3799 (1.2); 7.3647 (1.5); 7.3603 (2.0); 7.3458 (1.4); 7.3410 (1.0); 7.3281 (0.5); 7.2609 (11.9); 7.2085 (0.8); 7.1894 (1.2); 7.0390 (0.6); 7.0148 (1.1); 6.9931 (0.6); 6.9140 (1.0); 6.9071 (1.0); 6.8927 (1.0); 6.8860 (0.9); 5.2997 (0.6); 4.9662 (9.5); 4.3106 (1.2); 4.2928 (3.6); 4.2750 (3.7); 4.2571 (1.2); 2.5702 (16.0); 1.3203 (4.3); 1.3025 (8.7); 1.2846 (4.6); 1.2550 (4.0); 0.8800 (0.6); 0.0079 (0.5); −0.0002 (15.8); −0.00084 (0.5)

VII-053: $^1$H-NMR(400.6 MHz, CDCl3):

δ = 7.9474 (1.0); 7.9412 (1.1); 7.8408 (0.6); 7.8347 (0.6); 7.3801 (1.0); 7.3649 (1.2); 7.3603 (1.5); 7.3464 (1.0); 7.3410 (0.9); 7.2604 (31.9); 7.2088 (0.6); 7.1915 (0.9); 7.1896 (0.9); 7.0178 (0.5); 7.0149 (0.9); 7.0117 (0.6); 6.9932 (0.6); 6.9154 (0.8); 6.9139 (0.8); 6.9081 (0.8); 6.9066 (0.8); 6.8941 (0.8); 6.8926 (0.8); 6.8869 (0.8); 6.8854 (0.8); 4.9662 (8.2); 4.3107 (1.0); 4.2929 (3.2); 4.2750 (3.3); 4.2572 (1.1); 2.5811 (0.7); 2.5702 (16.0); 1.5412 (4.0); 1.3205 (4.2); 1.3027 (8.6); 1.2848 (4.2); 1.2549 (0.9); 1.2009 (0.6); 1.1836 (0.6); 0.0079 (1.1); −0.0002 (44.6); −0.00061 (0.6); −0.00085 (1.4)

VII-053: $^1$H-NMR(400.6 MHz, CDCl3):

δ = 7.9491 (1.3); 7.9430 (1.5); 7.8602 (0.6); 7.8540 (0.5); 7.8393 (0.8); 7.8347 (0.7); 7.8201 (0.6); 7.8139 (0.5); 7.3797 (1.1); 7.3645 (1.5); 7.3599 (1.8); 7.3548 (0.6); 7.3458 (1.4); 7.3410 (1.0); 7.3276 (0.5); 7.2625 (4.1); 7.2082 (0.8); 7.1890 (1.2); 7.0385 (0.6); 7.0146 (1.1); 6.9928 (0.6); 6.9129 (0.9); 6.9068 (1.0); 6.8916 (0.9); 6.8855 (0.9); 5.2989 (6.0); 4.9663 (8.9); 4.3102 (1.2); 4.2924 (3.5); 4.2745 (3.5); 4.2567 (1.2); 2.5806 (0.5); 2.5698 (16.0); 1.5757 (1.8); 1.3198 (4.2); 1.3020 (8.6); 1.2841 (4.1); −0.0002 (6.1)

VII-032: $^1$H-NMR(400.0 MHz, CDCl3):

δ = 8.6625 (0.8); 8.6587 (0.8); 8.6500 (0.8); 8.6462 (0.7); 8.5786 (1.2); 8.5744 (1.1); 7.7219 (0.6); 7.7174 (0.8); 7.7124 (0.6); 7.7020 (0.7); 7.6973 (0.9); 7.6924 (0.6); 7.4333 (0.6); 7.4208 (0.6); 7.4135 (0.6); 7.4004 (0.6); 7.3195 (0.5); 7.3041 (2.0); 7.3003 (0.8); 7.2965 (0.9); 7.2898 (1.0); 7.2857 (3.0); 7.2814 (1.8); 7.2773 (1.2); 7.2662 (1.0); 7.2605 (17.1); 7.1267 (1.8); 7.1221 (1.9); 7.1167 (0.5); 7.1108 (0.8); 7.1059 (1.7); 7.1023 (1.6); 5.2749 (1.6); 5.2575 (1.6); 3.7934 (16.0); 1.7087 (6.5); 1.6913 (6.4); 0.0080 (0.6); −0.0002 (22.7); −0.00085 (0.7)

VII-088: $^1$H-NMR(400.6 MHz, CDCl3):

δ = 8.1769 (1.2); 8.1749 (1.8); 8.1729 (1.4); 8.1707 (1.4); 8.1685 (1.9); 8.1666 (1.3); 7.8312 (1.1); 7.8249 (1.1); 7.8125 (1.2); 7.8099 (1.3); 7.8062 (1.2); 7.8036 (1.2); 7.7912 (1.1); 7.7849 (1.1); 7.4530 (0.7); 7.4486 (0.8); 7.4338 (1.3); 7.4294 (1.5); 7.4149 (0.9); 7.4106 (1.0); 7.3843 (0.5); 7.3798 (0.5); 7.3776 (0.8); 7.3757 (0.7); 7.3732 (0.7); 7.3713 (0.6); 7.3654 (0.8); 7.3636 (0.6); 7.3610 (0.7); 7.3591 (0.7); 7.3569 (0.8); 7.3524 (0.6); 7.3447 (0.7); 7.3403 (0.6); 7.2609 (27.9); 7.2479 (0.9); 7.2463 (1.0); 7.2446 (1.0); 7.2431 (0.9); 7.2249 (1.4); 7.2094 (0.6); 7.2077 (0.6); 7.2060 (0.6); 7.2044 (0.6); 7.0756 (1.0); 7.0724 (1.0); 7.0548 (0.9); 7.0511 (1.6); 7.0473 (1.0); 7.0298 (0.8); 7.0265 (0.8); 6.9298 (1.3); 6.9282 (1.4); 6.9223 (1.3); 6.9207 (1.4); 6.9085 (1.3); 6.9069 (1.3); 6.9010 (1.3); 6.8994 (1.3); 4.9013 (14.3); 4.2919 (1.8); 4.2741 (5.8); 4.2563 (5.9); 4.2385 (1.9); 3.2052 (11.9); 1.3021 (7.6); 1.2843 (16.0); 1.2664 (7.5); 1.2544 (0.6); 0.0080 (1.1); 0.0041 (0.6); −0.0002 (38.3); −0.00050 (0.6); −0.00058 (0.5); −0.00084 (1.1)

VI-010: $^1$H-NMR(400.0 MHz, CDCl3):

δ = 9.1936 (1.6); 8.6598 (1.4); 7.3518 (0.5); 7.3364 (1.9); 7.3325 (0.8); 7.3288 (0.7); 7.3221 (1.0); 7.3180 (2.9); 7.3137 (1.7); 7.3096 (1.1); 7.2987 (0.7); 7.2962 (0.6); 7.2615 (17.8); 7.1388 (1.7); 7.1342 (1.9); 7.1288 (0.6); 7.1229 (0.8); 7.1180 (1.7); 7.1145 (1.6); 5.2998 (2.4); 5.2720 (1.6); 5.2545 (1.6); 3.7913 (16.0); 1.7095 (6.5); 1.6920 (6.5); −0.0002 (12.4)

VII-119: $^1$H-NMR(400.6 MHz, CDCl3):

δ = 8.1165 (1.7); 8.1144 (1.3); 8.1122 (1.4); 8.1103 (1.7); 7.6766 (0.9); 7.6704 (0.8); 7.6576 (1.0); 7.6555 (1.1); 7.6514 (1.0); 7.6494 (1.0); 7.6365 (0.9); 7.6303 (0.9); 7.3818 (0.7); 7.3774 (0.8); 7.3625 (1.3); 7.3581 (1.5); 7.3436 (0.9); 7.3392 (1.0); 7.2955 (0.5); 7.2934 (0.7); 7.2916 (0.6); 7.2890 (0.6); 7.2871 (0.5); 7.2813 (0.7); 7.2796 (0.6); 7.2767 (0.6); 7.2749 (0.6); 7.2727 (0.7); 7.2693 (0.5); 7.2685 (0.7); 7.2670 (0.5); 7.2661 (0.6); 7.2621 (44.0); 7.2587 (1.0); 7.2579 (0.8); 7.2570 (0.8); 7.2563 (1.0); 7.1845 (0.8); 7.1830 (0.9); 7.1810 (0.9); 7.1798 (0.8); 7.1643 (1.2); 7.1615 (1.3); 7.1461 (0.5); 7.1445 (0.6); 7.1426 (0.5); 7.0180 (0.9); 7.0147 (0.9); 6.9974 (0.8); 6.9932 (1.3); 6.9893 (0.9); 6.9719 (0.8); 6.9686 (0.7); 6.8968 (1.2); 6.8953 (1.2); 6.8894 (1.3); 6.8878 (1.2); 6.8757 (1.2); 6.8742 (1.2); 6.8682 (1.2); 6.8667 (1.1); 4.8941 (0.8); 4.8515 (13.2); 4.2803 (1.6); 4.2625 (5.2); 4.2577 (0.5); 4.2447 (5.2); 4.2269 (1.7); 1.5839 (1.6); 1.5675 (4.8); 1.5569 (0.9); 1.5500 (1.3); 1.5333 (0.5); 1.3056 (6.9); 1.2878 (14.5); 1.2699 (6.7); 0.7740 (16.0); 0.7632 (1.0); 0.7566 (6.2); 0.7524 (1.1); 0.7506 (1.0); 0.0080 (0.8); −0.0002 (29.4); −0.00085 (0.8)

VII-091: $^1$H-NMR(400.6 MHz, CDCl3):

δ = 8.1128 (2.3); 8.1107 (1.7); 8.1085 (1.8); 8.1065 (2.3); 7.7721 (1.2); 7.7658 (1.2); 7.7534 (1.4); 7.7508 (1.4); 7.7471 (1.4); 7.7446 (1.4); 7.7322 (1.3); 7.7259 (1.2); 7.4163 (0.9); 7.4120 (1.0); 7.3971 (1.6); 7.3928 (1.9); 7.3779 (1.5); 7.3736 (1.6); 7.3654 (0.6); 7.3608 (0.7); 7.3587 (1.0); 7.3569 (0.8); 7.3542 (0.8); 7.3525 (0.7); 7.3464 (1.0); 7.3448 (0.8); 7.3420 (0.8); 7.3401 (0.8); 7.3380 (0.9); 7.3335 (0.7); 7.3258 (0.8); 7.3213 (0.6); 7.2629 (14.6); 7.2303 (1.1); 7.2287 (1.2); 7.2270 (1.2); 7.2094 (1.2); 7.2075 (1.7); 7.1918 (0.7); 7.1901 (0.8); 7.1884 (0.7); 7.1870 (0.6); 7.0561 (1.2); 7.0529 (1.1); 7.0352 (1.1); 7.0314 (1.9); 7.0277 (1.2); 7.0102 (1.0); 7.0070 (1.0); 6.9490 (1.6); 6.9475 (1.6); 6.9416 (1.7); 6.9401 (1.6); 6.9278 (1.6); 6.9263 (1.6); 6.9203 (1.6); 6.9188 (1.5); 4.9162 (16.0); 4.2474 (1.4); 4.2313 (1.4); 4.2205 (2.2); 4.2043 (2.2); 4.1318 (2.3); 4.1121 (2.4); 4.1048 (1.5); 4.0851 (1.5); 3.8493 (0.7); 3.8355 (0.8); 3.8285 (1.5); 3.8146 (1.5); 3.8081 (1.2); 3.8028 (1.7); 3.7943 (1.1); 3.7849 (1.8); 3.7806

-continued (2.0); 3.7628 (2.0); 3.7454 (1.2); 3.7278 (1.7); 3.7265 (1.7); 3.7089 (1.4); 3.7068 (1.2); 3.6877 (0.8); 3.5455 (1.9); 3.5315 (2.0); 3.5233 (1.6); 3.5093 (1.6); 2.6120 (0.6); 2.5948 (0.8); 2.5775 (0.6); 2.0243 (0.5); 2.0187 (0.6); 2.0082 (7.8); 1.9977 (0.5); 1.9930 (0.6); 1.9872 (0.8); 1.9850 (0.8); 1.9733 (0.7); 1.9664 (0.5); 1.6551 (0.5); 1.6379 (0.7); 1.6355 (0.6); 1.6231 (1.0); 1.6201 (0.7); 1.6064 (0.6); 1.6035 (0.9); 1.5912 (0.5); 1.5887 (0.6); −0.0002 (17.1)

VII-090: $^1$H-NMR(400.6 MHz, CDCl3):

δ = 8.1014 (2.2); 8.0995 (1.7); 8.0972 (1.7); 8.0951 (2.3); 7.7655 (1.1); 7.7593 (1.1); 7.7468 (1.3); 7.7443 (1.4); 7.7405 (1.3); 7.7381 (1.4); 7.7256 (1.2); 7.7194 (1.2); 7.4364 (0.9); 7.4320 (1.0); 7.4171 (1.6); 7.4128 (1.8); 7.3983 (1.1); 7.3939 (1.2); 7.3692 (0.5); 7.3647 (0.5); 7.3570 (0.6); 7.3524 (0.6); 7.3503 (0.9); 7.3484 (0.8); 7.3459 (0.8); 7.3440 (0.7); 7.3381 (0.9); 7.3363 (0.7); 7.3336 (0.8); 7.3317 (0.7); 7.3296 (0.9); 7.3251 (0.7); 7.3174 (0.8); 7.3129 (0.7); 7.2610 (47.1); 7.2285 (1.0); 7.2269 (1.0); 7.2250 (1.2); 7.2054 (1.7); 7.1883 (0.7); 7.1866 (0.7); 7.0435 (1.1); 7.0402 (1.1); 7.0227 (1.1); 7.0189 (1.8); 7.0151 (1.2); 6.9975 (1.3); 6.9943 (1.0); 6.9448 (1.5); 6.9434 (1.6); 6.9374 (1.6); 6.9359 (1.6); 6.9237 (1.5); 6.9222 (1.6); 6.9162 (1.5); 6.9147 (1.5); 4.9517 (16.0); 4.2859 (0.5); 4.2801 (1.7); 4.2613 (2.4); 4.2554 (1.2); 4.1828 (1.7); 4.1677 (3.4); 4.1541 (1.6); 4.1496 (0.9); 4.1433 (3.7); 4.1382 (1.6); 4.1289 (0.8); 4.1223 (0.7); 3.8830 (0.8); 3.8661 (1.5); 3.8622 (1.4); 3.8496 (0.9); 3.8453 (2.3); 3.8290 (1.1); 3.7924 (1.0); 3.7749 (1.4); 3.7592 (1.2); 3.7545 (1.0); 3.7386 (0.6); 2.0080 (1.1); 1.9753 (0.5); 1.9717 (0.6); 1.9680 (0.5); 1.9544 (0.8); 1.9420 (0.7); 1.9252 (0.7); 1.9122 (0.6); 1.8972 (0.8); 1.8922 (0.8); 1.8824 (1.5); 1.8771 (1.1); 1.8657 (1.4); 1.8618 (1.4); 1.8480 (0.7); 1.8451 (1.1); 1.6389 (0.8); 1.6176 (0.8); 1.6088 (0.7); 1.6008 (0.6); 1.5887 (0.6); 1.5552 (4.2); 0.0080 (1.5); 0.0041 (0.6); −0.0002 (55.1); −0.00057 (0.8); −0.00065 (0.7); −0.00085 (1.7)

VII-098: $^1$H-NMR(400.6 MHz, CDCl3):

δ = 8.0965 (2.0); 8.0945 (1.6); 8.0924 (1.6); 8.0902 (2.1); 8.0885 (1.4); 7.7641 (1.1); 7.7578 (1.1); 7.7454 (1.2); 7.7429 (1.4); 7.7391 (1.2); 7.7366 (1.3); 7.7242 (1.2); 7.7179 (1.2); 7.4005 (3.3); 7.3984 (3.7); 7.3959 (3.7); 7.3937 (3.9); 7.3780 (1.4); 7.3736 (1.8); 7.3679 (0.7); 7.3634 (0.6); 7.3590 (1.0); 7.3552 (1.6); 7.3511 (0.7); 7.3489 (1.0); 7.3472 (0.8); 7.3445 (0.7); 7.3427 (0.7); 7.3366 (1.0); 7.3351 (0.8); 7.3321 (0.7); 7.3305 (0.7); 7.3283 (0.9); 7.3238 (0.7); 7.3161 (0.8); 7.3116 (0.6); 7.2608 (24.0); 7.2234 (1.0); 7.2219 (1.1); 7.2200 (1.1); 7.2187 (1.0); 7.2040 (1.4); 7.2026 (1.5); 7.2005 (1.6); 7.1850 (0.6); 7.1833 (0.7); 7.1815 (0.6); 7.1801 (0.6); 7.0398 (1.1); 7.0365 (1.0); 7.0189 (1.0); 7.0152 (1.7); 7.0113 (1.1); 6.9939 (1.0); 6.9907 (0.9); 6.9445 (1.5); 6.9429 (1.5); 6.9370 (1.5); 6.9355 (1.5); 6.9232 (1.4); 6.9217 (1.5); 6.9158 (1.4); 6.9142 (1.4); 6.4352 (1.9); 6.4344 (2.0); 6.4279 (2.4); 6.4272 (2.3); 6.4262 (2.4); 6.3517 (2.2); 6.3471 (2.3); 6.3436 (2.0); 6.3389 (1.8); 5.1910 (12.7); 4.9293 (16.0); 0.0079 (0.8); −0.0002 (26.8); −0.00051 (0.5); −0.00085 (0.9)

VII-103: $^1$H-NMR(400.6 MHz, CDCl3):

δ = 8.1052 (1.4); 8.1034 (2.1); 8.1013 (1.6); 8.0992 (1.7); 8.0971 (2.2); 8.0951 (1.5); 7.7669 (1.2); 7.7606 (1.1); 7.7481 (1.3); 7.7456 (1.4); 7.7419 (1.3); 7.7394 (1.4); 7.7269 (1.2); 7.7207 (1.2); 7.4456 (0.9); 7.4413 (1.0); 7.4263 (1.5); 7.4220 (1.7); 7.4075 (1.1); 7.4031 (1.2); 7.3701 (0.5); 7.3657 (0.5); 7.3580 (0.6); 7.3534 (0.6); 7.3513 (0.9); 7.3494 (0.8); 7.3468 (0.8); 7.3450 (0.7); 7.3391 (0.9); 7.3373 (0.7); 7.3347 (0.8); 7.3327 (0.7); 7.3306 (0.9); 7.3261 (0.7); 7.3184 (0.8); 7.3139 (0.7); 7.2617 (24.5); 7.2313 (1.0); 7.2297 (1.1); 7.2279 (1.1); 7.2265 (1.1); 7.2082 (1.6); 7.1928 (0.6); 7.1912 (0.7); 7.1894 (0.7); 7.1880 (0.6); 7.0440 (1.1); 7.0408 (1.1); 7.0232 (1.0); 7.0194 (1.8); 7.0156 (1.2); 6.9981 (1.1); 6.9949 (1.0); 6.9455 (1.5); 6.9439 (1.6); 6.9380 (1.6); 6.9364 (1.6); 6.9242 (1.4); 6.9226 (1.6); 6.9167 (1.5); 6.9151 (1.5); 5.1834 (2.3); 5.1740 (5.1); 5.1646 (2.4); 4.9639 (16.0); 4.2600 (8.8); 4.2506 (8.7); 4.0052 (1.7); 3.9920 (2.1); 3.9891 (3.2); 3.9873 (4.1); 3.9827 (3.0); 3.9775 (2.7); 3.9706 (3.6); 3.9469 (1.2); 3.9316 (1.1); 3.9078 (3.4); 3.9010 (2.5); 3.8958 (2.7); 3.8911 (4.1); 3.8893 (3.2); 3.8865 (2.1); 3.8733 (1.7); 2.0079 (3.3); 1.5997 (0.7); 0.0080 (0.8); −0.0002 (27.2); −0.00084 (0.8)

VII-064: $^1$H-NMR(400.6 MHz, CDCl3):

δ = 8.1188 (1.4); 8.1126 (1.4); 7.7713 (0.7); 7.7651 (0.7); 7.7526 (0.8); 7.7501 (0.8); 7.7464 (0.8); 7.7439 (0.8); 7.7314 (0.7); 7.7252 (0.7); 7.4661 (0.6); 7.4617 (0.6); 7.4468 (1.0); 7.4425 (1.1); 7.4279 (0.7); 7.4235 (0.8); 7.3575 (0.5); 7.3531 (0.5); 7.3453 (0.6); 7.3409 (0.5); 7.3368 (0.5); 7.2613 (25.2); 7.2391 (0.6); 7.2376 (0.7); 7.2357 (0.7); 7.2161 (1.0); 7.0480 (0.7); 7.0447 (0.7); 7.0272 (0.7); 7.0233 (1.1); 7.0196 (0.7); 7.0020 (0.6); 6.9986 (0.6); 6.9478 (0.9); 6.9463 (1.0); 6.9403 (1.0); 6.9389 (1.0); 6.9265 (0.9); 6.9251 (1.0); 6.9192 (0.9); 6.9177 (0.9); 5.5359 (1.2); 5.5130 (1.6); 5.4913 (1.2); 5.0660 (0.7); 5.0255 (5.3); 5.0151 (5.2); 4.9745 (0.7); 4.4959 (0.5); 4.4891 (0.6); 4.4732 (1.1); 4.4663 (1.1); 4.4505 (0.7); 4.4436 (0.7); 4.3398 (0.8); 4.3234 (0.9); 4.3161 (1.4); 4.2998 (1.4); 4.2926 (0.7); 4.2762 (0.6); 2.7294 (0.5); 2.3647 (0.8); 2.3423 (0.8); 2.3320 (0.8); 2.3096 (0.7); 2.0085 (16.0); 0.0080 (0.8); −0.0002 (29.3); −0.00084 (0.9)

VII-110: $^1$H-NMR(400.6 MHz, CDCl3):

δ = 8.1262 (1.5); 8.1199 (1.6); 7.7700 (0.8); 7.7637 (0.8); 7.7513 (1.0); 7.7488 (1.0); 7.7451 (0.9); 7.7425 (0.9); 7.7301 (0.9); 7.7239 (0.8); 7.4489 (0.7); 7.4446 (0.8); 7.4296 (1.2); 7.4252 (1.3); 7.4108 (0.8); 7.4064 (0.9); 7.3667 (0.5); 7.3645 (0.7); 7.3627 (0.6); 7.3602 (0.6); 7.3583 (0.5); 7.3523 (0.7); 7.3506 (0.6); 7.3479 (0.6); 7.3460 (0.6); 7.3439 (0.7); 7.3394 (0.5); 7.3316 (0.6); 7.2608 (39.6); 7.2575 (1.0); 7.2567 (0.8); 7.2394 (0.8); 7.2378 (0.8); 7.2360 (0.8); 7.2345 (0.8); 7.2162 (1.2); 7.2009 (0.5); 7.1991 (0.5); 7.1975 (0.5); 7.0545 (0.8); 7.0513 (0.8); 7.0336 (0.8); 7.0298 (1.4); 7.0261 (0.9); 7.0085 (0.8); 7.0053 (0.7); 6.9527 (1.1); 6.9512 (1.1); 6.9453 (1.2); 6.9438 (1.1); 6.9315 (1.1); 6.9300 (1.1); 6.9241 (1.1); 6.9225 (1.0); 5.0026 (13.1); 4.9814 (0.6); 4.8464 (16.0); 2.0089 (7.9); 0.0080 (1.3); −0.0002 (48.2); −0.00058 (0.6); −0.00085 (1.4)

VII-104: $^1$H-NMR(400.6 MHz, CDCl3):

δ = 8.1259 (2.2); 8.1197 (2.3); 7.7773 (1.1); 7.7710 (1.1); 7.7585 (1.3); 7.7560 (1.3); 7.7523 (1.3); 7.7498 (1.2); 7.7373 (1.2); 7.7311 (1.1); 7.4245 (0.8); 7.4202 (1.0); 7.4052 (1.5); 7.4009 (1.8); 7.3864 (1.0); 7.3820 (1.3); 7.3790 (0.6); 7.3746 (0.5); 7.3668 (0.6); 7.3622 (0.6); 7.3601 (0.9); 7.3583 (0.8); 7.3557 (0.8); 7.3539 (0.7); 7.3478 (1.0); 7.3461 (0.7); 7.3433 (0.8); 7.3415 (0.8); 7.3394 (0.8); 7.3350 (0.7); 7.3272 (0.8); 7.3228 (0.6); 7.2611 (33.3); 7.2262 (1.0); 7.2245 (1.1); 7.2228 (1.1); 7.2033 (1.6); 7.1876 (0.7); 7.1860 (0.7); 7.1843 (0.7); 7.0622 (1.1); 7.0590 (1.1); 7.0414 (1.0); 7.0376 (1.8); 7.0339 (1.2); 7.0164 (1.0); 7.0131 (0.9); 6.9457 (1.5); 6.9442 (1.5); 6.9384 (1.6); 6.9369 (1.4); 6.9245 (1.5);

-continued 6.9230 (1.4); 6.9171 (1.5); 6.9156 (1.4); 4.9689 (16.0); 4.4254 (4.0); 4.4096 (8.2); 4.3939 (4.1); 2.7434 (4.8); 2.7277 (9.6); 2.7119 (4.5); 2.0090 (3.4); 0.0080 (1.0); −0.0002 (39.3); −0.00029 (1.6); −0.00053 (0.5); −0.00085 (1.2)

VII-052: $^1$H-NMR(400.6 MHz, CDCl3):

δ = 8.1052 (0.9); 8.1010 (0.7); 8.0989 (0.9); 7.7510 (0.5); 7.7484 (0.6); 7.7447 (0.5); 7.7422 (0.6); 7.4139 (0.6); 7.4096 (0.7); 7.3907 (0.5); 7.2615 (10.4); 7.2244 (0.5); 7.2052 (0.7); 7.0209 (0.8); 6.9465 (0.6); 6.9451 (0.7); 6.9391 (0.6); 6.9377 (0.6); 6.9253 (0.6); 6.9238 (0.6); 6.9179 (0.6); 6.9164 (0.5); 4.9551 (6.9); 4.3697 (1.7); 4.3615 (0.8); 4.3580 (1.7); 4.3543 (0.8); 4.3462 (1.8); 3.6295 (2.0); 3.6215 (0.9); 3.6177 (1.8); 3.6144 (0.9); 3.6060 (1.9); 3.3589 (16.0); −0.0002 (12.0)

VII-124: $^1$H-NMR(400.6 MHz, CDCl3):

δ = 8.1097 (1.0); 8.1076 (0.7); 8.1054 (0.8); 8.1034 (1.0); 7.7693 (0.5); 7.7631 (0.5); 7.7506 (0.6); 7.7481 (0.6); 7.7444 (0.6); 7.7418 (0.6); 7.7294 (0.6); 7.7231 (0.5); 7.4094 (0.7); 7.4050 (0.8); 7.3862 (0.6); 7.2610 (17.4); 7.2282 (0.5); 7.2085 (0.7); 7.0286 (0.8); 7.0249 (0.5); 6.9471 (0.7); 6.9455 (0.7); 6.9397 (0.7); 6.9381 (0.7); 6.9259 (0.7); 6.9243 (0.7); 6.9184 (0.7); 6.9168 (0.6); 4.9300 (7.3); 4.3973 (1.8); 4.3802 (3.8); 4.3631 (1.9); 2.7594 (2.0); 2.7423 (4.0); 2.7252 (1.9); 2.1371 (16.0); 2.0083 (1.1); 0.0079 (0.6); −0.0002 (20.9); −0.00027 (0.9); −0.00085 (0.6)

VII-108: $^1$H-NMR(400.6 MHz, CDCl3):

δ = 8.1138 (2.0); 8.1118 (1.5); 8.1095 (1.6); 8.1075 (2.1); 7.7733 (1.0); 7.7670 (1.0); 7.7546 (1.2); 7.7520 (1.3); 7.7484 (1.2); 7.7458 (1.2); 7.7334 (1.1); 7.7271 (1.1); 7.4261 (0.8); 7.4218 (1.0); 7.4069 (1.4); 7.4025 (1.7); 7.3881 (1.0); 7.3837 (1.2); 7.3756 (0.6); 7.3712 (0.5); 7.3634 (0.6); 7.3589 (0.6); 7.3568 (0.9); 7.3549 (0.7); 7.3523 (0.7); 7.3505 (0.7); 7.3445 (0.9); 7.3427 (0.7); 7.3401 (0.7); 7.3382 (0.7); 7.3360 (0.8); 7.3316 (0.7); 7.3239 (0.8); 7.3194 (0.6); 7.2611 (28.0); 7.2299 (0.9); 7.2283 (1.0); 7.2265 (1.1); 7.2252 (1.0); 7.2069 (1.5); 7.1914 (0.6); 7.1898 (0.7); 7.1880 (0.6); 7.1866 (0.6); 7.0530 (1.1); 7.0498 (1.0); 7.0322 (1.0); 7.0284 (1.7); 7.0246 (1.1); 7.0071 (0.9); 7.0039 (0.9); 6.9508 (1.4); 6.9493 (1.4); 6.9434 (1.5); 6.9419 (1.4); 6.9295 (1.4); 6.9280 (1.4); 6.9222 (1.4); 6.9207 (1.3); 4.9635 (16.0); 4.4706 (4.0); 4.4565 (4.7); 4.4543 (3.0); 4.4419 (4.3); 3.7075 (5.1); 3.6952 (3.5); 3.6930 (5.4); 3.6915 (3.8); 3.6788 (4.8); 2.0089 (4.7); 0.0079 (0.9); −0.0002 (33.2); −0.00052 (0.5); −0.00085 (1.0)

X-011: $^1$H-NMR(400.0 MHz, CDCl3):

δ = 8.1016 (2.8); 8.0955 (2.7); 7.7711 (1.2); 7.7647 (1.2); 7.7498 (1.6); 7.7435 (1.5); 7.7310 (1.3); 7.7247 (1.4); 7.4293 (1.1); 7.4248 (1.2); 7.4100 (1.9); 7.4057 (2.2); 7.3912 (1.3); 7.3868 (1.4); 7.3640 (0.6); 7.3595 (0.7); 7.3518 (0.6); 7.3450 (1.0); 7.3327 (1.0); 7.3244 (1.0); 7.3197 (0.8); 7.3122 (0.9); 7.3078 (0.8); 7.2604 (51.4); 7.2204 (1.4); 7.2008 (2.1); 7.1834 (0.9); 7.0410 (1.4); 7.0378 (1.4); 7.0202 (1.3); 7.0164 (2.2); 7.0126 (1.5); 6.9954 (1.4); 6.9919 (1.2); 6.9399 (1.9); 6.9324 (1.4); 6.9185 (1.5); 6.9111 (1.8); 5.4435 (16.0); 5.2998 (8.7); 4.2178 (3.8); 4.1996 (6.6); 4.1811 (4.2); 3.4017 (5.2); 3.3831 (7.6); 3.3650 (4.7); 2.2838 (1.7); 2.2264 (1.3); 2.2187 (1.0); 2.1742 (0.5); 1.2555 (2.0); 0.0080 (1.6); −0.0002 (66.1); −0.00085 (2.0)

VII-056-a: $^1$H-NMR(400.6 MHz, CDCl3):

δ = 8.1148 (1.2); 8.1131 (1.9); 8.1109 (1.5); 8.1088 (1.5); 8.1067 (1.9); 8.1047 (1.3); 7.6692 (1.1); 7.6629 (1.1); 7.6505 (1.2); 7.6479 (1.3); 7.6442 (1.2); 7.6417 (1.3); 7.6292 (1.2); 7.6229 (1.2); 7.2954 (0.6); 7.2800 (1.4); 7.2767 (1.4); 7.2617 (13.6); 7.2583 (1.7); 7.2317 (1.3); 7.2289 (1.6); 7.2276 (1.7); 7.2126 (0.8); 7.2112 (0.8); 7.2099 (0.8); 7.2084 (0.7); 7.1836 (0.6); 7.1823 (0.7); 7.1793 (0.6); 7.1781 (0.6); 7.1641 (1.3); 7.1627 (1.2); 7.1614 (1.0); 7.1599 (1.2); 7.1461 (0.6); 7.1447 (0.7); 7.1418 (0.6); 7.1405 (0.6); 7.0685 (1.7); 7.0652 (1.8); 7.0489 (1.2); 7.0456 (1.2); 6.8843 (1.4); 6.8828 (1.4); 6.8768 (1.4); 6.8752 (1.4); 6.8630 (1.3); 6.8615 (1.4); 6.8555 (1.3); 6.8539 (1.3); 5.2997 (9.0); 4.8934 (14.4); 4.2734 (1.8); 4.2556 (5.8); 4.2378 (5.8); 4.2200 (1.9); 2.0285 (13.4); 2.0072 (4.2); 1.5621 (3.6); 1.2980 (7.7); 1.2802 (16.0); 1.2623 (7.5); −0.0002 (14.2)

VII-058: $^1$H-NMR(400.6 MHz, CDCl3):

δ = 8.1159 (2.1); 8.1141 (1.7); 8.1097 (2.2); 7.6611 (1.1); 7.6548 (1.1); 7.6423 (1.3); 7.6399 (1.4); 7.6361 (1.3); 7.6336 (1.4); 7.6211 (1.2); 7.6148 (1.2); 7.2815 (0.5); 7.2782 (0.6); 7.2615 (14.0); 7.2445 (1.6); 7.2412 (1.7); 7.2149 (2.0); 7.1999 (0.9); 7.1958 (0.8); 7.1667 (0.7); 7.1635 (0.7); 7.1484 (1.4); 7.1472 (1.3); 7.1441 (1.3); 7.1292 (0.8); 7.1260 (0.7); 7.0489 (2.0); 7.0459 (2.0); 7.0294 (1.4); 7.0263 (1.4); 6.8821 (1.4); 6.8808 (1.5); 6.8746 (1.5); 6.8732 (1.5); 6.8608 (1.4); 6.8595 (1.5); 6.8533 (1.4); 6.8520 (1.5); 5.2996 (11.2); 4.8870 (15.6); 4.2688 (2.0); 4.2509 (6.3); 4.2331 (6.4); 4.2153 (2.1); 2.0288 (15.7); 2.0072 (2.0); 1.5635 (2.3); 1.2965 (7.7); 1.2787 (16.0); 1.2608 (7.7); 1.2552 (0.7); −0.0002 (14.2)

VII-056: $^1$H-NMR(400.0 MHz, d$_6$-DMSO):

δ = 8.1520 (1.5); 8.1458 (1.6); 7.9115 (0.6); 7.9052 (0.6); 7.8906 (0.9); 7.8843 (0.9); 7.8708 (0.6); 7.8645 (0.6); 7.5684 (0.6); 7.5531 (1.0); 7.5489 (1.2); 7.5337 (0.6); 7.5294 (0.7); 7.4771 (0.6); 7.4723 (0.5); 7.4643 (0.6); 7.4571 (0.6); 7.3314 (0.7); 7.3284 (0.8); 7.3090 (0.9); 7.2967 (1.0); 7.2936 (1.1); 7.2759 (0.8); 7.2707 (1.0); 7.2634 (1.2); 7.2572 (1.1); 7.2497 (0.7); 7.2462 (0.7); 7.2421 (1.0); 7.2352 (1.0); 4.8502 (6.9); 2.5199 (0.5); 2.5110 (9.5); 2.5065 (21.4); 2.5019 (30.1); 2.4973 (21.3); 2.4928 (9.7); 2.2595 (16.0); 2.0745 (6.4); 1.9888 (1.4); 1.9092 (1.2); 1.3560 (0.8); 1.1745 (0.8); 0.0080 (0.6); −0.0002 (21.0); −0.00085 (0.6)

X-007: $^1$H-NMR(400.6 MHz, CDCl3):

δ = 8.0770 (1.1); 8.0710 (1.2); 7.7237 (0.6); 7.7187 (0.6); 7.4453 (0.6); 7.4304 (0.8); 7.4262 (1.0); 7.4116 (0.7); 7.4075 (0.8); 7.3955 (0.6); 7.3830 (0.6); 7.3747 (0.6); 7.2623 (22.9); 7.2505 (0.6); 7.2489 (0.7); 7.2473 (0.8); 7.2278 (1.0); 7.0617 (0.8); 7.0586 (0.9); 7.0409 (1.0); 7.0373 (1.4); 7.0338 (1.0); 7.0160 (0.7); 7.0129 (0.6); 6.9491 (0.9); 6.9477 (0.9); 6.9416 (0.9); 6.9402 (0.9); 6.9278 (0.9); 6.9264 (1.0); 6.9204 (0.9); 6.9189 (0.9); 4.8956 (7.2); 4.8849 (0.6); 4.1730 (3.4); 4.1598 (3.4); 3.7990 (16.0); 1.5729 (1.6); −0.0002 (16.7); −0.00085 (0.6)

VII-071: $^1$H-NMR(400.6 MHz, CDCl3):

δ = 8.0203 (1.0); 8.0140 (1.2); 7.8709 (0.5); 7.8691 (0.6); 7.8647 (0.5); 7.8630 (0.5); 7.3784 (0.8); 7.3766 (0.7); 7.3741 (0.9); 7.3682 (0.6); 7.3599 (0.9); 7.3577 (0.9); 7.3558 (1.1); 7.3402 (0.7); 7.3360 (0.5); 7.2617 (10.3); 7.2272 (0.5); 7.2255 (0.6); 7.2239 (0.6); 7.2227 (0.6); 7.2070 (0.9); 7.2055 (0.9); 7.2040 (0.9); 7.0626 (0.6); 7.0596 (0.5); 7.0416 (0.6); 7.0382 (1.0); 7.0349 (0.6); 7.0171 (0.5); 6.9398

(0.8); 6.9383 (0.9); 6.9325 (0.9); 6.9310 (0.8); 6.9186 (0.8); 6.9171 (0.8); 6.9112 (0.8); 6.9097 (0.8); 5.3001 (2.5); 4.9944 (8.4); 4.2982 (1.1); 4.2803 (3.6); 4.2625 (3.7); 4.2447 (1.2); 3.2838 (16.0); 1.3202 (4.7); 1.3024 (10.0); 1.2846 (4.8); −0.0002 (15.3); −0.00028 (0.6)

VII-072: $^1$H-NMR(599.6 MHz, CDCl3):

δ = 8.0505 (7.4); 8.0470 (7.0); 7.8241 (2.3); 7.8200 (2.2); 7.8101 (3.8); 7.8078 (3.6); 7.7977 (2.4); 7.7937 (2.1); 7.4024 (4.6); 7.3899 (8.0); 7.3818 (3.9); 7.3773 (4.7); 7.3699 (2.1); 7.2625 (34.6); 7.2378 (3.5); 7.2245 (5.7); 7.2121 (2.6); 7.0685 (2.9); 7.0521 (5.0); 7.0376 (2.7); 6.9646 (4.2); 6.9601 (4.0); 6.9504 (4.1); 6.9459 (3.8); 5.2996 (0.4); 5.1377 (7.7); 5.1110 (9.3); 4.9934 (0.5); 4.8566 (9.2); 4.8299 (7.7); 4.2886 (3.7); 4.2767 (10.9); 4.2648 (11.1); 4.2529 (3.7); 3.2825 (0.8); 3.2281 (1.2); 3.2137 (49.4); 2.9860 (1.0); 2.6165 (50.0); 2.0753 (2.0); 1.6661 (0.7); 1.3333 (0.8); 1.3108 (13.8); 1.2989 (27.4); 1.2869 (13.8); 1.2703 (0.5); 1.2557 (1.9); 1.1891 (0.9); 1.1776 (0.9); 0.8802 (0.3); −0.00001 (36.8)

VII-123: $^1$H-NMR(400.0 MHz, CDCl3):

δ = 8.0733 (1.2); 8.0670 (1.2); 7.7519 (0.6); 7.7456 (0.6); 7.7329 (0.7); 7.7307 (0.7); 7.7267 (0.6); 7.7245 (0.7); 7.7118 (0.6); 7.7056 (0.6); 7.4279 (0.5); 7.4129 (0.8); 7.4086 (1.0); 7.3940 (0.6); 7.3896 (0.6); 7.2616 (7.3); 7.2211 (0.6); 7.2191 (0.6); 7.1996 (0.9); 7.0447 (0.6); 7.0414 (0.6); 7.0239 (0.6); 7.0200 (0.9); 7.0162 (0.6); 6.9986 (0.5); 6.9954 (0.5); 6.9339 (0.8); 6.9264 (0.8); 6.9125 (0.8); 6.9063 (0.8); 5.2996 (1.2); 4.9602 (7.6); 3.9240 (0.6); 3.8008 (14.1); 2.3125 (16.0); 2.3055 (0.8); 1.5601 (0.6); −0.0002 (9.6)

VII-057: $^1$H-NMR(400.6 MHz, CDCl3):

δ = 8.0963 (1.6); 8.0943 (1.3); 8.0922 (1.4); 8.0901 (1.8); 8.0883 (1.2); 7.7494 (0.9); 7.7431 (0.9); 7.7306 (1.0); 7.7283 (1.0); 7.7244 (1.0); 7.7220 (1.0); 7.7095 (0.9); 7.7032 (0.9); 7.3777 (0.7); 7.3734 (0.8); 7.3585 (1.2); 7.3542 (1.5); 7.3398 (0.9); 7.3355 (1.1); 7.3292 (0.5); 7.3247 (0.5); 7.3225 (0.8); 7.3207 (0.6); 7.3181 (0.6); 7.3162 (0.6); 7.3102 (0.8); 7.3086 (0.6); 7.3058 (0.6); 7.3040 (0.6); 7.3018 (0.7); 7.2973 (0.6); 7.2897 (0.6); 7.2852 (0.5); 7.2613 (12.9); 7.1983 (0.8); 7.1967 (0.8); 7.1949 (0.9); 7.1936 (0.9); 7.1775 (1.2); 7.1753 (1.3); 7.1598 (0.5); 7.1582 (0.6); 7.1564 (0.6); 7.1550 (0.5); 7.0235 (0.9); 7.0202 (0.9); 7.0027 (0.8); 6.9988 (1.4); 6.9950 (0.9); 6.9775 (0.8); 6.9744 (0.8); 6.9335 (1.2); 6.9320 (1.2); 6.9261 (1.3); 6.9245 (1.3); 6.9123 (1.2); 6.9107 (1.2); 6.9049 (1.2); 6.9033 (1.2); 5.2053 (0.7); 5.1879 (2.6); 5.1705 (2.7); 5.1532 (0.7); 4.2603 (1.0); 4.2585 (1.0); 4.2425 (3.1); 4.2407 (3.3); 4.2246 (3.3); 4.2230 (3.3); 4.2068 (1.1); 4.2053 (1.1); 2.0451 (1.3); 1.6900 (0.6); 1.6856 (10.2); 1.6682 (10.1); 1.5565 (3.3); 1.5560 (3.3); 1.2772 (7.5); 1.2594 (16.0); 1.2416 (7.1); 0.8987 (0.8); 0.8818 (3.1); 0.8641 (1.1); −0.0002 (17.7); −0.00085 (0.5)

VII-111: $^1$H-NMR(400.6 MHz, CDCl3):

δ = 8.1183 (0.7); 8.1164 (1.0); 8.1143 (0.8); 8.1122 (0.8); 8.1101 (1.1); 8.1082 (0.8); 7.7745 (0.6); 7.7683 (0.6); 7.7558 (0.6); 7.7533 (0.7); 7.7496 (0.6); 7.7471 (0.7); 7.7346 (0.6); 7.7284 (0.6); 7.4458 (0.5); 7.4309 (0.8); 7.4265 (0.9); 7.4120 (0.6); 7.4077 (0.6); 7.2625 (7.2); 7.2332 (0.5); 7.2315 (0.6); 7.2301 (0.5); 7.2145 (0.7); 7.2117 (0.8); 7.0485 (0.6); 7.0452 (0.6); 7.0277 (0.5); 7.0238 (0.9); 7.0200 (0.6); 6.9992 (0.5); 6.9447 (0.8); 6.9431 (0.8); 6.9372 (0.8); 6.9356 (0.8); 6.9234 (0.7); 6.9218 (0.8); 6.9159 (0.8); 6.9143 (0.8); 5.3004 (3.7); 4.9039 (8.1); 4.4975 (2.0); 4.4816 (4.2); 4.4657 (2.0); 3.6695 (16.0); 2.6997 (1.9); 2.6838 (3.9); 2.6679 (1.8); 1.5643 (1.6); 1.3381 (0.6); −0.0002 (9.8)

VII-073: $^1$H-NMR(400.6 MHz, d$_6$-DMSO):

δ = 8.2556 (2.6); 8.2497 (2.7); 8.0425 (0.9); 8.0363 (0.9); 8.0224 (1.5); 8.0164 (1.5); 8.0021 (1.0); 7.9958 (0.9); 7.6317 (0.8); 7.6271 (1.0); 7.6112 (1.7); 7.6077 (1.9); 7.5927 (1.1); 7.5885 (1.1); 7.5309 (0.5); 7.5223 (0.6); 7.5156 (1.1); 7.5031 (1.0); 7.4987 (1.1); 7.4912 (0.7); 7.4828 (0.8); 7.4785 (0.6); 7.3285 (1.9); 7.3245 (1.6); 7.3214 (1.3); 7.3098 (2.6); 7.3037 (1.5); 7.2990 (2.0); 7.2954 (1.6); 7.2777 (1.2); 7.2292 (1.6); 7.2231 (1.7); 7.2076 (1.6); 7.2020 (1.7); 4.9285 (10.8); 3.6175 (0.6); 3.6071 (0.6); 3.6009 (1.5); 3.5949 (0.6); 3.5844 (0.7); 3.3341 (2.0); 3.3134 (20.8); 3.2806 (0.7); 2.6702 (0.5); 2.5366 (0.5); 2.5236 (2.2); 2.5102 (35.3); 2.5058 (71.2); 2.5013 (95.2); 2.4968 (68.6); 2.4924 (34.0); 2.3284 (0.6); 2.1831 (0.5); 2.0741 (16.0); 1.9085 (1.2); 1.7760 (0.6); 1.7669 (1.2); 1.7594 (1.8); 1.7505 (0.7); 1.7429 (0.6); 1.3554 (4.0); 1.2357 (1.7); 0.0080 (2.5); −0.0002 (60.3); −0.00085 (2.7)

X-006: $^1$H-NMR(400.0 MHz, CDCl3):

δ = 8.0838 (2.0); 8.0779 (2.0); 7.7500 (0.7); 7.7439 (0.6); 7.7288 (1.0); 7.7104 (0.7); 7.7041 (0.7); 7.4343 (0.5); 7.4216 (0.7); 7.4156 (0.9); 7.4058 (1.6); 7.4019 (1.4); 7.3950 (1.0); 7.3866 (2.1); 7.3826 (1.9); 7.3679 (1.3); 7.3638 (0.9); 7.2609 (51.2); 7.2558 (1.3); 7.2341 (1.7); 7.2153 (0.7); 7.0854 (1.1); 7.0826 (1.0); 7.0644 (1.0); 7.0610 (1.8); 7.0576 (1.0); 7.0398 (1.0); 7.0369 (0.9); 6.9671 (1.4); 6.9597 (1.4); 6.9447 (1.4); 6.9386 (1.4); 4.9602 (16.0); 4.3209 (1.7); 4.2995 (5.4); 4.2780 (5.5); 4.2566 (1.8); 2.1062 (1.4); 2.0081 (11.0); 1.2559 (0.9); 0.0080 (1.0); −0.0002 (37.5); −0.00086 (1.1)

VII-074: $^1$H-NMR(400.6 MHz, CDCl3):

δ = 8.0561 (1.5); 8.0498 (1.5); 7.7580 (0.6); 7.7516 (0.6); 7.7396 (0.8); 7.7367 (0.8); 7.7333 (0.8); 7.7304 (0.8); 7.7185 (0.7); 7.7121 (0.7); 7.4745 (0.5); 7.4703 (0.6); 7.4553 (0.9); 7.4510 (1.1); 7.4371 (0.9); 7.4326 (1.0); 7.4185 (0.6); 7.4166 (0.5); 7.4141 (0.5); 7.4061 (0.6); 7.4044 (0.5); 7.4017 (0.5); 7.3977 (0.6); 7.3855 (0.6); 7.2732 (0.8); 7.2724 (0.8); 7.2717 (1.0); 7.2710 (1.0); 7.2701 (1.1); 7.2693 (1.1); 7.2685 (1.2); 7.2679 (1.0); 7.2670 (0.7); 7.2661 (0.9); 7.2653 (1.2); 7.2645 (1.6); 7.2613 (74.2); 7.2579 (1.7); 7.2571 (1.3); 7.2562 (1.1); 7.2554 (1.1); 7.2546 (1.2); 7.2538 (1.3); 7.2531 (1.4); 7.2523 (1.4); 7.2515 (1.2); 7.2507 (1.3); 7.2499 (1.2); 7.2492 (1.1); 7.2348 (0.6); 7.2328 (0.8); 7.2310 (0.5); 7.0884 (0.7); 7.0853 (0.7); 7.0675 (0.7); 7.0639 (1.2); 7.0605 (0.8); 7.0427 (0.7); 7.0395 (0.6); 6.9734 (1.0); 6.9720 (1.0); 6.9660 (1.0); 6.9646 (1.0); 6.9523 (1.0); 6.9508 (1.0); 6.9448 (1.0); 6.9433 (1.0); 5.0763 (1.0); 5.0424 (0.7); 5.0360 (4.7); 5.0223 (4.6); 4.9820 (0.9); 3.2521 (16.0); 2.1062 (0.6); 2.0084 (2.0); 1.4322 (3.6); 1.2843 (0.6); 1.2542 (1.0); 0.0080 (1.4); 0.0040 (0.5); 0.0024 (1.6); −0.0002 (48.1); −0.00049 (0.8); −0.00058 (0.7); −0.00085 (1.4)

VII-096: $^1$H-NMR(400.6 MHz, CDCl3):

δ = 8.1083 (2.7); 8.1021 (3.0); 7.7660 (1.4); 7.7599 (1.5); 7.7474 (1.6); 7.7448 (1.7); 7.7412 (1.7); 7.7386 (1.7); 7.7262 (1.5); 7.7199 (1.5); 7.5187 (1.0); 7.4195 (1.3); 7.4154 (1.2); 7.4004 (1.9); 7.3960 (2.3); 7.3817 (1.3); 7.3773 (0.9); 7.3728 (0.9); 7.3683 (0.7); 7.3605 (0.8); 7.3539 (1.1); 7.3477 (1.0); 7.3416 (1.2); 7.3397 (1.0); 7.3333 (1.1); 7.3287 (0.8); 7.3209 (1.0); 7.3165 (0.7); 7.2858 (0.6); 7.2650 (0.9); 7.2643 (1.4); 7.2602 (198.8); 7.2240 (1.8); 7.2223 (1.7); 7.2026 (2.2); 7.1854 (1.1); 7.1837 (1.1); 7.0485 (1.5); 7.0453 (1.5); 7.0277 (1.4); 7.0238 (2.4); 7.0201 (1.7); 7.0026 (1.3); 6.9992 (1.3); 6.9966 (1.4); 6.9480 (2.0); 6.9465 (2.1); 6.9405 (2.1); 6.9390 (2.1); 6.9268 (1.9); 6.9251 (2.1); 6.9177 (2.1); 5.3180 (1.1); 5.3006 (4.5); 5.2831 (4.5); 5.2658 (1.2); 2.2718 (0.7); 2.1066 (8.0); 2.0459 (1.7); 1.7534

(15.8); 1.7359 (16.0); 1.5821 (0.9); 1.5647 (0.9); 1.5066 (0.6); 1.4892 (0.6); 1.4322 (7.0); 1.2775 (0.7); 1.2596 (1.7); 1.2550 (1.4); 1.2418 (0.7); 0.1456 (0.8); 0.0276 (0.8); 0.0118 (0.6); 0.0110 (0.6); 0.0101 (0.9); 0.0079 (7.2); 0.0063 (1.7); 0.0054 (1.8); 0.0046 (2.7); 0.0037 (3.8); −0.0002 (264.9); −0.00052 (5.0); −0.00060 (4.4); −0.00069 (3.8); −0.00085 (8.9); −0.0124 (1.3); −0.0132 (1.3); −0.0140 (1.4); −0.0164 (0.8); −0.0172 (0.7); −0.0188 (0.8); −0.0227 (0.5); −0.1494 (0.8)

VII-066: $^1$H-NMR(400.6 MHz, CDCl3):

δ = 8.0469 (1.8); 8.0409 (1.9); 7.7250 (0.6); 7.7190 (0.6); 7.7043 (1.0); 7.6992 (0.9); 7.6854 (0.6); 7.6792 (0.6); 7.3698 (0.7); 7.3639 (1.1); 7.3618 (0.7); 7.3594 (1.2); 7.3574 (1.0); 7.3515 (1.2); 7.3484 (0.7); 7.3438 (1.8); 7.3401 (2.6); 7.3336 (1.2); 7.3291 (0.6); 7.3259 (1.1); 7.3210 (1.7); 7.2609 (17.8); 7.2010 (0.9); 7.1994 (1.0); 7.1978 (1.1); 7.1965 (1.0); 7.1810 (1.5); 7.1790 (1.6); 7.1771 (1.7); 7.1624 (0.6); 7.1608 (0.7); 7.1592 (0.7); 7.0324 (1.2); 7.0295 (1.1); 7.0110 (1.2); 7.0075 (2.1); 6.9861 (1.1); 6.9824 (0.7); 6.9252 (1.5); 6.9238 (1.5); 6.9177 (1.5); 6.9163 (1.5); 6.9040 (1.4); 6.9025 (1.5); 6.8965 (1.4); 6.8950 (1.4); 5.2251 (0.8); 5.2077 (2.8); 5.1903 (2.8); 5.1728 (0.8); 4.2574 (1.0); 4.2525 (1.0); 4.2396 (3.3); 4.2348 (3.3); 4.2217 (3.4); 4.2170 (3.3); 4.2039 (1.2); 4.1993 (1.1); 1.6855 (0.8); 1.6759 (11.8); 1.6683 (1.0); 1.6585 (11.7); 1.5484 (5.2); 1.2774 (0.8); 1.2696 (8.1); 1.2597 (1.7); 1.2519 (16.0); 1.2420 (0.7); 1.2341 (7.5); 0.8819 (1.8); 0.8642 (0.7); 0.0080 (0.7); −0.0002 (23.5); −0.00085 (0.7)

VII-118: $^1$H-NMR(400.6 MHz, CDCl3):

δ = 8.1043 (2.9); 8.0980 (3.2); 7.7557 (1.4); 7.7495 (1.4); 7.7370 (1.6); 7.7346 (1.8); 7.7308 (1.7); 7.7283 (1.8); 7.7159 (1.6); 7.7096 (1.5); 7.3989 (1.2); 7.3946 (1.4); 7.3796 (2.0); 7.3753 (2.4); 7.3609 (1.4); 7.3561 (2.2); 7.3511 (0.8); 7.3433 (0.8); 7.3388 (0.8); 7.3366 (1.2); 7.3322 (1.0); 7.3244 (1.3); 7.3199 (1.0); 7.3182 (1.0); 7.3159 (1.2); 7.3115 (1.0); 7.3088 (1.1); 7.2992 (0.9); 7.2602 (89.4); 7.2323 (0.6); 7.2074 (1.4); 7.2055 (1.5); 7.1858 (2.3); 7.1688 (1.0); 7.1670 (0.9); 7.0342 (1.5); 7.0309 (1.5); 7.0134 (1.4); 7.0096 (2.4); 7.0058 (1.6); 6.9965 (0.6); 6.9882 (1.3); 6.9851 (1.3); 6.9453 (2.0); 6.9438 (2.1); 6.9380 (2.1); 6.9364 (2.1); 6.9242 (2.0); 6.9227 (2.1); 6.9167 (2.1); 6.9152 (2.0); 5.3043 (1.2); 5.2869 (4.6); 5.2694 (4.7); 5.2520 (1.2); 4.1314 (0.7); 4.1136 (1.7); 2.1076 (5.6); 2.0459 (3.5); 1.7475 (15.7); 1.7300 (16.0); 1.7133 (0.6); 1.4322 (4.4); 1.2773 (1.1); 1.2595 (2.4); 1.2417 (1.1); 0.0080 (3.0); 0.0058 (0.6); −0.0002 (121.4); −0.00085 (3.9); −0.0280 (0.7)

VII-067: $^1$H-NMR(400.6 MHz, CDCl3):

δ = 8.1183 (1.5); 8.1166 (1.3); 8.1142 (1.2); 8.1120 (1.6); 7.6716 (0.8); 7.6653 (0.8); 7.6529 (0.8); 7.6503 (1.0); 7.6466 (0.9); 7.6440 (1.0); 7.6316 (0.8); 7.6253 (0.8); 7.2855 (1.1); 7.2823 (1.2); 7.2670 (1.1); 7.2653 (0.9); 7.2611 (31.9); 7.2207 (1.3); 7.2194 (1.4); 7.2016 (0.8); 7.1874 (0.6); 7.1846 (0.5); 7.1691 (1.0); 7.1679 (1.0); 7.1651 (1.0); 7.1497 (0.6); 7.1469 (0.6); 7.1457 (0.5); 7.0753 (1.4); 7.0722 (1.5); 7.0558 (1.0); 7.0526 (1.0); 6.8920 (1.0); 6.8905 (1.1); 6.8845 (1.0); 6.8831 (1.1); 6.8706 (0.9); 6.8692 (1.1); 6.8632 (1.0); 6.8617 (1.0); 4.9579 (10.7); 4.1499 (1.1); 4.1321 (3.3); 4.1142 (3.4); 4.0964 (1.1); 2.1098 (0.6); 2.0470 (16.0); 2.0217 (10.5); 1.4321 (0.9); 1.2773 (4.7); 1.2595 (9.5); 1.2416 (4.6); 0.0081 (0.6); −0.0002 (21.2); −0.00085 (0.7)

VII-097: $^1$H-NMR(400.6 MHz, CDCl3):

δ = 8.1209 (1.4); 8.1147 (1.4); 7.6645 (0.7); 7.6582 (0.7); 7.6457 (0.8); 7.6432 (0.8); 7.6395 (0.8); 7.6370 (0.8); 7.6246 (0.7); 7.6183 (0.7); 7.2690 (1.1); 7.2660 (1.2); 7.2611 (13.6); 7.2506 (1.0); 7.2474 (1.0); 7.2095 (1.2); 7.1931 (0.6); 7.1538 (0.9); 7.1499 (0.8); 7.0560 (1.3); 7.0531 (1.3); 7.0366 (0.9); 7.0336 (0.8); 6.8905 (1.0); 6.8892 (0.9); 6.8831 (1.0); 6.8818 (0.9); 6.8693 (0.9); 6.8679 (0.9); 6.8618 (0.9); 4.9467 (8.6); 2.1078 (2.0); 2.0236 (9.5); 2.0081 (16.0); 1.4321 (2.0); −0.0002 (17.9); −0.00085 (0.5)

VII-105: $^1$H-NMR(599.6 MHz, CDCl3):

δ = 8.1149 (0.9); 8.1109 (1.0); 8.0411 (7.5); 8.0374 (7.6); 7.6529 (0.4); 7.6487 (0.4); 7.6388 (0.6); 7.6347 (0.6); 7.6275 (2.5); 7.6235 (2.6); 7.6139 (3.8); 7.6107 (3.7); 7.6012 (2.4); 7.5971 (2.3); 7.2872 (2.4); 7.2855 (2.6); 7.2746 (6.3); 7.2730 (6.6); 7.2609 (35.5); 7.2481 (0.6); 7.2463 (0.6); 7.2172 (7.1); 7.2047 (4.6); 7.1533 (2.9); 7.1403 (5.6); 7.1280 (2.9); 7.0440 (0.9); 7.0286 (7.0); 7.0274 (7.0); 7.0154 (5.6); 6.8753 (5.4); 6.8705 (5.5); 6.8611 (5.2); 6.8563 (5.2); 5.2987 (4.0); 4.8991 (41.3); 4.8866 (5.2); 4.2580 (5.8); 4.2460 (17.6); 4.2341 (17.6); 4.2222 (5.8); 2.0396 (50.0); 2.0288 (6.4); 1.5658 (6.2); 1.2880 (19.7); 1.2761 (39.3); 1.2642 (19.4); 1.2553 (1.0); 0.0053 (1.2); −0.00001 (29.8); −0.00056 (1.0)

X-026: $^1$H-NMR(400.0 MHz, CDCl3):

δ = 8.0745 (2.5); 7.7356 (1.0); 7.7178 (1.4); 7.7012 (1.0); 7.5193 (1.1); 7.4390 (1.2); 7.4201 (2.2); 7.4013 (1.8); 7.3835 (1.3); 7.3632 (1.1); 7.2604 (184.7); 7.2492 (1.7); 7.2284 (2.5); 7.2099 (1.3); 7.0599 (1.3); 7.0383 (2.8); 7.0172 (2.3); 6.9965 (1.2); 6.9796 (1.0); 6.9472 (1.8); 6.9412 (1.9); 6.9261 (2.0); 6.9188 (2.0); 4.9115 (12.8); 4.2350 (5.3); 4.2214 (5.4); 2.2719 (1.2); 2.0082 (16.0); 1.4323 (12.3); 1.3327 (1.2); 1.2842 (1.3); 1.2547 (4.1); 0.0689 (1.0); 0.0080 (6.4); −0.0002 (255.5); −0.00085 (7.4); −0.1495 (0.9)

X-026: $^1$H-NMR(400.0 MHz, d$_6$-DMSO):

δ = 4.8276 (1.0); 3.3165 (16.0); 2.5051 (39.9); 2.5007 (55.1); 2.4963 (40.6); 2.4921 (19.9); 0.0081 (0.6); −0.0002 (21.2); −0.00083 (1.0)

VII-106: $^1$H-NMR(400.6 MHz, CDCl3):

δ = 8.0581 (3.1); 8.0521 (3.3); 7.7411 (1.0); 7.7349 (1.0); 7.7203 (1.6); 7.7150 (1.6); 7.7014 (1.1); 6.9852 (1.0); 7.3734 (2.9); 7.3628 (0.6); 7.3580 (3.2); 7.3538 (5.3); 7.3494 (1.4); 7.3446 (0.7); 7.3403 (2.5); 7.3374 (3.2); 7.3343 (2.6); 7.3303 (1.2); 7.3222 (1.5); 7.3178 (0.8); 7.2608 (18.0); 7.1968 (1.5); 7.1953 (1.8); 7.1937 (1.8); 7.1766 (2.6); 7.1745 (3.0); 7.1583 (1.1); 7.1568 (1.3); 7.1551 (1.2); 7.0299 (1.4); 7.0280 (1.3); 7.0252 (0.9); 7.0092 (1.7); 7.0062 (2.8); 7.0034 (2.0); 6.9969 (0.6); 6.9846 (1.6); 6.9809 (1.4); 6.9370 (2.3); 6.9357 (2.3); 6.9297 (2.4); 6.9283 (2.3); 6.9158 (2.3); 6.9144 (2.3); 6.9084 (2.3); 6.9071 (2.2); 5.3199 (1.1); 5.3025 (4.4); 5.2849 (4.6); 5.2675 (1.2); 2.1095 (1.2); 2.0468 (1.0); 1.7459 (0.7); 1.7418 (1.1); 1.7322 (16.0); 1.7245 (1.7); 1.7147 (16.0); 1.4321 (1.6); 1.2588 (0.6); 0.0079 (0.6); −0.0002 (22.9); −0.00085 (0.8)

VII-065: $^1$H-NMR(400.6 MHz, CDCl3):

δ = 8.1740 (1.2); 8.1721 (1.8); 8.1701 (1.4); 8.1680 (1.5); 8.1658 (1.9); 8.1638 (1.4); 7.7041 (1.0); 7.6978 (1.0); 7.6854 (1.2); 7.6828 (1.3); 7.6792 (1.2); 7.6766 (1.3); 7.6642 (1.1); 7.6579 (1.1); 7.2613 (47.4); 7.2548 (0.5); 7.1290 (2.1); 7.1232 (0.8); 7.1171 (2.3); 7.1117 (1.4); 7.1061 (3.5); 7.1002 (1.0); 7.0980 (0.7); 7.0943 (3.3); 7.0281 (3.4); 7.0221 (1.0); 7.0109 (0.9); 7.0080 (3.7); 7.0052 (2.6); 7.0022 (1.1); 6.9976 (0.5); 6.9910 (0.8); 6.9852 (2.3); 6.9771 (1.4); 6.9756 (1.4); 6.9695 (1.4); 6.9680 (1.4);

6.9559 (1.2); 6.9543 (1.3); 6.9483 (1.3); 6.9468 (1.3); 4.9083 (14.3); 4.3039 (1.8); 4.2861 (5.7); 4.2683 (5.8); 4.2504 (1.9); 1.5605 (0.7); 1.3197 (7.6); 1.3019 (16.0); 1.2841 (7.4); 0.0080 (0.8); −0.0002 (31.9); −0.00085 (1.0)

VII-102: $^1$H-NMR(400.6 MHz, CDCl3):
δ = 8.1696 (2.0); 8.1677 (1.5); 8.1655 (1.5); 8.1633 (2.0); 8.1615 (1.4); 7.6940 (1.1); 7.6877 (1.1); 7.6754 (1.2); 7.6729 (1.3); 7.6691 (1.2); 7.6666 (1.3); 7.6542 (1.2); 7.6479 (1.2); 7.2623 (23.9); 7.1111 (2.2); 7.1053 (0.8); 7.0992 (2.4); 7.0938 (1.5); 7.0882 (3.8); 7.0822 (1.0); 7.0802 (0.8); 7.0763 (3.6); 7.0144 (3.7); 7.0085 (1.1); 7.0026 (0.5); 6.9973 (1.0); 6.9944 (3.9); 6.9917 (2.7); 6.9886 (1.1); 6.9775 (2.1); 6.9714 (3.0); 6.9689 (1.7); 6.9567 (1.3); 6.9552 (1.4); 6.9492 (1.4); 6.9477 (1.4); 5.3003 (6.4); 4.9017 (14.8); 4.3002 (1.9); 4.2824 (6.0); 4.2646 (6.1); 4.2468 (2.0); 1.5681 (0.6); 1.3187 (7.7); 1.3009 (16.0); 1.2830 (7.5); −0.0002 (16.4)

11-016: $^1$H-NMR(400.2 MHz, d$_6$-DMSO):
δ = 8.5087 (3.3); 8.5016 (3.4); 7.9335 (0.9); 7.9262 (0.9); 7.9118 (2.1); 7.9044 (2.0); 7.8901 (1.3); 7.8828 (1.2); 7.7929 (1.9); 7.7819 (2.1); 7.7709 (1.6); 7.7599 (1.5); 7.4825 (0.8); 7.4785 (1.0); 7.4631 (1.7); 7.4591 (2.1); 7.4439 (1.4); 7.4399 (1.5); 7.4330 (0.7); 7.4262 (1.1); 7.4217 (1.0); 7.4135 (1.1); 7.4068 (1.1); 7.4018 (0.8); 7.3935 (0.8); 7.3893 (0.6); 7.2886 (1.5); 7.2720 (2.0); 7.2693 (2.3); 7.2530 (2.0); 7.2347 (1.2); 7.2289 (1.5); 7.2260 (1.3); 7.2079 (1.0); 7.2053 (1.0); 5.1311 (5.7); 3.7233 (16.0); 3.3392 (25.6); 3.1196 (15.2); 2.5117 (8.4); 2.5075 (17.5); 2.5031 (24.0); 2.4986 (17.9); 2.4944 (9.1); 2.0780 (0.5); 0.0000 (4.1)

11-003: $^1$H-NMR(400.2 MHz, d$_6$-DMSO):
δ = 11.4205 (3.2); 8.5090 (6.3); 8.5018 (6.6); 7.9290 (1.8); 7.9217 (1.7); 7.9072 (4.0); 7.8999 (3.9); 7.8856 (2.5); 7.8783 (2.4); 7.7842 (3.1); 7.7732 (3.4); 7.7623 (2.5); 7.7513 (2.4); 7.4776 (1.5); 7.4738 (2.0); 7.4579 (3.6); 7.4544 (4.8); 7.4352 (4.2); 7.4244 (2.3); 7.4184 (2.1); 7.4045 (1.4); 7.2896 (3.0); 7.2701 (5.0); 7.2637 (2.7); 7.2539 (2.2); 7.2510 (2.5); 7.2376 (2.8); 7.2162 (1.8); 6.5436 (0.4); 5.0706 (0.4); 5.0363 (0.4); 4.6709 (8.2); 3.6094 (16.0); 3.3319 (27.2); 2.9583 (0.5); 2.8407 (0.5); 2.6761 (0.4); 2.6714 (0.6); 2.6670 (0.5); 2.5113 (31.1); 2.5070 (64.9); 2.5025 (89.0); 2.4981 (67.2); 2.4939 (34.8); 2.3340 (0.4); 2.3294 (0.6); 2.3252 (0.4); 0.0081 (0.4); 0.0000 (9.8); −0.00081 (0.5)

II-017: $^1$H-NMR(400.2 MHz, d$_6$-DMSO):
δ = 10.8029 (3.2); 10.2111 (0.9); 9.2275 (1.0); 8.9881 (6.4); 8.5076 (7.9); 8.5005 (8.0); 7.9292 (2.1); 7.9220 (2.0); 7.9076 (4.8); 7.9002 (4.5); 7.8859 (2.9); 7.8785 (2.7); 7.7804 (3.7); 7.7694 (3.9); 7.7585 (3.0); 7.7477 (2.7); 7.5115 (1.8); 7.4921 (3.5); 7.4726 (2.3); 7.4541 (1.5); 7.4356 (2.6); 7.4198 (2.6); 7.4061 (1.6); 7.2988 (2.8); 7.2795 (4.4); 7.2593 (4.6); 7.2327 (3.6); 7.2112 (2.3); 5.0329 (1.8); 4.6682 (16.0); 3.3336 (106.0); 3.3101 (4.4); 2.6714 (1.7); 2.5065 (208.0); 2.5023 (274.3); 2.4980 (201.8); 2.3291 (1.6); 2.3246 (1.2); 2.0769 (0.7); 1.2344 (0.4); 0.0001 (31.1); −0.00080 (1.4)

VII-095: $^1$H-NMR(400.6 MHz, CDCl3):
δ = 8.1809 (2.1); 8.1788 (1.6); 8.1766 (1.7); 8.1746 (2.2); 7.7062 (1.1); 7.6999 (1.1); 7.6876 (1.2); 7.6850 (1.3); 7.6814 (1.2); 7.6788 (1.3); 7.6664 (1.2); 7.6602 (1.2); 7.2607 (51.3); 7.1403 (2.4); 7.1345 (0.9); 7.1285 (2.7); 7.1231 (1.6); 7.1175 (3.7); 7.1115 (1.1); 7.1093 (0.8); 7.1056 (3.5); 7.0349 (3.8); 7.0290 (1.1); 7.0231 (0.6); 7.0177 (1.2); 7.0149 (4.1); 7.0121 (2.7); 7.0091 (1.2); 6.9977 (1.2); 6.9921 (2.4); 6.9836 (1.7); 6.9821 (1.5); 6.9761 (1.5); 6.9745 (1.4); 6.9623 (1.4); 6.9608 (1.4); 6.9548 (1.5); 6.9532 (1.4); 4.9834 (16.0); 4.9586 (0.6); 4.1499 (0.9); 4.1321 (2.7); 4.1143 (2.7); 4.0964 (0.9); 2.2837 (0.8); 2.2271 (0.6); 2.2188 (0.5); 2.1108 (6.1); 2.0470 (13.2); 1.4420 (0.9); 1.4322 (1.1); 1.2776 (3.9); 1.2598 (8.0); 1.2419 (4.1); 1.2390 (1.1); 0.0080 (3.6); 0.0065 (0.6); 0.0057 (0.6); 0.0048 (0.6); −0.0002 (147.7); −0.00066 (1.7); −0.00085 (4.7)

VII-051: $^1$H-NMR(400.6 MHz, d$_6$-DMSO):
δ = 11.9140 (0.6); 7.4551 (2.2); 7.3288 (2.2); 7.3222 (1.3); 7.3159 (3.0); 7.3055 (6.6); 7.2989 (2.6); 7.2928 (6.2); 7.2829 (6.9); 7.2764 (1.5); 7.2618 (7.4); 7.2556 (1.5); 7.2448 (1.1); 7.2386 (2.5); 7.1778 (1.9); 7.1713 (1.8); 7.1543 (2.0); 7.1478 (1.9); 6.3189 (2.8); 6.2953 (2.6); 4.7909 (16.0); 3.5073 (0.7); 3.3373 (60.6); 2.6792 (0.9); 2.6745 (2.1); 2.6699 (2.9); 2.6653 (2.1); 2.6607 (1.0); 2.5447 (0.7); 2.5404 (50.0); 2.5237 (7.2); 2.5190 (9.7); 2.5102 (151.3); 2.5057 (339.9); 2.5011 (483.5); 2.4965 (338.4); 2.4919 (156.0); 2.4630 (0.9); 2.4585 (0.6); 2.3375 (0.9); 2.3281 (3.0); 2.3236 (2.1); 2.3189 (0.9); 2.0740 (4.4); 1.9885 (0.7); 1.3528 (1.3); 1.2980 (4.6); 1.2584 (7.4); 1.2351 (5.8); 1.1744 (0.6); 0.8537 (0.9); 0.1458 (0.8); 0.0081 (8.1); 0.0057 (0.6); 0.0049 (0.8); −0.0002 (335.8); −0.00085 (10.9); −0.0263 (1.0); −0.0338 (0.9); −0.1494 (0.9)

VII-051: $^1$H-NMR(400.0 MHz, CDCl3):
δ = 7.5188 (1.6); 7.2600 (281.3); 6.9960 (1.6); 1.6557 (2.7); 1.4274 (2.1); 1.3326 (12.3); 1.2844 (16.0); 1.2548 (10.0); 0.8799 (1.4); 0.0080 (9.4); −0.0002 (364.9); −0.00085 (11.0); −0.1490 (1.4)

VII-069: $^1$H-NMR(400.0 MHz, CDCl3):
δ = 8.1796 (2.6); 8.1734 (2.5); 7.6980 (1.2); 7.6916 (1.2); 7.6791 (1.4); 7.6767 (1.5); 7.6730 (1.3); 7.6704 (1.4); 7.6581 (1.2); 7.6517 (1.1); 7.2603 (56.4); 7.1225 (2.5); 7.1168 (1.0); 7.1106 (2.8); 7.1053 (1.8); 7.0997 (4.1); 7.0879 (3.9); 7.0230 (4.0); 7.0171 (1.1); 7.0030 (4.5); 6.9860 (2.5); 6.9801 (3.3); 6.9638 (1.6); 6.9573 (1.5); 4.9791 (16.0); 2.0084 (4.7); 1.4274 (0.6); 1.3315 (1.9); 1.2843 (2.6); 1.2546 (3.1); 0.8801 (0.6); 0.0080 (2.8); −0.0002 (71.5); −0.00085 (2.0)

VII-069: $^1$H-NMR(400.0 MHz, CDCl3):
δ = 8.1770 (2.3); 8.1705 (2.3); 7.6950 (1.0); 7.6887 (1.1); 7.6737 (1.3); 7.6675 (1.3); 7.6551 (1.1); 7.6489 (1.1); 7.2600 (66.0); 7.1226 (2.2); 7.1168 (1.0); 7.1108 (2.5); 7.1054 (1.5); 7.0998 (3.7); 7.0880 (3.6); 7.0227 (3.7); 7.0169 (1.0); 7.0027 (4.0); 6.9800 (3.3); 6.9763 (1.9); 6.9610 (1.5); 6.9536 (1.4); 4.9778 (16.0); 3.7699 (1.9); 3.7594 (1.6); 3.7532 (5.0); 3.7470 (1.7); 3.7366 (2.1); 2.2714 (1.0); 1.8729 (2.0); 1.8650 (2.0); 1.8563 (5.9); 1.8477 (1.9); 1.8397 (2.0); 1.4321 (9.7); 1.2543 (0.9); 1.2433 (0.7); 0.0080 (2.8); −0.0002 (104.2); −0.00085 (3.0)

VII-059: $^1$H-NMR(400.6 MHz, CDCl3):
δ = 8.1050 (1.5); 8.0989 (1.6); 7.6864 (0.6); 7.6801 (0.6); 7.6660 (0.9); 7.6613 (0.8); 7.6598 (0.8); 7.6469 (0.7); 7.6406 (0.6); 7.2613 (16.7); 7.1043 (2.0); 7.0984 (0.8); 7.0924 (2.2); 7.0871 (1.4); 7.0813 (3.6); 7.0755 (1.1); 7.0736 (0.8); 7.0695 (3.5); 7.0214 (3.5); 7.0154 (1.0); 7.0095 (0.6); 7.0043 (1.0); 7.0015 (3.7); 6.9995 (1.9); 6.9984 (2.4); 6.9956 (1.1); 6.9845 (0.9); 6.9786 (2.2); 6.9749 (1.4); 6.9732 (1.5); 6.9673 (1.4); 6.9657 (1.4); 6.9537 (1.3); 6.9520 (1.3); 6.9461 (1.3); 6.9445 (1.3); 5.3002 (4.7); 4.9156 (13.2); 4.9088 (0.8); 4.2980 (1.8); 4.2802 (5.7); 4.2624 (5.8); 4.2446 (1.9); 1.5490 (4.4); 1.3148 (7.5); 1.3010 (0.9); 1.2970 (16.0); 1.2832 (0.5); 1.2792 (7.4); 0.0080 (0.7); 0.0024 (0.8); −0.0002 (22.7); −0.00041 (0.6); −0.00084 (0.7)

VII-045: ¹H-NMR(400.2 MHz, d₆-DMSO):
δ = 8.2324 (1.0); 8.2193 (1.7); 8.2063 (1.0); 7.4097 (11.0); 4.1033 (2.4); 4.0855 (7.2); 4.0677 (7.2); 4.0499 (2.4); 3.5001 (1.7); 3.4834 (4.5); 3.4687 (4.5); 3.4521 (1.8); 3.3456 (34.2); 3.3405 (49.0); 2.8946 (1.8); 2.7358 (1.6); 2.5809 (3.8); 2.5640 (7.7); 2.5470 (3.5); 2.5099 (22.3); 2.5055 (28.6); 2.5011 (21.6); 1.2602 (0.3); 1.2394 (1.5); 1.2057 (8.0); 1.1880 (16.0); 1.1702 (7.7); 0.8542 (0.3); −0.0002 (0.8)

II-004: ¹H-NMR(400.2 MHz, d₆-DMSO):
δ = 11.4010 (3.2); 8.5200 (7.2); 8.5129 (7.0); 7.9346 (2.1); 7.9273 (2.0); 7.9129 (4.6); 7.9056 (4.2); 7.8913 (2.8); 7.8840 (2.5); 7.8129 (3.8); 7.8018 (4.0); 7.7910 (2.8); 7.7799 (2.4); 7.5474 (1.7); 7.5322 (2.0); 7.5253 (3.4); 7.5103 (3.4); 7.5033 (2.0); 7.4883 (1.6); 7.3811 (1.5); 7.3745 (1.6); 7.3531 (2.5); 7.3321 (1.4); 7.3256 (1.4); 7.1948 (1.6); 7.1910 (1.5); 7.1747 (2.8); 7.1523 (1.4); 5.0611 (0.4); 4.8421 (0.3); 4.6629 (7.5); 3.6062 (16.0); 3.3140 (24.0); 2.6732 (0.9); 2.6685 (1.2); 2.6639 (1.0); 2.5082 (76.2); 2.5039 (153.2); 2.4995 (206.2); 2.4951 (150.3); 2.4909 (74.4); 2.3307 (0.9); 2.3263 (1.2); 2.3218 (0.9); 0.1446 (0.4); 0.0066 (4.0); −0.00016 (102.9); −0.00097 (5.0); −0.1509 (0.4)

II-005: ¹H-NMR(400.2 MHz, d₆-DMSO):
δ = 8.5094 (5.2); 8.5022 (5.3); 8.4479 (1.5); 8.4338 (2.7); 8.4194 (1.4); 7.9273 (1.5); 7.9200 (1.4); 7.9056 (3.3); 7.8983 (3.1); 7.8839 (2.0); 7.8766 (1.8); 7.7749 (3.0); 7.7639 (3.2); 7.7531 (2.4); 7.7420 (2.2); 7.5106 (1.5); 7.5066 (1.6); 7.4912 (3.1); 7.4872 (3.2); 7.4717 (1.9); 7.4677 (1.9); 7.4506 (0.9); 7.4463 (0.9); 7.4378 (1.1); 7.4314 (1.8); 7.4270 (1.7); 7.4188 (1.8); 7.4144 (1.8); 7.4070 (1.3); 7.3986 (1.2); 7.3944 (1.0); 7.2843 (2.2); 7.2819 (2.4); 7.2652 (3.4); 7.2625 (3.7); 7.2503 (2.7); 7.2472 (2.9); 7.2298 (2.2); 7.2242 (2.6); 7.2031 (1.7); 7.2005 (1.5); 4.7547 (16.0); 3.3906 (2.2); 3.3747 (5.6); 3.3594 (5.8); 3.3434 (2.8); 3.3281 (28.5); 3.3047 (1.0); 2.6926 (5.0); 2.6764 (10.1); 2.6601 (4.5); 2.5109 (15.9); 2.5067 (30.6); 2.5022 (39.9); 2.4978 (29.2); 2.4936 (14.4); 0.0000 (5.0)

X-027: ¹H-NMR(599.6 MHz, CDCl3):
δ = 8.1023 (5.3); 8.0984 (5.2); 7.7586 (1.9); 7.7544 (1.9); 7.7458 (2.7); 7.7445 (2.8); 7.7418 (2.7); 7.7319 (1.9); 7.7278 (1.8); 7.4430 (1.8); 7.4403 (1.9); 7.4301 (3.5); 7.4277 (3.5); 7.4175 (2.0); 7.4148 (2.0); 7.3560 (1.0); 7.3532 (1.0); 7.3478 (1.1); 7.3433 (1.9); 7.3406 (1.8); 7.3341 (1.8); 7.3323 (1.9); 7.3268 (1.2); 7.3214 (1.2); 7.3187 (1.0); 7.2638 (11.9); 7.2201 (2.6); 7.2071 (4.2); 7.1945 (1.9); 7.0385 (2.3); 7.0368 (2.2); 7.0222 (3.9); 7.0078 (2.3); 7.0062 (2.0); 6.9963 (0.5); 6.9575 (0.3); 6.9330 (3.2); 6.9283 (3.2); 6.9189 (3.1); 6.9141 (3.2); 5.2993 (3.1); 4.9996 (24.7); 3.1119 (1.2); 3.0637 (34.6); 3.0312 (1.4); 3.0288 (1.5); 3.0093 (31.2); 2.9513 (0.8); 2.7170 (2.7); 2.2917 (0.5); 2.2831 (1.6); 2.2759 (0.7); 2.2262 (1.6); 2.2181 (1.3); 2.1738 (0.5); 2.0441 (0.8); 1.6337 (17.2); 1.2752 (0.4); 1.2707 (0.3); 1.2633 (0.8); 1.2587 (0.9); 1.2514 (0.4); 1.2470 (0.3); 0.0052 (2.4); −0.00001 (50.0); −0.00056 (1.6)

X-027: ¹H-NMR(599.6 MHz, CDCl3):
δ = 8.1013 (1.2); 8.0974 (1.3); 7.7586 (0.4); 7.7545 (0.5); 7.7446 (0.7); 7.7419 (0.6); 7.7405 (0.6); 7.7320 (0.5); 7.7278 (0.4); 7.4422 (0.4); 7.4395 (0.5); 7.4292 (0.8); 7.4267 (0.9); 7.4167 (0.5); 7.4140 (0.5); 7.3419 (0.4); 7.3402 (0.4); 7.3337 (0.4); 7.3320 (0.5); 7.3263 (0.3); 7.2609 (11.9); 7.2190 (0.6); 7.2062 (1.0); 7.1933 (0.4); 7.0382 (0.5); 7.0365 (0.6); 7.0220 (0.9); 7.0076 (0.5); 7.0059 (0.5); 6.9320 (0.8); 6.9272 (0.8); 6.9178 (0.8); 6.9130 (0.8); 4.9992 (6.1); 3.0639 (8.5); 3.0293 (0.3); 3.0098 (7.7); 2.7180 (0.6); 1.5636 (20.8); 0.0053 (2.0); −0.00001 (50.0); −0.00056 (1.8)

X-027: ¹H-NMR(400.0 MHz, CDCl3):
δ = 8.1024 (1.6); 8.0962 (1.6); 7.7671 (0.8); 7.7609 (0.8); 7.7483 (0.9); 7.7459 (1.0); 7.7421 (0.9); 7.7396 (0.8); 7.7272 (0.8); 7.7209 (0.8); 7.4506 (0.6); 7.4463 (0.7); 7.4313 (1.2); 7.4270 (1.3); 7.4125 (0.8); 7.4080 (0.8); 7.3467 (0.6); 7.3424 (0.6); 7.3346 (0.6); 7.3261 (0.6); 7.3139 (0.6); 7.2607 (29.7); 7.2251 (0.8); 7.2057 (1.2); 7.1882 (0.5); 7.0464 (0.8); 7.0431 (0.8); 7.0254 (0.8); 7.0217 (1.3); 7.0179 (0.8); 7.0004 (0.8); 6.9970 (0.9); 6.9374 (1.1); 6.9313 (1.1); 6.9161 (1.1); 6.9086 (1.0); 5.2999 (1.9); 5.0000 (8.8); 3.0639 (13.5); 3.0304 (0.6); 3.0103 (11.2); 2.7183 (1.1); 1.5534 (16.0); 0.0080 (1.0); −0.0002 (39.0); −0.00085 (1.1)

VII-012: ¹H-NMR(400.2 MHz, d₆-DMSO):
δ = 8.2023 (4.4); 8.1969 (4.3); 7.9638 (1.3); 7.9576 (1.3); 7.9435 (2.4); 7.9379 (2.2); 7.9232 (1.5); 7.9172 (1.3); 7.5759 (1.4); 7.5566 (2.8); 7.5407 (1.6); 7.5370 (1.6); 7.5115 (0.7); 7.5075 (0.7); 7.4927 (1.6); 7.4744 (1.7); 7.4594 (1.0); 7.3366 (2.1); 7.3166 (5.3); 7.3001 (4.4); 7.2949 (5.0); 7.2795 (2.8); 7.2725 (2.9); 6.6237 (0.4); 4.9352 (14.9); 4.1926 (2.3); 4.1750 (7.2); 4.1572 (7.2); 4.1396 (2.5); 3.3408 (148.1); 3.3182 (6.1); 2.6698 (0.9); 2.5050 (122.2); 2.5010 (152.4); 2.4971 (114.5); 2.3279 (0.9); 1.2315 (0.4); 1.2029 (7.9); 1.1852 (16.0); 1.1675 (7.8); 1.1511 (0.6); −0.00021 (12.9)

VII-121: ¹H-NMR(400.6 MHz, CDCl3):
δ = 8.1020 (1.2); 8.1001 (1.8); 8.0980 (1.4); 8.0959 (1.4); 8.0939 (1.9); 8.0919 (1.3); 7.7612 (1.0); 7.7550 (1.0); 7.7425 (1.2); 7.7400 (1.2); 7.7362 (1.2); 7.7337 (1.2); 7.7213 (1.1); 7.7150 (1.1); 7.3961 (0.8); 7.3918 (0.9); 7.3769 (1.3); 7.3725 (1.6); 7.3578 (1.0); 7.3537 (1.2); 7.3443 (0.6); 7.3397 (0.6); 7.3375 (0.8); 7.3357 (0.7); 7.3331 (0.7); 7.3313 (0.6); 7.3253 (0.9); 7.3236 (0.6); 7.3209 (0.7); 7.3190 (0.6); 7.3169 (0.8); 7.3124 (0.6); 7.3047 (0.7); 7.3002 (0.6); 7.2621 (23.5); 7.2121 (0.9); 7.2105 (1.0); 7.2087 (1.0); 7.2072 (0.9); 7.1910 (1.4); 7.1891 (1.4); 7.1736 (0.6); 7.1719 (0.6); 7.1702 (0.6); 7.1687 (0.6); 7.0362 (1.0); 7.0329 (1.0); 7.0154 (0.9); 7.0115 (1.6); 7.0078 (1.0); 6.9902 (0.9); 6.9871 (0.8); 6.9369 (1.4); 6.9354 (1.4); 6.9295 (1.4); 6.9279 (1.4); 6.9157 (1.3); 6.9141 (1.3); 6.9082 (1.4); 6.9067 (1.3); 5.2999 (1.2); 5.2154 (0.8); 5.1980 (2.9); 5.1807 (3.0); 5.1633 (0.8); 4.2641 (1.1); 4.2623 (1.2); 4.2463 (3.6); 4.2445 (3.7); 4.2284 (3.8); 4.2268 (3.7); 4.2106 (1.3); 4.2091 (1.2); 1.6903 (1.4); 1.6729 (11.4); 1.2780 (7.4); 1.2602 (16.0); 1.2424 (7.4); −0.0002 (15.7)

II-011: ¹H-NMR(400.2 MHz, d₆-DMSO):
δ = 8.5190 (3.1); 8.5118 (3.1); 7.9363 (0.9); 7.9289 (0.8); 7.9146 (2.0); 7.9072 (1.8); 7.8929 (1.3); 7.8856 (1.1); 7.8187 (1.8); 7.8078 (1.9); 7.7967 (1.3); 7.7858 (1.2); 7.5518 (0.7); 7.5368 (0.8); 7.5297 (1.5); 7.5148 (1.5); 7.5077 (0.9); 7.4927 (0.8); 7.3699 (0.8); 7.3630 (0.8); 7.3471 (1.0); 7.3413 (1.2); 7.3364 (1.0); 7.3206 (0.8); 7.3138 (0.8); 7.1899 (0.7); 7.1863 (0.7); 7.1696 (1.2); 7.1503 (0.6); 7.1473 (0.6); 7.1432 (0.5); 5.1198 (5.9); 3.7175 (16.0); 3.3141 (32.9); 3.1171 (15.0); 2.9230 (0.4); 2.6731 (0.4); 2.6686 (0.5); 2.6642 (0.4); 2.5082 (29.0); 2.5040 (59.2); 2.4995 (79.6); 2.4951 (57.5); 2.4910 (27.4); 2.3311 (0.3); 2.3264 (0.5); 2.3221 (0.3); 0.0066 (1.7); −0.00014 (41.8); −0.00097 (1.7)

X-025: ¹H-NMR(300.1 MHz, d₆-DMSO):
δ = 8.2245 (2.2); 8.2164 (2.2); 7.9756 (0.8); 7.9672 (0.8); 7.9477 (1.2); 7.9393 (1.2); 7.9216 (0.8); 7.9132 (0.8); 7.6967 (0.7); 7.6766 (0.8); 7.6672 (1.4); 7.6472 (1.4); 7.6378 (0.8); 7.6178 (0.7); 7.4355 (0.7); 7.4262 (0.8); 7.4052 (0.9); 7.4000 (1.0); 7.3967 (1.0); 7.3911 (0.9); 7.3703 (0.7); 7.3610 (0.8); 7.3152 (1.4); 7.3064 (1.4); 7.2867 (1.3); 7.2774 (1.3); 7.2668 (0.5); 7.2619 (0.6); 7.2571 (0.5); 7.2352

(1.0); 7.2095 (0.5); 7.2054 (0.5); 5.1135 (5.6); 3.7149 (16.0); 3.3225 (13.2); 3.2987 (0.4); 3.1178 (14.6); 2.7277 (0.4); 2.5132 (25.0); 2.5073 (47.7); 2.5014 (62.5); 2.4955 (43.0); 2.4899 (19.8); 2.2712 (0.4); 2.0753 (0.8); 0.0109 (2.0); 0.0000 (49.7); −0.0111 (1.7)

X-023: $^1$H-NMR(300.1 MHz, $d_6$-DMSO):
δ = 10.7754 (0.4); 8.9808 (1.4); 8.1907 (2.0); 8.1828 (2.1); 7.9603 (0.6); 7.9523 (0.6); 7.9329 (1.1); 7.9250 (1.0); 7.9063 (0.7); 7.8976 (0.6); 7.6259 (0.5); 7.6050 (1.0); 7.5995 (1.1); 7.5738 (0.7); 7.5000 (0.7); 7.4744 (0.8); 7.4563 (0.5); 7.3530 (0.9); 7.3270 (1.5); 7.3193 (1.4); 7.3058 (1.9); 7.2970 (1.8); 7.2848 (1.4); 7.2785 (1.8); 7.2687 (1.3); 7.2570 (0.8); 5.0232 (0.5); 4.6580 (5.0); 3.3235 (20.9); 3.2996 (0.3); 2.7275 (0.4); 2.5134 (25.0); 2.5075 (49.4); 2.5015 (65.8); 2.4955 (44.9); 2.4897 (20.3); 2.2713 (0.4); 2.0751 (16.0); 0.0108 (2.2); −0.00001 (62.1); −0.0112 (1.8)

II-018: $^1$H-NMR(400.2 MHz, $d_6$-DMSO):
δ = 10.7883 (4.0); 10.1957 (0.8); 9.2151 (0.9); 8.9768 (7.6); 8.5191 (8.0); 8.5120 (8.1); 7.9350 (2.3); 7.9276 (2.1); 7.9133 (5.1); 7.9059 (4.9); 7.8916 (3.2); 7.8843 (3.0); 7.8098 (3.8); 7.7988 (4.0); 7.7879 (2.8); 7.7769 (2.5); 7.5817 (1.2); 7.5666 (1.5); 7.5598 (2.5); 7.5448 (2.7); 7.5380 (1.8); 7.5229 (1.6); 7.3770 (1.6); 7.3704 (1.8); 7.3485 (3.0); 7.3279 (1.7); 7.3212 (1.7); 7.1993 (1.4); 7.1824 (2.7); 7.1633 (1.6); 5.0262 (1.5); 4.6599 (16.0); 3.3180 (104.8); 3.2945 (0.9); 2.6732 (0.5); 2.6688 (0.7); 2.5085 (43.8); 2.5042 (89.4); 2.4998 (120.7); 2.4953 (87.1); 2.4911 (41.3); 2.3313 (0.5); 2.3267 (0.7); 2.3223 (0.5); 2.0728 (0.9); 0.1446 (0.4); 0.0064 (4.1); −0.00016 (103.0); −0.00099 (3.9); −0.1512 (0.4)

X-032: $^1$H-NMR(300.1 MHz, $d_6$-DMSO):
δ = 8.4432 (1.1); 8.4249 (2.3); 8.4067 (1.2); 8.1857 (4.1); 8.1775 (4.3); 7.9500 (1.5); 7.9416 (1.5); 7.9218 (2.3); 7.9136 (2.2); 7.8958 (1.7); 7.8874 (1.6); 7.6173 (1.6); 7.5967 (2.5); 7.5916 (3.2); 7.5713 (1.6); 7.5655 (1.8); 7.5194 (0.7); 7.5137 (0.7); 7.5026 (0.8); 7.4940 (1.6); 7.4873 (1.5); 7.4772 (1.5); 7.4676 (1.7); 7.4611 (1.2); 7.4497 (1.2); 7.4439 (0.9); 7.3384 (2.5); 7.3128 (6.5); 7.2972 (3.1); 7.2860 (3.3); 7.2779 (4.9); 7.2699 (2.9); 7.2505 (1.5); 7.2461 (1.5); 7.0701 (0.5); 6.8998 (0.4); 4.7462 (16.0); 3.3938 (3.2); 3.3727 (6.9); 3.3522 (6.8); 3.3313 (2.5); 2.7333 (0.6); 2.7271 (0.7); 2.7212 (0.6); 2.6922 (4.8); 2.6707 (10.0); 2.6488 (4.1); 2.5133 (48.4); 2.5074 (96.8); 2.5014 (129.3); 2.4955 (89.3); 2.4897 (41.2); 2.2775 (0.6); 2.2714 (0.8); 2.2656 (0.6); 2.0749 (0.8); 0.1952 (0.5); 0.0108 (4.6); −0.00001 (128.7); −0.0112 (4.1); −0.1989 (0.5)

II-008: $^1$H-NMR(400.2 MHz, $d_6$-DMSO):
δ = 8.5222 (5.3); 8.5151 (5.1); 8.4362 (1.5); 8.4223 (2.7); 8.4079 (1.3); 7.9354 (1.5); 7.9281 (1.4); 7.9138 (3.2); 7.9065 (2.9); 7.8921 (2.0); 7.8848 (1.7); 7.8052 (3.0); 7.7942 (3.2); 7.7834 (2.2); 7.7722 (2.1); 7.5768 (1.2); 7.5616 (1.5); 7.5546 (2.5); 7.5396 (2.4); 7.5327 (1.5); 7.5178 (1.1); 7.3675 (1.3); 7.3605 (1.4); 7.3445 (1.8); 7.3391 (2.2); 7.3183 (1.3); 7.3115 (1.2); 7.1816 (1.3); 7.1612 (2.2); 7.1386 (1.1); 4.7447 (16.0); 3.3833 (2.2); 3.3675 (5.8); 3.3522 (6.1); 3.3359 (3.6); 3.3169 (33.4); 2.6847 (4.9); 2.6685 (10.3); 2.6523 (4.4); 2.5038 (86.7); 2.4994 (114.4); 2.4951 (86.1); 2.3264 (0.7); 2.3224 (0.6); 0.9710 (1.1); 0.1442 (0.4); 0.0059 (4.6); −0.00019 (94.5); −0.00098 (5.8); −0.1512 (0.5)

VII-125: $^1$H-NMR(400.6 MHz, CDCl3):
δ = 8.1138 (1.7); 8.1078 (1.8); 7.6923 (0.6); 7.6858 (0.7); 7.6676 (0.9); 7.6527 (0.8); 7.6466 (0.7); 7.5189 (1.4); 7.2916 (0.7); 7.2878 (0.8); 7.2701 (0.6); 7.2693 (0.6); 7.2685 (0.9); 7.2677 (1.0); 7.2669 (1.2); 7.2604 (246.8); 7.2547 (2.8); 7.2531 (1.8); 7.2491 (1.1); 7.2467 (0.6); 7.2459 (0.6); 7.2255 (0.7); 7.1166 (2.2); 7.1107 (1.0); 7.1048 (2.4); 7.0994 (1.6); 7.0937 (3.8); 7.0878 (1.1); 7.0819 (3.6); 7.0376 (0.6); 7.0297 (3.9); 7.0237 (1.1); 7.0178 (0.7); 7.0098 (4.0); 7.0067 (2.6); 7.0040 (1.2); 6.9968 (1.6); 6.9928 (1.0); 6.9869 (2.4); 6.9807 (1.9); 6.9749 (1.6); 6.9611 (1.4); 6.9536 (1.4); 6.9520 (1.4); 4.9946 (16.0); 4.9834 (0.5); 4.7418 (0.9); 2.2719 (1.2); 2.1098 (2.0); 2.0463 (1.6); 1.4322 (11.9); 1.3325 (0.6); 1.2842 (0.9); 1.2775 (0.7); 1.2598 (1.6); 1.2549 (1.4); 1.2420 (0.6); 1.2390 (0.6); 0.1458 (0.6); 0.0310 (0.6); 0.0272 (0.7); 0.0128 (0.5); 0.0080 (5.4); −0.0002 (183.8); −0.00058 (1.8); −0.00085 (5.0); −0.1494 (0.5)

VII-125: $^1$H-NMR(400.0 MHz, CDCl3):
δ = 8.1086 (1.2); 7.6710 (0.6); 7.2600 (33.2); 7.1158 (1.2); 7.1040 (1.3); 7.0986 (1.0); 7.0930 (2.1); 7.0812 (2.0); 7.0283 (2.0); 7.0222 (0.6); 7.0084 (2.2); 6.9856 (1.4); 6.9799 (1.7); 6.9741 (1.0); 6.9590 (0.8); 6.9515 (0.8); 5.0064 (0.7); 4.9934 (7.9); 3.7544 (0.6); 2.2717 (1.8); 1.8572 (0.6); 1.4322 (16.0); 1.2544 (5.3); 0.8799 (0.8); 0.0080 (1.5); −0.0002 (51.4); −0.00085 (2.0)

VII-092: $^1$H-NMR(400.6 MHz, CDCl3):
δ = 8.1075 (2.6); 8.1055 (2.0); 8.1033 (2.1); 8.1012 (2.8); 8.0993 (1.8); 7.7663 (1.4); 7.7601 (1.3); 7.7476 (1.5); 7.7451 (1.7); 7.7414 (1.5); 7.7389 (1.6); 7.7265 (1.5); 7.7202 (1.4); 7.4194 (1.0); 7.4151 (1.2); 7.4002 (1.8); 7.3958 (2.1); 7.3813 (1.3); 7.3770 (1.5); 7.3629 (0.7); 7.3585 (0.7); 7.3507 (0.7); 7.3462 (0.8); 7.3440 (1.1); 7.3422 (0.9); 7.3396 (1.0); 7.3377 (0.9); 7.3318 (1.1); 7.3301 (0.9); 7.3274 (1.0); 7.3255 (0.9); 7.3234 (1.1); 7.3188 (0.9); 7.3112 (1.0); 7.3067 (0.8); 7.2661 (0.6); 7.2654 (0.7); 7.2645 (1.1); 7.2611 (72.6); 7.2556 (0.9); 7.2532 (0.5); 7.2161 (1.1); 7.2144 (1.3); 7.2126 (1.4); 7.2112 (1.3); 7.1929 (2.0); 7.1775 (0.8); 7.1758 (0.9); 7.1741 (0.9); 7.1727 (0.8); 7.0402 (1.4); 7.0370 (1.3); 7.0195 (1.3); 7.0156 (2.2); 7.0119 (1.4); 6.9975 (0.5); 6.9943 (1.3); 6.9911 (1.2); 6.9466 (1.8); 6.9450 (1.9); 6.9392 (1.9); 6.9376 (1.8); 6.9254 (1.8); 6.9238 (1.8); 6.9179 (1.8); 6.9163 (1.8); 5.3159 (1.0); 5.2984 (4.0); 5.2809 (4.1); 5.2635 (1.0); 2.2717 (0.8); 2.1083 (2.3); 2.0081 (16.0); 1.7477 (13.7); 1.7302 (13.6); 1.4321 (7.8); 1.3323 (0.5); 1.2841 (0.8); 1.2541 (1.2); 0.0080 (1.1); −0.0002 (46.1); −0.0085 (1.4)

X-020: $^1$H-NMR(400.6 MHz, CDCl3):
δ = 8.1258 (1.0); 8.1196 (1.1); 7.6723 (0.6); 7.6680 (0.5); 7.2666 (0.5); 7.2657 (0.6); 7.2607 (81.1); 7.1447 (1.3); 7.1389 (0.5); 7.1329 (1.4); 7.1274 (1.0); 7.1218 (2.2); 7.1159 (0.7); 7.1101 (2.1); 7.0481 (2.2); 7.0422 (0.8); 7.0364 (0.6); 7.0282 (2.6); 7.0253 (2.0); 7.0226 (1.0); 7.0171 (0.5); 7.0112 (0.7); 7.0055 (1.5); 6.9971 (0.7); 6.9894 (0.9); 6.9880 (0.9); 6.9819 (0.9); 6.9803 (0.9); 6.9683 (0.8); 6.9668 (0.9); 6.9607 (0.8); 6.9592 (0.8); 5.3003 (1.0); 4.9079 (6.8); 4.1721 (3.2); 4.1589 (3.2); 3.7971 (16.0); 1.5490 (2.7); 1.4322 (1.2); 0.0080 (1.2); −0.0002 (48.1); −0.00085 (1.5)

X-019: $^1$H-NMR(300.1 MHz, $d_6$-DMSO):
δ = 8.1940 (2.1); 8.1858 (2.2); 7.9649 (0.8); 7.9566 (0.8); 7.9368 (1.2); 7.9285 (1.1); 7.9108 (0.8); 7.9023 (0.8); 7.5938 (0.8); 7.5734 (1.3); 7.5679 (1.7); 7.5477 (0.9); 7.5420 (0.9); 7.5143 (0.4); 7.5085 (0.4); 7.4972 (0.4); 7.4885 (0.8); 7.4820 (0.7); 7.4719 (0.8); 7.4619 (0.8); 7.4556 (0.6); 7.4446 (0.6); 7.4387 (0.5); 7.3412 (1.2); 7.3156 (3.3); 7.3036 (1.6); 7.2946 (2.0); 7.2890 (1.8); 7.2809 (1.5); 7.2765

(2.2); 7.2672 (1.3); 7.2533 (0.8); 7.2491 (0.7); 5.1191 (5.6); 3.7166 (16.0); 3.3247 (5.8); 3.1180 (14.4); 2.5135 (11.7); 2.5076 (23.1); 2.5017 (30.5); 2.4958 (20.9); 2.4900 (9.6); 2.0755 (2.5); 0.0108 (1.3); −0.0001 (33.9);−0.0112 (1.2)

VII-068: $^1$H-NMR(300.1 MHz, $d_6$-DMSO):
δ = 11.4070 (2.8); 8.1956 (4.8); 8.1875 (5.0); 7.9635 (1.8); 7.9551 (1.6); 7.9354 (2.8); 7.9271 (2.5); 7.9094 (1.9); 7.9010 (1.8); 7.6049 (1.0); 7.5989 (1.7); 7.5777 (2.7); 7.5730 (3.6); 7.5526 (1.8); 7.5469 (2.1); 7.5238 (0.7); 7.5181 (0.7); 7.5064 (0.8); 7.4974 (1.8); 7.4811 (1.7); 7.4715 (1.9); 7.4655 (1.2); 7.4542 (1.3); 7.4482 (1.0); 7.3441 (2.7); 7.3192 (7.2); 7.3044 (3.6); 7.2944 (6.3); 7.2762 (3.2); 7.2679 (3.1); 7.2598 (1.9); 4.6607 (6.3); 3.6087 (16.0); 3.3243 (10.0); 2.7273 (0.6); 2.5132 (35.5); 2.5074 (70.6); 2.5014 (93.6); 2.4955 (64.8); 2.4898 (29.9); 2.2776 (0.4); 2.2714 (0.6); 0.1952 (0.3); 0.0108 (3.2); −0.0002 (85.8); −0.0112 (2.8); −0.1987 (0.4)

X-024: $^1$H-NMR(300.1 MHz, $d_6$-DMSO):
δ = 11.3996 (1.0); 11.3579 (0.4); 8.2248 (4.7); 8.2167 (5.3); 7.9740 (1.7); 7.9657 (1.6); 7.9462 (2.8); 7.9375 (2.6); 7.9197 (2.1); 7.9114 (1.9); 7.7030 (1.4); 7.6828 (1.5); 7.6733 (3.0); 7.6535 (3.0); 7.6441 (1.8); 7.6244 (1.6); 7.4447 (1.3); 7.4357 (1.5); 7.4147 (1.7); 7.4084 (2.1); 7.4007 (1.9); 7.3797 (1.4); 7.3704 (1.5); 7.3172 (3.1); 7.3089 (3.1); 7.2889 (3.0); 7.2792 (3.1); 7.2693 (1.4); 7.2422 (2.2); 7.2121 (1.3); 5.0676 (0.4); 4.6544 (6.3); 3.6063 (16.0); 3.3236 (43.4); 3.2993 (1.4); 2.7332 (1.0); 2.7275 (1.4); 2.5545 (0.5); 2.5133 (82.7); 2.5074 (163.6); 2.5014 (216.9); 2.4955 (148.0); 2.4896 (66.7); 2.2714 (1.3); 2.2655 (1.0); 2.0752 (0.9); 1.7524 (0.3); 0.1956 (0.8); 0.0446 (0.5); 0.0108 (9.8); −0.0002 (244.1); −0.0113 (6.4);−0.1986 (0.8)

X-028: $^1$H-NMR(400.2 MHz, $d_6$-DMSO):
δ = 10.7845 (1.6); 10.1993 (0.9); 9.2209 (1.0); 8.9852 (4.4); 8.2173 (7.3); 8.2120 (7.2); 7.9608 (2.0); 7.9549 (2.0); 7.9403 (3.7); 7.9348 (3.5); 7.9202 (2.3); 7.9143 (1.9); 7.7157 (1.2); 7.7003 (1.7); 7.6937 (2.8); 7.6789 (3.0); 7.6720 (2.2); 7.6568 (1.8); 7.4305 (1.6); 7.4240 (1.9); 7.4025 (3.2); 7.3820 (1.8); 7.3757 (2.0); 7.3120 (4.4); 7.3055 (4.5); 7.2906 (4.3); 7.2842 (4.4); 7.2695 (1.6); 7.2475 (3.0); 7.2277 (1.9); 5.0178 (1.8); 4.6510 (16.0); 3.3244 (81.6); 3.3015 (1.3); 2.6735 (1.2); 2.6693 (1.0); 2.6648 (0.8); 2.5090 (63.9); 2.5047 (132.3); 2.5003 (179.2); 2.4958 (129.8); 2.4915 (61.6); 2.3315 (0.8); 2.3272 (1.0); 2.3227 (0.7); 2.0740 (5.5); 0.1445 (0.5); 0.0064 (4.3); −0.00016 (103.0); −0.00098 (3.7); −0.1509 (0.4)

X-029: $^1$H-NMR(400.2 MHz, $d_6$-DMSO):
δ = 8.4379 (1.1); 8.4234 (2.2); 8.4089 (1.1); 8.2135 (4.0); 8.2074 (4.2); 7.9520 (1.4); 7.9456 (1.4); 7.9309 (2.2); 7.9259 (2.0); 7.9247 (2.0); 7.9113 (1.6); 7.9051 (1.5); 7.7063 (1.2); 7.6913 (1.3); 7.6842 (2.4); 7.6693 (2.4); 7.6622 (1.4); 7.6472 (1.3); 7.4212 (1.2); 7.4143 (1.3); 7.3986 (1.5); 7.3947 (1.8); 7.3920 (1.7); 7.3881 (1.6); 7.3725 (1.3); 7.3655 (1.3); 7.3125 (2.3); 7.3063 (2.4); 7.2911 (2.3); 7.2849 (2.3); 7.2519 (1.0); 7.2485 (1.0); 7.2448 (0.9); 7.2420 (0.9); 7.2284 (1.7); 7.2261 (1.6); 7.2222 (1.6); 7.2092 (0.9); 7.2058 (1.0); 7.2021 (0.8); 7.1991 (0.8); 4.7401 (16.0); 3.3819 (1.8); 3.3660 (5.1); 3.3507 (5.4); 3.3345 (3.1); 3.3254 (11.5); 2.6826 (4.8); 2.6664 (10.5); 2.6501 (4.4); 2.5097 (18.3); 2.5053 (38.6); 2.5007 (53.6); 2.4961 (37.6); 2.4916 (17.6); 2.0740 (15.9); 0.0070 (1.7); −0.00011 (52.8); −0.00095 (1.7)

V-006: $^1$H-NMR(400.0 MHz, CDCl3):
δ = 9.0195 (2.4); 9.0162 (2.3); 8.8404 (2.2); 8.8274 (2.3); 7.7711 (1.6); 7.7676 (1.6); 7.7581 (1.6); 7.7543 (1.6); 7.5193 (0.8); 7.5047 (1.1); 7.5008 (1.1); 7.4859 (0.7); 7.3401 (0.6); 7.3321 (0.6); 7.2602 (73.3); 7.2462 (0.8); 7.2297 (1.2); 7.0158 (0.8); 6.9959 (1.0); 6.9909 (1.0); 6.9788 (1.0); 6.9660 (0.6); 5.3368 (0.6); 5.3197 (1.9); 5.3022 (2.0); 5.2848 (0.6); 5.0075 (0.6); 3.7675 (0.7); 3.7507 (1.8); 3.7342 (0.8); 2.2716 (1.7); 1.8715 (0.7); 1.8639 (0.8); 1.8550 (2.1); 1.8385 (0.8); 1.7555 (7.1); 1.7381 (7.2); 1.4323 (16.0); 1.3328 (0.8); 1.2841 (1.1); 1.2546 (6.3); 0.8803 (1.0); 0.0080 (2.6); −0.0002 (100.5); −0.0085 (3.0)

VI-014: $^1$H-NMR(400.0 MHz, CDCl3):
δ = 9.1946 (6.4); 8.6892 (9.9); 7.4599 (1.8); 7.4559 (1.7); 7.4403 (3.2); 7.4215 (1.9); 7.4173 (1.7); 7.3790 (1.2); 7.3642 (2.1); 7.3510 (2.0); 7.3313 (1.3); 7.2620 (17.5); 7.2413 (2.4); 7.2220 (3.4); 7.2024 (1.4); 7.0481 (2.1); 7.0234 (3.0); 7.0019 (1.8); 5.3199 (1.5); 5.3023 (4.1); 5.2847 (4.0); 5.2673 (1.2); 2.0084 (16.0); 1.7546 (14.7); 1.7371 (14.1); −0.0002 (22.9); −0.00084 (1.2)

VII-076: $^1$H-NMR(400.0 MHz, CDCl3):
δ = 8.1891 (2.5); 8.1828 (2.4); 7.7082 (1.0); 7.7019 (1.1); 7.6895 (1.4); 7.6870 (1.4); 7.6833 (1.3); 7.6683 (1.1); 7.6621 (1.2); 7.3434 (0.8); 7.3366 (1.0); 7.3213 (3.6); 7.3028 (5.3); 7.2986 (3.2); 7.2944 (2.0); 7.2838 (1.6); 7.2602 (97.8); 7.1496 (3.3); 7.1450 (3.5); 7.1288 (3.0); 7.1253 (2.9); 6.9962 (0.5); 6.9641 (1.7); 6.9580 (1.7); 6.9440 (1.6); 6.9354 (1.5); 5.0025 (16.0); 2.0080 (2.7); 0.0079 (3.6); −0.0002 (130.2); −0.00085 (3.7)

VI-015: $^1$H-NMR(400.0 MHz, CDCl3):
δ = 9.2050 (8.2); 8.6671 (13.7); 7.3558 (0.9); 7.3474 (1.3); 7.3427 (1.0); 7.3334 (5.1); 7.3236 (1.8); 7.3198 (4.4); 7.3146 (11.2); 7.3103 (3.3); 7.3012 (1.9); 7.2977 (1.3); 7.2608 (50.8); 7.1463 (5.3); 7.1410 (4.6); 7.1360 (1.6); 7.1315 (2.0); 7.1258 (4.7); 7.1220 (4.2); 5.3524 (1.2); 5.3351 (4.5); 5.3175 (4.6); 5.3001 (1.2); 2.0081 (11.7); 1.7621 (16.0); 1.7446 (15.9); 0.0080 (1.9); −0.0002 (67.0); −0.00085 (2.1)

VII-077: $^1$H-NMR(400.0 MHz, CDCl3):
δ = 8.1262 (2.7); 8.1200 (2.7); 7.6823 (1.1); 7.6761 (1.1); 7.6614 (1.5); 7.6551 (1.5); 7.6422 (1.2); 7.6361 (1.2); 7.3974 (0.9); 7.3930 (1.1); 7.3780 (1.9); 7.3738 (2.0); 7.3591 (1.2); 7.3546 (1.3); 7.3279 (0.6); 7.3236 (0.5); 7.3159 (0.6); 7.3092 (1.0); 7.3045 (0.9); 7.2968 (1.1); 7.2886 (1.0); 7.2839 (1.3); 7.2763 (0.8); 7.2720 (0.7); 7.2607 (35.8); 7.1909 (1.3); 7.1717 (2.0); 7.1545 (0.8); 7.0292 (1.3); 7.0260 (1.3); 7.0083 (1.2); 7.0044 (2.0); 7.0006 (1.3); 6.9830 (1.2); 6.9799 (1.1); 6.9054 (1.8); 6.8980 (1.7); 6.8841 (1.7); 6.8778 (1.6); 4.9148 (16.0); 2.0080 (5.9); 1.6008 (0.5); 1.5873 (1.1); 1.5798 (1.1); 1.5746 (0.7); 1.5667 (1.8); 1.5532 (1.1); 1.5458 (1.2); 1.5325 (0.6); 0.7989 (0.8); 0.7942 (0.6); 0.7854 (1.8); 0.7813 (2.8); 0.7726 (2.0); 0.7649 (2.5); 0.7595 (2.6); 0.7519 (1.9); 0.7402 (0.8); 0.7328 (1.8); 0.7236 (3.0); 0.7194 (3.8); 0.7116 (3.1); 0.7066 (2.8); 0.6931 (0.8); 0.0080 (1.2); −0.0002 (47.0); −0.00085 (1.4)

VII-101: $^1$H-NMR(400.2 MHz, $d_6$-DMSO):
δ = 8.2339 (4.3); 8.2284 (4.4); 7.9759 (1.4); 7.9698 (1.4); 7.9553 (2.4); 7.9499 (2.3); 7.9354 (1.5); 7.9293 (1.4); 7.6786 (1.1); 7.6634 (1.4); 7.6565 (2.3); 7.6416 (2.3); 7.6346 (1.5); 7.6196 (1.2); 7.4356 (1.2); 7.4289 (1.4); 7.4086 (2.1); 7.3869 (1.3); 7.3802 (1.3); 7.3117 (2.6); 7.3054 (2.6); 7.2904 (2.5);

7.2841 (2.4); 7.2590 (1.2); 7.2553 (1.2); 7.2385 (2.1); 7.2193 (1.1); 7.2164 (1.1); 5.0762 (0.4); 4.9338 (15.0); 4.7763 (0.4); 4.1966 (2.5); 4.1789 (7.3); 4.1611 (7.4); 4.1434 (2.6); 3.3241 (9.6); 2.5524 (0.4); 2.5082 (20.8); 2.5040 (26.3); 2.4999 (20.1); 1.2361 (0.4); 1.2077 (8.0); 1.1900 (16.0); 1.1723 (7.8); 1.1618 (1.0); 1.1439 (0.4); 0.0013 (9.1)

VII-100: $^1$H-NMR(400.2 MHz, d$_6$-DMSO):

δ = 13.0482 (1.4); 12.9628 (0.4); 8.2295 (11.1); 8.2240 (11.5); 7.9737 (3.3); 7.9675 (3.6); 7.9529 (6.0); 7.9477 (5.8); 7.9331 (3.8); 7.9269 (3.6); 7.6900 (2.3); 7.6679 (5.0); 7.6528 (5.0); 7.6457 (3.2); 7.6310 (2.6); 7.4280 (2.8); 7.4211 (3.2); 7.3992 (5.2); 7.3788 (3.2); 7.3721 (3.0); 7.3100 (7.0); 7.3037 (7.1); 7.2887 (6.9); 7.2821 (6.7); 7.2570 (3.2); 7.2364 (5.4); 7.2152 (2.8); 5.0206 (0.5); 4.8129 (16.0); 3.5084 (0.6); 3.4258 (0.3); 3.3208 (50.6); 2.9525 (1.1); 2.8909 (0.4); 2.8419 (1.0); 2.7318 (0.5); 2.6757 (2.3); 2.6711 (3.0); 2.6666 (2.4); 2.5110 (201.9); 2.5066 (405.8); 2.5022 (549.1); 2.4977 (396.3); 2.4935 (189.7); 2.3640 (0.3); 2.3333 (2.2); 2.3291 (3.2); 2.3245 (2.2); 2.2067 (0.4); 2.0754 (2.7); 1.7541 (7.3); 1.2369 (0.8); 0.7594 (0.5); 0.1470 (1.5); 0.1273 (0.3); 0.0700 (0.8); 0.0614 (0.7); 0.0089 (17.2); 0.0009 (369.4); −0.00074 (13.3); −0.1485 (1.6)

II-014: $^1$H-NMR(400.2 MHz, d$_6$-DMSO):

δ = 8.5108 (4.8); 8.5038 (4.7); 7.9316 (1.3); 7.9244 (1.2); 7.9099 (2.8); 7.9026 (2.6); 7.8883 (1.7); 7.8810 (1.5); 7.7955 (2.8); 7.7844 (2.9); 7.7736 (2.2); 7.7626 (2.0); 7.4567 (2.5); 7.4398 (4.6); 7.4374 (4.6); 7.4215 (4.0); 7.4042 (1.2); 7.2880 (2.4); 7.2682 (4.8); 7.2468 (2.5); 7.2406 (2.4); 7.2189 (1.5); 5.0908 (0.3); 4.9471 (15.5); 4.7827 (0.4); 4.1976 (2.6); 4.1799 (7.5); 4.1622 (7.4); 4.1444 (2.5); 3.3408 (4.3); 3.3171 (0.5); 2.5075 (14.7); 2.5039 (17.9); 2.0789 (3.7); 1.2055 (8.2); 1.1878 (16.0); 1.1701 (7.6); 1.1557 (0.5); 0.0000 (4.9)

II-015: $^1$H-NMR(400.2 MHz, d$_6$-DMSO):

δ = 13.1071 (1.8); 8.5101 (8.5); 8.5031 (8.8); 7.9317 (2.2); 7.9244 (2.1); 7.9100 (5.1); 7.9028 (4.8); 7.8883 (3.2); 7.8811 (3.0); 7.7953 (4.7); 7.7843 (5.1); 7.7735 (3.8); 7.7624 (3.6); 7.4731 (2.3); 7.4537 (5.8); 7.4350 (5.4); 7.4244 (3.4); 7.4193 (3.0); 7.4044 (2.0); 7.2909 (3.6); 7.2715 (5.7); 7.2616 (4.0); 7.2552 (3.2); 7.2354 (4.1); 7.2142 (2.8); 4.8445 (16.0); 3.3429 (1.7); 2.6725 (0.4); 2.5077 (46.9); 2.5035 (61.6); 2.4992 (46.1); 2.3305 (0.4); 2.3259 (0.3); 2.0781 (1.4); 0.0080 (0.7); 0.0000 (16.6); −0.0082 (1.0)

VIII-003: $^1$H-NMR(400.0 MHz, CDCl3):

δ = 8.1928 (2.8); 8.1798 (2.9); 7.4342 (0.8); 7.4298 (1.0); 7.4149 (1.5); 7.4106 (1.8); 7.4029 (0.6); 7.3962 (1.0); 7.3914 (1.5); 7.3838 (0.9); 7.3795 (0.7); 7.3716 (1.0); 7.3654 (0.7); 7.3633 (0.8); 7.3588 (0.6); 7.3510 (0.8); 7.3465 (0.6); 7.2618 (29.0); 7.2497 (1.1); 7.2481 (1.2); 7.2287 (1.7); 7.2111 (0.7); 7.0741 (1.2); 7.0711 (2.3); 7.0672 (2.1); 7.0633 (1.3); 7.0581 (1.3); 7.0538 (2.8); 7.0500 (2.8); 7.0457 (1.2); 7.0282 (1.0); 7.0249 (0.9); 6.8730 (1.9); 6.8698 (3.0); 5.3000 (1.7); 4.9006 (16.0); 4.2964 (2.0); 4.2786 (6.2); 4.2607 (6.3); 4.2429 (2.1); 1.3074 (7.6); 1.2896 (15.4); 1.2718 (7.4); −0.0002 (17.4); −0.0085 (0.5)

II-012: $^1$H-NMR(400.0 MHz, CDCl3):

δ = 8.3057 (3.0); 8.2985 (3.0); 7.6718 (1.4); 7.6608 (1.4); 7.6489 (1.7); 7.6391 (1.8); 7.4769 (1.4); 7.4696 (1.7); 7.4531 (2.0); 7.4486 (3.1); 7.4350 (1.8); 7.4285 (1.5); 7.2979 (0.5); 7.2912 (0.8); 7.2866 (0.8); 7.2792 (0.9); 7.2707 (1.0); 7.2601 (41.3); 7.2542 (0.9); 7.1975 (1.2); 7.1780 (1.7); 7.1592 (0.7); 6.9821 (1.1); 6.9787 (1.1); 6.9614 (1.1); 6.9567 (1.5); 6.9530 (1.2); 6.9357 (1.0); 6.9322 (0.9); 5.2998 (1.2); 4.9012 (16.0); 4.2881 (1.9); 4.2703 (6.2); 4.2524 (6.3); 4.2434 (0.5); 4.2345 (2.2); 1.5404 (12.3); 1.3112 (0.6); 1.3032 (7.7); 1.2933 (1.3); 1.2854 (15.8); 1.2755 (0.8); 1.2675 (7.6); 1.2555 (0.8); 0.0690 (0.6); 0.0080 (1.4); −0.0002 (54.5); −0.00085 (1.6)

X-021-a: $^1$H-NMR(400.0 MHz, d$_6$-DMSO):

δ = 4.7863 (1.2); 3.8307 (0.6); 3.8161 (0.6); 3.3214 (16.0); 2.5102 (7.3); 2.5057 (16.0); 2.5012 (22.6); 2.4966 (16.1); 2.4921 (7.4); −0.0002 (10.8)

II-013: $^1$H-NMR(400.0 MHz, CDCl3):

δ = 8.3002 (2.1); 8.2932 (2.0); 7.7156 (1.0); 7.7047 (1.1); 7.6937 (1.2); 7.6830 (1.2); 7.5369 (0.6); 7.5329 (0.6); 7.5178 (1.2); 7.5134 (1.2); 7.5014 (1.0); 7.4943 (1.5); 7.4811 (1.1); 7.4740 (1.0); 7.4599 (0.6); 7.4526 (0.6); 7.3256 (0.6); 7.3091 (0.7); 7.3010 (0.5); 7.2605 (19.9); 7.2409 (0.9); 7.2211 (1.2); 7.2031 (0.5); 7.1233 (0.6); 7.0014 (0.7); 6.9982 (0.7); 6.9764 (1.0); 6.9552 (0.6); 5.2998 (2.1); 4.8952 (8.7); 4.1777 (4.1); 4.1643 (4.0); 3.7932 (16.0); 1.5459 (4.8); 1.2553 (0.8); 0.0079 (1.0); −0.0002 (26.9); −0.00085 (1.0)

VIII-009: $^1$H-NMR(400.0 MHz, CDCl3):

δ = 8.2091 (1.7); 8.1961 (1.8); 7.4876 (0.5); 7.4833 (0.6); 7.4683 (1.0); 7.4641 (1.1); 7.4495 (0.6); 7.4451 (0.7); 7.4083 (0.5); 7.3960 (0.5); 7.3877 (0.5); 7.2793 (0.7); 7.2622 (9.5); 7.0873 (1.0); 7.0841 (1.0); 7.0755 (1.0); 7.0716 (1.4); 7.0673 (1.2); 7.0625 (1.9); 7.0587 (1.9); 7.0548 (0.8); 7.0413 (0.6); 7.0380 (0.6); 6.8815 (1.8); 5.3001 (1.4); 4.8849 (8.0); 4.1812 (3.7); 4.1678 (3.6); 3.7985 (16.0); 1.5735 (2.1); −0.0002 (10.8)

VII-044: $^1$H-NMR(400.0 MHz, CDCl3):

δ = 8.1913 (0.6); 8.1782 (0.6); 7.2594 (55.4); 7.2497 (0.6); 7.0701 (0.5); 7.0529 (0.7); 7.0490 (0.7); 6.8677 (0.7); 4.8991 (3.6); 4.2780 (1.4); 4.2601 (1.4); 2.0048 (0.5); 1.5328 (16.0); 1.3067 (1.7); 1.2889 (3.5); 1.2711 (1.7); 0.0079 (0.9); −0.0002 (28.2); −0.00085 (1.0)

VII-046: $^1$H-NMR(400.2 MHz, d$_6$-DMSO):

δ = 8.0577 (2.5); 8.0548 (2.8); 7.9509 (2.6); 7.9480 (2.6); 7.8809 (0.7); 7.8761 (0.8); 7.8636 (0.8); 7.8588 (0.8); 7.7505 (0.4); 7.7451 (0.4); 7.7384 (0.4); 7.7304 (0.6); 7.7237 (0.5); 7.7170 (0.5); 7.7117 (0.4); 7.5583 (0.8); 7.5363 (0.7); 7.5317 (0.9); 7.5098 (0.6); 5.3171 (5.5); 3.7244 (16.0); 3.3315 (7.6); 2.5237 (0.4); 2.5149 (6.0); 2.5105 (12.3); 2.5060 (16.2); 2.5014 (11.6); 2.4968 (5.5); 0.0080 (0.4); −0.0002 (12.6); −0.00085 (0.4)

VII-128: $^1$H-NMR(400.0 MHz, DMSO_5 mm):

δ = 3.3527 (16.0); 2.5212 (0.6); 2.5125 (4.3); 2.5080 (9.0); 2.5034 (12.4); 2.4987 (8.7); 2.4941 (3.8); 1.5698 (1.0); 1.5523 (0.9); −0.0002 (2.3)

VII-114: $^1$H-NMR(400.0 MHz, CDCl3):

δ = 9.9314 (9.5); 8.0532 (2.4); 8.0473 (2.5); 7.8830 (1.1); 7.8767 (1.0); 7.8619 (1.4); 7.8580 (1.3); 7.8557 (1.2); 7.8431 (1.1); 7.8369 (1.0); 7.4498 (0.9); 7.4455 (1.1); 7.4305 (1.7); 7.4265 (2.0); 7.4182 (0.6); 7.4112 (1.3); 7.4076 (1.6); 7.4035 (1.1); 7.3905 (1.1); 7.3831 (0.9); 7.3785 (0.6); 7.3704 (0.8); 7.3661 (0.6); 7.2625 (8.0); 7.2543 (1.4); 7.2349 (2.0); 7.2157 (0.8); 7.0739 (1.2); 7.0708 (1.2); 7.0528 (1.2); 7.0494 (2.0); 7.0460 (1.2); 7.0281 (1.1); 7.0250 (1.0); 6.9664 (1.7); 6.9592 (1.7); 6.9451 (1.6);

6.9378 (1.6); 5.2998 (2.6); 4.9546 (16.0); 4.3048 (2.1); 4.2870 (6.3); 4.2691 (6.3); 4.2513 (2.1); 1.5705 (5.3); 1.3125 (7.2); 1.2946 (14.3); 1.2768 (6.9); 0.0078 (0.5); −0.0002 (11.6)

X-034: $^1$H-NMR(400.6 MHz, CDCl3):

δ = 8.4434 (1.3); 8.4367 (1.3); 8.2854 (1.5); 7.4463 (0.7); 7.4424 (0.8); 7.4217 (1.0); 7.4172 (0.8); 7.4148 (0.8); 7.4104 (0.7); 7.3994 (0.8); 7.3950 (0.8); 7.3925 (0.8); 7.3881 (0.7); 7.2628 (8.3); 7.2390 (0.6); 7.2197 (0.9); 7.0564 (0.5); 7.0534 (0.5); 7.0354 (0.5); 7.0318 (0.8); 7.0283 (0.6); 5.3003 (10.1); 5.0650 (0.8); 5.0588 (0.9); 4.9961 (0.6); 4.9872 (0.6); 3.6885 (16.0); 2.0452 (1.6); 1.5954 (1.2); 1.2594 (1.0); −0.0002 (12.7)

X-037: $^1$H-NMR(400.6 MHz, CDCl3):

δ = 8.4441 (1.4); 8.4383 (1.5); 8.2841 (1.7); 7.4597 (0.7); 7.4554 (0.8); 7.4405 (1.4); 7.4364 (1.6); 7.4218 (1.4); 7.4177 (1.7); 7.4158 (1.7); 7.4128 (1.0); 7.4086 (0.7); 7.4000 (0.6); 7.3959 (0.9); 7.3931 (1.2); 7.3905 (0.9); 7.3863 (0.7); 7.3573 (0.8); 7.3529 (0.7); 7.3451 (0.8); 7.3407 (0.8); 7.3380 (0.8); 7.3327 (0.6); 7.3250 (0.6); 7.3206 (0.5); 7.2640 (9.1); 7.2396 (1.1); 7.2377 (1.2); 7.2180 (1.8); 7.2010 (0.7); 7.1992 (0.7); 7.0551 (0.9); 7.0525 (0.9); 7.0308 (1.5); 7.0091 (0.8); 7.0065 (0.8); 5.3004 (12.2); 4.9332 (2.6); 4.9226 (5.3); 3.8394 (0.9); 3.8206 (3.1); 3.8022 (3.1); 3.7834 (0.9); 3.7236 (14.2); 3.7177 (16.0); 3.6972 (0.9); 3.6218 (0.8); 3.5962 (0.7); 3.5756 (0.7); 3.1968 (0.6); 3.1780 (0.8); 3.1593 (0.6); 3.0951 (0.6); 3.0776 (0.7); 3.0583 (0.5); 2.2890 (0.8); 2.2709 (0.8); 2.2582 (0.6); 2.2436 (0.7); 2.2044 (0.6); 2.1856 (0.9); 2.1725 (0.6); 2.1646 (1.1); 2.1449 (1.0); 2.0449 (1.9); 1.6275 (1.9); 1.2770 (0.6); 1.2592 (1.3); 1.2413 (0.5); −0.0002 (14.8)

X-035: $^1$H-NMR(400.6 MHz, CDCl3):

δ = 8.4410 (1.7); 8.4342 (1.7); 8.2798 (1.9); 8.2762 (1.4); 7.4954 (0.5); 7.4804 (0.9); 7.4762 (0.9); 7.4615 (0.6); 7.4571 (0.6); 7.4161 (0.9); 7.4117 (0.9); 7.4092 (0.8); 7.4048 (0.8); 7.3938 (0.7); 7.3894 (0.9); 7.3870 (0.8); 7.3826 (0.8); 7.3529 (0.5); 7.3406 (0.6); 7.2620 (11.4); 7.2396 (0.7); 7.2202 (1.0); 7.0464 (0.6); 7.0432 (0.6); 7.0258 (0.6); 7.0217 (1.0); 7.0179 (0.6); 7.0004 (0.5); 6.9972 (0.5); 5.3003 (6.3); 5.0301 (0.8); 4.9943 (2.8); 4.9679 (2.8); 4.9321 (1.1); 4.8970 (0.6); 4.8393 (0.5); 4.5900 (0.5); 4.5809 (0.6); 4.5698 (0.6); 4.5593 (0.6); 3.7291 (4.4); 3.7250 (16.0); 3.7143 (0.7); 3.7014 (0.6); 3.6490 (0.7); 2.1895 (0.5); 2.0453 (1.8); 2.0317 (0.8); 2.0168 (0.8); 2.0104 (0.6); 2.0012 (0.5); 1.5839 (4.0); 1.2594 (0.9); 0.0079 (0.5); −0.0002 (17.9); −0.00085 (0.6)

X-036: $^1$H-NMR(400.6 MHz, CDCl3):

δ = 8.4437 (2.7); 8.4369 (2.8); 8.2863 (2.9); 7.4650 (0.8); 7.4606 (0.9); 7.4457 (1.5); 7.4415 (1.6); 7.4268 (1.1); 7.4227 (2.3); 7.4184 (1.5); 7.4159 (1.4); 7.4115 (1.2); 7.4005 (1.3); 7.3961 (1.5); 7.3937 (1.3); 7.3893 (1.2); 7.3651 (0.5); 7.3605 (0.7); 7.3584 (0.9); 7.3565 (0.7); 7.3540 (0.8); 7.3462 (0.9); 7.3444 (0.7); 7.3417 (0.8); 7.3398 (0.8); 7.3377 (0.8); 7.3333 (0.7); 7.3256 (0.7); 7.3211 (0.6); 7.2619 (21.1); 7.2441 (1.1); 7.2425 (1.2); 7.2408 (1.2); 7.2212 (1.7); 7.2056 (0.7); 7.2039 (0.8); 7.2022 (0.7); 7.0544 (1.1); 7.0512 (1.0); 7.0335 (1.0); 7.0298 (1.7); 7.0261 (1.1); 7.0085 (1.0); 7.0053 (0.9); 5.3002 (13.7); 4.9962 (8.7); 4.3710 (0.5); 4.1814 (2.0); 4.1636 (6.3); 4.1458 (6.5); 4.1280 (2.1); 3.8195 (0.5); 3.1929 (0.6); 2.9398 (0.6); 2.5903 (0.6); 2.5741 (0.6); 2.5639 (1.2); 2.5539 (0.7); 2.5377 (0.7); 1.9928 (0.8); 1.9620 (1.1); 1.5753 (6.6); 1.2780 (7.5); 1.2602 (16.0); 1.2424 (7.2); 0.0079 (0.9); −0.0002 (32.8); −0.00085 (0.9)

X-012: $^1$H-NMR(400.6 MHz, CDCl3):

δ = 8.1474 (4.3); 8.1411 (4.4); 7.7714 (1.8); 7.7651 (1.8); 7.7528 (2.2); 7.7501 (2.3); 7.7465 (2.2); 7.7439 (2.2); 7.7316 (1.9); 7.7253 (1.9); 7.4918 (1.6); 7.4875 (1.8); 7.4725 (2.8); 7.4685 (3.0); 7.4537 (1.9); 7.4494 (2.0); 7.4165 (0.9); 7.4121 (0.9); 7.4042 (1.0); 7.3975 (1.1); 7.3932 (1.4); 7.3852 (1.6); 7.3808 (1.5); 7.3769 (1.4); 7.3724 (1.2); 7.3646 (1.3); 7.3602 (1.1); 7.2613 (35.0); 7.2438 (3.2); 7.2245 (1.3); 7.1147 (1.7); 7.0750 (2.0); 7.0719 (2.0); 7.0542 (2.0); 7.0505 (3.3); 7.0469 (2.1); 7.0292 (1.8); 7.0260 (1.7); 6.9790 (0.8); 6.9658 (2.7); 6.9586 (2.8); 6.9446 (2.6); 6.9374 (2.7); 6.6303 (6.4); 6.4894 (6.5); 4.2562 (8.7); 4.2430 (8.8); 4.1520 (1.1); 4.1342 (3.4); 4.1163 (3.4); 4.0985 (1.2); 3.7742 (0.7); 2.2717 (1.4); 2.0499 (16.0); 1.8712 (0.8); 1.4321 (13.4); 1.2788 (4.4); 1.2609 (9.1); 1.2548 (1.3); 1.2430 (4.5); 0.0079 (1.4); −0.0002 (50.1); −0.00084 (1.6)

X-010: $^1$H-NMR(400.6 MHz, d$_6$-DMSO):

δ = 8.1932 (2.4); 8.1870 (2.5); 7.9586 (1.0); 7.9523 (1.0); 7.9391 (1.3); 7.9374 (1.4); 7.9329 (1.3); 7.9311 (1.4); 7.9180 (1.1); 7.9117 (1.1); 7.6014 (0.9); 7.5975 (0.6); 7.5859 (0.9); 7.5819 (1.8); 7.5781 (1.2); 7.5665 (0.6); 7.5625 (1.0); 7.5586 (0.7); 7.5025 (0.5); 7.4942 (0.6); 7.4880 (0.9); 7.4835 (0.8); 7.4753 (0.9); 7.4709 (0.9); 7.4675 (0.9); 7.4629 (0.7); 7.4546 (0.7); 7.4502 (0.6); 7.3392 (1.2); 7.3199 (1.9); 7.3044 (1.7); 7.3011 (1.9); 7.2981 (2.2); 7.2911 (1.7); 7.2838 (1.2); 7.2753 (2.7); 7.2699 (1.6); 7.2685 (1.5); 7.2577 (1.0); 7.2545 (0.9); 4.9436 (2.2); 4.9346 (3.8); 4.0557 (1.0); 4.0379 (3.3); 4.0202 (3.4); 4.0024 (1.1); 3.7088 (0.5); 3.7035 (0.6); 3.6839 (0.6); 3.5854 (0.9); 3.5672 (0.9); 3.5608 (0.7); 3.5551 (0.9); 3.5425 (1.0); 3.5352 (0.9); 3.5281 (0.6); 3.5232 (0.5); 3.5094 (0.7); 3.5032 (0.8); 3.4919 (1.0); 3.4864 (1.0); 3.4738 (0.8); 3.4675 (0.6); 3.4576 (0.6); 3.3494 (0.6); 3.3509 (0.8); 3.3210 (7.6); 3.1342 (0.7); 3.0445 (0.5); 3.0273 (0.6); 2.6704 (0.5); 2.5410 (2.2); 2.5242 (1.3); 2.5195 (1.6); 2.5108 (26.1); 2.5062 (59.2); 2.5016 (84.7); 2.4970 (60.2); 2.4924 (28.0); 2.3286 (0.5); 2.1828 (0.5); 2.1399 (0.5); 2.0861 (0.7); 2.0678 (0.8); 2.0540 (0.7); 1.9887 (16.0); 1.9568 (0.5); 1.9367 (0.5); 1.9086 (0.8); 1.3554 (4.7); 1.2355 (1.7); 1.1922 (4.6); 1.1745 (9.9); 1.1567 (4.8); 0.0080 (1.7); 0.0040 (0.6); −0.0002 (60.4); −0.00057 (0.9); −0.00066 (0.7); −0.00085 (1.8)

X-009: $^1$H-NMR(400.6 MHz, d$_6$-DMSO):

δ = 8.1877 (2.3); 8.1833 (2.1); 8.1815 (2.4); 7.9549 (1.0); 7.9486 (1.0); 7.9352 (1.3); 7.9337 (1.4); 7.9291 (1.3); 7.9274 (1.3); 7.9143 (1.1); 7.9080 (1.0); 7.6296 (0.6); 7.6253 (0.8); 7.6101 (1.4); 7.6059 (1.5); 7.5908 (1.0); 7.5864 (0.9); 7.4879 (0.8); 7.4859 (0.8); 7.4835 (0.8); 7.4751 (0.9); 7.4707 (0.9); 7.4689 (0.8); 7.4628 (0.6); 7.4545 (0.6); 7.4501 (0.5); 7.3445 (1.0); 7.3419 (1.3); 7.3254 (1.6); 7.3225 (2.0); 7.3061 (1.0); 7.3031 (1.1); 7.2994 (2.4); 7.2914 (1.7); 7.2840 (0.5); 7.2782 (2.1); 7.2766 (2.2); 7.2735 (1.7); 7.2702 (2.4); 7.2526 (0.8); 7.2495 (0.7); 5.0419 (0.6); 5.0046 (3.4); 4.9926 (3.0); 4.9703 (0.7); 4.9552 (0.6); 4.6946 (0.6); 4.6584 (0.7); 4.2783 (1.0); 4.2682 (1.1); 4.2561 (1.1); 4.2465 (0.9); 4.0557 (1.1); 4.0380 (3.4); 4.0202 (3.4); 4.0024 (1.1); 3.6019 (0.9); 3.5844 (0.9); 3.5747 (0.7); 3.5590 (1.4); 3.5401 (1.4); 3.5222 (1.1); 3.5154 (0.5); 3.4206 (0.5); 3.3215 (8.9); 2.5410 (1.6); 2.5243 (1.2); 2.5196 (1.5); 2.5109 (22.6); 2.5063 (50.6); 2.5017 (71.5); 2.4971 (50.1); 2.4925 (22.7); 2.1828 (0.6); 2.1613 (0.6); 2.1398 (0.8); 2.1299 (0.8); 2.1203 (0.6); 2.1121 (0.7); 1.9888 (16.0); 1.9348 (1.1); 1.9176 (1.7); 1.9087 (3.2); 1.9001 (1.3); 1.8834 (0.9); 1.8721 (0.8); 1.8537 (0.6); 1.8430 (0.6); 1.8297 (0.5); 1.7594 (0.5); 1.3555 (4.5); 1.2355 (1.4); 1.1922 (4.9); 1.1744 (9.8); 1.1567 (4.6); 0.0080 (1.3); −0.0002 (49.2); −0.00052 (0.8); −0.00060 (0.6); −0.00069 (0.5); −0.00085 (1.5)

X-008: ¹H-NMR(400.6 MHz, CDCl3):
δ = 8.1090 (2.6); 8.1028 (2.7); 7.7660 (1.1); 7.7598 (1.1); 7.7472 (1.4); 7.7448 (1.5); 7.7410 (1.4); 7.7386 (1.4); 7.7261 (1.2); 7.7198 (1.2); 7.4453 (0.9); 7.4409 (1.1); 7.4260 (1.7); 7.4218 (2.0); 7.4072 (1.2); 7.4028 (1.2); 7.3684 (0.5); 7.3640 (0.5); 7.3562 (0.6); 7.3494 (1.0); 7.3450 (0.9); 7.3372 (1.0); 7.3328 (0.9); 7.3289 (0.9); 7.3244 (0.7); 7.3166 (0.8); 7.3122 (0.7); 7.2609 (43.2); 7.2260 (1.4); 7.2066 (1.9); 7.1894 (0.8); 7.0487 (1.2); 7.0456 (1.2); 7.0279 (1.2); 7.0242 (2.1); 7.0205 (1.3); 7.0029 (1.1); 6.9997 (1.1); 6.9423 (1.8); 6.9349 (1.8); 6.9211 (1.7); 6.9198 (1.7); 6.9137 (1.7); 4.9992 (5.1); 4.9932 (5.4); 4.9718 (0.6); 4.4127 (0.6); 4.3783 (0.6); 4.1494 (1.1); 4.1316 (3.2); 4.1138 (3.3); 4.0960 (1.1); 3.8794 (0.5); 3.8461 (0.6); 3.2176 (0.7); 2.9711 (0.7); 2.6629 (0.6); 2.6470 (0.7); 2.6368 (1.3); 2.6268 (0.7); 2.6108 (0.7); 2.2717 (0.7); 2.1073 (1.1); 2.0463 (16.0); 2.0311 (1.0); 1.9977 (1.4); 1.8560 (0.7); 1.8254 (0.6); 1.8001 (0.6); 1.7470 (0.6); 1.7225 (0.5); 1.4322 (6.8); 1.2776 (4.6); 1.2598 (9.5); 1.2420 (4.7); 0.0080 (2.0); −0.0002 (69.6); −0.00085 (2.1)

X-033: ¹H-NMR(400.6 MHz, d₆-DMSO):
δ = 12.4345 (0.6); 8.6443 (3.1); 8.6373 (3.1); 8.3537 (1.5); 8.3497 (2.8); 8.3459 (1.5); 7.7841 (0.6); 7.7777 (0.8); 7.7732 (0.6); 7.7606 (0.7); 7.7561 (0.8); 7.7496 (0.6); 7.6113 (0.5); 7.5954 (1.0); 7.5919 (1.0); 7.5760 (0.5); 7.5725 (0.6); 7.4941 (0.6); 7.4923 (0.6); 7.4895 (0.6); 7.4813 (0.7); 7.4769 (0.6); 7.4735 (0.7); 7.4689 (0.5); 7.4607 (0.5); 7.3476 (0.8); 7.3447 (1.0); 7.3286 (1.3); 7.3253 (1.6); 7.3064 (1.6); 7.2859 (0.8); 7.2807 (1.0); 7.2774 (0.9); 7.2597 (0.7); 7.2566 (0.6); 5.1278 (0.6); 5.0709 (0.7); 5.0539 (0.7); 5.0334 (0.8); 4.0559 (1.1); 4.0381 (3.4); 4.0203 (3.5); 4.0026 (1.2); 3.3222 (13.1); 2.5413 (1.2); 2.5245 (0.7); 2.5199 (1.0); 2.5111 (13.0); 2.5065 (29.0); 2.5019 (41.2); 2.4973 (29.1); 2.4927 (13.2); 1.9888 (16.0); 1.9090 (1.0); 1.3557 (2.8); 1.1923 (5.0); 1.1745 (9.9); 1.1567 (4.8); 0.0080 (0.8); −0.0002 (28.3); −0.00085 (0.9)

X-040: ¹H-NMR(400.6 MHz, d₆-DMSO):
δ = 12.5466 (0.9); 8.6455 (3.6); 8.6386 (3.6); 8.3529 (1.8); 8.3488 (3.4); 8.3451 (1.8); 7.7854 (1.1); 7.7811 (1.2); 7.7785 (1.2); 7.7742 (1.1); 7.7619 (1.2); 7.7575 (1.3); 7.7549 (1.1); 7.7506 (1.1); 7.6169 (0.8); 7.6130 (0.5); 7.6012 (0.8); 7.5974 (1.6); 7.5936 (1.0); 7.5819 (0.5); 7.5780 (0.9); 7.5741 (0.6); 7.4943 (0.8); 7.4897 (0.7); 7.4815 (0.8); 7.4771 (0.8); 7.4737 (0.8); 7.4691 (0.6); 7.4609 (0.6); 7.4564 (0.6); 7.3492 (1.1); 7.3299 (1.6); 7.3105 (0.8); 7.3064 (1.3); 7.3031 (1.0); 7.2854 (1.0); 7.2802 (1.3); 7.2769 (1.1); 7.2592 (0.9); 7.2561 (0.8); 4.9513 (2.1); 4.9429 (3.2); 4.0557 (1.1); 4.0379 (3.4); 4.0202 (3.4); 4.0024 (1.1); 3.7058 (0.6); 3.6860 (0.5); 3.5872 (0.8); 3.5689 (0.8); 3.5563 (0.8); 3.5441 (0.8); 3.5362 (0.8); 3.5105 (0.6); 3.5050 (0.8); 3.4935 (0.9); 3.4885 (0.9); 3.4757 (0.8); 3.4692 (0.6); 3.4594 (0.6); 3.3526 (0.6); 3.3212 (18.8); 3.1374 (0.6); 3.0298 (0.6); 2.5410 (1.5); 2.5242 (0.7); 2.5195 (1.5); 2.5108 (21.4); 2.5062 (47.6); 2.5016 (66.9); 2.4970 (47.0); 2.4925 (21.4); 2.0879 (0.6); 2.0697 (0.7); 2.0560 (0.7); 1.9887 (16.0); 1.9087 (0.6); 1.3555 (3.1); 1.1922 (4.7); 1.1744 (9.4); 1.1566 (4.6); 0.0080 (1.2); −0.0002 (44.3); −0.00085 (1.4)

X-039: ¹H-NMR(400.6 MHz, d₆-DMSO):
δ = 8.6474 (2.7); 8.6404 (2.8); 8.3478 (1.6); 8.3440 (2.6); 8.3405 (1.3); 7.7806 (0.9); 7.7763 (1.0); 7.7737 (1.0); 7.7693 (0.9); 7.7570 (1.0); 7.7526 (1.1); 7.7501 (0.9); 7.7458 (0.9); 7.6457 (0.5); 7.6414 (0.6); 7.6261 (1.1); 7.6219 (1.2); 7.6067 (0.8); 7.6024 (0.7); 7.4943 (0.6); 7.4922 (0.6); 7.4898 (0.6); 7.4815 (0.6); 7.4770 (0.6); 7.4752 (0.6); 7.3547 (0.7); 7.3523 (1.0); 7.3329 (1.5); 7.3163 (0.5); 7.3136 (0.7); 7.3007 (0.7); 7.2976 (0.6); 7.2800 (0.7); 7.2747 (0.8); 7.2713 (0.7); 7.2537 (0.6); 7.2505 (0.5); 5.0124 (2.5); 5.0018 (2.4); 4.9795 (0.5); 4.2801 (0.8); 4.2700 (0.9); 4.2580 (0.8); 4.2484 (0.7); 4.0559 (1.1); 4.0381 (3.4); 4.0203 (3.4); 4.0026 (1.1); 3.5766 (0.5); 3.5609 (1.1); 3.5414 (1.1); 3.5235 (0.5); 3.3228 (2.6); 2.5413 (0.9); 2.5246 (0.6); 2.5199 (0.9); 2.5111 (11.8); 2.5065 (26.1); 2.5020 (37.0); 2.4974 (26.0); 2.4928 (11.7); 2.1410 (0.6); 2.1312 (0.6); 2.1136 (0.5); 1.9888 (16.0); 1.9362 (0.8); 1.9191 (1.3); 1.9090 (1.1); 1.9017 (1.0); 1.8849 (0.7); 1.8736 (0.6); 1.3558 (1.8); 1.1923 (4.7); 1.1745 (9.8); 1.1567 (4.7); 0.0080 (0.7); −0.0002 (24.8); −0.00085 (0.7)

X-038: ¹H-NMR(400.6 MHz, d₆-DMSO):
δ = 12.2660 (1.2); 8.6440 (3.8); 8.6371 (3.9); 8.3522 (2.2); 8.3482 (3.8); 8.3445 (2.1); 7.7825 (1.2); 7.7781 (1.4); 7.7757 (1.4); 7.7713 (1.2); 7.7589 (1.3); 7.7546 (1.5); 7.7521 (1.3); 7.7477 (1.2); 7.6008 (0.8); 7.5966 (1.0); 7.5814 (1.8); 7.5772 (1.9); 7.5620 (1.0); 7.5578 (1.1); 7.4926 (0.5); 7.4864 (1.0); 7.4819 (0.9); 7.4736 (0.9); 7.4692 (1.0); 7.4614 (0.7); 7.4531 (0.7); 7.4488 (0.6); 7.3375 (1.4); 7.3210 (1.8); 7.3182 (2.1); 7.2976 (1.7); 7.2941 (1.2); 7.2760 (1.1); 7.2711 (1.5); 7.2677 (1.2); 7.2499 (1.0); 7.2469 (0.9); 5.0659 (2.2); 5.0294 (2.1); 4.1833 (0.6); 4.1525 (0.6); 4.0560 (1.3); 4.0381 (3.6); 4.0203 (3.6); 4.0026 (1.2); 3.7430 (0.6); 3.7089 (0.6); 3.3229 (20.1); 3.1042 (0.7); 2.7813 (0.7); 2.5413 (1.2); 2.5333 (0.8); 2.5244 (1.4); 2.5197 (2.0); 2.5110 (19.1); 2.5065 (39.7); 2.5020 (53.3); 2.4975 (38.3); 2.4930 (18.3); 1.9888 (16.0); 1.8447 (1.2); 1.8135 (1.4); 1.7593 (0.6); 1.5640 (0.5); 1.4032 (0.5); 1.3557 (2.8); 1.1922 (4.4); 1.1744 (8.9); 1.1567 (4.3); 0.0079 (0.9); −0.0002 (24.3); −0.00085 (1.0)

VII-078: ¹H-NMR(400.6 MHz, CDCl3):
δ = 8.0816 (1.9); 8.0753 (2.0); 7.7922 (0.8); 7.7859 (0.7); 7.7712 (1.0); 7.7652 (1.0); 7.7524 (0.8); 7.7461 (0.8); 7.4162 (0.8); 7.4119 (1.0); 7.3971 (1.3); 7.3928 (1.7); 7.3842 (0.6); 7.3787 (1.1); 7.3739 (1.2); 7.3673 (0.6); 7.3652 (0.9); 7.3635 (0.8); 7.3608 (0.7); 7.3590 (0.7); 7.3529 (0.9); 7.3484 (0.7); 7.3466 (0.7); 7.3446 (0.8); 7.3400 (0.6); 7.3322 (0.8); 7.3278 (0.6); 7.2606 (36.6); 7.2227 (1.0); 7.2209 (1.0); 7.2015 (1.6); 7.1841 (0.7); 7.1825 (0.7); 7.0527 (1.0); 7.0494 (1.2); 7.0318 (1.8); 7.0281 (1.8); 7.0245 (1.1); 7.0069 (0.9); 7.0037 (0.9); 6.9340 (1.3); 6.9326 (1.5); 6.9266 (1.4); 6.9252 (1.4); 6.9129 (1.3); 6.9114 (1.4); 6.9054 (1.4); 6.9040 (1.4); 6.8476 (1.8); 6.7123 (4.0); 6.5770 (2.0); 4.8949 (15.5); 4.2954 (1.9); 4.2776 (6.1); 4.2598 (6.2); 4.2420 (2.0); 2.9832 (2.0); 2.9067 (1.6); 2.9053 (1.7); 1.4050 (0.9); 1.3097 (7.8); 1.2919 (16.0); 1.2846 (0.5); 1.2740 (7.7); 1.2540 (0.7); 0.0080 (1.4); −0.0002 (54.5); −0.00085 (1.8)

VII-032: ¹H-NMR(400.6 MHz, CDCl3):
δ = 8.6099 (0.9); 8.6057 (1.0); 8.5977 (1.0); 8.5935 (1.0); 8.5389 (1.0); 8.5369 (1.1); 8.5333 (1.1); 8.5312 (1.1); 7.6141 (0.6); 7.6097 (0.8); 7.6085 (0.7); 7.6042 (0.7); 7.5943 (0.8); 7.5899 (0.9); 7.5887 (0.9); 7.5844 (0.8); 7.3205 (0.8); 7.3184 (0.8); 7.3083 (0.9); 7.3063 (1.0); 7.3009 (1.2); 7.2986 (0.8); 7.2884 (0.9); 7.2863 (1.8); 7.2848 (2.0); 7.2811 (0.7); 7.2784 (0.8); 7.2702 (0.8); 7.2663 (2.3); 7.2646 (1.6); 7.2617 (6.3); 7.2574 (1.5); 7.2534 (0.9); 7.2414 (0.7); 7.2397 (0.7); 7.1293 (1.6); 7.1252 (2.0);

7.1196 (0.5); 7.1129 (0.9); 7.1102 (0.6); 7.1083 (1.7); 7.1050 (1.4); 5.2992 (4.5); 5.2760 (1.5); 5.2586 (1.5); 3.7932 (16.0); 1.7067 (6.3); 1.6893 (6.2); −0.0002 (8.6)
VII-041: $^1$H-NMR(400.6 MHz, CDCl3):
δ = 8.6098 (0.9); 8.6057 (0.9); 8.5976 (0.9); 8.5935 (0.9); 8.5385 (1.0); 8.5368 (1.1); 8.5331 (1.1); 8.5312 (1.1); 7.6141 (0.6); 7.6097 (0.8); 7.6087 (0.8); 7.6043 (0.6); 7.5943 (0.8); 7.5899 (0.9); 7.5889 (0.9); 7.5845 (0.7); 7.3208 (0.7); 7.3186 (0.8); 7.3085 (0.9); 7.3066 (1.1); 7.3011 (1.2); 7.2998 (0.8); 7.2864 (1.8); 7.2850 (2.0); 7.2812 (0.8); 7.2786 (0.8); 7.2703 (0.8); 7.2664 (2.3); 7.2648 (1.7); 7.2614 (7.3); 7.2576 (1.6); 7.2536 (0.9); 7.2415 (0.8); 7.2400 (0.8); 7.1292 (1.6); 7.1250 (2.1); 7.1195 (0.5); 7.1128 (0.9); 7.1082 (1.7); 7.1049 (1.4); 5.2994 (1.3); 5.2759 (1.5); 5.2585 (1.5); 3.7934 (16.0); 3.7314 (0.6); 1.7067 (6.4); 1.6893 (6.3); −0.0002 (9.8)
VII-043: $^1$H-NMR(400.6 MHz, d$_6$-DMSO):
δ = 8.6229 (2.5); 8.6188 (2.7); 8.6108 (2.7); 8.6067 (2.7); 8.4928 (2.7); 8.4907 (3.0); 8.4872 (3.0); 8.4851 (2.9); 7.7553 (1.6); 7.7511 (1.9); 7.7498 (1.8); 7.7455 (1.6); 7.7355 (1.9); 7.7313 (2.0); 7.7299 (2.3); 7.7257 (1.8); 7.4963 (1.9); 7.4942 (1.9); 7.4842 (1.8); 7.4820 (1.9); 7.4765 (1.7); 7.4744 (1.7); 7.4644 (1.7); 7.4622 (1.8); 7.3988 (0.9); 7.3946 (1.6); 7.3901 (0.8); 7.3847 (0.5); 7.3821 (0.7); 7.3773 (4.6); 7.3737 (1.8); 7.3724 (2.0); 7.3624 (1.8); 7.3587 (4.8); 7.3569 (3.2); 7.3516 (0.7); 7.3455 (1.4); 7.3417 (3.0); 7.3381 (1.8); 7.3303 (0.8); 7.3242 (2.5); 7.3057 (0.8); 7.1986 (1.8); 7.1966 (3.8); 7.1928 (6.0); 7.1873 (1.2); 7.1797 (2.1); 7.1777 (1.6); 7.1755 (4.0); 7.1723 (3.4); 5.1165 (0.7); 5.0992 (3.8); 5.0818 (3.9); 5.0644 (0.8); 4.0556 (1.1); 4.0378 (3.3); 4.0201 (3.4); 4.0023 (1.1); 3.4052 (1.0); 2.5241 (1.0); 2.5195 (1.2); 2.5107 (16.2); 2.5061 (35.9); 2.5015 (50.5); 2.4969 (34.8); 2.4923 (15.4); 2.1828 (0.8); 1.9886 (16.0); 1.9089 (2.4); 1.5820 (10.2); 1.5645 (10.1); 1.3555 (7.0); 1.1921 (4.9); 1.1810 (0.5); 1.1743 (9.8); 1.1565 (4.6); 0.0024 (0.5); −0.0002 (17.3)
VII-042: $^1$H-NMR(400.6 MHz, d$_6$-DMSO):
δ = 8.6217 (2.8); 8.6176 (3.0); 8.6097 (3.0); 8.6055 (3.0); 8.4913 (3.0); 8.4892 (3.2); 8.4857 (3.3); 8.4835 (3.1); 7.7530 (1.6); 7.7487 (2.1); 7.7474 (1.8); 7.7431 (1.7); 7.7332 (2.1); 7.7289 (2.2); 7.7276 (2.3); 7.7233 (2.0); 7.4941 (2.0); 7.4920 (2.0); 7.4820 (2.0); 7.4798 (1.9); 7.4744 (1.8); 7.4722 (1.8); 7.4622 (1.8); 7.4600 (1.8); 7.3987 (1.0); 7.3945 (1.7); 7.3899 (0.8); 7.3844 (0.5); 7.3820 (0.8); 7.3773 (4.8); 7.3734 (1.9); 7.3722 (2.0); 7.3623 (1.9); 7.3585 (5.0); 7.3568 (3.2); 7.3514 (0.7); 7.3453 (1.4); 7.3415 (3.1); 7.3379 (1.8); 7.3301 (0.9); 7.3240 (2.6); 7.3158 (0.5); 7.3088 (0.5); 7.3055 (0.8); 7.1983 (2.0); 7.1964 (4.0); 7.1926 (6.4); 7.1871 (1.3); 7.1795 (2.3); 7.1773 (1.7); 7.1753 (4.4); 7.1722 (3.4); 5.1164 (0.8); 5.0991 (4.1); 5.0816 (4.2); 5.0643 (0.8); 4.0556 (1.1); 4.0378 (3.4); 4.0201 (3.4); 4.0023 (1.1); 3.3876 (0.9); 2.6736 (1.4); 2.5240 (0.7); 2.5194 (1.0); 2.5106 (16.8); 2.5061 (37.1); 2.5015 (52.2); 2.4969 (35.8); 2.4923 (15.8); 2.1829 (0.6); 1.9885 (16.0); 1.9088 (1.5); 1.5819 (10.8); 1.5645 (10.8); 1.3556 (5.6); 1.1920 (4.7); 1.1743 (9.9); 1.1565 (4.8); −0.0002 (16.9); −0.00020 (0.8); −0.00029 (0.6)
VII-138: $^1$H-NMR(400.6 MHz, CDCl3):
δ = 8.4477 (0.8); 8.4418 (0.9); 8.2940 (1.0); 7.4578 (0.5); 7.4428 (0.8); 7.4385 (1.0); 7.4301 (0.7); 7.4236 (1.2); 7.4192 (1.1); 7.4078 (0.6); 7.4035 (0.7); 7.4010 (0.7); 7.3966 (0.6); 7.2606 (27.6); 7.2424 (0.6); 7.2405 (0.6); 7.2210 (0.9); 7.0549 (0.6); 7.0517 (0.6); 7.0342 (1.0); 7.0303 (1.0); 7.0265 (0.7); 7.0091 (0.5); 7.0057 (0.5); 5.3002 (4.7); 4.9074 (8.5); 4.4992 (2.0); 4.4834 (4.3); 4.4675 (2.1); 3.6713 (16.0); 2.7003 (2.0); 2.6844 (4.2); 2.6685 (2.0); 1.5439 (4.2); 0.0080 (1.2); −0.0002 (40.4); −0.00085 (1.4)
VII-138: $^1$H-NMR(400.0 MHz, CDCl3_5 mm):
δ = 8.4477 (1.6); 8.4408 (1.6); 8.2975 (1.0); 8.2939 (1.7); 8.2903 (1.0); 7.4625 (0.5); 7.4582 (0.6); 7.4432 (0.9); 7.4389 (1.0); 7.4304 (0.8); 7.4259 (1.0); 7.4237 (1.3); 7.4193 (1.2); 7.4081 (0.8); 7.4037 (0.8); 7.4012 (0.8); 7.3968 (0.7); 7.3624 (0.5); 7.3502 (0.5); 7.2625 (6.5); 7.2441 (0.6); 7.2425 (0.6); 7.2408 (0.7); 7.2211 (0.9); 7.0550 (0.6); 7.0518 (0.6); 7.0342 (0.6); 7.0304 (1.0); 7.0266 (0.7); 7.0090 (0.5); 7.0058 (0.5); 4.9074 (8.3); 4.4991 (2.0); 4.4832 (4.2); 4.4673 (2.1); 3.6774 (0.7); 3.6710 (16.0); 2.7004 (2.0); 2.6845 (4.1); 2.6686 (1.9); 1.5788 (2.3); 1.2610 (1.2); 1.2596 (1.1); 1.2434 (0.6); 0.8987 (0.6); 0.8818 (1.8); 0.8640 (0.7); −0.0002 (8.5)
VII-085: $^1$H-NMR(400.6 MHz, CDCl3):
δ = 8.1199 (1.2); 8.1178 (1.0); 8.1138 (1.2); 7.6788 (0.6); 7.6726 (0.6); 7.6597 (0.7); 7.6577 (0.7); 7.6535 (0.7); 7.6515 (0.7); 7.6387 (0.6); 7.6325 (0.6); 7.3886 (0.5); 7.3737 (0.9); 7.3693 (1.0); 7.3548 (0.6); 7.3504 (0.6); 7.2613 (41.2); 7.1898 (0.6); 7.1884 (0.6); 7.1864 (0.6); 7.1697 (0.9); 7.1669 (0.9); 7.0190 (0.6); 7.0156 (0.6); 6.9978 (0.7); 6.9942 (0.9); 6.9903 (0.6); 6.9729 (0.5); 6.9696 (0.5); 6.8974 (0.8); 6.8960 (0.8); 6.8899 (0.9); 6.8885 (0.8); 6.8763 (0.8); 6.8748 (0.8); 6.8688 (0.8); 6.8674 (0.7); 5.3002 (0.9); 4.8528 (8.4); 4.4836 (2.0); 4.4677 (4.3); 4.4518 (2.1); 3.6799 (16.0); 2.6972 (2.0); 2.6813 (4.2); 2.6654 (2.0); 1.5575 (1.4); 1.5519 (1.9); 1.5443 (0.6); 1.5412 (0.6); 1.5395 (0.6); 0.7726 (0.6); 0.7684 (2.3); 0.7659 (2.2); 0.7638 (2.3); 0.7618 (2.3); 0.7570 (0.8); 0.7479 (9.9); 0.0080 (0.7); −0.0002 (24.7); −0.00042 (0.6); −0.00050 (0.5); −0.00084 (0.7)
VII-075-a: $^1$H-NMR(400.6 MHz, CDCl3):
δ = 8.0973 (0.7); 8.0956 (1.0); 8.0935 (0.8); 8.0913 (0.8); 8.0893 (1.1); 7.7539 (0.6); 7.7477 (0.6); 7.7352 (0.6); 7.7327 (0.7); 7.7289 (0.6); 7.7264 (0.7); 7.7140 (0.7); 7.7077 (0.6); 7.3806 (0.7); 7.3762 (0.9); 7.3618 (0.7); 7.3574 (0.6); 7.2627 (9.5); 7.2200 (0.5); 7.2182 (0.6); 7.2169 (0.5); 7.2007 (0.9); 7.1987 (0.8); 7.0490 (0.5); 7.0457 (0.5); 7.0282 (0.5); 7.0242 (0.8); 7.0205 (0.6); 6.9427 (0.7); 6.9411 (0.7); 6.9352 (0.8); 6.9337 (0.7); 6.9214 (0.7); 6.9199 (0.7); 6.9139 (0.7); 6.9124 (0.7); 5.2998 (0.9); 5.2354 (1.5); 5.2180 (1.5); 3.7781 (16.0); 1.6967 (6.3); 1.6793 (6.3); −0.0002 (5.8)
VII-082: $^1$H-NMR(400.6 MHz, d$_6$-DMSO):
δ = 13.0133 (1.7); 8.1985 (4.2); 8.1922 (4.4); 7.9606 (1.8); 7.9543 (1.7); 7.9412 (2.3); 7.9394 (2.4); 7.9349 (2.3); 7.9331 (2.3); 7.9200 (1.9); 7.9137 (1.9); 7.5830 (1.3); 7.5788 (1.7); 7.5638 (3.0); 7.5593 (3.5); 7.5442 (1.8); 7.5399 (2.0); 7.5203 (0.9); 7.5159 (0.9); 7.5076 (1.0); 7.5013 (1.6); 7.4964 (1.5); 7.4886 (1.6); 7.4842 (1.5); 7.4809 (1.6); 7.4763 (1.2); 7.4681 (1.2); 7.4636 (1.0); 7.3460 (1.8); 7.3432 (2.4); 7.3271 (3.0); 7.3237 (4.3); 7.3178 (2.5); 7.3153 (1.7); 7.3082 (3.0); 7.3021 (3.2); 7.3007 (3.2); 7.2938 (4.6); 7.2888 (2.2); 7.2807 (2.7); 7.2793 (2.8); 7.2736 (3.0); 7.2721 (3.6); 7.2681 (1.7); 5.0736 (1.2); 5.0562 (5.8); 5.0388 (5.9); 5.0215 (1.2); 3.6220 (0.8); 3.6181 (4.5); 3.6159 (2.7); 3.6118 (2.6); 3.6095 (2.1); 3.6078 (3.5); 3.6015 (10.7); 3.5993 (4.1); 3.5953 (3.6); 3.5933 (2.0); 3.5912 (2.5); 3.5870 (2.6); 3.5849 (4.8); 3.5810 (0.9); 3.3247 (4.4); 2.5252 (1.1); 2.5205 (1.4); 2.5118 (20.2); 2.5072 (45.1); 2.5026 (63.6); 2.4980 (44.6); 2.4935 (20.1); 1.7807 (0.8); 1.7760 (4.7); 1.7684 (4.0); 1.7642 (2.4); 1.7594 (13.5); 1.7548 (2.6); 1.7505 (3.8); 1.7429 (4.5); 1.7384 (0.8); 1.5749 (16.0); 1.5575 (15.9);

1.3564 (3.9); 0.0080 (1.9); 0.0065 (0.5); 0.0056 (0.5); 0.0047 (0.7); −0.0002 (69.2); −0.00066 (0.8); −0.0085 (2.0)
VII-081: $^1$H-NMR(400.6 MHz, CDCl3):
δ = 8.1083 (1.2); 8.1062 (0.9); 8.1040 (1.0); 8.1021 (1.2); 7.7632 (0.6); 7.7569 (0.6); 7.7444 (0.7); 7.7419 (0.7); 7.7382 (0.7); 7.7357 (0.7); 7.7232 (0.6); 7.7170 (0.5); 7.4368 (0.5); 7.4218 (0.9); 7.4175 (1.0); 7.4029 (0.6); 7.3985 (0.6); 7.2617 (8.7); 7.2300 (0.6); 7.2284 (0.6); 7.2267 (0.6); 7.2071 (0.9); 7.0452 (0.6); 7.0420 (0.6); 7.0244 (0.6); 7.0206 (1.0); 7.0168 (0.6); 6.9992 (0.6); 6.9960 (0.5); 6.9418 (0.9); 6.9403 (0.8); 6.9343 (0.9); 6.9328 (0.8); 6.9205 (0.8); 6.9190 (0.8); 6.9130 (0.8); 6.9115 (0.8); 5.3001 (3.5); 5.1971 (1.7); 5.1797 (1.7); 4.4921 (0.6); 4.4802 (0.8); 4.4643 (1.4); 4.4477 (1.1); 4.4304 (1.5); 4.4148 (0.9); 4.4026 (0.6); 3.6368 (16.0); 2.6741 (1.1); 2.6710 (1.0); 2.6579 (1.8); 2.6552 (2.2); 2.6421 (1.0); 2.6394 (1.0); 1.6815 (6.3); 1.6641 (6.2); 1.5561 (2.8); −0.0002 (11.5)
VII-075: $^1$H-NMR(400.6 MHz, CDCl3):
δ = 8.1151 (1.1); 8.1130 (0.9); 8.1108 (0.9); 8.1088 (1.2); 7.7693 (0.6); 7.7631 (0.6); 7.7506 (0.7); 7.7481 (0.7); 7.7443 (0.7); 7.7419 (0.7); 7.7294 (0.6); 7.7232 (0.6); 7.4309 (0.5); 7.4160 (0.8); 7.4117 (0.9); 7.3971 (0.6); 7.3928 (0.6); 7.2618 (8.3); 7.2229 (0.5); 7.2213 (0.6); 7.2195 (0.6); 7.1999 (0.9); 7.0371 (0.6); 7.0338 (0.6); 7.0163 (0.6); 7.0124 (0.9); 7.0086 (0.6); 6.9911 (0.5); 6.9369 (0.8); 6.9354 (0.8); 6.9295 (0.8); 6.9279 (0.8); 6.9158 (0.8); 6.9142 (0.8); 6.9083 (0.8); 6.9067 (0.8); 5.3002 (4.7); 5.1939 (1.7); 5.1765 (1.7); 4.4915 (0.6); 4.4795 (0.8); 4.4637 (1.4); 4.4471 (1.1); 4.4429 (0.8); 4.4270 (1.4); 4.4116 (0.8); 4.3992 (0.6); 3.6371 (16.0); 2.6731 (1.0); 2.6698 (1.0); 2.6571 (1.6); 2.6539 (2.0); 2.6411 (1.0); 2.6382 (1.0); 1.6800 (6.2); 1.6626 (6.1); 1.5586 (2.5); −0.0002 (11.2)
X-021: $^1$H-NMR(400.6 MHz, CDCl3):
δ = 8.1263 (1.3); 8.1242 (1.0); 8.1219 (1.1); 8.1201 (1.3); 7.7644 (0.6); 7.7581 (0.6); 7.7456 (0.8); 7.7431 (0.8); 7.7394 (0.8); 7.7369 (0.7); 7.7245 (0.7); 7.7182 (0.6); 7.4636 (0.5); 7.4593 (0.6); 7.4443 (0.9); 7.4400 (1.0); 7.4255 (0.6); 7.4211 (0.7); 7.3664 (0.5); 7.3541 (0.5); 7.3497 (0.5); 7.2620 (9.4); 7.2470 (0.6); 7.2454 (0.7); 7.2436 (0.7); 7.2242 (1.0); 7.0547 (0.7); 7.0515 (0.6); 7.0338 (0.6); 7.0301 (1.1); 7.0264 (0.7); 7.0087 (0.6); 7.0056 (0.6); 6.9522 (1.1); 6.9507 (0.9); 6.9447 (1.0); 6.9432 (0.9); 6.9309 (0.9); 6.9294 (0.8); 6.9234 (0.9); 6.9219 (0.8); 5.3168 (1.5); 5.3001 (8.7); 4.1408 (1.8); 4.1280 (3.1); 4.1152 (1.7); 3.7810 (16.0); 1.7135 (6.9); 1.6965 (6.8); 1.5695 (2.8); −0.0002 (12.4)
VII-134: $^1$H-NMR(400.6 MHz, CDCl3):
δ = 8.4406 (1.8); 8.4338 (1.8); 8.2957 (1.0); 8.2921 (1.8); 8.2884 (1.0); 7.4430 (0.5); 7.4271 (1.4); 7.4228 (1.4); 7.4201 (0.9); 7.4156 (0.7); 7.4092 (0.6); 7.4047 (1.3); 7.4002 (0.8); 7.3977 (0.7); 7.3934 (0.7); 7.2618 (7.9); 7.2321 (0.6); 7.2304 (0.6); 7.2286 (0.6); 7.2116 (0.9); 7.2092 (0.9); 7.0439 (0.6); 7.0407 (0.6); 7.0231 (0.6); 7.0192 (1.0); 7.0155 (0.6); 6.9980 (0.6); 6.9947 (0.5); 5.3000 (1.3); 5.1964 (1.7); 5.1789 (1.7); 4.4923 (0.6); 4.4803 (0.8); 4.4645 (1.4); 4.4479 (1.1); 4.4447 (0.8); 4.4289 (1.4); 4.4134 (0.8); 4.4011 (0.6); 3.6390 (16.0); 2.6733 (1.1); 2.6700 (1.0); 2.6575 (1.7); 2.6541 (2.1); 2.6414 (1.0); 2.6383 (1.0); 1.6829 (6.3); 1.6655 (6.2); 1.5723 (0.9); 1.4321 (0.5); −0.0002 (11.0); −0.00028 (0.5)
VII-023: $^1$H-NMR(400.0 MHz, CDCl3):
δ = 8.1731 (0.7); 8.1711 (1.1); 8.1690 (0.9); 8.1670 (0.9); 8.1649 (1.1); 8.1629 (0.8); 7.6936 (0.6); 7.6873 (0.6); 7.6748 (0.7); 7.6723 (0.8); 7.6686 (0.7); 7.6661 (0.8); 7.6536 (0.7); 7.6473 (0.7); 7.3239 (0.5); 7.3223 (0.6); 7.3076 (1.3); 7.3061 (2.0); 7.3024 (0.9); 7.2997 (0.9); 7.2915 (1.0); 7.2876 (2.4); 7.2858 (1.7); 7.2830 (1.0); 7.2787 (1.7); 7.2747 (1.0); 7.2684 (0.5); 7.2610 (12.3); 7.1262 (1.7); 7.1221 (2.1); 7.1165 (0.7); 7.1098 (1.0); 7.1072 (0.8); 7.1053 (1.9); 7.1019 (1.6); 6.9554 (0.8); 6.9537 (0.8); 6.9478 (0.8); 6.9461 (0.8); 6.9341 (0.8); 6.9325 (0.8); 6.9265 (0.8); 6.9249 (0.8); 5.2975 (1.8); 5.2679 (1.5); 5.2504 (1.6); 3.7882 (16.0); 1.7023 (6.4); 1.6848 (6.4); 1.5639 (2.3); −0.0002 (4.5)
VII-017: $^1$H-NMR(400.0 MHz, CDCl3):
δ = 8.3176 (1.5); 8.3162 (1.8); 8.3116 (1.6); 8.3101 (1.8); 7.5533 (1.3); 7.5471 (1.3); 7.5325 (1.6); 7.5263 (1.6); 7.3364 (2.6); 7.3325 (0.8); 7.3311 (0.9); 7.3265 (0.5); 7.3151 (3.8); 7.3111 (1.2); 7.3084 (1.1); 7.2998 (1.1); 7.2960 (2.5); 7.2949 (2.5); 7.2915 (1.1); 7.2871 (1.8); 7.2832 (1.1); 7.2697 (1.1); 7.2606 (13.0); 7.2517 (0.5); 7.1279 (1.9); 7.1237 (2.5); 7.1183 (0.8); 7.1114 (1.0); 7.1068 (2.0); 7.1036 (1.8); 5.2979 (1.0); 5.2637 (1.7); 5.2463 (1.7); 5.2289 (0.5); 3.7853 (16.0); 1.6997 (6.9); 1.6823 (6.8); −0.0002 (7.4)
VIII-007: $^1$H-NMR(400.0 MHz, CDCl3):
δ = 8.2079 (1.5); 8.1949 (1.6); 7.3302 (1.6); 7.3263 (0.9); 7.3238 (0.5); 7.3197 (1.4); 7.3172 (1.4); 7.3135 (2.9); 7.3120 (3.1); 7.3091 (1.5); 7.3036 (0.5); 7.3010 (0.7); 7.2969 (0.5); 7.2610 (9.6); 7.1389 (2.1); 7.1332 (1.5); 7.1283 (0.7); 7.1251 (0.7); 7.1220 (0.7); 7.1184 (1.1); 7.1145 (1.6); 7.0478 (0.7); 7.0439 (1.1); 7.0400 (0.8); 7.0348 (0.7); 7.0309 (1.1); 7.0270 (0.7); 6.8890 (1.1); 6.8858 (1.7); 6.8826 (1.1); 6.8812 (0.9); 5.2975 (3.0); 5.2621 (1.6); 5.2446 (1.6); 3.7850 (16.0); 1.7016 (6.6); 1.6842 (6.6); 1.5649 (1.6); −0.0002 (4.8)
VIII-001: $^1$H-NMR(400.0 MHz, CDCl3):
δ = 8.3653 (1.7); 8.3637 (1.6); 8.3524 (1.7); 8.3508 (1.7); 7.3498 (0.5); 7.3368 (1.7); 7.3357 (1.7); 7.3317 (1.0); 7.3258 (0.9); 7.3225 (1.6); 7.3175 (3.9); 7.3134 (1.4); 7.3110 (0.7); 7.3046 (0.8); 7.3008 (0.7); 7.2976 (1.8); 7.2958 (2.0); 7.2940 (2.1); 7.2922 (1.7); 7.2622 (6.9); 7.1393 (0.5); 7.1357 (2.0); 7.1304 (1.7); 7.1252 (0.7); 7.1214 (0.8); 7.1199 (0.7); 7.1151 (1.8); 7.1113 (1.6); 7.0553 (1.6); 7.0516 (1.6); 7.0424 (1.6); 7.0387 (1.5); 5.2970 (3.2); 5.2587 (1.6); 5.2413 (1.6); 3.7830 (16.0); 1.6999 (6.6); 1.6825 (6.6); 1.5876 (0.5); −0.0002 (2.7)
VII-032: $^1$H-NMR(400.0 MHz, CDCl3):
δ = 8.6079 (1.2); 8.6038 (1.2); 8.5958 (1.2); 8.5916 (1.2); 8.5382 (1.3); 8.5362 (1.4); 8.5327 (1.5); 8.5306 (1.3); 7.6123 (0.7); 7.6079 (0.9); 7.6069 (0.8); 7.6025 (0.7); 7.5925 (0.8); 7.5880 (1.0); 7.5870 (1.0); 7.5826 (0.8); 7.3174 (0.9); 7.3152 (0.9); 7.3051 (1.2); 7.3029 (1.0); 7.3008 (0.7); 7.2991 (1.0); 7.2976 (1.0); 7.2953 (1.1); 7.2849 (2.0); 7.2831 (2.8); 7.2794 (1.0); 7.2767 (0.9); 7.2684 (1.1); 7.2644 (3.1); 7.2608 (13.2); 7.2557 (1.9); 7.2517 (1.0); 7.2396 (0.8); 7.2381 (0.8); 7.1293 (1.8); 7.1252 (2.3); 7.1196 (0.6); 7.1128 (1.0); 7.1082 (1.9); 7.1050 (1.5); 5.2970 (2.9); 5.2939 (0.6); 5.2763 (1.6); 5.2588 (1.6); 3.7915 (16.0); 1.7054 (6.5); 1.6879 (6.4); −0.0002 (6.3)
VI-010: $^1$H-NMR(400.0 MHz, CDCl3):
δ = 9.1887 (3.7); 8.6543 (8.7); 7.3569 (0.7); 7.3505 (1.1); 7.3349 (2.6); 7.3164 (3.5); 7.3123 (2.4); 7.3082 (1.7); 7.3031 (0.8); 7.2970 (1.3); 7.2948 (1.2); 7.2771 (1.0); 7.2597 (32.9); 7.1384 (2.2); 7.1339 (2.4); 7.1286 (0.9); 7.1222 (1.2); 7.1177 (2.1); 7.1143 (1.8); 5.2977 (1.6); 5.2894 (0.6); 5.2720 (1.7); 5.2546 (1.7); 5.2372 (0.5); 3.7898 (16.0); 3.7515 (1.0); 1.7082 (7.0); 1.6908 (7.0); 1.5456 (2.2); −0.0002 (18.3); −0.00083 (0.9)

-continued

VI-009: ¹H-NMR(400.0 MHz, CDCl3):
δ = 8.5224 (10.9); 7.3819 (0.6); 7.3663 (2.1); 7.3624 (1.0); 7.3592 (0.8); 7.3519 (1.2); 7.3477 (3.1); 7.3428 (1.8); 7.3388 (1.1); 7.3275 (0.8); 7.3252 (0.7); 7.2601 (25.0); 7.1418 (1.8); 7.1374 (2.1); 7.1320 (0.7); 7.1258 (1.0); 7.1210 (1.9); 7.1176 (1.7); 5.2981 (1.2); 5.2612 (1.6); 5.2438 (1.6); 3.7834 (16.0); 1.7031 (6.6); 1.6857 (6.5); 1.5407 (4.8); −0.0002 (12.0)

VII-014: ¹H-NMR(400.6 MHz, CDCl3):
δ = 8.1775 (1.0); 8.1753 (0.8); 8.1732 (0.9); 8.1713 (1.1); 8.1694 (0.7); 7.7853 (0.7); 7.6991 (0.6); 7.6928 (0.6); 7.6803 (0.7); 7.6779 (0.7); 7.6741 (0.7); 7.6717 (0.7); 7.6591 (0.6); 7.6529 (0.6); 7.3156 (0.5); 7.2994 (1.9); 7.2956 (0.7); 7.2930 (0.8); 7.2848 (0.9); 7.2809 (2.3); 7.2794 (1.5); 7.2766 (0.8); 7.2724 (1.5); 7.2684 (0.9); 7.2617 (10.7); 7.2564 (0.9); 7.2548 (0.8); 7.1152 (1.6); 7.1111 (2.0); 7.1054 (0.6); 7.0988 (0.9); 7.0942 (1.8); 7.0909 (1.4); 6.9552 (0.8); 6.9537 (0.8); 6.9477 (0.8); 6.9462 (0.7); 6.9340 (0.8); 6.9325 (0.7); 6.9265 (0.8); 6.9249 (0.7); 5.2990 (2.6); 5.2636 (1.5); 5.2461 (1.5); 3.7879 (16.0); 3.7703 (1.9); 1.7020 (6.3); 1.6846 (6.6); 1.6681 (0.8); −0.0002 (6.5)

VII-018: ¹H-NMR(400.0 MHz, CDCl3):
δ = 8.1829 (1.3); 8.1767 (1.4); 7.7062 (0.7); 7.6999 (0.7); 7.6874 (0.8); 7.6850 (0.9); 7.6811 (0.8); 7.6788 (0.8); 7.6662 (0.7); 7.6600 (0.7); 7.3300 (0.7); 7.3139 (2.4); 7.3102 (1.0); 7.3073 (1.0); 7.2994 (1.2); 7.2954 (2.9); 7.2880 (2.0); 7.2841 (1.1); 7.2781 (0.5); 7.2723 (1.0); 7.2706 (1.0); 7.2614 (14.4); 7.1394 (2.0); 7.1351 (2.4); 7.1295 (0.8); 7.1231 (1.1); 7.1184 (2.0); 7.1151 (1.7); 6.9591 (1.0); 6.9578 (1.0); 6.9516 (1.0); 6.9503 (1.0); 6.9379 (0.9); 6.9365 (1.0); 6.9303 (0.9); 6.9290 (0.9); 4.9458 (9.2); 3.8215 (0.7); 3.8143 (16.0); −0.0002 (9.0)

VII-008: ¹H-NMR(400.0 MHz, CDCl3):
δ = 8.6130 (1.1); 8.6088 (1.2); 8.6008 (1.2); 8.5966 (1.1); 8.5451 (1.3); 8.5431 (1.4); 8.5395 (1.4); 8.5376 (1.3); 7.6197 (0.7); 7.6153 (0.9); 7.6099 (0.7); 7.5999 (0.8); 7.5956 (1.0); 7.5946 (1.0); 7.5901 (0.8); 7.3198 (0.9); 7.3177 (0.9); 7.3076 (0.9); 7.3055 (0.9); 7.2999 (1.0); 7.2978 (1.2); 7.2933 (0.6); 7.2919 (0.7); 7.2877 (1.2); 7.2857 (1.0); 7.2758 (2.2); 7.2719 (0.9); 7.2692 (1.0); 7.2606 (9.4); 7.2572 (2.8); 7.2534 (1.0); 7.2490 (1.7); 7.2449 (1.0); 7.2329 (0.8); 7.2314 (0.8); 7.1178 (1.8); 7.1136 (2.3); 7.1080 (0.6); 7.1014 (1.0); 7.0968 (1.8); 7.0935 (1.6); 5.2722 (1.6); 5.2548 (1.6); 3.7911 (16.0); 1.7049 (6.7); 1.6874 (6.6); 1.2552 (0.6); −0.0002 (10.1)

VI-013: ¹H-NMR(599.6 MHz, CDCl3):
δ = 9.1912 (13.2); 8.6642 (27.2); 7.3393 (1.9); 7.3367 (2.9); 7.3335 (1.6); 7.3252 (8.5); 7.3226 (4.2); 7.3125 (8.2); 7.3077 (1.6); 7.3042 (2.9); 7.3020 (4.8); 7.2997 (3.0); 7.2943 (1.5); 7.2904 (4.2); 7.2848 (0.8); 7.2799 (0.9); 7.2779 (1.2); 7.2641 (9.0); 7.1239 (7.0); 7.1215 (9.6); 7.1180 (2.5); 7.1124 (4.5); 7.1097 (7.8); 7.1031 (0.6); 5.2774 (1.7); 5.2658 (5.6); 5.2542 (5.7); 5.2426 (1.7); 3.7889 (50.0); 3.4853 (3.5); 1.7045 (22.4); 1.6929 (22.2); 1.6444 (0.4); 1.6315 (0.5); 1.6182 (1.2); 1.3662 (0.5); 1.3537 (0.6); 1.3414 (0.4); 1.3103 (0.6); 1.2967 (0.6); 1.2887 (0.4); 1.2838 (0.7); 1.2769 (0.5); 1.2649 (0.5); 1.2557 (1.6); 0.9354 (1.0); 0.9231 (1.9); 0.9109 (0.9); 0.8796 (0.3); 0.0052 (0.3); −0.00001 (6.3)

VII-020: ¹H-NMR(599.7 MHz, CDCl3):
δ = 8.1762 (5.0); 8.1721 (4.9); 7.7835 (0.4); 7.6907 (1.8); 7.6866 (1.9); 7.6780 (2.5); 7.6767 (2.6); 7.6740 (2.5); 7.6726 (2.4); 7.6641 (1.9); 7.6599 (1.8); 7.3115 (1.8); 7.3092 (3.0); 7.3062 (1.4); 7.2976 (8.2); 7.2949 (4.0); 7.2871 (3.0); 7.2847 (7.0); 7.2803 (1.0); 7.2713 (2.3); 7.2692 (4.3); 7.2670 (2.8); 7.2604 (26.3); 7.2574 (5.0); 7.2524 (0.9); 7.2469 (0.8); 7.2449 (1.2); 7.1114 (6.0); 7.1090 (9.2); 7.1055 (2.1); 7.0971 (6.6); 7.0962 (6.6); 7.0906 (0.6); 6.9481 (3.0); 6.9436 (3.0); 6.9339 (2.9); 6.9294 (2.9); 5.2725 (1.6); 5.2609 (5.4); 5.2492 (5.4); 5.2376 (1.6); 3.7877 (50.0); 3.7702 (1.1); 1.6988 (21.5); 1.6871 (21.4); 1.6709 (0.5); 1.5508 (7.9); 1.2556 (0.8); 0.0697 (1.6); 0.0053 (0.9); −0.00001 (23.4); −0.0056 (0.8)

VII-026: ¹H-NMR(599.7 MHz, CDCl3):
δ = 8.1741 (12.4); 7.7835 (2.0); 7.6882 (3.6); 7.6751 (6.8); 7.6620 (3.6); 7.5061 (1.6); 7.4931 (2.0); 7.4100 (1.0); 7.3977 (1.8); 7.3851 (0.9); 7.3090 (5.3); 7.2970 (13.9); 7.2847 (11.3); 7.2601 (24.2); 7.2458 (2.2); 7.2304 (0.7); 7.2185 (1.0); 7.2061 (0.4); 7.1095 (15.5); 7.0971 (13.7); 6.9457 (6.6); 6.9316 (6.2); 5.2985 (0.4); 5.2723 (2.1); 5.2608 (6.2); 5.2494 (6.2); 5.2377 (2.1); 5.2097 (0.8); 5.1977 (0.8); 3.7876 (50.0); 3.7701 (6.4); 1.6987 (24.9); 1.6869 (25.7); 1.6709 (3.4); 1.5548 (9.4); 1.4271 (0.4); 1.2830 (0.6); 1.2565 (2.9); 0.8812 (0.5); 0.8414 (0.3); 0.0706 (0.8); −0.00001 (16.0)

VII-107: ¹H-NMR(400.6 MHz, CDCl3):
δ = 8.1085 (1.2); 8.1066 (0.9); 8.1044 (1.0); 8.1023 (1.2); 7.7792 (0.6); 7.7729 (0.6); 7.7605 (0.7); 7.7580 (0.7); 7.7543 (0.7); 7.7518 (0.7); 7.7393 (0.6); 7.7331 (0.6); 7.2617 (6.7); 7.1488 (0.7); 7.1422 (0.5); 7.0336 (0.5); 7.0247 (0.6); 7.0152 (0.5); 6.9966 (0.6); 6.9847 (0.6); 6.9723 (1.1); 6.9706 (1.0); 6.9626 (1.5); 6.9507 (1.1); 6.9432 (0.8); 6.9417 (0.9); 5.2145 (1.5); 5.1971 (1.6); 3.7871 (16.0); 1.6992 (6.4); 1.6818 (6.4); 1.5554 (2.8); 1.2643 (0.6); 1.2596 (0.6); 0.8818 (1.1); −0.0002 (8.7)

VII-089: ¹H-NMR(400.6 MHz, CDCl3):
δ = 8.1168 (1.2); 8.1146 (0.9); 8.1124 (1.0); 8.1105 (1.2); 7.7892 (0.6); 7.7829 (0.6); 7.7705 (0.7); 7.7680 (0.8); 7.7642 (0.7); 7.7617 (0.7); 7.7494 (0.7); 7.7431 (0.6); 7.2615 (9.2); 7.2016 (0.5); 7.1950 (0.5); 7.1878 (0.7); 7.1815 (0.5); 7.1671 (0.5); 7.0477 (0.5); 7.0464 (0.5); 7.0377 (0.6); 7.0295 (0.5); 7.0063 (0.6); 6.9944 (0.7); 6.9835 (1.0); 6.9788 (1.0); 6.9773 (1.0); 6.9714 (1.8); 6.9576 (0.9); 6.9561 (0.9); 6.9499 (1.0); 6.9486 (1.1); 4.9174 (8.5); 3.8160 (16.0); 2.0454 (0.9); 1.5529 (5.0); 1.2596 (0.8); 0.8819 (1.0); −0.0002 (12.0)

VII-062: ¹H-NMR(400.0 MHz, CDCl3):
δ = 12.9997 (1.4); 12.9934 (1.5); 12.7492 (0.6); 12.7429 (0.5); 12.7281 (0.8); 12.7219 (0.8); 12.7086 (0.6); 12.7023 (0.6); 12.2687 (0.7); 12.1477 (0.5); 12.1411 (1.1); 12.1363 (0.6); 12.1292 (1.4); 12.1251 (1.1); 12.1201 (0.9); 12.1081 (0.8); 12.0723 (0.9); 12.0660 (0.9); 12.0509 (0.9); 12.0448 (0.8); 9.9323 (1.7); 9.9150 (1.8); 8.4482 (15.2); 8.0735 (10.4); 7.2662 (8.0); 7.2617 (17.9); 7.2571 (25.1); 7.2525 (17.9); 7.2479 (8.1); 6.3407 (5.6); 6.3234 (5.6); 6.0021 (0.6); 5.6129 (1.1); 4.7547 (16.0)

VII-063: ¹H-NMR(400.6 MHz, CDCl3):
δ = 8.1212 (1.2); 8.1192 (0.9); 8.1166 (1.0); 8.1148 (1.3); 7.8944 (0.6); 7.8880 (0.6); 7.8762 (0.7); 7.8730 (0.8); 7.8698 (0.7); 7.8666 (0.7); 7.8550 (0.7); 7.8485 (0.6); 7.2636 (7.5); 7.2552 (0.6); 7.2414 (0.6); 7.2359 (0.5); 7.2217 (0.5); 7.1344 (0.6); 7.0801 (0.6); 7.0685 (0.6); 7.0573 (0.9); 7.0492 (0.9); 7.0477 (1.1); 7.0459 (1.1); 7.0418 (0.9); 7.0404 (0.9); 7.0280 (0.8); 7.0266 (0.8); 7.0206 (0.9); 7.0191 (0.8); 4.9218 (8.2); 3.8192 (16.0); 2.0451 (1.5); 1.5738 (1.7); 1.2775 (0.5); 1.2597 (1.1); 0.8820 (0.8); −0.0002 (5.6)

VII-099: ¹H-NMR(400.0 MHz, CDCl3):
δ = 8.1100 (1.2); 8.1037 (1.2); 7.8855 (0.6); 7.8791 (0.6); 7.8673 (0.7); 7.8641 (0.7); 7.8609 (0.7); 7.8577 (0.7); 7.8460 (0.6); 7.8396 (0.6); 7.2615 (28.8); 7.2149 (0.6); 7.2012 (0.7); 7.1955 (0.6); 7.1813 (0.5); 7.1317 (0.6); 7.1227 (0.6); 7.1134 (0.5); 7.0713 (0.6); 7.0598 (0.6); 7.0484 (1.0); 7.0413 (0.9); 7.0364 (1.3); 7.0200 (0.8); 7.0135 (1.1); 5.2059 (1.6); 5.1884 (1.6); 3.7869 (16.0); 1.7019 (6.4); 1.6844 (6.4); 1.5523 (6.0); 0.8819 (0.5); 0.0079 (0.5); −0.0002 (17.6); −0.00085 (0.5)

VII-132: ¹H-NMR(400.0 MHz, CDCl3):
δ = 8.4735 (1.7); 8.4666 (1.7); 8.2823 (1.0); 8.2786 (1.7); 8.2751 (1.0); 7.4408 (0.6); 7.4363 (0.7); 7.4339 (0.7); 7.4295 (0.6); 7.4186 (0.7); 7.4142 (0.7); 7.4118 (0.7); 7.4073 (0.6); 7.2609 (22.8); 7.1601 (0.8); 7.1535 (0.5); 7.0410 (0.5); 7.0320 (0.6); 7.0025 (0.6); 6.9905 (0.6); 6.9795 (0.9); 6.9677 (0.9); 5.2169 (1.6); 5.1995 (1.6); 3.7885 (16.0); 1.7019 (6.3); 1.6845 (6.3); 1.5757 (0.5); 1.2650 (0.5); 0.8822 (0.9); −0.0002 (12.9)

VII-147: ¹H-NMR(400.0 MHz, CDCl3):
δ = 8.5489 (1.4); 8.5422 (1.4); 8.2971 (1.5); 7.4966 (0.7); 7.4920 (0.8); 7.4899 (0.8); 7.4852 (0.6); 7.4755 (0.7); 7.4708 (0.8); 7.4688 (0.7); 7.4641 (0.6); 7.2615 (7.8); 7.2237 (0.6); 7.2100 (0.7); 7.2043 (0.6); 7.1902 (0.5); 7.1382 (0.5); 7.1292 (0.6); 7.0751 (0.6); 7.0635 (0.6); 7.0523 (0.9); 7.0407 (0.9); 5.2109 (1.6); 5.1934 (1.6); 3.7892 (16.0); 1.7061 (6.4); 1.6886 (6.3); 1.5560 (0.9); 1.2646 (0.6); 1.2598 (0.6); 0.8819 (1.1); −0.0002 (10.3)

VII-149: ¹H-NMR(400.6 MHz, CDCl3):
δ = 7.8335 (1.0); 7.8289 (1.6); 7.8244 (1.1); 7.5784 (0.5); 7.5733 (0.5); 7.5562 (0.7); 7.5552 (0.7); 7.5511 (0.7); 7.5501 (0.7); 7.5331 (0.5); 7.5280 (0.5); 7.3925 (0.7); 7.3880 (1.0); 7.3743 (0.6); 7.3696 (0.9); 7.3556 (0.5); 7.2613 (9.5); 7.2407 (0.5); 7.2389 (0.6); 7.2376 (0.5); 7.2229 (0.7); 7.2214 (0.8); 7.2194 (0.8); 7.0650 (0.5); 7.0617 (0.5); 7.0402 (0.8); 7.0365 (0.5); 5.2252 (1.5); 5.2078 (1.5); 3.7756 (16.0); 1.6949 (6.2); 1.6775 (6.2); 1.5569 (4.9); 1.5545 (6.0); −0.0002 (13.4)

VII-148: ¹H-NMR(400.6 MHz, CDCl3):
δ = 7.8417 (1.8); 7.8371 (2.7); 7.8326 (2.0); 7.5873 (1.0); 7.5822 (0.9); 7.5652 (1.2); 7.5642 (1.3); 7.5601 (1.2); 7.5590 (1.2); 7.5421 (1.0); 7.5370 (0.9); 7.4473 (0.7); 7.4430 (0.8); 7.4281 (1.3); 7.4237 (1.5); 7.4093 (0.9); 7.4049 (1.1); 7.3978 (0.5); 7.3856 (0.5); 7.3811 (0.5); 7.3790 (0.8); 7.3771 (0.6); 7.3745 (0.7); 7.3727 (0.6); 7.3667 (0.8); 7.3649 (0.6); 7.3622 (0.7); 7.3604 (0.6); 7.3582 (0.8); 7.3538 (0.6); 7.3460 (0.7); 7.3415 (0.6); 7.2613 (22.9); 7.2555 (1.0); 7.2538 (1.1); 7.2521 (1.1); 7.2507 (1.0); 7.2347 (1.3); 7.2323 (1.3); 7.2169 (0.6); 7.2153 (0.6); 7.2135 (0.6); 7.2121 (0.6); 7.0720 (1.6); 7.0687 (0.9); 7.0512 (0.9); 7.0474 (1.5); 7.0436 (1.0); 7.0260 (0.9); 7.0228 (0.8); 4.8983 (14.4); 4.2967 (1.8); 4.2788 (5.7); 4.2610 (5.8); 4.2433 (2.1); 4.2325 (0.7); 1.5546 (9.6); 1.5531 (11.2); 1.3085 (7.6); 1.2996 (0.5); 1.2907 (16.0); 1.2729 (7.5); 0.0080 (0.8); −0.0002 (28.6); −0.00084 (0.9)

VII-109: ¹H-NMR(400.0 MHz, CDCl3):
δ = 8.1443 (1.3); 8.1382 (1.3); 7.8118 (0.6); 7.8056 (0.6); 7.7931 (0.7); 7.7907 (0.8); 7.7869 (0.7); 7.7845 (0.7); 7.7720 (0.6); 7.7657 (0.6); 7.3767 (0.6); 7.3704 (0.5); 7.3553 (1.2); 7.3400 (0.5); 7.3339 (0.6); 7.2608 (11.7); 6.9679 (0.7); 6.9645 (1.7); 6.9561 (1.0); 6.9461 (2.3); 6.9429 (2.2); 6.9363 (1.0); 6.9273 (1.1); 6.9247 (1.6); 6.9211 (0.6); 4.9047 (9.0); 3.7951 (16.0); 1.5463 (4.8); −0.0002 (14.7)

VIII-010: ¹H-NMR(400.0 MHz, CDCl3):
δ = 8.2300 (1.6); 8.2171 (1.7); 7.2618 (17.8); 7.2188 (0.6); 7.2123 (0.5); 7.2052 (0.8); 7.1988 (0.6); 7.1921 (0.5); 7.1844 (0.5); 7.0805 (1.0); 7.0767 (1.7); 7.0728 (1.0); 7.0676 (1.3); 7.0635 (1.3); 7.0596 (1.2); 7.0299 (0.7); 7.0181 (0.7); 7.0069 (1.0); 6.9951 (1.0); 6.8866 (1.8); 4.9178 (8.9); 3.8161 (16.0); 1.2595 (0.5); 0.8818 (0.7); −0.0002 (10.5)

VII-061: ¹H-NMR(400.6 MHz, CDCl3):
δ = 8.1472 (1.1); 8.1408 (1.2); 7.9059 (0.6); 7.8995 (0.6); 7.8878 (0.7); 7.8846 (0.7); 7.8814 (0.7); 7.8782 (0.7); 7.8665 (0.7); 7.8601 (0.6); 7.4662 (0.6); 7.4447 (1.1); 7.4233 (0.6); 7.2626 (15.7); 7.0316 (1.4); 7.0304 (1.4); 7.0275 (1.6); 7.0243 (1.0); 7.0227 (1.0); 7.0092 (2.7); 7.0059 (2.1); 7.0031 (1.3); 7.0016 (1.1); 6.9878 (1.2); 6.9840 (0.7); 4.9104 (8.4); 3.8003 (16.0); 2.0454 (0.7); 1.5634 (1.1); 1.2596 (0.6); 0.8818 (0.6); −0.0002 (9.6)

VDI-008: ¹H-NMR(400.0 MHz, CDCl3):
δ = 8.3101 (1.6); 8.2971 (1.7); 7.2765 (0.5); 7.2689 (0.8); 7.2612 (40.1); 7.2495 (0.7); 7.2431 (0.5); 7.2354 (0.6); 7.1754 (0.6); 7.1665 (0.6); 7.1570 (0.5); 7.1497 (1.0); 7.1462 (1.4); 7.1424 (0.8); 7.1369 (0.8); 7.1331 (1.4); 7.1294 (0.7); 7.1039 (0.6); 7.0923 (0.6); 7.0811 (1.0); 7.0696 (1.0); 6.8648 (1.1); 6.8611 (1.7); 4.9268 (8.6); 3.8211 (16.0); 2.0455 (0.5); 1.5511 (5.3); 0.0079 (0.7); −0.0002 (24.4); −0.0085 (0.7)

VII-116: ¹H-NMR(400.0 MHz, CDCl3_5 mm):
δ = 8.1822 (2.0); 8.1802 (1.6); 8.1780 (1.6); 8.1760 (2.0); 8.1741 (1.4); 7.7065 (1.1); 7.7002 (1.1); 7.6877 (1.2); 7.6852 (1.4); 7.6815 (1.3); 7.6790 (1.3); 7.6665 (1.2); 7.6602 (1.1); 7.3329 (0.7); 7.3286 (0.9); 7.3270 (1.0); 7.3226 (0.7); 7.3188 (0.5); 7.3164 (0.6); 7.3110 (3.5); 7.3072 (1.4); 7.3044 (1.4); 7.2964 (1.7); 7.2925 (4.4); 7.2909 (3.1); 7.2850 (3.1); 7.2811 (1.7); 7.2752 (0.8); 7.2694 (1.6); 7.2675 (1.5); 7.2654 (0.8); 7.2612 (15.4); 7.1383 (3.1); 7.1341 (3.6); 7.1285 (1.0); 7.1221 (1.6); 7.1174 (3.2); 7.1140 (2.7); 6.9588 (1.4); 6.9573 (1.4); 6.9513 (1.4); 6.9497 (1.4); 6.9376 (1.4); 6.9361 (1.4); 6.9300 (1.4); 6.9285 (1.3); 5.2998 (1.2); 4.9232 (14.8); 4.3064 (1.9); 4.2886 (5.9); 4.2707 (6.0); 4.2529 (1.9); 2.0452 (1.3); 1.5611 (5.1); 1.3332 (0.7); 1.3215 (7.7); 1.3037 (16.0); 1.2933 (0.6); 1.2858 (7.9); 1.2773 (0.8); 1.2593 (2.2); 1.2551 (2.2); 1.2441 (0.8); 1.2416 (0.9); 0.0079 (0.6); −0.0002 (19.6); −0.00085 (0.6)

VII-132: ¹H-NMR(400.0 MHz, CDCl3_5 mm):
δ = 8.4736 (2.2); 8.4668 (2.1); 8.2822 (1.4); 8.2786 (2.2); 8.2750 (1.3); 7.4407 (0.8); 7.4362 (0.9); 7.4339 (0.9); 7.4294 (0.7); 7.4186 (0.8); 7.4141 (0.9); 7.4118 (0.8); 7.4073 (0.7); 7.2612 (8.1); 7.1818 (0.5); 7.1741 (0.6); 7.1675 (0.6); 7.1605 (0.9); 7.1540 (0.6); 7.1474 (0.6); 7.1396 (0.5); 7.0501 (0.6); 7.0451 (0.5); 7.0421 (0.7); 7.0324 (0.7); 7.0238 (0.6); 7.0029 (0.7); 6.9909 (0.7); 6.9799 (1.0); 6.9681 (1.0); 5.2346 (0.5); 5.2172 (1.7); 5.1997 (1.7); 3.7886 (16.0); 1.7021 (6.8); 1.6847 (6.6); 1.5562 (5.0); 0.0078 (0.8); −0.0002 (12.3)

VII-135: ¹H-NMR(400.0 MHz, CDCl3_5 mm):
δ = 8.4716 (2.0); 8.4647 (2.0); 8.2834 (1.2); 8.2797 (2.0); 8.2761 (1.1); 7.4260 (0.7); 7.4216 (0.8); 7.4192 (0.8); 7.4147 (0.7); 7.4040 (0.7); 7.3995 (0.8); 7.3971 (0.8); 7.3927 (0.6); 7.2627 (3.6); 7.1542

(0.6); 7.1476 (0.5); 7.1404 (0.8); 7.1340 (0.5); 7.0274 (0.6); 7.0261 (0.6); 7.0174 (0.6); 7.0092 (0.5); 7.0077 (0.5); 6.9896 (0.6); 6.9777 (0.7); 6.9667 (0.9); 6.9548 (0.9); 5.3001 (2.2); 5.2041 (1.6); 5.1867 (1.6); 3.7849 (16.0); 1.6974 (6.5); 1.6800 (6.4); 1.5841 (1.4); −0.0002 (5.3)

VII-136: $^1$H-NMR(400.6 MHz, CDCl3):
δ = 8.4722 (2.1); 8.4654 (2.2); 8.2823 (1.4); 8.2788 (2.3); 8.2753 (1.4); 7.4419 (1.1); 7.4375 (1.2); 7.4351 (1.2); 7.4307 (1.1); 7.4199 (1.2); 7.4155 (1.2); 7.4130 (1.2); 7.4086 (1.1); 7.2610 (21.0); 7.1881 (0.7); 7.1806 (0.8); 7.1740 (0.8); 7.1669 (1.2); 7.1604 (0.8); 7.1537 (0.8); 7.1461 (0.8); 7.0517 (0.5); 7.0468 (0.7); 7.0420 (0.6); 7.0390 (0.8); 7.0376 (0.8); 7.0288 (1.0); 7.0208 (0.7); 7.0192 (0.8); 7.0114 (0.6); 6.9975 (1.1); 6.9858 (1.0); 6.9747 (1.4); 6.9629 (1.4); 6.9517 (0.6); 9.9400 (0.5); 5.1999 (0.8); 5.1825 (2.9); 5.1651 (3.0); 5.1478 (0.8); 4.2753 (2.0); 4.2575 (6.5); 4.2397 (6.6); 4.2219 (2.1); 1.6974 (11.2); 1.6800 (11.1); 1.5533 (7.9); 1.2922 (7.6); 1.2744 (16.0); 1.2679 (1.2); 1.2642 (1.3); 1.2566 (7.6); 0.8988 (0.6); 0.8819 (2.4); 0.8642 (0.9); 0.0080 (0.8); −0.0002 (30.5); −0.00084 (0.9)

VII-137: $^1$H-NMR(400.6 MHz, CDCl3):
δ = 8.4896 (2.9); 8.4829 (3.3); 8.2894 (3.3); 7.5187 (0.5); 7.4545 (1.8); 7.4501 (1.8); 7.4477 (1.9); 7.4433 (1.7); 7.4326 (1.8); 7.4282 (2.0); 7.4257 (1.8); 7.4213 (1.7); 7.2603 (93.5); 7.2024 (1.1); 7.1947 (1.3); 7.1882 (1.3); 7.1810 (1.8); 7.1747 (1.4); 7.1680 (1.3); 7.1604 (1.4); 7.0776 (0.6); 7.0684 (0.8); 7.0601 (0.9); 7.0547 (1.1); 7.0500 (1.0); 7.0467 (1.4); 7.0422 (0.8); 7.0368 (1.6); 7.0272 (1.3); 7.0193 (0.9); 7.0036 (1.6); 6.9966 (0.7); 6.9917 (1.6); 6.9805 (2.6); 6.9687 (2.4); 6.9576 (0.9); 6.9459 (0.9); 5.3057 (1.1); 5.2882 (4.8); 5.2767 (0.7); 5.2708 (4.9); 5.2593 (0.7); 5.2533 (1.2); 2.2718 (0.5); 1.7598 (16.0); 1.7544 (2.9); 1.7423 (16.0); 1.7369 (2.9); 1.6972 (0.5); 1.4322 (5.2); 1.2917 (0.7); 1.2740 (1.4); 1.2651 (2.0); 0.8990 (1.1); 0.8820 (3.9); 0.8643 (1.4); 0.0080 (3.6); −0.0002 (136.5); −0.00085 (4.2)

VII-080: $^1$H-NMR(400.6 MHz, CDCl3):
δ = 8.2290 (0.6); 8.2220 (5.8); 8.2165 (1.9); 8.2044 (1.8); 8.1989 (6.4); 8.1919 (0.8); 8.1504 (2.0); 8.1486 (1.6); 8.1462 (1.6); 8.1441 (2.2); 7.9076 (1.0); 7.9013 (1.0); 7.8895 (1.2); 7.8864 (1.3); 7.8832 (1.2); 7.8800 (1.2); 7.8682 (1.1); 7.8619 (1.1); 7.3289 (0.7); 7.3218 (6.1); 7.3163 (1.9); 7.3043 (1.8); 7.2988 (6.2); 7.2917 (0.7); 7.2611 (32.0); 7.1092 (1.4); 7.1077 (1.4); 7.1016 (1.4); 7.1002 (1.4); 7.0880 (1.3); 7.0865 (1.4); 7.0804 (1.3); 7.0789 (1.4); 5.0340 (13.4); 5.0212 (0.8); 4.3238 (1.8); 4.3060 (5.9); 4.2882 (6.0); 4.2704 (2.0); 2.0453 (1.0); 1.5441 (16.0); 1.3340 (7.4); 1.3162 (15.5); 1.3024 (1.0); 1.2984 (7.2); 1.2917 (0.6); 1.2846 (0.5); 1.2596 (0.7); 0.0081 (1.2); −0.0002 (47.4); −0.00085 (1.4)

VII-079: $^1$H-NMR(400.6 MHz, CDCl3):
δ = 8.1094 (1.9); 8.1074 (1.5); 8.1052 (1.5); 8.1031 (2.0); 8.1012 (1.3); 7.8474 (1.1); 7.8411 (1.1); 7.8290 (1.2); 7.8261 (1.3); 7.8227 (1.2); 7.8199 (1.2); 7.8077 (1.2); 7.8015 (1.1); 7.5192 (0.6); 7.3638 (0.5); 7.3590 (0.7); 7.3562 (0.9); 7.3525 (6.2); 7.3483 (4.8); 7.3401 (2.4); 7.3347 (3.0); 7.3336 (2.7); 7.3309 (0.8); 7.3277 (0.6); 7.3233 (1.1); 7.2674 (0.6); 7.2608 (103.1); 7.1284 (3.2); 7.1240 (2.8); 7.1178 (1.0); 7.1153 (1.9); 7.1110 (1.9); 7.1093 (1.3); 7.1039 (3.0); 7.0183 (1.4); 7.0167 (1.4); 7.0108 (1.4); 7.0092 (1.4); 6.9971 (1.9); 6.9955 (1.4); 6.9895 (1.4); 6.9880 (1.4); 5.3002 (7.3); 5.0215 (14.2); 4.3130 (1.8); 4.2951 (5.9); 4.2773 (6.0); 4.2595 (1.9); 1.5456 (2.7); 1.3203 (7.5); 1.3025 (16.0); 1.2847 (7.5); 0.0080 (1.8); −0.0002 (62.7); −0.00085 (1.7)

VII-145: $^1$H-NMR(400.6 MHz, CDCl3):
δ = 8.4727 (1.3); 8.4659 (1.3); 8.2780 (0.7); 8.2742 (1.3); 8.2706 (0.8); 7.4389 (0.6); 7.4345 (0.6); 7.4321 (0.6); 7.4276 (0.5); 7.4169 (0.6); 7.4124 (0.6); 7.4100 (0.6); 7.4056 (0.5); 7.2613 (25.4); 7.1938 (0.6); 6.9715 (0.7); 6.9597 (0.7); 5.2352 (1.4); 5.2177 (1.4); 4.3523 (1.0); 4.3505 (1.0); 4.3426 (1.1); 4.3411 (1.1); 4.3381 (1.1); 4.3362 (1.0); 4.3287 (1.1); 4.3267 (1.1); 3.6095 (1.9); 3.5998 (1.1); 3.5977 (1.7); 3.5955 (1.1); 3.5858 (1.8); 3.3342 (16.0); 1.7149 (5.1); 1.6975 (5.0); −0.0002 (16.1)

VII-144: $^1$H-NMR(400.6 MHz, CDCl3):
δ = 8.4729 (1.1); 8.4661 (1.2); 8.2976 (1.2); 7.4547 (0.6); 7.4503 (0.7); 7.4478 (0.7); 7.4434 (0.6); 7.4326 (0.6); 7.4282 (0.7); 7.4257 (0.7); 7.4213 (0.6); 7.2610 (51.1); 7.2519 (0.5); 7.2370 (0.5); 7.2299 (0.6); 7.0332 (0.5); 6.9977 (0.7); 6.9866 (0.6); 6.9755 (0.8); 6.9637 (0.8); 5.1811 (1.6); 5.1637 (1.7); 4.4858 (0.8); 4.4706 (1.1); 4.4692 (1.0); 4.4536 (1.4); 4.4375 (1.2); 4.4226 (0.8); 3.6447 (16.0); 2.6792 (0.9); 2.6745 (0.9); 2.6643 (1.2); 2.6627 (1.2); 2.6588 (1.7); 2.6477 (0.9); 2.6434 (0.9); 1.6869 (6.0); 1.6695 (6.0); 0.0080 (0.8); −0.0002 (31.9); −0.00085 (0.9)

VII-143: $^1$H-NMR(400.6 MHz, CDCl3):
δ = 8.5473 (2.7); 8.5406 (2.8); 8.2997 (1.6); 8.2962 (2.6); 8.2927 (1.6); 7.5192 (0.6); 7.4975 (1.2); 7.4928 (1.3); 7.4907 (1.3); 7.4860 (1.2); 7.4764 (1.3); 7.4717 (1.4); 7.4695 (1.3); 7.4650 (1.2); 7.2607 (115.7); 7.2559 (1.6); 7.2551 (1.3); 7.2348 (0.5); 7.2336 (0.5); 7.2269 (0.9); 7.2205 (0.8); 7.2129 (1.1); 7.2073 (0.9); 7.2010 (0.8); 7.1932 (0.9); 7.1579 (0.6); 7.1492 (0.6); 7.1443 (0.7); 7.1396 (0.7); 7.1350 (0.8); 7.1263 (0.9); 7.1167 (0.8); 7.1088 (0.5); 7.0706 (1.0); 7.0590 (1.0); 7.0478 (1.5); 7.0362 (1.5); 7.0249 (0.6); 7.0133 (0.6); 6.9971 (0.6); 5.1916 (0.8); 5.1742 (2.9); 5.1568 (3.0); 5.1394 (0.8); 4.2746 (1.9); 4.2568 (6.2); 4.2390 (6.4); 4.2213 (2.1); 1.7010 (11.2); 1.6836 (11.1); 1.5478 (5.6); 1.2907 (7.5); 1.2730 (16.0); 1.2597 (0.8); 1.2552 (7.5); 0.8821 (0.8); 0.0080 (2.0); −0.0002 (71.8); −0.00085 (2.0)

VII-086: $^1$H-NMR(400.6 MHz, CDCl3):
δ = 8.2243 (0.9); 8.2221 (0.7); 8.2200 (0.7); 8.2180 (1.0); 8.1733 (2.9); 8.1679 (0.8); 8.1557 (0.9); 8.1502 (3.0); 7.7546 (0.5); 7.7484 (0.5); 7.7362 (0.6); 7.7335 (0.6); 7.7299 (0.6); 7.7272 (0.6); 7.7150 (0.5); 7.7087 (0.5); 7.2804 (3.1); 7.2750 (0.9); 7.2607 (48.3); 7.2582 (3.4); 7.2574 (3.6); 7.0583 (0.6); 7.0567 (0.6); 7.0507 (0.7); 7.0491 (0.6); 7.0371 (0.6); 7.0355 (0.6); 7.0295 (0.6); 7.0279 (0.6); 5.2544 (1.3); 5.2370 (1.3); 3.8009 (14.1); 2.0456 (0.7); 1.7233 (5.2); 1.7058 (5.2); 1.5414 (16.0); 1.2639 (0.5); 1.2598 (0.7); 0.8820 (1.1); 0.0080 (1.3); −0.0002 (41.0); −0.00085 (1.0)

VII-087: $^1$H-NMR(400.6 MHz, CDCl3):
δ = 8.2282 (1.7); 8.2261 (1.3); 8.2239 (1.4); 8.2219 (1.8); 8.1881 (0.5); 8.1809 (5.2); 8.1755 (1.5); 8.1633 (1.6); 8.1578 (5.4); 8.1506 (0.6); 7.7600 (0.9); 7.7537 (0.9); 7.7415 (1.0); 7.7388 (1.1); 7.7352 (1.0); 7.7325 (1.0); 7.7204 (1.0); 7.7141 (1.0); 7.3122 (0.6); 7.3051 (5.5); 7.2996 (1.5); 7.2874 (1.5); 7.2820 (5.0); 7.2748 (0.5); 7.2610 (48.3); 7.0615 (1.2); 7.0600 (1.2); 7.0539 (1.2); 7.0524 (1.1); 7.0403 (1.2); 7.0388 (1.1); 7.0327 (1.2); 7.0312 (1.1); 4.9364 (12.0); 4.3214 (1.6); 4.3036 (5.0); 4.2858 (5.1); 4.2680 (1.6); 4.1310 (0.5); 4.1132 (0.5); 2.7762 (0.8); 2.0455 (2.5); 1.5447 (16.0); 1.3362 (6.3); 1.3184 (13.2); 1.3006 (6.3); 1.2776 (1.0); 1.2598 (2.0); 1.2419 (0.8); 0.8820 (1.7); 0.8644 (0.6); 0.0080 (1.0); −0.0002 (40.6); −0.00085 (1.2)

VII-142: $^1$H-NMR(400.6 MHz, CDCl3):
δ = 8.5599 (3.4); 8.5533 (3.5); 8.3115 (4.0); 7.5190 (2.8); 7.5142 (2.2); 7.5120 (2.0); 7.5074 (1.7); 7.4978 (1.9); 7.4932 (2.4); 7.4911 (2.0); 7.4865 (1.7); 7.2688 (0.5); 7.2606 (196.2); 7.2550 (1.7);

VII-146: ¹H-NMR(400.6 MHz, CDCl3):
δ = 8.4331 (1.1); 8.4265 (1.2); 8.2991 (1.3); 7.3374 (0.5); 7.3330 (0.6); 7.3308 (0.6); 7.3265 (0.5); 7.3149 (0.5); 7.3105 (0.7); 7.3083 (0.6); 7.3040 (0.5); 7.2615 (18.3); 7.1089 (0.8); 6.9795 (0.5); 6.9775 (0.5); 6.9692 (0.8); 6.9637 (0.8); 6.9591 (0.6); 6.9515 (1.0); 6.9415 (0.8); 6.9293 (0.8); 5.1951 (1.6); 5.1777 (1.6); 3.7717 (16.0); 1.6400 (6.5); 1.6226 (6.5); 1.5866 (0.5); 1.5672 (0.9); 1.2643 (0.7); 0.8818 (1.2); 0.8181 (0.9); 0.8137 (1.0); 0.8081 (1.7); 0.8022 (0.8); 0.7963 (2.1); 0.7911 (1.8); 0.7857 (0.8); 0.7784 (0.9); 0.7728 (1.3); 0.7646 (0.6); −0.0002 (10.9)

VII-141: ¹H-NMR(400.6 MHz, CDCl3):
δ = 8.4552 (1.6); 8.3167 (1.8); 7.5193 (0.8); 7.3575 (1.3); 7.3534 (1.5); 7.3510 (1.6); 7.3468 (1.4); 7.3353 (1.4); 7.3312 (1.6); 7.3288 (1.5); 7.3246 (1.2); 7.2665 (0.6); 7.2607 (149.3); 7.2543 (2.3); 7.2503 (0.8); 7.2495 (0.8); 7.2336 (0.7); 7.1557 (1.0); 7.1484 (1.2); 7.1415 (1.3); 7.1343 (2.2); 7.1278 (1.3); 7.1207 (1.3); 7.1134 (1.3); 7.0127 (0.7); 7.0046 (0.8); 6.9994 (1.3); 6.9971 (1.6); 6.9919 (1.5); 6.9899 (1.5); 6.9816 (2.1); 6.9719 (3.0); 6.9639 (1.3); 6.9602 (1.9); 6.9496 (2.3); 6.9375 (2.3); 6.9267 (0.8); 6.9148 (0.7); 5.2607 (1.2); 5.2433 (4.8); 5.2259 (4.9); 5.2085 (1.2); 1.6962 (16.0); 1.6788 (16.0); 1.6001 (0.7); 1.5871 (0.7); 1.5821 (1.5); 1.5735 (1.0); 1.5658 (2.6); 1.5594 (1.0); 1.5532 (1.1); 1.5477 (1.6); 1.5318 (0.9); 1.4322 (3.4); 1.2642 (1.2); 0.8989 (0.6); 0.8820 (2.2); 0.8642 (0.9); 0.8168 (0.5); 0.8006 (1.8); 0.7957 (3.4); 0.7933 (4.7); 0.7825 (3.2); 0.7763 (9.2); 0.7681 (4.2); 0.7639 (6.1); 0.0080 (2.0); −0.0002 (88.7); −0.00066 (1.9); −0.00085 (3.2); −0.0273 (0.5)

VII-140: ¹H-NMR(400.6 MHz, CDCl3):
δ = 8.4317 (3.0); 8.4249 (3.1); 8.3030 (1.8); 8.2991 (3.2); 8.2953 (1.8); 7.3395 (1.2); 7.3352 (1.3); 7.3326 (1.3); 7.3283 (1.2); 7.3170 (1.2); 7.3126 (1.4); 7.3102 (1.3); 7.3058 (1.2); 7.2613 (47.8); 7.1389 (0.7); 7.1317 (0.8); 7.1247 (0.8); 7.1175 (1.5); 7.1115 (0.8); 7.1038 (0.8); 7.0966 (0.8); 6.9974 (0.6); 6.9891 (0.5); 6.9840 (0.8); 6.9765 (0.9); 6.9745 (0.9); 6.9662 (1.4); 6.9590 (1.9); 6.9562 (1.0); 6.9479 (1.6); 6.9368 (1.5); 6.9247 (1.4); 5.1841 (0.8); 5.1668 (3.1); 5.1495 (3.1); 5.1321 (0.8); 4.2559 (2.0); 4.2381 (6.6); 4.2204 (6.8); 4.2026 (2.2); 1.6358 (12.0); 1.6185 (12.1); 1.6009 (0.8); 1.5875 (0.8); 1.5836 (0.9); 1.5801 (0.7); 1.5736 (0.7); 1.5670 (2.1); 1.5590 (0.7); 1.5529 (0.7); 1.5497 (0.9); 1.5458 (0.6); 1.5326 (0.6); 1.2871 (7.6); 1.2693 (16.0); 1.2515 (7.5); 0.8525 (0.7); 0.8475 (0.8); 0.8422 (0.8); 0.8381 (1.3); 0.8290 (0.9); 0.8247 (1.5); 0.8190 (1.2); 0.8095 (1.6); 0.8060 (1.5); 0.7976 (3.1); 0.7893 (2.4); 0.7815 (1.3); 0.7799 (1.4); 0.7755 (2.1); 0.7677 (1.6); 0.7607 (1.3); 0.7496 (0.6); 0.7475 (0.6); 0.0080 (0.9); −0.0002 (27.3); −0.00084 (0.8)

VII-084: ¹H-NMR(400.6 MHz, CDCl3):
δ = 8.1549 (2.0); 8.1527 (1.5); 8.1505 (1.6); 8.1485 (2.0); 7.8130 (1.1); 7.8066 (1.1); 7.7948 (1.2); 7.7917 (1.3); 7.7884 (1.2); 7.7853 (1.2); 7.7735 (1.2); 7.7671 (1.1); 7.3902 (1.5); 7.3868 (6.0); 7.3832 (2.6); 7.3792 (4.6); 7.3756 (2.0); 7.3702 (4.4); 7.3638 (1.1); 7.2614 (46.0); 7.1942 (3.0); 7.1908 (1.5); 7.1879 (2.2); 7.1833 (1.8); 7.1791 (2.7); 7.1755 (1.1); 7.1726 (1.3); 7.1698 (2.3); 7.0135 (1.4); 7.0120 (1.4); 7.0059 (1.5); 7.0044 (1.4); 6.9922 (1.4); 6.9907 (1.3); 6.9846 (1.4); 6.9830 (1.3); 4.9209 (14.6); 4.3057 (1.8); 4.2878 (5.8); 4.2700 (5.9); 4.2522 (1.9); 1.5586 (2.6); 1.3209 (7.6); 1.3031 (16.0); 1.2852 (7.5); 0.0080 (0.8); −0.0002 (27.5); −0.00085 (0.8)

VII-083: ¹H-NMR(400.6 MHz, CDCl3):
δ = 8.1668 (2.6); 8.1604 (2.6); 7.8170 (1.2); 7.8106 (1.2); 7.7988 (1.4); 7.7956 (1.5); 7.7924 (1.4); 7.7893 (1.4); 7.7775 (1.3); 7.7711 (1.2); 7.4014 (0.7); 7.3912 (6.8); 7.3842 (5.4); 7.3797 (2.4); 7.3765 (4.0); 7.3742 (4.6); 7.3700 (1.0); 7.3667 (1.2); 7.2614 (33.3); 7.2101 (0.5); 7.2037 (3.7); 7.2000 (2.0); 7.1977 (3.2); 7.1920 (2.2); 7.1883 (3.2); 7.1849 (1.3); 7.1815 (1.6); 7.1793 (2.6); 7.0180 (1.7); 7.0116 (1.6); 7.0105 (1.6); 6.9977 (1.7); 6.9903 (1.6); 6.9891 (1.6); 4.9994 (16.0); 1.4319 (0.9); 1.2644 (1.1); 0.8986 (0.6); 0.8818 (2.1); 0.8641 (0.8); 0.0080 (0.5); −0.0002 (19.1); −0.00085 (0.6)

VIII-002: ¹H-NMR(400.0 MHz, CDCl3):
δ = 8.3893 (2.4); 8.3763 (2.5); 8.1937 (2.3); 8.1808 (2.4); 7.4278 (2.7); 7.4246 (2.6); 7.4118 (4.0); 7.3902 (2.0); 7.3668 (1.7); 7.3516 (1.1); 7.2611 (25.4); 7.2335 (1.2); 7.2118 (1.6); 7.1631 (3.7); 7.0663 (2.2); 7.0533 (3.5); 7.0298 (1.3); 6.9982 (0.5); 6.9762 (0.7); 6.8684 (3.0); 4.9213 (10.0); 4.8550 (1.8); 4.8443 (2.7); 3.8054 (16.0); 3.7706 (6.4); 2.7718 (1.7); 1.5614 (1.9); 1.2563 (0.7); 0.0701 (2.2); −0.0002 (9.6)

II-002: ¹H-NMR(400.0 MHz, CDCl3):
δ = 7.8797 (0.6); 7.8605 (1.8); 7.8404 (2.0); 7.8208 (0.8); 7.7214 (1.1); 7.7064 (1.2); 7.6264 (1.7); 7.6210 (1.7); 7.6077 (1.6); 7.6027 (1.5); 7.4974 (0.9); 7.4814 (1.8); 7.4622 (1.2); 7.4157 (0.7); 7.3947 (1.6); 7.3772 (1.2); 7.3496 (0.5); 7.3300 (1.1); 7.3122 (1.3); 7.2973 (0.8); 7.2606 (30.8); 7.2594 (32.3); 7.2265 (1.6); 7.2083 (2.2); 7.1893 (1.0); 7.0181 (1.1); 6.9944 (1.7); 6.9716 (1.0); 6.8799 (1.5); 6.8727 (1.6); 6.8593 (1.5); 6.8522 (1.5); 4.9271 (10.2); 4.0990 (0.9); 3.7969 (16.0); 2.7707 (0.7); 1.5460 (1.5); 1.2473 (2.6); 1.0708 (7.2); 1.0014 (0.7); 0.0009 (11.2); −0.0002 (12.0)

VII-001: ¹H-NMR(400.0 MHz, CDCl3):
δ = 8.1087 (1.2); 8.1066 (0.9); 8.1043 (1.0); 8.1024 (1.2); 7.7681 (0.6); 7.7619 (0.6); 7.7494 (0.7); 7.7469 (0.8); 7.7431 (0.8); 7.7407 (0.8); 7.7282 (0.7); 7.7219 (0.7); 7.4251 (0.5); 7.4207 (0.6); 7.4058 (0.9); 7.4014 (1.1); 7.3870 (0.6); 7.3826 (0.7); 7.3525 (0.5); 7.3402 (0.7); 7.3318 (0.5); 7.2603 (36.9); 7.2284 (0.6); 7.2268 (0.6); 7.2250 (0.7); 7.2056 (1.0); 7.0499 (0.7); 7.0467 (0.7); 7.0291 (0.6); 7.0253 (1.1); 7.0215 (0.7); 7.0040 (0.6); 7.0007 (0.6); 6.9424 (0.9); 6.9410 (0.9); 6.9349 (0.9); 6.9335 (0.9); 6.9212 (0.8); 6.9197 (0.8); 6.9136 (0.9); 6.9122 (0.8); 5.2988 (0.5); 4.9216 (8.8); 3.8059 (16.0); 2.7731 (4.4); 1.5444 (1.8); 1.4213 (0.5); −0.0002 (16.0)

VII-009: ¹H-NMR(400.0 MHz, CDCl3):
δ = 8.1060 (3.0); 8.1001 (3.2); 7.7767 (1.1); 7.7704 (1.1); 7.7578 (1.6); 7.7554 (1.8); 7.7516 (1.7); 7.7369 (1.3); 7.7306 (1.2); 7.3576 (0.9); 7.3378 (1.3); 7.3204 (1.2); 7.3159 (1.4); 7.2961 (1.0); 7.2600 (42.8); 6.9958 (2.1); 6.9883 (2.0); 6.9744 (1.9); 6.9670 (2.0); 6.9390 (0.9); 6.9217 (1.0); 6.9154 (1.8); 6.8981 (1.8); 6.8918 (1.1); 6.8746 (0.9); 5.2983 (0.6); 4.8822 (16.0); 4.3049 (2.0); 4.2870 (6.3); 4.2692 (6.5); 4.2513 (2.3); 1.5399 (1.0); 1.3180 (7.1); 1.3002 (14.5); 1.2823 (7.3); 1.2569 (0.8); −0.0002 (15.5)

-continued

VII-016: ¹H-NMR(400.0 MHz, CDCl3):
δ = 8.1020 (2.2); 8.0957 (2.2); 7.7648 (1.1); 7.7585 (1.1); 7.7461 (1.3); 7.7435 (1.3); 7.7398 (1.3); 7.7373 (1.3); 7.7249 (1.2); 7.7186 (1.2); 7.4295 (0.9); 7.4151 (1.0); 7.4078 (1.5); 7.3935 (1.5); 7.3864 (1.0); 7.3720 (1.0); 7.2609 (34.4); 6.9779 (0.7); 6.9714 (2.2); 6.9673 (1.0); 6.9642 (1.8); 6.9629 (1.6); 6.9588 (0.9); 6.9553 (1.3); 6.9504 (2.3); 6.9488 (2.6); 6.9429 (1.7); 6.9415 (1.5); 6.9366 (0.6); 6.9328 (0.6); 6.9298 (0.7); 6.9260 (0.6); 6.8261 (1.0); 6.8193 (0.9); 6.8053 (1.1); 6.8012 (1.2); 6.7986 (1.1); 6.7944 (1.0); 6.7805 (1.0); 6.7737 (0.9); 5.2988 (1.0); 4.8874 (16.0); 4.8733 (0.8); 4.2972 (2.1); 4.2794 (6.5); 4.2616 (6.6); 4.2437 (2.2); 1.3088 (7.8); 1.2909 (15.9); 1.2731 (7.6); −0.0002 (12.9)

VI-002: ¹H-NMR(400.0 MHz, CDCl3):
δ = 9.1759 (0.7); 8.6525 (1.6); 8.0189 (1.6); 7.3464 (0.6); 7.3342 (0.6); 7.3268 (0.5); 7.3199 (1.0); 7.3130 (0.7); 7.2609 (39.3); 5.2512 (1.6); 4.9621 (2.0); 2.9556 (16.0); 2.8842 (13.9); 2.8828 (13.9); 2.8079 (0.9); 1.5840 (0.9); 0.0079 (0.6); −0.0002 (17.1)

VII-028: ¹H-NMR(400.0 MHz, CDCl3):
δ = 8.0183 (1.6); 7.2632 (17.6); 4.9366 (1.7); 3.8155 (3.2); 2.9557 (16.0); 2.8842 (13.1); 2.8828 (13.5); −0.0002 (7.6)

VII-002: ¹H-NMR(400.0 MHz, CDCl3):
δ = 8.1724 (1.4); 8.1704 (1.2); 8.1683 (1.2); 8.1663 (1.4); 7.7025 (0.7); 7.6962 (0.7); 7.6838 (0.8); 7.6812 (0.9); 7.6775 (0.9); 7.6750 (0.9); 7.6626 (0.8); 7.6563 (0.7); 7.2597 (69.4); 7.1295 (1.5); 7.1238 (0.7); 7.1177 (1.7); 7.1124 (1.2); 7.1067 (2.4); 7.1006 (1.0); 7.0948 (2.6); 7.0866 (0.7); 7.0826 (0.6); 7.0748 (0.8); 7.0521 (0.5); 7.0295 (2.4); 7.0236 (0.8); 7.0176 (0.5); 7.0094 (2.7); 7.0068 (1.9); 7.0037 (1.0); 6.9957 (0.8); 6.9924 (0.8); 6.9866 (1.6); 6.9751 (1.2); 6.9735 (1.2); 6.9675 (1.2); 6.9660 (1.2); 6.9538 (1.0); 6.9523 (1.0); 6.9462 (1.1); 6.9447 (1.1); 4.9297 (8.8); 3.8121 (16.0); 1.5389 (1.1); 1.0075 (0.9); 0.3184 (0.6); 0.0691 (6.8); 0.0080 (1.1); −0.0002 (31.4); −0.00085 (1.4)

VIII-005: ¹H-NMR(400.0 MHz, CDCl3):
δ = 8.2338 (1.6); 8.2208 (1.6); 7.2598 (57.1); 7.1415 (1.3); 7.1356 (0.6); 7.1296 (1.5); 7.1242 (1.0); 7.1186 (2.3); 7.1127 (0.7); 7.1106 (0.5); 7.1068 (2.2); 7.0497 (2.2); 7.0437 (1.8); 7.0397 (1.0); 7.0344 (1.0); 7.0299 (3.4); 7.0269 (2.4); 7.0127 (0.5); 7.0070 (1.4); 6.9004 (1.1); 6.8970 (1.8); 5.2985 (0.5); 4.9278 (8.7); 3.8109 (16.0); 3.8059 (1.4); 1.5438 (2.2); 0.0079 (0.8); −0.0002 (24.4); −0.00085 (0.7)

VI-004: ¹H-NMR(400.0 MHz, CDCl3):
δ = 9.1760 (4.0); 8.6700 (8.6); 7.5186 (0.6); 7.4670 (0.5); 7.4625 (0.6); 7.4476 (1.0); 7.4434 (1.1); 7.4287 (0.6); 7.4244 (0.7); 7.3752 (0.5); 7.3629 (0.5); 7.3546 (0.5); 7.3423 (0.5); 7.2597 (111.1); 7.2347 (1.1); 7.2172 (0.5); 7.0621 (0.7); 7.0589 (0.7); 7.0412 (0.7); 7.0374 (1.1); 7.0336 (0.8); 7.0161 (0.6); 7.0128 (0.6); 6.9957 (0.6); 4.9286 (9.3); 3.8101 (16.0); 2.9555 (1.3); 2.8832 (1.1); 2.7734 (2.2); 1.5597 (4.5); 0.0080 (1.5); −0.0002 (48.2); −0.00085 (1.6)

VIII-003: ¹H-NMR(400.0 MHz, CDCl3):
δ = 8.1913 (0.6); 8.1782 (0.6); 7.2594 (55.4); 7.2497 (0.6); 7.0701 (0.5); 7.0529 (0.7); 7.0490 (0.7); 6.8677 (0.7); 4.8991 (3.6); 4.2780 (1.4); 4.2601 (1.4); 2.0048 (0.5); 1.5328 (16.0); 1.3067 (1.7); 1.2889 (3.5); 1.2711 (1.7); 0.0079 (0.9); −0.0002 (28.2); −0.00085 (1.0)

VIII-004: ¹H-NMR(400.0 MHz, CDCl3):
δ = 8.2034 (2.8); 8.1904 (3.0); 7.5187 (0.6); 7.4485 (0.8); 7.4441 (1.0); 7.4291 (1.5); 7.4248 (1.8); 7.4105 (1.3); 7.4062 (1.5); 7.3992 (0.7); 7.3925 (1.0); 7.3880 (0.9); 7.3802 (1.0); 7.3718 (1.0); 7.3674 (0.8); 7.3598 (0.7); 7.3551 (0.6); 7.2756 (0.7); 7.2729 (0.6); 7.2705 (1.1); 7.2672 (1.4); 7.2598 (119.1); 7.2551 (5.9); 7.2503 (2.2); 7.2474 (1.7); 7.2448 (1.3); 7.2417 (1.5); 7.2384 (2.2); 7.2367 (2.5); 7.2312 (1.0); 7.2272 (0.7); 7.2256 (0.7); 7.2237 (0.7); 7.2215 (0.9); 7.2182 (1.1); 7.2165 (1.2); 7.0793 (1.2); 7.0759 (1.3); 7.0738 (1.6); 7.0695 (2.1); 7.0659 (1.6); 7.0606 (1.8); 7.0561 (2.8); 7.0333 (1.0); 7.0301 (1.0); 6.9958 (0.6); 6.8751 (2.0); 6.8718 (3.2); 4.9783 (16.0); 4.1315 (0.5); 4.1137 (0.5); 2.0448 (2.5); 1.2766 (0.8); 1.2587 (1.8); 1.2409 (0.9); 0.0691 (0.6); 0.0080 (1.8); −0.0002 (61.1); −0.00085 (2.6); −0.0126 (1.0); −0.0183 (0.8); −0.0217 (0.5); −0.0234 (0.5)

VII-012: ¹H-NMR(600.4 MHz, d6-DMSO):
δ = 8.1973 (3.1); 8.1933 (3.2); 7.9509 (1.0); 7.9467 (1.0); 7.9370 (1.7); 7.9336 (1.6); 7.9239 (1.1); 7.9197 (1.0); 7.5684 (1.0); 7.5658 (1.1); 7.5555 (2.1); 7.5528 (2.2); 7.5426 (1.2); 7.5398 (1.3); 7.5006 (0.5); 7.4978 (0.6); 7.4921 (0.7); 7.4879 (1.2); 7.4851 (1.1); 7.4794 (1.2); 7.4766 (1.2); 7.4714 (0.8); 7.4658 (0.8); 7.4631 (0.7); 7.3277 (1.6); 7.3148 (2.7); 7.3033 (2.6); 7.3020 (2.5); 7.2874 (3.6); 7.2840 (3.3); 7.2729 (2.6); 7.2698 (2.8); 5.7520 (1.5); 4.9321 (14.8); 4.9120 (0.6); 4.8902 (0.6); 4.8850 (0.4); 4.8806 (0.3); 4.1869 (2.2); 4.1751 (6.9); 4.1690 (0.7); 4.1633 (7.0); 4.1573 (0.6); 4.1514 (2.3); 3.3062 (196.4); 2.6151 (1.2); 2.6121 (1.7); 2.6091 (1.2); 2.5211 (1.8); 2.5181 (5.2); 2.5149 (5.4); 2.5061 (97.2); 2.5032 (198.9); 2.5001 (269.5); 2.4971 (201.7); 2.4942 (100.3); 2.3871 (1.2); 2.3841 (1.7); 2.3811 (1.2); 1.1998 (7.8); 1.1947 (0.8); 1.1879 (16.0); 1.1829 (1.3); 1.1761 (7.7); 1.1492 (0.4); 1.1373 (0.7); 1.1255 (0.4); 1.1096 (0.6); 0.0052 (1.2); −0.0002 (32.4); −0.00057 (1.3)

VII-003: ¹H-NMR(400.0 MHz, CDCl3):
δ = 8.1127 (1.7); 8.1066 (1.7); 7.7664 (0.7); 7.7601 (0.7); 7.7476 (0.9); 7.7451 (1.0); 7.7413 (0.9); 7.7389 (0.9); 7.7264 (0.8); 7.7202 (0.7); 7.4356 (0.6); 7.4313 (0.7); 7.4163 (1.2); 7.4122 (1.3); 7.3975 (0.8); 7.3932 (0.8); 7.3536 (0.7); 7.3493 (0.6); 7.3413 (0.7); 7.3370 (0.6); 7.3331 (0.7); 7.3285 (0.5); 7.3207 (0.6); 7.3163 (0.5); 7.2602 (34.6); 7.2233 (0.9); 7.2043 (1.2); 7.1847 (0.6); 7.0471 (0.8); 7.0439 (0.8); 7.0264 (1.1); 7.0225 (1.4); 7.0188 (1.0); 7.0047 (0.9); 7.0013 (0.9); 6.9980 (0.9); 6.9918 (0.8); 6.9428 (1.1); 6.9367 (1.1); 6.9215 (1.1); 6.9155 (1.1); 6.8509 (0.8); 6.8441 (0.5); 6.7617 (0.6); 5.2980 (16.0); 4.9464 (5.8); 4.5515 (2.3); 4.1388 (1.9); 4.1325 (1.3); 4.1288 (1.1); 4.1197 (0.6); 4.1140 (0.5); 4.0728 (0.6); 4.0561 (0.9); 4.0522 (1.0); 4.0383 (1.1); 2.0454 (0.9); 1.5666 (6.8); 1.3316 (0.6); 1.2840 (1.0); 1.2761 (0.5); 1.2581 (1.8); 0.0080 (0.7); −0.0002 (19.6); −0.00085 (0.8)

VII-009: ¹H-NMR(400.0 MHz, CDCl3):
δ = 8.1005 (3.4); 7.8839 (0.8); 7.8782 (0.9); 7.7772 (1.1); 7.7710 (1.1); 7.7559 (1.9); 7.7524 (1.9); 7.7499 (1.8); 7.7374 (1.2); 7.7312 (1.2); 7.3582 (0.9); 7.3385 (1.6); 7.3346 (1.4); 7.3169 (1.5); 7.2970 (0.9); 7.2612 (24.1); 6.9953 (2.1); 6.9887 (2.0); 6.9740 (1.9); 6.9675 (1.8); 6.9395 (0.9); 6.9221 (1.0); 6.9160 (1.8); 6.8986 (1.7); 6.8751 (0.8); 5.2988 (2.7); 4.8824 (16.0); 4.8745 (4.1); 4.8077 (4.4); 4.3048 (2.2); 4.2870 (6.6); 4.2691 (7.2); 4.2514 (3.9); 4.2336 (1.7); 4.2158 (0.6); 1.5494 (5.7); 1.3250 (1.7); 1.3181 (6.8); 1.3072 (3.4); 1.3003 (13.6); 1.2873 (3.4); 1.2825 (7.1); 1.2696 (3.8); 1.2517 (1.8); −0.0002 (13.6)

-continued

VII-033: ¹H-NMR(400.0 MHz, CDCl3):
δ = 8.1164 (2.8); 8.1101 (2.9); 7.7824 (1.2); 7.7761 (1.2); 7.7638 (1.5); 7.7611 (1.6); 7.7575 (1.6); 7.7548 (1.5); 7.7426 (1.3); 7.7363 (1.3); 7.5185 (0.6); 7.3671 (0.9); 7.3476 (1.2); 7.3431 (1.1); 7.3303 (1.0); 7.3259 (1.2); 7.3062 (0.9); 7.2596 (106.1); 7.0024 (1.8); 6.9957 (2.3); 6.9823 (1.7); 6.9810 (1.7); 6.9749 (1.8); 6.9469 (0.8); 6.9298 (0.9); 6.9233 (1.7); 6.9061 (1.6); 6.8997 (0.9); 6.8825 (0.8); 5.2982 (5.6); 4.9625 (16.0); 4.9571 (2.6); 4.8874 (4.5); 3.8607 (0.7); 2.6567 (0.8); 2.5992 (0.8); 2.5857 (0.6); 2.5776 (0.6); 1.5763 (0.7); 0.0080 (1.9); −0.0002 (60.0); −0.00085 (2.1)

VIII-002: ¹H-NMR(400.0 MHz, CDCl3):
δ = 8.1928 (1.7); 8.1798 (1.8); 7.4319 (0.5); 7.4276 (0.6); 7.4127 (0.9); 7.4084 (1.2); 7.3937 (0.7); 7.3897 (1.0); 7.3869 (0.6); 7.3846 (0.7); 7.3829 (0.6); 7.3801 (0.5); 7.3784 (0.5); 7.3722 (0.7); 7.3678 (0.5); 7.3661 (0.5); 7.3639 (0.6); 7.3517 (0.5); 7.2607 (18.6); 7.2514 (0.9); 7.2497 (0.9); 7.2481 (0.9); 7.2287 (1.1); 7.2110 (0.5); 7.0758 (0.7); 7.0724 (0.8); 7.0701 (1.0); 7.0661 (1.3); 7.0622 (0.9); 7.0568 (1.1); 7.0525 (1.9); 7.0298 (0.7); 7.0268 (0.6); 6.8715 (1.3); 6.8683 (2.0); 6.8650 (1.3); 5.2983 (0.9); 4.9210 (8.8); 3.8052 (16.0); 1.5535 (1.1); −0.0002 (10.0)

VI-004: ¹H-NMR(400.0 MHz, CDCl3):
δ = 9.1758 (3.6); 8.6697 (5.4); 7.4668 (0.6); 7.4625 (0.6); 7.4475 (1.0); 7.4432 (1.1); 7.4287 (0.7); 7.4243 (0.7); 7.3749 (0.5); 7.3626 (0.6); 7.3581 (0.5); 7.3541 (0.5); 7.2605 (28.6); 7.2341 (1.0); 7.0619 (0.7); 7.0587 (0.7); 7.0411 (0.7); 7.0372 (1.1); 7.0335 (0.7); 7.0159 (0.6); 7.0126 (0.6); 4.9286 (8.7); 3.8098 (16.0); 1.5567 (1.2); −0.0002 (14.9); −0.00084 (0.5)

VIII-002: ¹H-NMR(400.0 MHz, CDCl3):
δ = 8.1926 (1.8); 8.1796 (1.8); 7.4321 (0.5); 7.4278 (0.6); 7.4128 (1.0); 7.4088 (1.3); 7.3940 (0.7); 7.3901 (1.0); 7.3868 (0.6); 7.3843 (0.7); 7.3799 (0.5); 7.3719 (0.6); 7.3660 (0.6); 7.3638 (0.6); 7.2621 (4.9); 7.2480 (0.8); 7.2287 (1.2); 7.2108 (0.5); 7.0755 (0.8); 7.0705 (1.1); 7.0662 (1.4); 7.0625 (1.0); 7.0531 (2.0); 7.0296 (0.7); 7.0265 (0.6); 6.8687 (2.0); 5.2980 (4.5); 4.9209 (9.3); 3.8046 (16.0); 1.5765 (1.1); −0.0002(4.0)

VII-012: ¹H-NMR(600.4 MHz, d₆-DMSO):
δ = 8.1973 (3.2); 8.1933 (3.2); 7.9509 (1.0); 7.9467 (1.0); 7.9371 (1.7); 7.9335 (1.6); 7.9238 (1.1); 7.9197 (1.0); 7.5684 (1.0); 7.5658 (1.2); 7.5555 (2.1); 7.5528 (2.3); 7.5426 (1.2); 7.5399 (1.2); 7.5006 (0.6); 7.4979 (0.6); 7.4921 (0.7); 7.4879 (1.2); 7.4851 (1.2); 7.4793 (1.2); 7.4767 (1.2); 7.4714 (0.8); 7.4658 (0.8); 7.4631 (0.7); 7.3277 (1.7); 7.3148 (2.7); 7.3034 (2.5); 7.3019 (2.5); 7.2874 (3.6); 7.2840 (3.3); 7.2729 (2.6); 7.2698 (2.8); 5.7521 (1.7); 4.9322 (15.1); 4.8431 (0.6); 4.1869 (2.2); 4.1751 (7.0); 4.1632 (7.1); 4.1514 (2.3); 4.1228 (0.3); 3.3052 (127.1); 2.6151 (1.2); 2.6121 (1.7); 2.6091 (1.2); 2.6062 (0.6); 2.5211 (4.1); 2.5180 (5.2); 2.5149 (5.6); 2.5060 (98.8); 2.5031 (200.8); 2.5001 (271.8); 2.4970 (203.1); 2.4941 (100.6); 2.3870 (1.3); 2.3840 (1.7); 2.3810 (1.2); 1.2369 (0.4); 1.1998 (7.8); 1.1879 (16.0); 1.1761 (7.7); 1.1653 (0.4); 1.1534 (0.7); 1.1416 (0.4); 0.0052 (1.3); −0.0002 (31.9); −0.0057 (1.3)

VI-004: ¹H-NMR(400.0 MHz, CDCl3):
δ = 9.1767 (3.0); 8.6698 (6.8); 7.4489 (0.7); 7.4449 (0.8); 7.4259 (0.5); 7.2603 (21.4); 7.2362 (0.9); 7.0378 (0.8); 4.9296 (6.4); 3.8109 (10.5); 2.0447 (1.4); 1.5401 (16.0); 1.2772 (0.6); 1.2593 (1.1); 0.8821 (0.9); 0.0078 (1.2); −0.0002 (26.5); −0.00079 (0.8)

VI-007: ¹H-NMR(400.0 MHz, CDCl3):
δ = 9.2020 (5.1); 8.7056 (7.6); 7.4740 (1.0); 7.4697 (1.1); 7.4546 (1.9); 7.4506 (2.0); 7.4357 (1.2); 7.4315 (1.3); 7.4016 (0.5); 7.3973 (0.6); 7.3893 (0.6); 7.3827 (1.0); 7.3784 (1.0); 7.3702 (1.0); 7.3659 (1.0); 7.3622 (1.0); 7.3576 (0.8); 7.3497 (0.8); 7.3454 (0.7); 7.2610 (23.3); 7.2388 (2.1); 7.2211 (0.9); 7.0642 (1.3); 7.0611 (1.3); 7.0433 (1.3); 7.0396 (2.1); 7.0359 (1.4); 7.0181 (1.1); 7.0151 (1.1); 4.9785 (16.0); 3.7772 (0.8); 3.7666 (0.8); 3.7605 (2.0); 3.7545 (0.8); 3.7440 (0.9); 1.8765 (0.8); 1.8684 (0.8); 1.8600 (2.3); 1.8513 (0.8); 1.8434 (0.8); 1.4320 (0.7); 0.0079 (1.2); −0.0002 (26.8); −0.00084 (1.0)

VII-003: ¹H-NMR(600.4 MHz, d₆-DMSO):
δ = 13.0358 (0.6); 8.1959 (6.6); 8.1926 (5.8); 7.9519 (2.1); 7.9477 (2.2); 7.9381 (3.6); 7.9343 (3.5); 7.9249 (2.3); 7.9207 (2.2); 7.5830 (1.6); 7.5804 (1.8); 7.5701 (3.5); 7.5675 (3.6); 7.5631 (1.9); 7.5602 (2.0); 7.5572 (2.2); 7.5545 (2.1); 7.5502 (1.1); 7.5475 (1.0); 7.5010 (1.3); 7.4985 (1.4); 7.4927 (1.5); 7.4884 (2.6); 7.4859 (2.6); 7.4774 (2.6); 7.4665 (1.7); 7.4642 (1.4); 7.3298 (3.4); 7.3170 (5.6); 7.3040 (3.7); 7.2993 (2.7); 7.2874 (5.9); 7.2836 (7.4); 7.2734 (4.9); 7.2690 (5.4); 5.7520 (10.0); 4.9574 (8.4); 4.8674 (0.4); 4.8263 (11.5); 4.7841 (0.4); 4.7371 (0.5); 3.8434 (1.0); 3.6996 (16.0); 3.6851 (0.4); 3.6606 (0.7); 3.3055 (116.8); 3.1727 (0.5); 3.1648 (0.5); 2.6151 (2.8); 2.6121 (3.8); 2.6091 (2.8); 2.5984 (0.3); 2.5211 (10.1); 2.5180 (13.9); 2.5148 (17.2); 2.5060 (233.1); 2.5031 (462.2); 2.5001 (624.6); 2.4971 (470.2); 2.4942 (237.8); 2.3899 (1.4); 2.3870 (2.8); 2.3840 (3.8); 2.3811 (2.8); 2.2915 (0.3); 1.9077 (0.7); 1.2364 (1.1); 0.0051 (3.3); −0.0002 (68.1); −0.00056 (3.0)

VII-123-a: ¹H-NMR(400.0 MHz, CDCl3):
δ = 8.1022 (1.2); 8.0960 (1.2); 7.7606 (0.6); 7.7543 (0.6); 7.7418 (0.7); 7.7394 (0.8); 7.7355 (0.7); 7.7331 (0.7); 7.7206 (0.6); 7.7143 (0.6); 7.3865 (0.6); 7.3716 (0.8); 7.3673 (1.0); 7.3528 (0.6); 7.3481 (0.8); 7.3404 (0.5); 7.3281 (0.5); 7.2614 (16.3); 7.2124 (0.6); 7.2107 (0.6); 7.1912 (0.9); 7.0412 (0.6); 7.0379 (0.6); 7.0203 (0.6); 7.0165 (1.0); 7.0127 (0.6); 6.9952 (0.5); 6.9920 (0.5); 6.9385 (0.8); 6.9373 (0.8); 6.9311 (0.8); 6.9299 (0.8); 6.9174 (0.8); 6.9160 (0.8); 6.9099 (0.8); 6.9086 (0.8); 5.2312 (1.6); 5.2138 (1.6); 3.7764 (16.0); 1.6951 (6.6); 1.6776 (6.5); −0.0002 (9.9)

VII-038: ¹H-NMR(400.6 MHz, CDCl3):
δ = 8.0970 (0.6); 8.0951 (1.0); 8.0930 (0.8); 8.0909 (0.8); 8.0888 (1.0); 8.0868 (0.7); 7.7540 (0.6); 7.7477 (0.6); 7.7352 (0.6); 7.7327 (0.7); 7.7290 (0.6); 7.7264 (0.7); 7.7140 (0.6); 7.7077 (0.6); 7.3803 (0.7); 7.3759 (0.9); 7.3617 (0.7); 7.3572 (0.6); 7.2610 (48.0); 7.2202 (0.5); 7.2184 (0.6); 7.2170 (0.5); 7.2009 (0.7); 7.1990 (0.8); 7.0492 (0.5); 7.0459 (0.5); 7.0245 (0.8); 7.0207 (0.5); 6.9425 (0.7); 6.9408 (0.8); 6.9350 (0.8); 6.9333 (0.8); 6.9212 (0.7); 6.9196 (0.7); 6.9137 (0.7); 6.9121 (0.7); 6.4172 (0.7); 5.2352 (1.4); 5.2178 (1.5); 3.9793 (2.4); 3.9293 (3.0); 3.7786 (16.0); 2.5560 (2.4); 2.5461 (1.5); 1.6970 (6.2); 1.6796 (6.2); 1.5468 (1.7); 1.2844 (0.5); 1.2548 (0.6); 0.0080 (0.8); −0.0002 (29.0); −0.00084 (0.9)

VI-011: ¹H-NMR(400.0 MHz, CDCl3):
δ = 9.1701 (3.8); 8.6612 (9.1); 7.4283 (0.5); 7.4134 (0.8); 7.4091 (0.9); 7.3946 (0.6); 7.3902 (0.6); 7.2621 (18.0); 7.2419 (0.6); 7.2400 (0.6); 7.2204 (0.9); 7.0534 (0.6); 7.0502 (0.6); 7.0326 (0.6); 7.0287 (0.9); 7.0249 (0.6); 7.0073 (0.5); 5.2346 (1.5); 5.2172 (1.6); 3.7804 (16.0); 1.7019 (6.4); 1.6845 (6.3); 1.5722 (3.3); 1.2643 (0.8); 0.8818 (1.5); 0.8641 (0.6); −0.0002 (10.4)

-continued

VI-008: ¹H-NMR(400.0 MHz, CDCl3):
δ = 9.1700 (4.0); 8.6613 (9.7); 7.4286 (0.5); 7.4136 (0.8); 7.4094 (0.9); 7.3948 (0.6); 7.3904 (0.6); 7.2634 (10.8); 7.2418 (0.6); 7.2400 (0.6); 7.2205 (0.9); 7.0534 (0.6); 7.0502 (0.6); 7.0326 (0.6); 7.0287 (0.9); 7.0249 (0.6); 7.0073 (0.5); 5.2998 (1.2); 5.2347 (1.5); 5.2173 (1.6); 3.7802 (16.0); 1.7018 (6.3); 1.6844 (6.3); 1.5952 (1.9); −0.0002 (6.2)

IV-001: ¹H-NMR(400.0 MHz, CDCl3):
δ = 9.2187 (2.6); 9.2157 (2.7); 9.2054 (2.7); 9.2023 (2.7); 9.0675 (2.5); 9.0644 (2.7); 9.0616 (2.8); 9.0585 (2.4); 7.4826 (0.9); 7.4782 (1.0); 7.4633 (1.6); 7.4590 (1.8); 7.4516 (2.8); 7.4455 (3.3); 7.4383 (3.1); 7.4323 (2.7); 7.4182 (0.5); 7.4138 (0.5); 7.4059 (0.6); 7.3992 (0.9); 7.3948 (0.8); 7.3869 (0.9); 7.3825 (0.8); 7.3807 (0.8); 7.3786 (0.9); 7.3740 (0.7); 7.3663 (0.8); 7.3618 (0.6); 7.2755 (1.2); 7.2627 (11.7); 7.2384 (0.8); 7.0682 (1.2); 7.0650 (1.1); 7.0473 (1.1); 7.0435 (1.8); 7.0397 (1.2); 7.0222 (1.0); 7.0189 (1.0); 5.3000 (2.2); 4.9087 (16.0); 4.2997 (2.0); 4.2819 (6.2); 4.2640 (6.3); 4.2462 (2.1); 1.3106 (7.4); 1.2928 (15.2); 1.2750 (7.3); −0.0002 (15.3); −0.00085 (0.5)

VI-012: ¹H-NMR(400.0 MHz, CDCl3):
δ = 9.1872 (8.6); 8.6773 (16.0); 7.4584 (1.2); 7.4541 (1.4); 7.4391 (2.3); 7.4348 (2.4); 7.4202 (1.5); 7.4159 (1.6); 7.3839 (0.8); 7.3795 (0.7); 7.3717 (0.8); 7.3650 (1.2); 7.3606 (1.1); 7.3527 (1.3); 7.3484 (1.2); 7.3444 (1.2); 7.3399 (0.9); 7.3321 (1.0); 7.3277 (0.9); 7.2602 (50.1); 7.2495 (0.8); 7.2392 (1.7); 7.2196 (2.5); 7.2006 (1.7); 7.1876 (0.9); 7.1813 (0.9); 7.1687 (0.6); 7.1577 (1.4); 7.1499 (0.9); 7.1296 (0.6); 7.1088 (0.6); 7.0840 (2.3); 7.0498 (1.6); 7.0465 (1.5); 7.0289 (1.6); 7.0250 (2.5); 7.0212 (1.6); 7.0037 (1.5); 7.0005 (1.4); 5.3209 (1.1); 5.3035 (4.4); 5.2860 (4.4); 5.2684 (1.2); 3.9880 (1.4); 3.9421 (1.8); 2.3115 (3.3); 2.2419 (3.2); 1.7562 (15.0); 1.7387 (14.8); 1.7255 (0.7); 1.7084 (0.6); 1.7006 (0.5); 0.0080 (2.1); −0.0002 (65.4); −0.00085 (1.9)

III-002: ¹H-NMR(400.0 MHz, CDCl3):
δ = 8.7084 (9.5); 8.6962 (9.7); 7.5202 (1.0); 7.5158 (1.0); 7.5008 (1.8); 7.4965 (1.8); 7.4818 (1.1); 7.4773 (1.1); 7.3175 (0.5); 7.3128 (0.6); 7.3107 (0.9); 7.3062 (0.8); 7.2986 (0.9); 7.2941 (0.9); 7.2902 (0.9); 7.2856 (0.8); 7.2782 (0.8); 7.2736 (0.8); 7.2612 (11.9); 7.2277 (1.2); 7.2253 (1.3); 7.2132 (2.8); 7.2089 (1.8); 7.2058 (2.0); 7.2010 (5.2); 7.1888 (3.2); 7.0058 (1.2); 7.0024 (1.2); 6.9851 (1.1); 6.9803 (1.4); 6.9764 (1.2); 6.9593 (1.0); 6.9558 (1.0); 5.2992 (2.3); 4.9201 (16.0); 4.2930 (2.0); 4.2751 (6.2); 4.2573 (6.4); 4.2395 (2.1); 1.5582 (4.8); 1.3019 (7.5); 1.2840 (15.2); 1.2662 (7.3); 0.0080 (0.6); −0.0002 (15.9); −0.00085 (0.5)

III-005: ¹H-NMR(400.0 MHz, CDCl3):
δ = 8.7074 (5.3); 8.6952 (5.3); 7.4919 (0.6); 7.4874 (0.6); 7.4725 (1.2); 7.4682 (1.2); 7.4535 (0.7); 7.4490 (0.7); 7.2982 (0.6); 7.2938 (0.6); 7.2861 (0.6); 7.2817 (0.6); 7.2779 (0.6); 7.2732 (0.6); 7.2619 (4.6); 7.2113 (1.9); 7.1988 (3.7); 7.1866 (1.5); 7.1776 (0.5); 6.9954 (1.2); 6.9921 (0.7); 6.9747 (0.8); 6.9698 (1.0); 6.9660 (0.8); 6.9488 (0.6); 6.9455 (0.6); 5.2990 (2.3); 5.2782 (0.5); 5.2608 (1.7); 5.2434 (1.7); 5.2260 (0.5); 3.7666 (16.0); 1.7001 (7.0); 1.6827 (6.9); 1.5708 (1.7); −0.0002 (5.8)

IV-002: ¹H-NMR(400.0 MHz, CDCl3):
δ = 9.2346 (1.5); 9.2240 (1.6); 9.0730 (2.3); 7.5189 (1.3); 7.5004 (0.9); 7.4960 (0.8); 7.4770 (2.9); 7.4709 (1.8); 7.4629 (2.3); 7.4576 (2.3); 7.4124 (0.9); 7.4001 (0.8); 7.2886 (1.0); 7.2600 (230.4); 7.0755 (0.9); 7.0510 (1.6); 7.0264 (0.8); 6.9960 (1.0); 4.9934 (16.0); 4.9092 (1.9); 4.2823 (0.7); 4.2646 (0.7); 1.7043 (0.6); 1.3109(1.1); 1.2932 (2.0); 1.2753 (1.0); 0.1460 (1.0); 0.0080 (8.2); −0.0002 (305.3); −0.00085 (8.9); −0.1496 (1.0)

III-003: ¹H-NMR(400.0 MHz, CDCl3):
δ = 8.7204 (14.6); 8.7081 (14.7); 7.5187 (1.6); 7.5138 (1.3); 7.4989 (2.3); 7.4945 (2.4); 7.4799 (1.4); 7.4754 (1.4); 7.3262 (0.6); 7.3218 (0.7); 7.3142 (0.7); 7.3074 (1.2); 7.3030 (1.1); 7.2953 (1.2); 7.2909 (1.2); 7.2868 (1.2); 7.2824 (1.1); 7.2748 (1.4); 7.2704 (1.5); 7.2601 (102.9); 7.2285 (4.0); 7.2163 (8.5); 7.2040 (3.8); 7.1985 (2.2); 7.1786 (1.0); 6.9998 (1.5); 6.9962 (1.0); 6.9792 (1.5); 6.9743 (1.8); 6.9704 (1.5); 6.9533 (1.3); 6.9497 (1.2); 5.3399 (1.1); 5.3225 (4.6); 5.3050 (4.6); 5.2877 (1.2); 1.7547 (16.0); 1.7372 (15.9); 0.0080 (4.5); −0.0002 (140.3); −0.00085 (3.8)

IV-003: ¹H-NMR(400.6 MHz, CDCl3):
δ = 9.3232 (2.4); 9.3201 (2.5); 9.3098 (2.6); 9.3066 (2.6); 8.9834 (2.3); 8.9803 (2.5); 8.9774 (2.5); 8.9743 (2.2); 7.5749 (2.7); 7.5688 (2.7); 7.5615 (2.7); 7.5554 (2.7); 7.5289 (0.6); 7.5248 (0.9); 7.5145 (0.6); 7.5101 (1.4); 7.5057 (1.7); 7.5021 (0.9); 7.4976 (0.6); 7.4953 (1.0); 7.4937 (0.9); 7.4909 (1.2); 7.4877 (1.4); 7.4826 (1.2); 7.4770 (0.7); 7.4747 (0.8); 7.4703 (0.6); 7.4623 (0.8); 7.4579 (0.5); 7.3438 (0.8); 7.3421 (0.9); 7.3406 (1.0); 7.3391 (0.9); 7.3245 (1.2); 7.3227 (1.4); 7.3211 (1.4); 7.3052 (0.5); 7.3033 (0.7); 7.2612 (48.2); 7.1370 (0.9); 7.1336 (0.9); 7.1161 (0.9); 7.1126 (1.5); 7.1093 (1.0); 7.0911 (0.8); 7.0878 (0.9); 5.3003 (6.8); 5.0012 (0.6); 4.9176 (13.4); 4.8635 (0.5); 4.3037 (1.8); 4.2859 (5.7); 4.2680 (5.9); 4.2502 (2.0); 2.3118 (0.6); 1.5557 (4.7); 1.3175 (0.9); 1.3137 (7.6); 1.2995 (0.8); 1.2959 (16.0); 1.2780 (7.7); 0.0080 (1.4); −0.0002 (52.1); −0.00050 (1.1); −0.00067 (0.7); −0.00084 (1.8)

V-003: ¹H-NMR(400.0 MHz, CDCl3):
δ = 7.6633 (4.1); 7.6462 (4.3); 7.5423 (0.8); 7.5379 (0.9); 7.5229 (1.6); 7.5186 (1.6); 7.5039 (1.0); 7.4994 (1.0); 7.4015 (1.1); 7.3346 (0.6); 7.3325 (0.8); 7.3280 (0.7); 7.3203 (0.8); 7.3157 (0.8); 7.3120 (0.8); 7.3074 (0.7); 7.2998 (0.8); 7.2952 (0.7); 7.2613 (47.5); 7.2478 (1.0); 7.2453 (1.1); 7.2290 (1.5); 7.2258 (1.5); 7.2091 (0.6); 7.2068 (0.6); 7.0659 (1.1); 7.0626 (1.0); 7.0453 (1.0); 7.0401 (1.2); 7.0364 (1.0); 7.0192 (0.9); 7.0158 (0.8); 6.8462 (4.7); 6.8292 (4.6); 5.3594 (0.8); 4.8947 (14.0); 4.5902 (11.8); 4.2801 (2.0); 4.2698 (2.0); 4.2623 (6.1); 4.2519 (6.0); 4.2444 (6.2); 4.2340 (6.0); 4.2266 (2.1); 4.2161 (1.9); 1.3330 (1.1); 1.3003 (7.4); 1.2931 (7.8); 1.2824 (15.5); 1.2753 (16.0); 1.2699 (1.3); 1.2645 (7.4); 1.2574 (8.6); 0.0080 (1.0); −0.0002 (35.6); −0.00085 (1.1)

X-001: ¹H-NMR(400.6 MHz, CDCl3):
δ = 8.1305 (2.3); 8.1244 (2.3); 7.7600 (1.3); 7.7538 (1.3); 7.7413 (1.6); 7.7388 (1.6); 7.7351 (1.6); 7.7325 (1.5); 7.7202 (1.4); 7.7139 (1.3); 7.4636 (1.1); 7.4592 (1.2); 7.4442 (1.9); 7.4400 (2.0); 7.4255 (1.3); 7.4211 (1.4); 7.3989 (0.6); 7.3945 (0.7); 7.3866 (0.7); 7.3820 (0.9); 7.3800 (1.1); 7.3781 (1.0); 7.3756 (1.0); 7.3737 (0.8); 7.3677 (1.2); 7.3659 (0.9); 7.3633 (1.0); 7.3613 (1.0); 7.3593 (1.0); 7.3548 (0.9); 7.3471 (1.0); 7.3426 (0.8); 7.2613 (68.3); 7.2577 (2.1); 7.2562 (1.7); 7.2395 (1.8); 7.2329 (0.7); 7.2206 (0.9); 7.2189 (1.0); 7.2173 (0.9); 7.0648 (1.4); 7.0617 (1.3); 7.0440 (1.3); 7.0402 (2.1); 7.0365 (1.3); 7.0189 (1.2); 7.0157 (1.1); 6.9558 (1.6); 6.9483 (1.7); 6.9346 (1.6); 6.9271 (1.6); 6.6563 (0.6); 5.9493 (0.6); 5.9357 (1.3); 5.9235 (0.9); 5.9221 (0.7); 5.9099 (1.5); 5.9064 (0.8); 5.8963 (0.7); 5.8928 (1.5); 5.8806 (1.0); 5.8792 (0.8); 5.8671 (1.6); 5.8534 (0.8); 5.2795 (0.9); 5.2752 (2.1); 5.2720 (2.3); 5.2677 (0.9); 5.2366 (0.8); 5.2323 (1.8); 5.2292 (2.0); 5.2248 (0.8); 5.1968 (1.0); 5.1932 (2.4); 5.1899

(2.3); 5.1863 (0.9); 5.1711 (0.9); 5.1675 (2.2); 5.1642 (2.2); 5.1606 (0.9); 4.8586 (16.0); 4.7735 (0.5); 4.0397 (1.2); 4.0358 (2.2); 4.0318 (1.3); 4.0217 (3.8); 4.0180 (2.1); 4.0113 (1.3); 4.0073 (2.1); 4.0033 (1.1); 1.3333 (0.5); 1.2845 (0.7); 1.2548 (0.9); 0.0080 (1.5); −0.0002 (53.8); −0.00085 (1.4)

VII-006: $^1$H-NMR(400.0 MHz, CDCl3):
δ = 8.0897 (2.2); 8.0834 (2.2); 7.7569 (1.1); 7.7506 (1.1); 7.7381 (1.3); 7.7356 (1.4); 7.7318 (1.2); 7.7294 (1.3); 7.7169 (1.2); 7.7106 (1.1); 7.3684 (0.5); 7.3639 (0.7); 7.3564 (1.0); 7.3515 (1.8); 7.3497 (2.0); 7.3432 (2.4); 7.3397 (2.2); 7.3357 (3.4); 7.3326 (4.7); 7.3247 (3.8); 7.3218 (2.2); 7.3169 (9.1); 7.3141 (4.5); 7.3101 (4.8); 7.3057 (3.3); 7.3003 (3.5); 7.2981 (2.0); 7.2938 (1.2); 7.2599 (34.4); 7.2087 (1.2); 7.2068 (1.2); 7.1901 (1.6); 7.1886 (1.7); 7.1701 (0.7); 7.0393 (1.1); 7.0361 (1.0); 7.0185 (1.0); 7.0146 (1.7); 7.0109 (1.1); 6.9933 (1.0); 6.9903 (0.9); 6.9434 (1.5); 6.9420 (1.6); 6.9360 (1.5); 6.9346 (1.5); 6.9222 (1.4); 6.9208 (1.5); 6.9147 (1.4); 6.9133 (1.4); 5.2488 (12.6); 4.9564 (16.0); 4.8824 (0.6); 1.5459 (7.1); 1.4321 (0.9); 1.2844 (0.6); 1.2553 (1.4); 0.0080 (1.4); −0.0002 (47.2); −0.00085 (1.3)

I-001: $^1$H-NMR(400.0 MHz, CDCl3):
δ = 8.9579 (1.9); 8.9541 (1.9); 8.5086 (1.8); 8.5024 (2.0); 8.4138 (1.4); 8.4099 (1.5); 8.4076 (1.4); 8.4036 (1.2); 7.4746 (0.5); 7.4596 (0.9); 7.4553 (0.9); 7.4406 (0.6); 7.4362 (0.6); 7.2784 (0.5); 7.2597 (32.1); 7.2172 (0.7); 7.1974 (0.9); 6.9898 (0.6); 6.9865 (0.6); 6.9691 (0.6); 6.9644 (0.7); 6.9606 (0.6); 6.9432 (0.5); 5.2990 (0.7); 5.2554 (1.5); 5.2380 (1.5); 3.7950 (4.3); 3.7747 (16.0); 3.7679 (0.5); 3.7377 (1.7); 2.7544 (2.1); 1.7080 (2.4); 1.7032 (6.4); 1.6905 (2.5); 1.6858 (6.4); 1.5824 (0.9); 1.5642 (1.0); 1.5401 (1.3); 0.0080 (1.1); −0.0002 (41.6); −0.00085 (1.2)

I-004: $^1$H-NMR(400.0 MHz, CDCl3):
δ = 8.9676 (3.9); 8.9638 (3.8); 8.5126 (3.7); 8.5063 (4.0); 8.4160 (2.8); 8.4121 (2.9); 8.4097 (2.6); 8.4058 (2.3); 7.5094 (1.0); 7.5049 (1.0); 7.4900 (1.7); 7.4857 (1.7); 7.4710 (1.1); 7.4665 (1.1); 7.3409 (0.5); 7.3364 (0.6); 7.3288 (0.6); 7.3221 (0.9); 7.3175 (0.8); 7.3099 (0.9); 7.3054 (0.9); 7.3014 (0.9); 7.2970 (0.8); 7.2893 (0.9); 7.2848 (0.9); 7.2596 (66.1); 7.2309 (1.0); 7.2286 (1.1); 7.2121 (1.6); 7.1923 (0.7); 6.9982 (1.1); 6.9951 (1.3); 6.9775 (1.0); 6.9729 (1.4); 6.9690 (1.1); 6.9518 (0.9); 6.9484 (0.9); 5.2989 (1.4); 4.9193 (15.7); 4.2984 (2.0); 4.2805 (6.2); 4.2627 (4.3); 4.2391 (1.9); 4.2448 (2.2); 4.2315 (1.0); 4.2229 (0.9); 4.2049 (0.8); 3.8281 (0.5); 2.8026 (4.5); 1.5397 (3.3); 1.3083 (8.1); 1.3014 (1.5); 1.2905 (16.0); 1.2835 (2.7); 1.2727 (7.7); 1.2656 (1.5); 0.0080 (2.5); −0.0002 (87.0); −0.00085 (2.4)

III-001: $^1$H-NMR(400.0 MHz, CDCl3):
δ = 8.5636 (8.8); 8.4513 (1.6); 7.4864 (0.7); 7.4821 (0.6); 7.4671 (1.0); 7.4628 (1.0); 7.4481 (0.6); 7.4436 (0.6); 7.3140 (0.6); 7.3095 (0.5); 7.3019 (0.5); 7.2623 (7.1); 7.2290 (0.6); 7.2258 (0.7); 7.2104 (0.9); 7.2071 (0.9); 7.0079 (0.6); 7.0045 (0.6); 6.9873 (0.6); 6.9821 (0.8); 6.9783 (0.7); 6.9612 (0.6); 6.9577 (0.5); 6.6254 (1.0); 5.3013 (3.7); 5.2537 (1.6); 5.2363 (1.6); 3.7727 (3.9); 3.7694 (16.0); 1.7008 (6.5); 1.6834 (6.4); 1.6527 (1.3); 1.6354 (1.3); 1.5623 (1.2); −0.0002 (9.5)

I-002: $^1$H-NMR(400.0 MHz, CDCl3):
δ = 8.9713 (4.9); 8.9678 (4.9); 8.5315 (4.0); 8.5252 (4.7); 8.4708 (3.0); 8.4669 (3.4); 8.4609 (2.5); 7.5189 (0.5); 7.5020 (1.4); 7.4976 (1.5); 7.4825 (2.5); 7.4782 (2.6); 7.4635 (1.6); 7.4591 (1.6); 7.3294 (0.7); 7.3250 (0.8); 7.3172 (0.9); 7.3105 (1.4); 7.3062 (1.4); 7.2984 (1.5); 7.2899 (1.4); 7.2854 (1.3); 7.2778 (1.4); 7.2733 (1.5); 7.2600 (93.1); 7.2419 (0.6); 7.2253 (1.0); 7.2146 (2.3); 7.1953 (2.9); 7.1784 (1.5); 6.9960 (0.7); 6.9840 (1.6); 6.9809 (1.7); 6.9634 (1.6); 6.9587 (2.1); 6.9550 (1.7); 6.9375 (1.4); 6.9342 (1.4); 5.3351 (1.2); 5.3176 (4.8); 5.3001 (4.8); 5.2827 (1.2); 4.1489 (1.6); 2.1033 (0.5); 1.7562 (16.0); 1.7387 (15.9); 1.6251 (0.8); 1.5943 (4.9); 1.5785 (0.5); 1.3324 (0.6); 1.2841 (0.9); 1.2745 (0.7); 1.2551 (2.4); 1.2221 (0.8); 1.2180 (0.6); 1.1303 (2.2); 1.1093 (4.9); 1.0918 (2.9); 1.0520 (3.6); 0.0693 (4.0); 0.0080 (2.9); −0.0002 (93.4); −0.00085 (2.6)

I-003: $^1$H-NMR(400.0 MHz, CDCl3):
δ = 8.9694 (2.2); 8.5279 (1.8); 8.5220 (2.0); 8.4307 (1.6); 7.5216 (1.1); 7.5183 (2.1); 7.5028 (1.5); 7.4849 (1.0); 7.4837 (1.0); 7.3230 (0.9); 7.2594 (375.5); 7.2449 (1.3); 7.2211 (0.9); 7.2027 (0.9); 7.0088 (1.0); 6.9955 (2.1); 6.9837 (1.2); 6.9625 (0.8); 5.0007 (16.0); 1.8963 (1.1); 0.1459 (1.4); 0.0688 (2.2); 0.0080 (11.1); −0.0002 (373.0); −0.00085 (10.7); −0.1495 (1.2)

III-006: $^1$H-NMR(400.0 MHz, CDCl3):
δ = 8.5633 (15.6); 8.4520 (2.6); 7.4223 (1.3); 7.4186 (1.2); 7.4032 (2.3); 7.3993 (2.1); 7.3839 (1.4); 7.3799 (1.3); 7.3543 (3.3); 7.3407 (3.9); 7.3260 (6.3); 7.3161 (6.4); 7.3109 (8.8); 7.3024 (6.7); 7.2931 (3.9); 7.2598 (49.3); 7.2145 (1.9); 7.1961 (2.6); 7.1772 (1.0); 7.0097 (1.4); 6.9849 (1.9); 6.9630 (1.2); 6.6624 (1.3); 5.2990 (4.2); 5.2497 (16.0); 5.1926 (1.7); 4.9711 (15.0); 4.9170 (2.6); 4.2859 (1.8); 1.5457 (5.4); 1.2565 (2.7); −0.0002 (33.9)

V-002: $^1$H-NMR(400.6 MHz, CDCl3):
δ = 8.5201 (4.9); 8.5173 (4.8); 7.5071 (0.9); 7.5026 (0.9); 7.4878 (1.6); 7.4834 (1.7); 7.4687 (1.0); 7.4643 (1.0); 7.3322 (0.6); 7.3300 (0.8); 7.3255 (0.7); 7.3179 (0.8); 7.3134 (0.8); 7.3095 (0.8); 7.3050 (0.7); 7.2975 (0.8); 7.2930 (0.7); 7.2602 (62.6); 7.2317 (1.4); 7.2219 (1.6); 7.1949 (0.7); 7.1356 (5.3); 7.1328 (5.3); 7.0282 (1.0); 7.0249 (1.0); 7.0076 (1.0); 7.0032 (1.4); 6.9991 (1.1); 6.9819 (0.9); 6.9785 (0.9); 6.4011 (0.8); 5.3000 (1.4); 4.9015 (15.1); 4.8521 (1.1); 4.4659 (1.8); 4.4482 (6.1); 4.4305 (6.2); 4.4128 (1.9); 4.4074 (0.5); 4.2881 (1.9); 4.2772 (0.6); 4.2702 (6.2); 4.2594 (0.7); 4.2524 (6.4); 4.2344 (2.5); 4.2330 (2.4); 3.8297 (3.3); 1.5394 (14.2); 1.4409 (6.4); 1.4232 (13.9); 1.4055 (6.2); 1.3977 (0.6); 1.3800 (1.1); 1.3623 (0.5); 1.3241 (1.3); 1.3113 (0.5); 1.3062 (3.2); 1.2999 (7.8); 1.2934 (1.2); 1.2882 (2.6); 1.2821 (16.0); 1.2756 (0.8); 1.2701 (0.9); 1.2643 (7.7); 1.2538 (0.8); 0.0079 (2.7); −0.0002 (101.4); −0.00085 (2.9); −0.0284 (0.7)

V-005: $^1$H-NMR(400.6 MHz, CDCl3):
δ = 9.0097 (2.0); 9.0062 (2.0); 8.8261 (2.2); 8.8131 (2.2); 7.7661 (1.4); 7.7625 (1.4); 7.7530 (1.4); 7.7494 (1.4); 7.6977 (0.6); 7.6805 (0.7); 7.6768 (0.6); 7.6678 (0.6); 7.6506 (0.7); 7.6469 (0.6); 7.4915 (0.6); 7.4867 (0.5); 7.4766 (1.0); 7.4720 (1.2); 7.4677 (0.8); 7.4637 (0.6); 7.4602 (0.8); 7.4578 (0.7); 7.4534 (0.7); 7.2607 (19.0); 7.2432 (0.6); 7.2410 (0.7); 7.2215 (1.0); 7.0110 (0.6); 7.0077 (0.6); 6.9904 (0.5); 6.9855 (0.7); 6.9818 (0.6); 6.9645 (0.5); 6.9611 (0.5); 5.2997 (1.9); 5.2501 (1.5); 5.2327 (1.5); 3.7955 (1.1); 3.7691 (16.0); 1.7084 (0.6); 1.6984 (6.4); 1.6911 (0.8); 1.6810(6.4); 1.5641 (0.6); 0.0080 (0.7); −0.0002 (26.0); −0.00085 (0.8)

V-001: $^1$H-NMR(400.6 MHz, CDCl3):
δ = 9.0117 (3.7); 9.0083 (3.7); 8.8317 (3.8); 8.8186 (4.0); 7.7764 (2.6); 7.7728 (2.7); 7.7634 (2.6); 7.7597 (2.7); 7.7010 (0.6); 7.6978 (0.8); 7.6806 (1.0); 7.6769 (0.9); 7.6711 (0.6); 7.6678 (0.8); 7.6506 (1.0); 7.6470 (0.9); 7.5513 (0.6); 7.5469 (0.6); 7.5325 (0.6); 7.5288 (0.6); 7.5254 (1.1); 7.5211 (1.0); 7.5061 (1.6); 7.5018 (1.7); 7.4870 (1.7); 7.4828 (1.5); 7.4795 (0.8); 7.4712 (0.6); 7.4678 (1.0); 7.4638

(0.8); 7.4605 (1.0); 7.3662 (0.6); 7.3618 (0.6); 7.3541 (0.6); 7.3494 (0.7); 7.3474 (0.9); 7.3430 (0.9); 7.3352 (1.0); 7.3307 (0.9); 7.3269 (1.0); 7.3223 (0.8); 7.3148 (0.9); 7.3102 (0.8); 7.2606 (50.3); 7.2565 (1.8); 7.2542 (1.6); 7.2525 (1.5); 7.2327 (2.0); 7.2157 (0.9); 7.2122 (1.0); 7.0194 (1.1); 7.0161 (1.1); 6.9987 (1.1); 6.9941 (1.4); 6.9902 (1.2); 6.9730 (1.2); 6.9696 (1.0); 5.3000 (6.4); 5.0533 (0.9); 4.9144 (15.7); 4.8358 (0.7); 4.7153 (0.9); 4.2935 (2.0); 4.2757 (6.2); 4.2579 (6.6); 4.2401 (2.3); 4.2326 (1.2); 4.2257 (0.6); 2.8043 (1.5); 1.5543 (2.8); 1.3110 (1.0); 1.3083 (1.2); 1.3043 (7.8); 1.2982 (0.8); 1.2932 (1.8); 1.2865 (16.0); 1.2754 (1.1); 1.2687 (7.7); 1.2638 (1.4); 1.2542 (1.3); 1.2460 (0.6); 0.0080 (1.7); −0.0002 (69.8); −0.00085 (2.4); −0.0282 (0.6)

V-004: $^1$H-NMR(400.6 MHz, CDCl3):

δ = 9.0251 (2.8); 9.0218 (2.9); 8.8497 (1.3); 8.8366 (1.4); 7.7826 (2.0); 7.7791 (2.0); 7.7695 (2.0); 7.7659 (2.0); 7.5413 (0.8); 7.5370 (0.9); 7.5220 (1.5); 7.5178 (1.7); 7.5030 (1.0); 7.4986 (1.0); 7.3547 (0.8); 7.3502 (0.7); 7.3425 (0.8); 7.3380 (0.8); 7.3341 (0.8); 7.3296 (0.7); 7.3219 (0.7); 7.3175 (0.6); 7.2603 (67.2); 7.2380 (1.7); 7.2210 (0.8); 7.0229 (1.0); 7.0196 (1.0); 7.0022 (1.1); 6.9970 (1.6); 6.9937 (1.2); 6.9764 (1.0); 6.9730 (1.0); 4.9911 (16.0); 4.9658 (0.5); 4.9178 (0.8); 4.9112 (0.8); 1.2549 (0.6); 0.0691 (0.7); 0.0272 (0.6); 0.0080 (2.4); −0.0002 (92.1); −0.00085 (3.0)

III-001: $^1$H-NMR(400.0 MHz, CDCl3):

δ = 8.5602 (8.8); 8.4480 (0.6); 7.4832 (0.6); 7.4788 (0.5); 7.4639 (1.0); 7.4595 (1.0); 7.4448 (0.6); 7.4404 (0.6); 7.3123 (0.5); 7.2609 (6.9); 7.2257 (0.6); 7.2233 (0.7); 7.2070 (0.9); 7.2039 (1.0); 7.0072 (0.6); 7.0039 (0.6); 6.9866 (0.6); 6.9815 (0.8); 6.9777 (0.6); 6.9605 (0.5); 6.9571 (0.5); 5.2995 (1.0); 5.2538 (1.6); 5.2364 (1.6); 3.7678 (16.0); 1.6992 (6.5); 1.6818 (6.5); 1.5513 (1.6); −0.0002 (9.2)

III-004: $^1$H-NMR(400.0 MHz, CDCl3):

δ = 8.5613 (16.0); 8.4503 (1.0); 7.5115 (1.0); 7.5072 (1.0); 7.4922 (1.8); 7.4878 (1.9); 7.4731 (1.1); 7.4687 (1.1); 7.3431 (0.5); 7.3386 (0.5); 7.3310 (0.5); 7.3242 (0.9); 7.3197 (0.8); 7.3120 (0.9); 7.3076 (0.9); 7.3037 (0.9); 7.2991 (0.7); 7.2916 (0.8); 7.2871 (0.7); 7.2612 (10.2); 7.2364 (1.1); 7.2341 (1.2); 7.2176 (1.7); 7.2146 (1.8); 7.1978 (0.7); 7.1958 (0.7); 7.0171 (1.1); 7.0137 (1.1); 6.9965 (1.1); 6.9915 (1.4); 6.9877 (1.2); 6.9705 (1.0); 6.9671 (1.0); 6.6674 (0.6); 5.2994 (1.9); 4.9162 (1.0); 4.8608 (1.1); 4.2930 (2.0); 4.2802 (0.6); 4.2751 (6.2); 4.2573 (6.3); 4.2394 (2.1); 4.2326 (1.2); 1.5558 (1.9); 1.3108 (0.6); 1.3075 (0.7); 1.3019 (7.5); 1.2929 (1.4); 1.2898 (1.4); 1.2840 (15.3); 1.2750 (0.8); 1.2720 (0.9); 1.2662 (7.3); −0.0002 (13.4)

VIII-003: $^1$H-NMR(400.6 MHz, CDCl3):

δ = 8.1927 (2.4); 8.1797 (2.5); 7.4335 (0.6); 7.4291 (0.8); 7.4145 (1.2); 7.4101 (1.5); 7.4025 (0.6); 7.3956 (0.8); 7.3909 (1.3); 7.3858 (0.6); 7.3836 (0.8); 7.3818 (0.7); 7.3791 (0.6); 7.3774 (0.6); 7.3713 (0.8); 7.3669 (0.6); 7.3651 (0.6); 7.3629 (0.8); 7.3584 (0.6); 7.3507 (0.7); 7.3463 (0.6); 7.2728 (0.8); 7.2685 (1.1); 7.2598 (70.0); 7.2496 (2.0); 7.2319 (1.8); 7.2210 (0.7); 7.2094 (0.7); 7.1992 (0.6); 7.1877 (0.9); 7.1817 (1.0); 7.1690 (0.7); 7.1674 (0.7); 7.1580 (1.7); 7.1502 (1.1); 7.1452 (0.5); 7.1348 (1.0); 7.1297 (0.8); 7.1124 (0.6); 7.1090 (0.7); 7.0838 (2.6); 7.0737 (1.1); 7.0705 (2.1); 7.0664 (1.8); 7.0627 (1.4); 7.0575 (1.2); 7.0532 (2.5); 7.0495 (2.5); 7.0455 (1.1); 7.0278 (0.8); 7.0247 (0.8); 6.9962 (0.5); 6.8724 (1.5); 6.8691 (2.6); 6.8659 (1.6); 6.8643 (1.4); 4.9004 (14.2); 4.8356 (1.4); 4.2965 (1.8); 4.2787 (5.6); 4.2609 (5.7); 4.2431 (2.1); 3.9882 (1.6); 3.9423 (1.8); 2.3118 (3.6); 2.2421 (3.8); 1.5379 (16.0); 1.3076 (7.5); 1.2956 (0.6); 1.2898 (15.3); 1.2720 (8.1); 1.2542 (2.1); 1.2364 (0.8); 0.8820 (0.6); 0.0080 (2.3); −0.0002 (96.2); −0.00085 (3.0); −0.0280 (0.7)

VIII-006: $^1$H-NMR(400.6 MHz, CDCl3):

δ = 8.1861 (1.5); 8.1731 (1.5); 7.3921 (0.7); 7.3771 (1.1); 7.3740 (1.1); 7.3722 (1.2); 7.3584 (1.4); 7.3543 (0.8); 7.3523 (0.6); 7.2681 (0.6); 7.2602 (22.6); 7.2372 (0.6); 7.2338 (0.7); 7.2165 (1.0); 7.2147 (0.9); 7.1987 (0.6); 7.1580 (0.7); 7.0839 (1.2); 7.0673 (0.6); 7.0645 (0.5); 7.0609 (0.8); 7.0569 (1.1); 7.0530 (0.7); 7.0476 (1.1); 7.0434 (1.7); 7.0400 (1.2); 7.0212 (0.6); 6.8666 (1.0); 6.8634 (1.6); 6.8602 (1.0); 5.2997 (1.4); 5.2262 (1.5); 5.2088 (1.6); 3.9881 (1.6); 3.9422 (0.8); 3.7753 (16.0); 3.7382 (1.4); 3.7145 (0.6); 2.7559 (1.8); 2.3117 (1.6); 2.2420 (1.6); 1.6962 (6.4); 1.6788 (6.3); 1.5824 (0.8); 1.5642 (0.9); 1.5479 (2.5); 1.2543 (0.7); 0.0079 (0.8); −0.0002 (30.0); −0.00085 (0.9)

VI-001: $^1$H-NMR(400.6 MHz, CDCl3):

δ = 9.1753 (1.4); 8.6702 (3.5); 7.2626 (7.1); 5.3007 (1.1); 4.9081 (3.3); 4.2832 (1.3); 4.2654 (1.3); 2.9641 (16.0); 2.7740 (3.3); 1.5691 (1.7); 1.3122 (1.7); 1.2944 (3.5); 1.2766 (1.7); −0.0002 (9.6)

VI-003: $^1$H-NMR(400.6 MHz, CDCl3):

δ = 9.1767 (2.9); 8.6628 (6.4); 7.4762 (0.5); 7.4717 (0.6); 7.4568 (0.8); 7.4525 (0.8); 7.4336 (0.5); 7.2622 (13.5); 7.2431 (0.7); 7.2414 (0.7); 7.0449 (0.8); 7.0411 (0.7); 5.3004 (1.8); 4.9097 (7.2); 4.3034 (1.0); 4.2856 (3.0); 4.2677 (3.0); 4.2499 (1.0); 2.9220 (16.0); 2.7733 (5.8); 1.3136 (1.0); 1.2958 (8.3); 1.2780 (4.0); 1.2581 (0.7); 0.0022 (0.8); −0.0002 (17.3); −0.00026 (0.9); −0.00084 (0.6)

VI-005: $^1$H-NMR(400.6 MHz, CDCl3):

δ = 9.2205 (6.7); 8.8682 (0.7); 8.7213 (0.6); 8.6968 (11.2); 7.4636 (0.6); 7.4611 (1.8); 7.4459 (2.2); 7.4414 (3.2); 7.4368 (0.7); 7.4278 (1.6); 7.4255 (1.7); 7.4219 (1.7); 7.4177 (0.6); 7.4096 (0.9); 7.2860 (0.9); 7.2843 (1.0); 7.2828 (1.0); 7.2812 (0.9); 7.2678 (0.8); 7.2633 (15.2); 7.2473 (0.7); 7.2456 (0.7); 7.2442 (0.7); 7.2426 (0.6); 7.0825 (0.9); 7.0796 (0.8); 7.0769 (0.5); 7.0607 (1.0); 7.0578 (1.7); 7.0550 (1.1); 7.0362 (1.0); 7.0326 (0.7); 5.3008 (2.8); 5.0164 (0.6); 5.0054 (14.3); 4.3088 (1.9); 4.2910 (6.0); 4.2731 (6.1); 4.2553 (2.0); 2.9222 (2.8); 1.3165 (0.9); 1.3116 (7.6); 1.3052 (1.0); 1.2938 (16.0); 1.2874 (0.8); 1.2760 (7.6); 1.2538 (0.6); 1.2359 (0.7); 0.0079 (0.5); −0.0002 (18.5); −0.00085 (0.5)

VI-006: $^1$H-NMR(400.6 MHz, CDCl3):

δ = 9.2464 (4.0); 8.7607 (0.5); 8.7448 (6.7); 7.4477 (0.6); 7.4436 (1.4); 7.4289 (1.1); 7.4246 (1.4); 7.4107 (0.7); 7.4096 (0.7); 7.4079 (0.7); 7.2896 (0.6); 7.2881 (0.6); 7.2867 (0.5); 7.2710 (0.9); 7.2700 (0.8); 7.2678 (0.8); 7.2661 (0.5); 7.2625 (8.3); 7.0849 (0.6); 7.0629 (0.8); 7.0596 (0.8); 7.0567 (0.5); 5.3143 (1.5); 5.3005 (6.3); 5.2968 (1.6); 3.7997 (1.2); 3.7926 (16.0); 3.7387 (0.6); 1.7712 (6.1); 1.7648 (0.7); 1.7537 (6.1); 0.1728 (0.5); 0.0944 (5.4); 0.0791 (1.7); 0.0770 (0.9); −0.0002 (10.8)

VI-017: $^1$H-NMR(400.6 MHz, CDCl3):

δ = 7.2641 (2.4); 3.7820 (1.0); 2.9235 (16.0); −0.0002 (3.1)

VI-017: $^1$H-NMR(400.6 MHz, CDCl3):

δ = 8.5682 (0.8); 7.2618 (6.2); 6.1762 (0.9); 3.7820 (2.6); 2.9225 (16.0); 1.6573 (1.0); 1.6399 (1.0); 1.5498 (0.7); −0.0002(8.1)

VI-007: $^1$H-NMR(400.6 MHz, CDCl3):

δ = 9.1867 (6.6); 8.6820 (14.1); 7.6936 (0.6); 7.6764 (0.7); 7.6728 (0.7); 7.6634 (0.6); 7.6462 (0.8); 7.6426 (0.7); 7.5202 (0.5); 7.4870 (0.5); 7.4797 (1.3); 7.4756 (1.0); 7.4680 (0.8); 7.4605 (2.0); 7.4562

(1.6); 7.4416 (1.1); 7.4372 (1.1); 7.3892 (0.5); 7.3826 (0.8); 7.3781 (0.7); 7.3702 (0.8); 7.3658 (0.7); 7.3619 (0.8); 7.3573 (0.6); 7.3495 (0.7); 7.3451 (0.6); 7.2666 (0.6); 7.2616 (90.5); 7.2394 (1.4); 7.2335 (0.8); 7.2205 (0.7); 7.0646 (1.0); 7.0613 (1.0); 7.0437 (0.9); 7.0399 (1.5); 7.0362 (1.0); 7.0186 (0.9); 7.0154 (0.8); 6.9980 (0.6); 4.9775 (16.0); 4.9101 (0.6); 4.9063 (0.6); 1.9555 (1.0); 1.4321 (0.8); 1.2222 (0.9); 0.0079 (3.2); −0.0002 (127.9); −0.00052 (1.9); −0.00060 (1.6); −0.00085 (3.8); −0.0117 (0.6); −0.0284 (1.0)

VI-016: $^1$H-NMR(400.6 MHz, CDCl3):
δ = 9.2235 (9.0); 8.7018 (13.3); 7.5206 (0.9); 7.4630 (1.0); 7.4582 (1.7); 7.4432 (3.2); 7.4406 (2.9); 7.4382 (2.7); 7.4326 (1.1); 7.4242 (3.9); 7.4207 (1.8); 7.4181 (1.4); 7.4136 (0.9); 7.4054 (1.2); 7.4010 (0.8); 7.2780 (1.7); 7.2621 (148.6); 7.2410 (1.0); 7.2340 (1.2); 7.0751 (1.3); 7.0513 (2.1); 7.0295 (1.2); 7.0262 (0.8); 6.9985 (0.8); 5.4007 (1.0); 5.3832 (4.4); 5.3656 (4.5); 5.3481 (1.1); 5.3406 (1.0); 5.3231 (0.9); 1.9551 (4.2); 1.8578 (2.4); 1.8218 (16.0); 1.8042 (15.8); 1.7908 (3.9); 1.7820 (1.8); 1.7733 (3.6); 1.7647 (1.6); 1.7457 (1.1); 1.7289 (0.9); 1.2222 (0.7); 0.1458 (0.6); 0.0080 (5.2); 0.0057 (1.4); 0.0049 (1.4); 0.0040 (2.2); −0.0002 (203.0); −0.00085 (6.0); −0.0283 (1.6); −0.1493 (0.6)

IX-001: $^1$H-NMR(400.6 MHz, CDCl3):
δ = 9.1924 (6.1); 9.1774 (1.0); 8.6770 (16.0); 8.6661 (2.4); 7.7000 (0.6); 7.6966 (0.8); 7.6795 (1.1); 7.6758 (1.0); 7.6700 (0.6); 7.6667 (0.8); 7.6495 (1.0); 7.6459 (0.9); 7.5332 (0.6); 7.5293 (0.6); 7.5080 (0.7); 7.5036 (0.8); 7.4888 (1.7); 7.4841 (1.7); 7.4816 (0.7); 7.4797 (0.9); 7.4764 (0.5); 7.4695 (1.4); 7.4681 (1.3); 7.4649 (1.4); 7.4608 (1.1); 7.4047 (0.5); 7.4026 (0.7); 7.4008 (0.7); 7.3982 (0.7); 7.3963 (0.6); 7.3903 (0.8); 7.3885 (0.6); 7.3859 (0.7); 7.3840 (0.6); 7.3819 (0.8); 7.3774 (0.7); 7.3696 (0.8); 7.3651 (0.7); 7.2889 (0.9); 7.2872 (0.9); 7.2854 (1.0); 7.2840 (0.9); 7.2679 (1.6); 7.2672 (1.7); 7.2663 (1.7); 7.2656 (1.9); 7.2623 (31.3); 7.2598 (1.3); 7.2582 (0.7); 7.2550 (0.8); 7.2486 (0.9); 7.2469 (0.9); 7.2454 (0.8); 7.0762 (0.9); 7.0730 (0.9); 7.0554 (0.9); 7.0516 (1.4); 7.0478 (1.0); 7.0302 (0.9); 7.0271 (0.9); 5.9377 (1.0); 5.9256 (0.6); 5.9241 (0.6); 5.9120 (1.0); 5.9086 (0.6); 5.8983 (0.6); 5.8948 (1.2); 5.8827 (0.6); 5.8812 (0.7); 5.8691 (1.2); 5.8555 (0.6); 5.3003 (7.2); 5.2817 (0.9); 5.2774 (1.9); 5.2743 (1.8); 5.2700 (0.8); 5.2389 (0.6); 5.2345 (1.3); 5.2314 (1.4); 5.2271 (1.6); 5.2015 (0.7); 5.1978 (1.7); 5.1945 (1.6); 5.1910 (0.7); 5.1758 (0.6); 5.1722 (1.5); 5.1689 (1.6); 5.1653 (0.7); 4.8662 (10.6); 4.0432 (0.8); 4.0392 (1.4); 4.0352 (0.9); 4.0287 (1.4); 4.0250 (2.5); 4.0212 (1.5); 4.0147 (0.9); 4.0107 (1.5); 4.0067 (1.0); 2.7881 (0.7); 2.7339 (0.6); 2.2717 (0.6); 1.4322 (5.5); 1.2539 (1.1); 1.2218 (1.1); 1.2107 (0.6); 1.1927 (1.4); 1.1745 (0.6); 0.0695 (1.4); 0.0080 (1.1); 0.0030 (0.6); 0.0022 (1.3); −0.0002 (41.4); −0.00027 (2.3); −0.00034 (1.7); −0.00043 (1.0); −0.00051 (0.7); −0.00060 (0.6); −0.00068 (0.5); −0.00085 (1.4)

IX-002: $^1$H-NMR(400.6 MHz, CDCl3):
δ = 9.2343 (9.6); 9.2134 (0.5); 8.9495 (0.5); 8.7205 (0.7); 8.7044 (16.0); 7.5197 (0.6); 7.5016 (0.9); 7.4972 (1.2); 7.4838 (1.8); 7.4794 (2.2); 7.4714 (1.1); 7.4646 (2.0); 7.4601 (2.3); 7.4522 (1.9); 7.4477 (1.2); 7.4441 (1.3); 7.4397 (0.9); 7.4316 (1.3); 7.4271 (0.8); 7.3123 (1.6); 7.2961 (1.8); 7.2927 (2.3); 7.2882 (0.5); 7.2749 (1.0); 7.2612 (92.2); 7.2531 (1.0); 7.2331 (0.9); 7.1928 (0.5); 7.1879 (0.5); 7.0966 (1.4); 7.0933 (1.4); 7.0757 (1.8); 7.0721 (2.7); 7.0683 (1.9); 7.0508 (1.7); 7.0482 (1.6); 6.9976 (0.6); 5.9459 (0.6); 5.9322 (1.4); 5.9201 (0.9); 5.9184 (0.9); 5.9064 (1.6); 5.9031 (0.8); 5.8926 (1.0); 5.8893 (1.7); 5.8773 (1.0); 5.8756 (1.1); 5.8635 (1.8); 5.8498 (1.0); 5.3953 (0.8); 5.3785 (3.0); 5.3616 (3.1); 5.3447 (1.0); 5.3004 (7.5); 5.2816 (1.0); 5.2774 (2.1); 5.2743 (2.4); 5.2700 (1.2); 5.2387 (0.9); 5.2345 (1.9); 5.2314 (2.0); 5.2272 (1.0); 5.2157 (0.6); 5.2126 (0.6); 5.2050 (1.2); 5.2014 (2.7); 5.1982 (2.6); 5.1947 (1.2); 5.1792 (1.2); 5.1757 (2.7); 5.1725 (2.4); 5.1690 (1.0); 5.1528 (0.5); 5.1489 (0.7); 4.0065 (1.2); 4.0026 (2.2); 3.9986 (1.4); 3.9924 (2.4); 3.9884 (4.2); 3.9844 (2.8); 3.9784 (1.9); 3.9743 (2.6); 3.9702 (1.8); 3.9658 (1.0); 3.9519 (0.5); 3.8709 (0.5); 2.8213 (0.8); 2.8094 (0.8); 2.6167 (2.5); 2.2718 (0.8); 1.7757 (14.7); 1.7588 (14.6); 1.7375 (0.5); 1.7288 (0.9); 1.7232 (2.4); 1.7121 (1.0); 1.7063 (2.3); 1.5637 (3.8); 1.4322 (8.3); 1.2539 (3.6); 1.2225 (0.6); 1.1237 (0.7); 0.0691 (0.7); 0.0080 (3.2); −0.0002 (127.4); −0.0049 (2.9); −0.00085 (4.1); −0.0282 (1.1)

VIII-003: $^1$H-NMR(400.0 MHz, CDCl3):
δ = 8.1930 (2.5); 8.1802 (2.6); 7.5200 (0.6); 7.4878 (0.5); 7.4794 (0.6); 7.4297 (1.1); 7.4104 (1.9); 7.3911 (1.7); 7.3836 (1.3); 7.3704 (1.3); 7.3506 (0.9); 7.2609 (42.6); 7.2304 (2.0); 7.2108 (0.9); 7.1763 (1.1); 7.0703 (2.4); 7.0667 (2.4); 7.0534 (3.0); 7.0499 (2.7); 7.0279 (1.0); 6.8696 (3.4); 5.0400 (1.0); 4.9003 (11.8); 4.7181 (1.1); 4.6655 (1.7); 4.5975 (0.9); 4.2964 (1.6); 4.2786 (4.7); 4.2607 (4.8); 4.2430 (1.8); 4.2312 (1.1); 4.2130 (1.0); 2.8159 (1.4); 2.3526 (0.8); 2.3336 (0.6); 1.6401 (0.6); 1.5515 (0.8); 1.3329 (2.0); 1.3075 (6.8); 1.2897 (13.0); 1.2844 (5.8); 1.2718 (9.2); 1.2550 (16.0); 1.2201 (1.6); 0.8966 (1.1); 0.8801 (2.5); 0.8625 (1.3); 0.0696 (0.6); −0.0002 (28.3)

VIII-012: $^1$H-NMR(400.6 MHz, CDCl3):
δ = 8.2247 (1.0); 8.2117 (1.1); 7.4434 (0.8); 7.4253 (1.0); 7.4231 (0.8); 7.4054 (0.6); 7.4013 (0.6); 7.2615 (23.7); 7.0855 (0.7); 7.0744 (0.6); 7.0706 (0.9); 7.0667 (0.6); 7.0642 (0.6); 7.0612 (0.8); 7.0576 (0.9); 7.0538 (0.6); 6.8791 (0.8); 6.8758 (1.2); 6.8725 (0.8); 6.8710 (0.6); 5.3005 (4.2); 4.9202 (3.5); 3.3648 (1.9); 3.1125 (16.0); 2.2839 (1.0); 2.2267 (0.7); 2.2188 (0.6); 2.1363 (0.6); 2.0458 (1.2); 2.1594 (1.2); 1.2555 (0.9); −0.0002 (17.4); −0.00084 (0.5)

VIII-003: $^1$H-NMR(400.0 MHz, CDCl3):
δ = 7.2626 (14.0); 4.9002 (1.2); 2.9654 (16.0); 2.7749 (3.4); 1.3078 (0.6); 1.2900 (1.2); 1.2722 (0.6); 1.2547 (0.6); −0.0002 (7.7)

VIII-003: $^1$H-NMR(400.6 MHz, CDCl3):
δ = 7.2617 (27.2); 6.2329 (1.2); 5.3008 (12.5); 4.8545 (1.8); 4.2833 (0.7); 4.2655 (0.7); 2.9651 (16.0); 2.7752 (3.2); 1.3115 (1.0); 1.2937 (2.1); 1.2759 (1.0); −0.0002 (15.9); −0.00085 (0.5)

| Ex. No. | NMR Data (400 MHz) |
| --- | --- |
| III-007 | CDCl$_3$: 5.0 (s, 2H), 7.0 (m, 1H), 7.3-7.4 (m, 4H), 7.5 (m, 1H), 8.7 (m, 2H) |
| III-008 | CDCl$_3$: 5.0 (s, 2H), 7.0 (m, 1H), 7.4 (m, 2H), 7.5 (m, 1H), 8.6 (s, 2H) |
| III-009 | CDCl$_3$: 1.6 (d, 3H), 5.4 (q, 1H), 7.0 (m, 1H), 7.4 (m, 2H), 7.5 (m, 1H), 8.5 (s, 2H) |
| IX-001 | CDCl$_3$: 4.0 (dd, 2H), 4.8 (s, 2H), 5.2-5.4 (qd, 2H), 6.0 (m, 1H), 6.7 (br, 1H), 7.0 (m, 1H), 7.4-7.5 (m, 3H), 86 (s, 2H), 9.2 (s, 1H) |

-continued

| Ex. No. | NMR Data (400 MHz) |
|---|---|
| V-007 | CDCl$_3$: 1.4 (t, 3H), 4.4 (q, 2H), 5.0 (s, 1H), 7.0 (t, 1H), 7.3-7.4 (m, 3H), 7.5 (m, 1H), 8.5 (s, 1H) |
| VI-018 | DMSO-d$_6$: 1.5 (d, 3H), 5.0 (q, 1H), 7.4 (m, 2H), 7.5 (m, 2H), 8.7 (s, 2H), 9.3 (s, 1H) |
| VII-001 | DMSO-d$_6$: 3.7 (s, 3H), 5.0 (s, 2H), 7.4 (m, 3H), 7.5 (m, 1H), 7.55 (m, 1H), 8.0 (t, 1H), 8.4 (s, 1H) |
| VII-013 | CDCl3: 1.6 (d, 3H), 3.7 (s, 3H), 5.2 (q, 1H), 7.1 (m, 3H), 7.2 (m, 3H), 7.5 (m, 1H), 8.4 (s, 1H) |
| VII-020 | CDCl3: 1.6 (d, 3H), 3.8 (s, 3H), 5.3 (q, 1H), 7.1 (m, 3H), 7.2 (m, 3H), 7.7 (m, 1H), 8.3 (s, 1H) |
| VII-022 | CDCl3: 2.9 (s, 3H), 3.9 (s, 3H), 4.9 (s, 2H), 7.1 (m, 1H), 7.2 (m, 1H), 7.4 (m, 3H), 7.5 (m, 1H), 8.1 (s, 1H) |
| VII-025 | DMSO-d$_6$: 4.88 (s, 2H), 7.4 (m. 2H), 7.5 (m, 1H), 7.6 (m, 1H), 7.8 (m, 1H), 8.4 (s, 1H), 8.6 (s, 1H) |
| VII-031 | CDCl$_3$: 3.8 (s, 3H), 4.9 (s, 2H), 6.9 (m, 1H), 7.0 (m, 1H), 7.2 (m, 1H), 7.4 (m, 2H), 7.8 (m 1H), 8.1 (s, 1H) |
| VII-035 | CDCl$_3$: 3.8 (s, 3H), 4.9 (s, 2H), 7.0 (t, 1H), 7.4 (m, 2H), 7.4 (m, 2H), 8.4 (s, 1H), 8.5 (s, 1H) |
| VII-040 | CDCl$_3$: 3.7 (s, 3H), 4.9 (s, 2H), 6.9 (m, 1H), 7.1 (m, 1H), 7.3 (m, 1H), 7.5 (m, 2H), 7.6 (m, 1H), 8.1 (s, 1H) |
| VII-047 | DMSO-d$_6$: 3.4 (s, 3H), 4.8 (s, 2H), 7.4 (m, 3H), 7.5 (m, 3H), 8.4 (s, 1H) |
| VII-048 | CDCl$_3$: 1.4 (t, 3H), 2.5 (s, 3H), 4.2 (q, 2H), 4.9 (s, 2H), 7.1-7.5 (m, 6H), 8.4 (s, 1H) |
| VII-049 | CDCl$_3$: 3.7 (s, 3H), 3.8 (s, 3H), 4.9 (s, 2H), 6.6 (d, 1H), 7.0 (m, 1H), 7.1 (m, 1H), 7.4 (m, 1H), 7.5 (m, 1H), 8.0 (s, 1H) |
| VII-050 | CDCl$_3$: 3.6 (s, 3H), 3.8 (s, 3H), 4.9 (s, 2H), 6.7 ((m, 1H), 7.0 (m, 1H), 7.2 (m, 1H), 7.4.-7.5 (m, 2H), 7.7 (m, 1H), 8.1 (s, 1H) |
| VII-057-a | DMSO-d$_6$: 6.5 (d, J = 4 Hz, 1H), 6.9 (m, 1H), 7.0 (m, 3H), 7.5-7.6 (m, 2H), 8.0 (m, 2H), 8.4 (s, 1H) |
| VII-060 | CDCl$_3$: 1.6 (d, 3H), 3.8 (s, 3H), 5.2 (q, 1H), 5.4 (s, 2H), 6.9 (m, 1H), 7.0 (m, 1H), 7.2 (m, 1H), 7.4 (m, 2H), 7.7 (m, 1H), 8.1 (s, 1H) |
| VII-071-a | CDCl$_3$: 1.4 (t, 3H), 4.4 (q, 2H), 6.5 (d, J = 4 Hz, 1H), 6.9 (m, 1H), 7.0 (m, 1H), 7.2-7.5 (m, 4H), 7.7 (m, 1H), 8.1 (s, 1H) |
| VII-092 | DMSO-d$_6$: 1.5 (d, 3H), 5.0 (q, 1H), 7.2-7.3 (m, 3H), 7.5 (m; 2H), 8.0 (m, 1H), 8.1 (s, 1H) |
| VII-111 | CDCl$_3$: 2.6 (t, 2H), 3.6 (s, 3H), 4.1 (q, 2H), 4.5 (t, 2H), 5.0 (s, 2H), 6.9 (m 1H), 7.0 (m, 1H), 7.4 (m, 1H), 7.5 (m, 1H), 7.8 (m, 1H), 8.1 (s, 1H) |
| VII-113 | CDCl$_3$: 3.8 (s, 3H), 4.9 (s, 2H), 6.9 (m, 1H), 7.1 (m, 1H), 7.2 (m, 1H), 7.4.-7.5 (m, 2H), 7.7 (m, 1H), 8.1 (s, 1H) |
| VII-115 | DMSO-d$_6$: 4.8 (s, 2H), 7.4 (m, 3H), 7.5 (m, 2H), 7.9 (m, 1H), 8.2 (s, 1H) |
| VII-119 | CDCl$_3$: 0.8 (m, 4H), 1.4 (t, 3H), 4.2 (q, 2H), 4.9 (s, 1H), 6.9 (m, 1H), 7.0 (m, 1H), 7.2 (m, 1H), 7.4 (m, 2H), 7.6 (m, 1H), 8.1 (s, 1H) |
| VII-121 | CDCl$_3$: 1.4 (t, 3H), 1.6 (2, 3H), 4.3 (q, 2H), 5.2 (t, 1H), 6.9 (m 1H), 7.0 (m, 1H), 7.4 (m, 1H), 7.5 (m, 2H), 7.8 (m, 1H), 8.1 (s, 1H) |
| VII-130 | CDCl$_3$:1.4 (t, 3H), 1.6 (d, 3H), 4.3 (q, 2H), 5.2 (q, 1H), 7.0 (m, 1H), 7.2-7.5 (m, 5H), 8.4 (s, 1H), 8.5 (s, 1H) |
| VIII-011 | CDCl$_3$: 1.6 (m, 1H), 2.0 (m, 1H), 2.6 (m, 1H), 3.6 (m, 1H), 3.7-3.8 (m, 2H), 4.1 (t, 1H), 4.3 (t, 1H), 4.9 (s, 2H) 6.9 (m, 1H), 7.1 (m, 2H), 7.4-7.5 (m, 4H), 8.2 (s, 1H) |
| X-005 | CDCl$_3$: 3.0 (s, 3H), 4.9 (s, 2H), 6.9 (m, 1H), 7.1 (m, 1H), 7.2 (m, 1H), 7.5 (m, 1H), 7.7 (m, 1H), 8.1 (s, 1H), 8.6 (s, 1H) |
| X-006 | CDCl$_3$: 4.4 (q, 2H), 5.0 (s, 2H), 6.9 (m, 1H), 7.1 (m, 1H), 7.4 (m, 1H), 7.5 (m, 1H), 7.6 (m, 1H), 8.1 (s, 1H), 9.0 (s, 1H) |
| X-013 | CDCl$_3$: 2.2-2.3 (m, 2H), 3.0-3.1 (m, 1H), 3.5 (m, 1H), 3.6 (s, 3H), 3.9 (m, 2H), 5.0 (s, 2H), 6.9 (m, 1H), 7.0 (m, 1H), 7.2-7.5 (m, 4H), 7.7 (m, 1H), 8.1 (s, 1H) |
| X-015 | CDCl$_3$: 1.3 (t, 3H), 1.9 (m, 2H), 2.0 (m, 2H), 2.5 (m, 1H), 2.9-3.1 (m, 2H), 3.9 (m, 1H), 4.1 (q, 2H), 4.5 (m, 1H( ), 5.0 (s, 2H), 6.9 (m, 1H), 7.0 (m, 1H), 7.2 -7.5 (m, 4H), 7.7 (m, 1H), 8.1 (s, 1H) |
| X-016 | CDCl$_3$: 2.2 (m, 2H), 3.4 (m, 2H), 3.6 (s, 3H), 1.5 (m, 1H), 5.0 (m, 2H), 6.9 (m, 1H), 7.0 (m, 1H), 7.2 (m, 1H), 7.4-7.5 (m, 2H), 7.8 (m, 1H), 8.1 (s, 1H) |
| X-018 | CDCl$_3$: 1.9 (m, 1H), 2.0 (m, 1H), 2.5 (m, 1H), 3.0 (m, 1H), 3.5 (m, 1H), 3.6 (s, 3H), 3.7 (m, 1H), 5.0 (m, 2H), 5.4 (m, 2H); 6.9 (m, 1H), 7.0 (m, 1H), 7.2-7.5 (m, 4H), 7.7 (m, 1H), 8.1 (m, 1H) |
| X-022 | CDCl$_3$: 4.4 (q, 2H), 5.0 (s, 2H), 7.0-7.2 (m, 5H), 7.6 (m, 1H), 8.1 (s, 1H) |
| X-030 | CDCl$_3$: 3.1 (s, 3H), 3.7 (s, 3H), 4.2 (s, 2H), 5.1 (s, 2H), 6.9 (m, 1H), 7.1 (m, 1H), 7.4 (m, 2H), 7.5 (m, 2H), 7.7 (m, 1H), 8.1 (s, 1H) |
| X-031 | CDCl$_3$: 1.4 (t, 3H), 3.1 (s, 3H), 4.1 (s, 2H), 4.2 (q, 2H), 4.9 (s, 2H), 6.9 (m, 1H), 7.1 (m, 1H), 7.4 (m, 2H), 7.7 (m, 1H), 8.1 (s, 1H), 9.1 (s, 1H) |
| X-041 | CDCl$_3$: 1.4 (t, 3H), 3.1 (s, 3H), 4.1 (s, 2H), 4.2 (q, 2H), 4.9 (s, 2H), 7.0 (m, 1H), 7.5 (m, 3h), 8.4 (s, 1H), 8.5 (s, 1H), 9.2 (s, 1H) |

B. Formulation Examples a) A dusting product is obtained by mixing 10 parts by weight of a compound of the formula (I) and/or salts thereof and 90 parts by weight of talc as inert substance and comminuting the mixture in an impact mill.

b) A readily water-dispersible, wettable powder is obtained by mixing 25 parts by weight of a compound of the formula (I) and/or salts thereof, 64 parts by weight of kaolin-containing quartz as inert substance, 10 parts by weight of potassium lignosulfonate and 1 part by weight of sodium oleoylmethyltaurate as wetting agent and dispersant and grinding in a pinned-disc mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range e.g. about 255 to more than 277° C.) and grinding to a fineness of below 5 microns in an attrition ball mill.

d) An emulsifiable concentrate is obtained from 15 parts by weight of a compound of the formula (I) and/or salts thereof, 75 parts by weight of cyclohexanone as solvent and 10 parts by weight of oxethylated nonylphenol as emulsifier.

e) Water-dispersible granules are obtained by mixing
75 parts by weight of a compound of the formula (I) and/or salts thereof,
10 parts by weight of calcium lignosulfonate,
5 parts by weight of sodium laurylsulfate,
3 parts by weight of polyvinyl alcohol and
7 parts by weight of kaolin,
grinding the mixture in a pinned-disc mill, and granulating the powder in a fluidized bed by spray application of water as a granulating liquid.

f) Water-dispersible granules are also obtained by homogenizing and precomminuting, in a colloid mill,
25 parts by weight of a compound of the formula (I) and/or salts thereof,
5 parts by weight of sodium 2,2'-dinaphthylmethane-6,6'-disulfonate,
2 parts by weight of sodium oleoylmethyltaurate,
1 part by weight of polyvinyl alcohol,
17 parts by weight of calcium carbonate and
50 parts by weight of water,
then grinding the mixture in a bead mill and atomizing and drying the resulting suspension in a spray tower by means of a one-phase nozzle.

C. Biological Examples

In Tables 1 to 39 below, the following abbreviations are used:
Undesired Plants/Weeds:

| ALOMY: | *Alopecurus myosuroides* | SETVI: | *Setaria viridis* |
|---|---|---|---|
| ABUTH: | *Abutilon theophrasti* | HORMU: | *Hordeum murinum* |
| AMARE: | *Amaranthus retroflexus* | KCHSC: | *Bassia scoparia* |
| DIGSA. | *Digitaria sanguinalis* | ECHCG: | *Echinochloa crus-galli* |
| LOLRI: | *Lolium rigidum* | STEME: | *Stellaria media* |
| VERPE: | *Veronica persica* | MATIN: | *Tripleurospermum inodorum* |
| | | | *Matricaria inodora* |
| POAAN: | *Poa annua* | POLCO: | *Fallopia convolvulus* |
| | | | *Polygonum convolvulus* |
| VIOTR: | *Viola tricolor* | | |

1. Pre-Emergence Herbicidal Effect and Crop Plant Compatibility a) Seeds of mono- and dicotyledonous weed plants are placed in plastic pots in sandy loam soil (doubly sown with one species each of mono- or dicotyledonous weed plants per pot) and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate equivalent to 600 litres per hectare. After the treatment, the pots are placed in a greenhouse and kept under good growth conditions for the trial plants. After about 3 weeks, the effect of the preparations is scored visually in comparison with untreated controls as percentages. For example, 100% activity=the plants have died, 0% activity=like control plants.

1. Pre-Emergence Effectiveness

Tables 1 to 12 below show the effects of selected compounds of the general formula (I) according to Tables 1 and 2 on various harmful plants and at an application rate corresponding to 1280 g/ha, which were obtained by the experimental procedure mentioned above.

TABLE 1

Pre-emergence action against ALOMY

| Example number | Dosage [g/ha] | ALOMY |
|---|---|---|
| I-001 | 1280 | 90 |
| I-002 | 1280 | 90 |
| II-004 | 1280 | 100 |
| II-012 | 1280 | 90 |
| II-013 | 1280 | 90 |
| II-014 | 1280 | 100 |
| VI-001 | 1280 | 90 |
| VI-003 | 1280 | 90 |
| VI-005 | 1280 | 90 |
| VI-007 | 1280 | 90 |
| VI-011 | 1280 | 90 |
| VI-012 | 1280 | 90 |
| VI-013 | 1280 | 90 |
| VI-016 | 1280 | 90 |
| VI-017 | 1280 | 90 |
| VI-018 | 1280 | 100 |
| VII-003 | 1280 | 90 |
| VII-008 | 1280 | 100 |
| VII-010 | 1280 | 100 |
| VII-012 | 1280 | 100 |
| VII-012 | 1280 | 90 |
| VII-014 | 1280 | 90 |
| VII-015 | 1280 | 90 |
| VII-018 | 1280 | 100 |
| VII-019 | 1280 | 90 |
| VII-025 | 1280 | 100 |
| VII-026 | 1280 | 100 |
| VII-029 | 1280 | 90 |
| VII-031 | 1280 | 100 |
| VII-035 | 1280 | 100 |
| VII-036 | 1280 | 100 |

TABLE 1-continued

Pre-emergence action against ALOMY

| Example number | Dosage [g/ha] | ALOMY |
|---|---|---|
| VII-037 | 1280 | 100 |
| VII-040 | 1280 | 100 |
| VII-052 | 1280 | 100 |
| VII-056-a | 1280 | 90 |
| VII-057 | 1280 | 100 |
| VII-058 | 1280 | 90 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |

TABLE 1-continued

Pre-emergence action against ALOMY

| Example number | Dosage [g/ha] | ALOMY |
|---|---|---|
| VII-066 | 1280 | 100 |
| VII-067 | 1280 | 100 |
| VII-068 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-098 | 1280 | 100 |
| VII-099 | 1280 | 90 |
| VII-101 | 1280 | 100 |
| VII-102 | 1280 | 90 |
| VII-103 | 1280 | 100 |
| VII-104 | 1280 | 100 |
| VII-105 | 1280 | 100 |
| VII-106 | 1280 | 100 |
| VII-107 | 1280 | 90 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123-a | 1280 | 100 |
| VII-124 | 1280 | 100 |
| VII-132 | 1280 | 100 |
| VII-147 | 1280 | 100 |
| VII-149 | 1280 | 100 |
| VIII-006 | 1280 | 100 |
| VIII-010 | 1280 | 100 |
| VIII-011 | 1280 | 90 |
| VIII-012 | 1280 | 100 |
| X-001 | 1280 | 90 |
| X-002 | 1280 | 100 |
| X-003 | 1280 | 90 |
| X-004 | 1280 | 90 |
| X-005 | 1280 | 100 |
| X-007 | 1280 | 100 |
| X-009 | 1280 | 100 |
| X-019 | 1280 | 100 |
| X-020 | 1280 | 100 |
| X-021-a | 1280 | 100 |
| X-023 | 1280 | 90 |
| X-024 | 1280 | 100 |
| X-025 | 1280 | 100 |
| X-026 | 1280 | 100 |
| X-027 | 1280 | 100 |
| X-028 | 1280 | 90 |
| X-032 | 1280 | 100 |
| X-033 | 1280 | 90 |
| X-039 | 1280 | 90 |

TABLE 2

Pre-emergence action against DIGSA

| Example number | Dosage [g/ha] | DIGSA |
|---|---|---|
| I-001 | 1280 | 90 |
| I-002 | 1280 | 100 |
| I-003 | 1280 | 90 |
| I-004 | 1280 | 90 |
| II-003 | 1280 | 100 |
| II-004 | 1280 | 100 |
| II-012 | 1280 | 100 |
| II-013 | 1280 | 100 |
| II-014 | 1280 | 100 |
| II-017 | 1280 | 100 |
| IV-002 | 1280 | 90 |
| IX-001 | 1280 | 100 |
| VI-001 | 1280 | 90 |

TABLE 2-continued

Pre-emergence action against DIGSA

| Example number | Dosage [g/ha] | DIGSA |
|---|---|---|
| VI-003 | 1280 | 100 |
| VI-005 | 1280 | 100 |
| VI-006 | 1280 | 100 |
| VI-007 | 1280 | 100 |
| VI-008 | 1280 | 100 |
| VI-011 | 1280 | 100 |
| VI-012 | 1280 | 90 |
| VI-013 | 1280 | 100 |
| VI-016 | 1280 | 100 |
| VI-018 | 1280 | 100 |
| VII-003 | 1280 | 100 |
| VII-008 | 1280 | 100 |
| VII-010 | 1280 | 100 |
| VII-012 | 1280 | 100 |
| VII-012 | 1280 | 100 |
| VII-013 | 1280 | 90 |
| VII-014 | 1280 | 100 |
| VII-015 | 1280 | 90 |
| VII-017 | 1280 | 90 |
| VII-018 | 1280 | 100 |
| VII-019 | 1280 | 100 |
| VII-023 | 1280 | 90 |
| VII-025 | 1280 | 100 |
| VII-026 | 1280 | 100 |
| VII-027 | 1280 | 90 |
| VII-029 | 1280 | 100 |
| VII-030 | 1280 | 90 |
| VII-031 | 1280 | 100 |
| VII-032 | 1280 | 90 |
| VII-035 | 1280 | 90 |
| VII-036 | 1280 | 100 |
| VII-037 | 1280 | 100 |
| VII-040 | 1280 | 100 |
| VII-052 | 1280 | 100 |
| VII-056 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 90 |
| VII-101 | 1280 | 100 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 100 |
| VII-123-a | 1280 | 100 |
| VII-124 | 1280 | 100 |

TABLE 2-continued

Pre-emergence action against DIGSA

| Example number | Dosage [g/ha] | DIGSA |
|---|---|---|
| VII-125 | 1280 | 100 |
| VII-132 | 1280 | 100 |
| VII-147 | 1280 | 100 |
| VII-148 | 1280 | 100 |
| VII-149 | 1280 | 100 |
| VIII-001 | 1280 | 90 |
| VIII-006 | 1280 | 100 |
| VIII-007 | 1280 | 90 |
| VIII-008 | 1280 | 100 |
| VIII-009 | 1280 | 100 |
| VIII-010 | 1280 | 100 |
| VIII-011 | 1280 | 90 |
| VIII-012 | 1280 | 100 |
| X-001 | 1280 | 100 |
| X-002 | 1280 | 100 |
| X-003 | 1280 | 100 |
| X-004 | 1280 | 90 |
| X-005 | 1280 | 100 |
| X-006 | 1280 | 100 |
| X-007 | 1280 | 100 |
| X-009 | 1280 | 90 |
| X-011 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 100 |
| X-032 | 1280 | 100 |
| X-033 | 1280 | 90 |
| X-038 | 1280 | 90 |
| X-039 | 1280 | 90 |
| X-040 | 1280 | 90 |

TABLE 3

Pre-emergence action against ECHCG

| Example number | Dosage [g/ha] | ECHCG |
|---|---|---|
| I-003 | 1280 | 90 |
| I-004 | 1280 | 90 |
| II-003 | 1280 | 100 |
| II-012 | 1280 | 90 |
| II-013 | 1280 | 90 |
| II-014 | 1280 | 100 |
| IV-001 | 1280 | 90 |
| IV-002 | 1280 | 100 |
| IX-001 | 1280 | 90 |
| VI-001 | 1280 | 100 |
| VI-002 | 1280 | 100 |
| VI-003 | 1280 | 100 |
| VI-004 | 1280 | 100 |
| VI-005 | 1280 | 90 |
| VI-006 | 1280 | 100 |
| VI-007 | 1280 | 100 |
| VI-011 | 1280 | 100 |
| VI-012 | 1280 | 90 |
| VI-013 | 1280 | 100 |
| VI-016 | 1280 | 100 |
| VI-018 | 1280 | 100 |
| VII-002 | 1280 | 100 |
| VII-003 | 1280 | 100 |
| VII-008 | 1280 | 100 |
| VII-009 | 1280 | 90 |
| VII-010 | 1280 | 100 |
| VII-012 | 1280 | 100 |
| VII-012 | 1280 | 100 |
| VII-014 | 1280 | 90 |
| VII-015 | 1280 | 100 |

TABLE 3-continued

Pre-emergence action against ECHCG

| Example number | Dosage [g/ha] | ECHCG |
|---|---|---|
| VII-016 | 1280 | 100 |
| VII-018 | 1280 | 100 |
| VII-019 | 1280 | 100 |
| VII-023 | 1280 | 100 |
| VII-025 | 1280 | 100 |
| VII-026 | 1280 | 90 |
| VII-027 | 1280 | 90 |
| VII-028 | 1280 | 100 |
| VII-029 | 1280 | 100 |
| VII-030 | 1280 | 90 |
| VII-031 | 1280 | 90 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-101 | 1280 | 90 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 90 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123-a | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 90 |
| VIII-001 | 1280 | 100 |
| VIII-002 | 1280 | 100 |
| VIII-003 | 1280 | 100 |
| VIII-004 | 1280 | 100 |
| VIII-006 | 1280 | 100 |
| VIII-007 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 100 |
| X-002 | 1280 | 90 |
| X-003 | 1280 | 100 |
| X-004 | 1280 | 100 |
| X-005 | 1280 | 100 |
| X-006 | 1280 | 100 |
| X-007 | 1280 | 100 |

TABLE 3-continued

Pre-emergence action against ECHCG

| Example number | Dosage [g/ha] | ECHCG |
|---|---|---|
| X-009 | 1280 | 100 |
| X-011 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 100 |
| X-032 | 1280 | 100 |
| X-039 | 1280 | 90 |
| X-040 | 1280 | 90 |

TABLE 4

Pre-emergence action against LOLRI

| Example number | Dosage [g/ha] | LOLRI |
|---|---|---|
| I-001 | 1280 | 90 |
| I-002 | 1280 | 90 |
| I-003 | 1280 | 90 |
| I-004 | 1280 | 90 |
| II-003 | 1280 | 100 |
| II-004 | 1280 | 90 |
| II-012 | 1280 | 100 |
| II-013 | 1280 | 100 |
| II-014 | 1280 | 100 |
| IV-001 | 1280 | 100 |
| IX-001 | 1280 | 100 |
| VI-001 | 1280 | 100 |
| VI-002 | 1280 | 100 |
| VI-003 | 1280 | 90 |
| VI-004 | 1280 | 100 |
| VI-005 | 1280 | 100 |
| VI-006 | 1280 | 100 |
| VI-007 | 1280 | 100 |
| VI-008 | 1280 | 100 |
| VI-011 | 1280 | 100 |
| VI-012 | 1280 | 100 |
| VI-013 | 1280 | 100 |
| VI-016 | 1280 | 100 |
| VI-018 | 1280 | 100 |
| VII-002 | 1280 | 100 |
| VII-003 | 1280 | 100 |
| VII-008 | 1280 | 100 |
| VII-009 | 1280 | 100 |
| VII-010 | 1280 | 100 |
| VII-012 | 1280 | 100 |
| VII-012 | 1280 | 100 |
| VII-014 | 1280 | 100 |
| VII-015 | 1280 | 100 |
| VII-016 | 1280 | 100 |
| VII-018 | 1280 | 100 |
| VII-019 | 1280 | 100 |
| VII-023 | 1280 | 100 |
| VII-025 | 1280 | 100 |
| VII-026 | 1280 | 90 |
| VII-027 | 1280 | 100 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 90 |
| VII-056-a | 1280 | 90 |
| VII-057 | 1280 | 100 |

TABLE 4-continued

Pre-emergence action against LOLRI

| Example number | Dosage [g/ha] | LOLRI |
|---|---|---|
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 90 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 90 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 90 |
| VII-123-a | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 90 |
| VII-149 | 1280 | 100 |
| VIII-001 | 1280 | 100 |
| VIII-002 | 1280 | 100 |
| VIII-003 | 1280 | 90 |
| VIII-004 | 1280 | 100 |
| VIII-006 | 1280 | 100 |
| VIII-007 | 1280 | 100 |
| VIII-008 | 1280 | 100 |
| VIII-009 | 1280 | 90 |
| VIII-010 | 1280 | 100 |
| VIII-011 | 1280 | 100 |
| VIII-012 | 1280 | 100 |
| X-001 | 1280 | 100 |
| X-002 | 1280 | 100 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-028 | 1280 | 100 |
| X-032 | 1280 | 100 |
| X-038 | 1280 | 90 |
| X-039 | 1280 | 90 |
| X-040 | 1280 | 90 |

TABLE 5

Pre-emergence action against POAAN

| Example number | Dosage [g/ha] | POAAN |
| --- | --- | --- |
| I-001 | 1280 | 100 |
| I-002 | 1280 | 100 |
| I-003 | 1280 | 100 |
| I-004 | 1280 | 100 |
| II-003 | 1280 | 100 |
| II-004 | 1280 | 100 |
| II-012 | 1280 | 100 |
| II-013 | 1280 | 100 |
| II-014 | 1280 | 100 |
| II-017 | 1280 | 100 |
| IV-001 | 1280 | 100 |
| IV-002 | 1280 | 100 |
| IV-003 | 1280 | 90 |
| IX-001 | 1280 | 100 |
| VI-001 | 1280 | 100 |
| VI-002 | 1280 | 100 |
| VI-003 | 1280 | 100 |
| VI-004 | 1280 | 100 |
| VI-005 | 1280 | 100 |
| VI-006 | 1280 | 100 |
| VI-007 | 1280 | 100 |
| VI-008 | 1280 | 100 |
| VI-011 | 1280 | 100 |
| VI-012 | 1280 | 100 |
| VI-013 | 1280 | 100 |
| VI-016 | 1280 | 100 |
| VI-017 | 1280 | 90 |
| VI-018 | 1280 | 100 |
| VII-002 | 1280 | 100 |
| VII-003 | 1280 | 100 |
| VII-008 | 1280 | 100 |
| VII-009 | 1280 | 100 |
| VII-010 | 1280 | 100 |
| VII-012 | 1280 | 100 |
| VII-012 | 1280 | 100 |
| VII-013 | 1280 | 100 |
| VII-014 | 1280 | 100 |
| VII-015 | 1280 | 100 |
| VII-016 | 1280 | 100 |
| VII-017 | 1280 | 90 |
| VII-018 | 1280 | 100 |
| VII-019 | 1280 | 100 |
| VII-021 | 1280 | 90 |
| VII-023 | 1280 | 100 |
| VII-025 | 1280 | 100 |
| VII-026 | 1280 | 100 |
| VII-027 | 1280 | 90 |
| VII-028 | 1280 | 100 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 90 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 100 |
| VII-123-a | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 100 |
| VII-149 | 1280 | 100 |
| VIII-001 | 1280 | 100 |
| VIII-002 | 1280 | 100 |
| VIII-003 | 1280 | 100 |
| VIII-004 | 1280 | 100 |
| VIII-006 | 1280 | 100 |
| VIII-007 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 100 |
| X-002 | 1280 | 100 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-011 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 100 |
| X-029 | 1280 | 100 |
| X-032 | 1280 | 100 |
| X-033 | 1280 | 100 |
| X-038 | 1280 | 100 |
| X-039 | 1280 | 100 |
| X-040 | 1280 | 90 |

TABLE 6

Pre-emergence action against SETVI

| Example number | Dosage [g/ha] | SETVI |
| --- | --- | --- |
| I-001 | 1280 | 90 |
| I-002 | 1280 | 100 |
| I-003 | 1280 | 90 |

TABLE 6-continued

Pre-emergence action against SETVI

| Example number | Dosage [g/ha] | SETVI |
|---|---|---|
| I-004 | 1280 | 100 |
| II-003 | 1280 | 100 |
| II-012 | 1280 | 100 |
| II-013 | 1280 | 100 |
| II-014 | 1280 | 90 |
| II-017 | 1280 | 100 |
| IV-001 | 1280 | 100 |
| IV-002 | 1280 | 100 |
| IV-003 | 1280 | 100 |
| IX-001 | 1280 | 100 |
| VI-001 | 1280 | 100 |
| VI-002 | 1280 | 100 |
| VI-003 | 1280 | 100 |
| VI-004 | 1280 | 100 |
| VI-005 | 1280 | 100 |
| VI-006 | 1280 | 100 |
| VI-007 | 1280 | 100 |
| VI-008 | 1280 | 100 |
| VI-011 | 1280 | 100 |
| VI-012 | 1280 | 100 |
| VI-013 | 1280 | 100 |
| VI-016 | 1280 | 100 |
| VI-018 | 1280 | 100 |
| VII-002 | 1280 | 100 |
| VII-003 | 1280 | 100 |
| VII-008 | 1280 | 100 |
| VII-009 | 1280 | 100 |
| VII-010 | 1280 | 100 |
| VII-012 | 1280 | 100 |
| VII-012 | 1280 | 100 |
| VII-014 | 1280 | 100 |
| VII-015 | 1280 | 100 |
| VII-016 | 1280 | 100 |
| VII-018 | 1280 | 100 |
| VII-019 | 1280 | 100 |
| VII-023 | 1280 | 100 |
| VII-025 | 1280 | 100 |
| VII-026 | 1280 | 100 |
| VII-027 | 1280 | 90 |
| VII-028 | 1280 | 100 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 90 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 90 |
| VII-101 | 1280 | 100 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123-a | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 90 |
| VII-149 | 1280 | 90 |
| VIII-001 | 1280 | 100 |
| VIII-002 | 1280 | 100 |
| VIII-003 | 1280 | 100 |
| VIII-004 | 1280 | 100 |
| VIII-006 | 1280 | 100 |
| VIII-007 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 100 |
| X-002 | 1280 | 100 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-011 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 100 |
| X-032 | 1280 | 100 |
| X-033 | 1280 | 90 |
| X-038 | 1280 | 100 |
| X-039 | 1280 | 90 |
| X-040 | 1280 | 90 |

TABLE 7

Pre-emergence action against ABUTH

| Example number | Dosage [g/ha] | ABUTH |
|---|---|---|
| IX-001 | 1280 | 100 |
| VI-001 | 1280 | 90 |
| VI-003 | 1280 | 90 |
| VI-004 | 1280 | 90 |
| VI-007 | 1280 | 90 |
| VI-011 | 1280 | 90 |
| VI-012 | 1280 | 90 |
| VI-013 | 1280 | 90 |
| VI-018 | 1280 | 90 |
| VII-008 | 1280 | 90 |
| VII-010 | 1280 | 100 |
| VII-015 | 1280 | 90 |
| VII-016 | 1280 | 100 |

TABLE 7-continued

Pre-emergence action against ABUTH

| Example number | Dosage [g/ha] | ABUTH |
|---|---|---|
| VII-018 | 1280 | 90 |
| VII-019 | 1280 | 90 |
| VII-025 | 1280 | 90 |
| VII-026 | 1280 | 90 |
| VII-029 | 1280 | 90 |
| VII-030 | 1280 | 90 |
| VII-031 | 1280 | 90 |
| VII-035 | 1280 | 90 |
| VII-036 | 1280 | 90 |
| VII-052 | 1280 | 100 |
| VII-057 | 1280 | 90 |
| VII-061 | 1280 | 90 |
| VII-062 | 1280 | 90 |
| VII-064 | 1280 | 90 |
| VII-064 | 1280 | 90 |
| VII-091 | 1280 | 90 |
| VII-099 | 1280 | 90 |
| VII-103 | 1280 | 90 |
| VII-104 | 1280 | 90 |
| VII-106 | 1280 | 90 |
| VII-108 | 1280 | 90 |
| VII-109 | 1280 | 90 |
| VII-110 | 1280 | 90 |
| VII-111 | 1280 | 90 |
| VII-117 | 1280 | 90 |
| VII-123-a | 1280 | 90 |
| VII-124 | 1280 | 90 |
| VII-132 | 1280 | 90 |
| VII-147 | 1280 | 90 |
| VII-149 | 1280 | 90 |
| VIII-006 | 1280 | 90 |
| X-003 | 1280 | 90 |
| X-007 | 1280 | 90 |
| X-027 | 1280 | 90 |
| X-039 | 1280 | 90 |

TABLE 8

Pre-emergence action against AMARE

| Example number | Dosage [g/ha] | AMARE |
|---|---|---|
| I-001 | 1280 | 100 |
| I-002 | 1280 | 100 |
| I-003 | 1280 | 90 |
| I-004 | 1280 | 100 |
| II-003 | 1280 | 100 |
| II-005 | 1280 | 90 |
| II-012 | 1280 | 90 |
| II-013 | 1280 | 90 |
| II-014 | 1280 | 90 |
| II-017 | 1280 | 100 |
| IV-001 | 1280 | 90 |
| IV-002 | 1280 | 100 |
| IV-003 | 1280 | 90 |
| IX-001 | 1280 | 100 |
| VI-001 | 1280 | 100 |
| VI-002 | 1280 | 100 |
| VI-003 | 1280 | 100 |
| VI-004 | 1280 | 100 |
| VI-005 | 1280 | 100 |
| VI-006 | 1280 | 90 |
| VI-007 | 1280 | 100 |
| VI-008 | 1280 | 100 |
| VI-011 | 1280 | 100 |
| VI-012 | 1280 | 100 |
| VI-013 | 1280 | 100 |
| VI-016 | 1280 | 100 |
| VI-017 | 1280 | 100 |
| VI-018 | 1280 | 100 |
| VII-002 | 1280 | 100 |
| VII-003 | 1280 | 100 |
| VII-008 | 1280 | 100 |

TABLE 8-continued

Pre-emergence action against AMARE

| Example number | Dosage [g/ha] | AMARE |
|---|---|---|
| VII-009 | 1280 | 100 |
| VII-010 | 1280 | 100 |
| VII-012 | 1280 | 100 |
| VII-012 | 1280 | 100 |
| VII-014 | 1280 | 100 |
| VII-015 | 1280 | 100 |
| VII-016 | 1280 | 100 |
| VII-017 | 1280 | 90 |
| VII-018 | 1280 | 100 |
| VII-019 | 1280 | 100 |
| VII-021 | 1280 | 90 |
| VII-023 | 1280 | 100 |
| VII-025 | 1280 | 100 |
| VII-026 | 1280 | 100 |
| VII-027 | 1280 | 90 |
| VII-028 | 1280 | 90 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 90 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 90 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 90 |
| VII-123-a | 1280 | 100 |
| VII-124 | 1280 | 100 |
| VII-125 | 1280 | 90 |
| VII-132 | 1280 | 100 |
| VII-147 | 1280 | 100 |
| VII-148 | 1280 | 100 |
| VII-149 | 1280 | 100 |
| VIII-001 | 1280 | 90 |
| VIII-002 | 1280 | 100 |
| VIII-003 | 1280 | 100 |
| VIII-004 | 1280 | 100 |

TABLE 8-continued

Pre-emergence action against AMARE

| Example number | Dosage [g/ha] | AMARE |
|---|---|---|
| VIII-006 | 1280 | 100 |
| VIII-007 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 100 |
| X-002 | 1280 | 100 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-011 | 1280 | 100 |
| X-019 | 1280 | 100 |
| X-020 | 1280 | 90 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 100 |
| X-029 | 1280 | 100 |
| X-032 | 1280 | 100 |
| X-033 | 1280 | 90 |
| X-038 | 1280 | 100 |
| X-039 | 1280 | 100 |
| X-040 | 1280 | 90 |

TABLE 9

Pre-emergence action against KCHSC

| Example number | Dosage [g/ha] | KCHSC |
|---|---|---|
| I-002 | 1280 | 100 |
| II-017 | 1280 | 100 |
| IV-002 | 1280 | 90 |
| IX-001 | 1280 | 100 |
| VI-005 | 1280 | 90 |
| VI-006 | 1280 | 100 |
| VI-008 | 1280 | 90 |
| VI-011 | 1280 | 100 |
| VI-012 | 1280 | 100 |
| VI-013 | 1280 | 100 |
| VI-016 | 1280 | 100 |
| VI-018 | 1280 | 100 |
| VII-008 | 1280 | 90 |
| VII-014 | 1280 | 100 |
| VII-018 | 1280 | 90 |
| VII-019 | 1280 | 100 |
| VII-025 | 1280 | 90 |
| VII-026 | 1280 | 100 |
| VII-029 | 1280 | 90 |
| VII-030 | 1280 | 90 |
| VII-035 | 1280 | 90 |
| VII-057 | 1280 | 100 |
| VII-058 | 1280 | 90 |
| VII-059 | 1280 | 100 |
| VII-062 | 1280 | 100 |
| VII-064 | 1280 | 100 |
| VII-064 | 1280 | 90 |
| VII-065 | 1280 | 100 |
| VII-095 | 1280 | 100 |
| VII-096 | 1280 | 100 |
| VII-099 | 1280 | 100 |
| VII-100 | 1280 | 100 |
| VII-101 | 1280 | 100 |
| VII-104 | 1280 | 90 |
| VII-108 | 1280 | 90 |

TABLE 9-continued

Pre-emergence action against KCHSC

| Example number | Dosage [g/ha] | KCHSC |
|---|---|---|
| VII-110 | 1280 | 90 |
| VII-118 | 1280 | 100 |
| VII-123-a | 1280 | 100 |
| VII-124 | 1280 | 90 |
| VII-125 | 1280 | 100 |
| VII-132 | 1280 | 100 |
| VII-147 | 1280 | 100 |
| VIII-006 | 1280 | 100 |
| X-003 | 1280 | 90 |
| X-005 | 1280 | 90 |
| X-009 | 1280 | 90 |
| X-020 | 1280 | 90 |
| X-021-a | 1280 | 90 |
| X-024 | 1280 | 100 |
| X-025 | 1280 | 100 |
| X-028 | 1280 | 100 |
| X-039 | 1280 | 100 |
| X-040 | 1280 | 90 |

TABLE 10

Pre-emergence action against MATIN

| Example number | Dosage [g/ha] | MATIN |
|---|---|---|
| I-001 | 1280 | 90 |
| I-002 | 1280 | 100 |
| I-003 | 1280 | 90 |
| I-004 | 1280 | 90 |
| II-003 | 1280 | 100 |
| II-012 | 1280 | 90 |
| II-013 | 1280 | 90 |
| II-014 | 1280 | 100 |
| II-017 | 1280 | 90 |
| IV-001 | 1280 | 90 |
| IV-002 | 1280 | 100 |
| IV-003 | 1280 | 90 |
| IX-001 | 1280 | 100 |
| VI-001 | 1280 | 100 |
| VI-002 | 1280 | 90 |
| VI-003 | 1280 | 100 |
| VI-004 | 1280 | 100 |
| VI-005 | 1280 | 100 |
| VI-006 | 1280 | 100 |
| VI-007 | 1280 | 100 |
| VI-008 | 1280 | 90 |
| VI-011 | 1280 | 90 |
| VI-012 | 1280 | 90 |
| VI-013 | 1280 | 90 |
| VI-016 | 1280 | 100 |
| VI-017 | 1280 | 100 |
| VI-018 | 1280 | 100 |
| VII-002 | 1280 | 90 |
| VII-003 | 1280 | 100 |
| VII-008 | 1280 | 100 |
| VII-009 | 1280 | 100 |
| VII-010 | 1280 | 90 |
| VII-012 | 1280 | 100 |
| VII-012 | 1280 | 100 |
| VII-014 | 1280 | 90 |
| VII-015 | 1280 | 100 |
| VII-016 | 1280 | 90 |
| VII-018 | 1280 | 90 |
| VII-019 | 1280 | 90 |
| VII-023 | 1280 | 90 |
| VII-025 | 1280 | 100 |
| VII-026 | 1280 | 90 |
| VII-027 | 1280 | 90 |
| VII-028 | 1280 | 100 |
| VII-029 | 1280 | 100 |
| VII-030 | 1280 | 90 |
| VII-031 | 1280 | 100 |
| VII-032 | 1280 | 90 |

TABLE 10-continued

Pre-emergence action against MATIN

| Example number | Dosage [g/ha] | MATIN |
|---|---|---|
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 90 |
| VII-056-a | 1280 | 100 |
| VII-057 | 1280 | 100 |
| VII-058 | 1280 | 100 |
| VII-059 | 1280 | 90 |
| VII-061 | 1280 | 100 |
| VII-062 | 1280 | 100 |
| VII-063 | 1280 | 90 |
| VII-064 | 1280 | 100 |
| VII-064 | 1280 | 100 |
| VII-065 | 1280 | 90 |
| VII-066 | 1280 | 90 |
| VII-067 | 1280 | 100 |
| VII-068 | 1280 | 100 |
| VII-069 | 1280 | 90 |
| VII-088 | 1280 | 100 |
| VII-089 | 1280 | 100 |
| VII-090 | 1280 | 100 |
| VII-091 | 1280 | 100 |
| VII-095 | 1280 | 90 |
| VII-096 | 1280 | 100 |
| VII-097 | 1280 | 90 |
| VII-098 | 1280 | 90 |
| VII-099 | 1280 | 100 |
| VII-100 | 1280 | 100 |
| VII-101 | 1280 | 100 |
| VII-102 | 1280 | 90 |
| VII-103 | 1280 | 100 |
| VII-104 | 1280 | 100 |
| VII-105 | 1280 | 90 |
| VII-106 | 1280 | 90 |
| VII-107 | 1280 | 90 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 100 |
| VII-123-a | 1280 | 100 |
| VII-124 | 1280 | 100 |
| VII-125 | 1280 | 90 |
| VII-132 | 1280 | 100 |
| VII-147 | 1280 | 100 |
| VII-148 | 1280 | 90 |
| VII-149 | 1280 | 90 |
| VIII-001 | 1280 | 90 |
| VIII-002 | 1280 | 100 |
| VIII-003 | 1280 | 100 |
| VIII-004 | 1280 | 100 |
| VIII-006 | 1280 | 100 |
| VIII-007 | 1280 | 90 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 90 |
| X-002 | 1280 | 90 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-011 | 1280 | 90 |
| X-019 | 1280 | 100 |
| X-020 | 1280 | 90 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 90 |
| X-028 | 1280 | 100 |
| X-032 | 1280 | 100 |
| X-033 | 1280 | 90 |
| X-038 | 1280 | 90 |
| X-039 | 1280 | 100 |
| X-040 | 1280 | 90 |

TABLE 11

Pre-emergence action against STEME

| Example number | Dosage [g/ha] | STEME |
|---|---|---|
| I-001 | 1280 | 100 |
| I-002 | 1280 | 100 |
| I-003 | 1280 | 100 |
| I-004 | 1280 | 100 |
| II-003 | 1280 | 90 |
| II-012 | 1280 | 100 |
| II-013 | 1280 | 100 |
| II-014 | 1280 | 90 |
| II-017 | 1280 | 90 |
| IV-001 | 1280 | 90 |
| IV-002 | 1280 | 100 |
| IV-003 | 1280 | 100 |
| IX-001 | 1280 | 100 |
| VI-001 | 1280 | 100 |
| VI-002 | 1280 | 100 |
| VI-003 | 1280 | 90 |
| VI-004 | 1280 | 100 |
| VI-005 | 1280 | 100 |
| VI-006 | 1280 | 90 |
| VI-007 | 1280 | 100 |
| VI-008 | 1280 | 100 |
| VI-011 | 1280 | 100 |
| VI-012 | 1280 | 100 |
| VI-013 | 1280 | 100 |
| VI-016 | 1280 | 100 |
| VI-017 | 1280 | 90 |
| VI-018 | 1280 | 100 |
| VII-002 | 1280 | 100 |
| VII-003 | 1280 | 100 |
| VII-008 | 1280 | 100 |
| VII-009 | 1280 | 100 |
| VII-010 | 1280 | 100 |
| VII-012 | 1280 | 90 |
| VII-012 | 1280 | 100 |
| VII-014 | 1280 | 100 |
| VII-015 | 1280 | 100 |
| VII-016 | 1280 | 100 |
| VII-018 | 1280 | 100 |
| VII-019 | 1280 | 100 |
| VII-023 | 1280 | 100 |
| VII-025 | 1280 | 100 |
| VII-026 | 1280 | 90 |
| VII-027 | 1280 | 100 |
| VII-028 | 1280 | 100 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 90 |
| VII-056-a | 1280 | 100 |
| VII-057 | 1280 | 100 |

TABLE 11-continued

Pre-emergence action against STEME

| Example number | Dosage [g/ha] | STEME |
|---|---|---|
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |
| VII-089 | 1280 | 90 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 90 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 90 |
| VII-118 | 1280 | 100 |
| VII-119 | 1280 | 100 |
| VII-123 | 1280 | 90 |
| VII-123-a | 1280 | 100 |
| VII-124 | 1280 | 100 |
| VII-125 | 1280 | 90 |
| VII-127 | 1280 | 90 |
| VII-132 | 1280 | 100 |
| VII-147 | 1280 | 100 |
| VII-148 | 1280 | 90 |
| VII-149 | 1280 | 100 |
| VIII-001 | 1280 | 90 |
| VIII-002 | 1280 | 90 |
| VIII-003 | 1280 | 100 |
| VIII-004 | 1280 | 100 |
| VIII-006 | 1280 | 100 |
| VIII-007 | 1280 | 90 |
| VIII-008 | 1280 | 100 |
| VIII-009 | 1280 | 100 |
| VIII-010 | 1280 | 100 |
| VIII-011 | 1280 | 100 |
| X-001 | 1280 | 100 |
| X-002 | 1280 | 100 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-019 | 1280 | 90 |
| X-020 | 1280 | 90 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 90 |
| X-028 | 1280 | 100 |
| X-029 | 1280 | 90 |
| X-032 | 1280 | 100 |
| X-033 | 1280 | 90 |
| X-038 | 1280 | 90 |
| X-039 | 1280 | 90 |
| X-040 | 1280 | 90 |

TABLE 12

Pre-emergence action against VERPE

| Example number | Dosage [g/ha] | VERPE |
|---|---|---|
| I-001 | 1280 | 100 |
| I-002 | 1280 | 100 |
| I-003 | 1280 | 90 |
| I-004 | 1280 | 90 |
| II-012 | 1280 | 90 |
| II-013 | 1280 | 100 |
| II-014 | 1280 | 100 |
| IV-003 | 1280 | 100 |
| IX-001 | 1280 | 100 |
| VI-001 | 1280 | 100 |
| VI-002 | 1280 | 90 |
| VI-003 | 1280 | 100 |
| VI-004 | 1280 | 90 |
| VI-005 | 1280 | 100 |
| VI-006 | 1280 | 100 |
| VI-007 | 1280 | 90 |
| VI-011 | 1280 | 100 |
| VI-012 | 1280 | 100 |
| VI-013 | 1280 | 100 |
| VI-016 | 1280 | 100 |
| VI-017 | 1280 | 100 |
| VI-018 | 1280 | 100 |
| VII-003 | 1280 | 90 |
| VII-008 | 1280 | 100 |
| VII-009 | 1280 | 90 |
| VII-010 | 1280 | 100 |
| VII-012 | 1280 | 100 |
| VII-012 | 1280 | 100 |
| VII-013 | 1280 | 100 |
| VII-014 | 1280 | 90 |
| VII-015 | 1280 | 100 |
| VII-016 | 1280 | 90 |
| VII-017 | 1280 | 100 |
| VII-018 | 1280 | 100 |
| VII-019 | 1280 | 100 |
| VII-022 | 1280 | 90 |
| VII-023 | 1280 | 100 |
| VII-025 | 1280 | 100 |
| VII-026 | 1280 | 100 |
| VII-028 | 1280 | 90 |
| VII-029 | 1280 | 100 |
| VII-030 | 1280 | 90 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |

TABLE 12-continued

Pre-emergence action against VERPE

| Example number | Dosage [g/ha] | VERPE |
|---|---|---|
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 90 |
| VII-123-a | 1280 | 100 |
| VII-124 | 1280 | 100 |
| VII-125 | 1280 | 90 |
| VII-132 | 1280 | 100 |
| VII-147 | 1280 | 100 |
| VII-148 | 1280 | 90 |
| VII-149 | 1280 | 100 |
| VIII-001 | 1280 | 100 |
| VIII-002 | 1280 | 90 |
| VIII-003 | 1280 | 90 |
| VIII-004 | 1280 | 90 |
| VIII-006 | 1280 | 100 |
| VIII-007 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 100 |
| X-002 | 1280 | 100 |
| X-003 | 1280 | 100 |
| X-004 | 1280 | 90 |
| X-005 | 1280 | 100 |
| X-006 | 1280 | 100 |
| X-007 | 1280 | 100 |
| X-009 | 1280 | 100 |
| X-011 | 1280 | 100 |
| X-019 | 1280 | 90 |
| X-020 | 1280 | 90 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 90 |
| X-032 | 1280 | 100 |
| X-033 | 1280 | 90 |
| X-038 | 1280 | 90 |
| X-039 | 1280 | 100 |
| X-040 | 1280 | 90 |

As shown by the results, compounds of the general formula (I) of the invention, in post-emergence treatment, have very good herbicidal efficacy (90% to 100% herbicidal action) against harmful plants such as *Abutilon theophrasti, Digitaria sanguinalis, Echinochloa crus-galli, Matricaria inodora, Poa annua*, at an application rate of 1.28 kg of active substance per hectare. The compounds of the invention are therefore suitable for control of unwanted plant growth by the pre-emergence method.

b) Seeds of monocotyledonous and dicotyledonous weed plants and crop plants are placed in plastic or organic planting pots and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate of 600 l/ha (converted). After the treatment, the pots are placed in a greenhouse and kept under good growth conditions for the trial plants. After about 3 weeks, the effect of the preparations is scored visually in comparison with untreated controls as percentages. For example, 100% activity=the plants have died, 0% activity=like control plants.

Tables 13 to 26 below show the effects of selected compounds of the general formula (I) on various harmful plants and at an application rate corresponding to 320 g/ha, which were obtained by the experimental procedure mentioned above.

TABLE 13

Pre-emergence action at 320 g/ha against ALOMY in %

| Example number | Dosage [g/ha] | ALOMY |
|---|---|---|
| VI-004 | 320 | 100 |
| VI-007 | 320 | 80 |
| VI-011 | 320 | 100 |
| VI-012 | 320 | 90 |
| VI-013 | 320 | 90 |
| VI-016 | 320 | 100 |
| VI-018 | 320 | 100 |
| VII-001 | 320 | 100 |
| VII-002 | 320 | 90 |
| VII-003 | 320 | 100 |
| VII-004 | 320 | 90 |
| VII-005 | 320 | 100 |
| VII-008 | 320 | 100 |
| VII-010 | 320 | 100 |
| VII-012 | 320 | 100 |
| VII-012 | 320 | 90 |
| VII-014 | 320 | 100 |
| VII-015 | 320 | 100 |
| VII-016 | 320 | 100 |
| VII-018 | 320 | 100 |
| VII-019 | 320 | 100 |
| VII-023 | 320 | 100 |
| VII-025 | 320 | 100 |
| VII-026 | 320 | 100 |
| VII-028 | 320 | 100 |
| VII-029 | 320 | 90 |
| VII-031 | 320 | 100 |
| VII-032 | 320 | 100 |
| VII-034 | 320 | 90 |
| VII-035 | 320 | 100 |
| VII-036 | 320 | 100 |
| VII-037 | 320 | 100 |
| VII-040 | 320 | 100 |
| VII-041 | 320 | 90 |
| VII-042 | 320 | 90 |
| VII-044 | 320 | 90 |
| VII-052 | 320 | 100 |
| VII-056-a | 320 | 100 |
| VII-057 | 320 | 100 |
| VII-060 | 320 | 100 |
| VII-062 | 320 | 100 |
| VII-064 | 320 | 100 |
| VII-064 | 320 | 100 |
| VII-066 | 320 | 100 |
| VII-071-a | 320 | 80 |
| VII-078 | 320 | 80 |
| VII-089 | 320 | 100 |
| VII-091 | 320 | 100 |

TABLE 13-continued

Pre-emergence action at 320 g/ha against ALOMY in %

| Example number | Dosage [g/ha] | ALOMY |
|---|---|---|
| VII-103 | 320 | 100 |
| VII-104 | 320 | 100 |
| VII-105 | 320 | 90 |
| VII-107 | 320 | 80 |
| VII-108 | 320 | 100 |
| VII-110 | 320 | 100 |
| VII-111 | 320 | 100 |
| VII-113 | 320 | 90 |
| VII-115 | 320 | 100 |
| VII-116 | 320 | 100 |
| VII-117 | 320 | 100 |
| VII-118 | 320 | 100 |
| VII-124 | 320 | 100 |
| VII-128 | 320 | 100 |
| VII-130 | 320 | 100 |
| VII-132 | 320 | 100 |
| VII-135 | 320 | 100 |
| VII-136 | 320 | 100 |
| VII-137 | 320 | 100 |
| VII-147 | 320 | 100 |
| VIII-002 | 320 | 90 |
| VIII-003 | 320 | 100 |
| VIII-004 | 320 | 100 |
| VIII-006 | 320 | 100 |
| VIII-011 | 320 | 100 |
| X-001 | 320 | 100 |
| X-002 | 320 | 100 |
| X-004 | 320 | 100 |
| X-005 | 320 | 100 |
| X-007 | 320 | 100 |
| X-012 | 320 | 90 |
| X-014 | 320 | 90 |
| X-016 | 320 | 100 |
| X-019 | 320 | 100 |
| X-021-a | 320 | 100 |
| X-030 | 320 | 90 |
| X-031 | 320 | 90 |
| X-041 | 320 | 100 |

TABLE 14

Pre-emergence action at 320 g/ha against AVEFA in %

| Example number | Dosage [g/ha] | AVEFA |
|---|---|---|
| VI-001 | 320 | 90 |
| VI-004 | 320 | 90 |
| VI-007 | 320 | 90 |
| VI-011 | 320 | 80 |
| VI-012 | 320 | 80 |
| VI-016 | 320 | 80 |
| VI-018 | 320 | 80 |
| VII-001 | 320 | 90 |
| VII-002 | 320 | 80 |
| VII-003 | 320 | 90 |
| VII-005 | 320 | 90 |
| VII-008 | 320 | 80 |
| VII-010 | 320 | 90 |
| VII-012 | 320 | 90 |
| VII-012 | 320 | 80 |
| VII-014 | 320 | 90 |
| VII-015 | 320 | 90 |
| VII-016 | 320 | 90 |
| VII-018 | 320 | 80 |
| VII-019 | 320 | 90 |
| VII-023 | 320 | 90 |
| VII-025 | 320 | 80 |
| VII-031 | 320 | 100 |
| VII-032 | 320 | 80 |
| VII-034 | 320 | 90 |
| VII-035 | 320 | 90 |
| VII-037 | 320 | 90 |
| VII-040 | 320 | 100 |

TABLE 14-continued

Pre-emergence action at 320 g/ha against AVEFA in %

| Example number | Dosage [g/ha] | AVEFA |
|---|---|---|
| VII-041 | 320 | 80 |
| VII-052 | 320 | 90 |
| VII-056-a | 320 | 90 |
| VII-057 | 320 | 90 |
| VII-057-a | 320 | 80 |
| VII-060 | 320 | 90 |
| VII-062 | 320 | 100 |
| VII-064 | 320 | 90 |
| VII-066 | 320 | 90 |
| VII-089 | 320 | 90 |
| VII-091 | 320 | 90 |
| VII-103 | 320 | 90 |
| VII-104 | 320 | 90 |
| VII-107 | 320 | 90 |
| VII-108 | 320 | 80 |
| VII-110 | 320 | 80 |
| VII-111 | 320 | 90 |
| VII-113 | 320 | 90 |
| VII-115 | 320 | 90 |
| VII-116 | 320 | 90 |
| VII-117 | 320 | 100 |
| VII-118 | 320 | 100 |
| VII-124 | 320 | 90 |
| VII-128 | 320 | 80 |
| VII-130 | 320 | 90 |
| VII-132 | 320 | 100 |
| VII-135 | 320 | 90 |
| VII-136 | 320 | 90 |
| VII-137 | 320 | 90 |
| VII-147 | 320 | 100 |
| VIII-003 | 320 | 90 |
| VIII-006 | 320 | 80 |
| X-001 | 320 | 90 |
| X-002 | 320 | 100 |
| X-004 | 320 | 90 |
| X-005 | 320 | 100 |
| X-007 | 320 | 100 |
| X-016 | 320 | 90 |
| X-019 | 320 | 80 |
| X-021-a | 320 | 100 |
| X-031 | 320 | 80 |
| X-041 | 320 | 80 |

TABLE 15

Pre-emergence action at 320 g/ha against DIGSA in %

| Example number | Dosage [g/ha] | DIGSA |
|---|---|---|
| VI-001 | 320 | 100 |
| VI-004 | 320 | 100 |
| VI-007 | 320 | 100 |
| VI-011 | 320 | 100 |
| VI-012 | 320 | 100 |
| VI-013 | 320 | 100 |
| VI-016 | 320 | 100 |
| VI-018 | 320 | 100 |
| VII-001 | 320 | 100 |
| VII-002 | 320 | 100 |
| VII-003 | 320 | 100 |
| VII-004 | 320 | 100 |
| VII-005 | 320 | 100 |
| VII-008 | 320 | 90 |
| VII-010 | 320 | 100 |
| VII-012 | 320 | 100 |
| VII-012 | 320 | 100 |
| VII-014 | 320 | 100 |
| VII-015 | 320 | 100 |
| VII-016 | 320 | 100 |
| VII-018 | 320 | 100 |
| VII-019 | 320 | 100 |
| VII-023 | 320 | 100 |
| VII-025 | 320 | 100 |

TABLE 15-continued

Pre-emergence action at 320 g/ha against DIGSA in %

| Example number | Dosage [g/ha] | DIGSA |
|---|---|---|
| VII-026 | 320 | 100 |
| VII-028 | 320 | 90 |
| VII-029 | 320 | 100 |
| VII-031 | 320 | 100 |
| VII-032 | 320 | 90 |
| VII-034 | 320 | 100 |
| VII-035 | 320 | 100 |
| VII-036 | 320 | 100 |
| VII-037 | 320 | 100 |
| VII-040 | 320 | 100 |
| VII-052 | 320 | 100 |
| VII-056-a | 320 | 100 |
| VII-057 | 320 | 100 |
| VII-057-a | 320 | 100 |
| VII-060 | 320 | 100 |
| VII-062 | 320 | 100 |
| VII-064 | 320 | 100 |
| VII-064 | 320 | 100 |
| VII-066 | 320 | 100 |
| VII-071-a | 320 | 90 |
| VII-089 | 320 | 100 |
| VII-091 | 320 | 100 |
| VII-103 | 320 | 100 |
| VII-104 | 320 | 100 |
| VII-105 | 320 | 100 |
| VII-107 | 320 | 100 |
| VII-108 | 320 | 100 |
| VII-110 | 320 | 100 |
| VII-111 | 320 | 100 |
| VII-115 | 320 | 100 |
| VII-116 | 320 | 100 |
| VII-117 | 320 | 100 |
| VII-118 | 320 | 100 |
| VII-124 | 320 | 100 |
| VII-128 | 320 | 100 |
| VII-130 | 320 | 100 |
| VII-132 | 320 | 100 |
| VII-147 | 320 | 100 |
| VIII-001 | 320 | 100 |
| VIII-002 | 320 | 100 |
| VIII-003 | 320 | 100 |
| VIII-004 | 320 | 100 |
| VIII-006 | 320 | 100 |
| VIII-011 | 320 | 100 |
| X-001 | 320 | 100 |
| X-002 | 320 | 100 |
| X-004 | 320 | 100 |
| X-005 | 320 | 100 |
| X-007 | 320 | 100 |
| X-019 | 320 | 100 |
| X-030 | 320 | 100 |
| X-031 | 320 | 100 |

TABLE 16

Pre-emergence action at 320 g/ha against ECHCG in %

| Example number | Dosage [g/ha] | ECHCG |
|---|---|---|
| VI-011 | 320 | 80 |
| VI-012 | 320 | 80 |
| VI-013 | 320 | 90 |
| VII-001 | 320 | 100 |
| VII-002 | 320 | 90 |
| VII-003 | 320 | 100 |
| VII-005 | 320 | 100 |
| VII-008 | 320 | 80 |
| VII-010 | 320 | 100 |
| VII-012 | 320 | 100 |
| VII-014 | 320 | 80 |
| VII-015 | 320 | 90 |
| VII-016 | 320 | 100 |
| VII-018 | 320 | 90 |

TABLE 16-continued

Pre-emergence action at 320 g/ha against ECHCG in %

| Example number | Dosage [g/ha] | ECHCG |
|---|---|---|
| VII-019 | 320 | 100 |
| VII-023 | 320 | 90 |
| VII-025 | 320 | 100 |
| VII-028 | 320 | 80 |
| VII-031 | 320 | 90 |
| VII-032 | 320 | 90 |
| VII-034 | 320 | 90 |
| VII-035 | 320 | 90 |
| VII-036 | 320 | 90 |
| VII-037 | 320 | 80 |
| VII-040 | 320 | 90 |
| VII-041 | 320 | 80 |
| VII-052 | 320 | 90 |
| VII-057-a | 320 | 80 |
| VII-060 | 320 | 90 |
| VII-064 | 320 | 100 |
| VII-064 | 320 | 90 |
| VII-066 | 320 | 90 |
| VII-089 | 320 | 80 |
| VII-103 | 320 | 80 |
| VII-104 | 320 | 100 |
| VII-108 | 320 | 100 |
| VII-110 | 320 | 100 |
| VII-111 | 320 | 100 |
| VII-113 | 320 | 90 |
| VII-117 | 320 | 90 |
| VII-118 | 320 | 90 |
| VII-124 | 320 | 100 |
| VII-128 | 320 | 90 |
| VII-130 | 320 | 90 |
| VII-132 | 320 | 90 |
| VII-135 | 320 | 90 |
| VII-136 | 320 | 90 |
| VII-137 | 320 | 90 |
| VII-147 | 320 | 100 |
| VIII-003 | 320 | 90 |
| VIII-004 | 320 | 90 |
| VIII-011 | 320 | 90 |
| X-001 | 320 | 100 |
| X-002 | 320 | 100 |
| X-004 | 320 | 90 |
| X-005 | 320 | 90 |
| X-016 | 320 | 90 |
| X-019 | 320 | 100 |
| X-021-a | 320 | 100 |
| X-031 | 320 | 80 |
| X-041 | 320 | 80 |

TABLE 17

Pre-emergence action at 320 g/ha against LOLRI in %

| Example number | Dosage [g/ha] | LOLRI |
|---|---|---|
| VI-004 | 320 | 90 |
| VI-007 | 320 | 100 |
| VI-011 | 320 | 100 |
| VI-012 | 320 | 90 |
| VI-013 | 320 | 90 |
| VI-016 | 320 | 100 |
| VI-018 | 320 | 100 |
| VII-001 | 320 | 100 |
| VII-003 | 320 | 100 |
| VII-004 | 320 | 80 |
| VII-005 | 320 | 100 |
| VII-008 | 320 | 100 |
| VII-010 | 320 | 100 |
| VII-012 | 320 | 90 |
| VII-012 | 320 | 80 |
| VII-014 | 320 | 100 |
| VII-015 | 320 | 90 |
| VII-016 | 320 | 100 |
| VII-018 | 320 | 100 |

TABLE 17-continued

Pre-emergence action at 320 g/ha against LOLRI in %

| Example number | Dosage [g/ha] | LOLRI |
|---|---|---|
| VII-019 | 320 | 100 |
| VII-023 | 320 | 100 |
| VII-025 | 320 | 90 |
| VII-026 | 320 | 80 |
| VII-029 | 320 | 90 |
| VII-031 | 320 | 100 |
| VII-032 | 320 | 100 |
| VII-034 | 320 | 90 |
| VII-035 | 320 | 90 |
| VII-037 | 320 | 100 |
| VII-040 | 320 | 100 |
| VII-041 | 320 | 90 |
| VII-042 | 320 | 100 |
| VII-052 | 320 | 100 |
| VII-056-a | 320 | 90 |
| VII-057 | 320 | 90 |
| VII-057-a | 320 | 90 |
| VII-060 | 320 | 100 |
| VII-062 | 320 | 100 |
| VII-064 | 320 | 100 |
| VII-064 | 320 | 100 |
| VII-066 | 320 | 90 |
| VII-071-a | 320 | 100 |
| VII-089 | 320 | 100 |
| VII-091 | 320 | 100 |
| VII-103 | 320 | 100 |
| VII-104 | 320 | 100 |
| VII-107 | 320 | 80 |
| VII-108 | 320 | 100 |
| VII-110 | 320 | 100 |
| VII-111 | 320 | 100 |
| VII-113 | 320 | 100 |
| VII-115 | 320 | 90 |
| VII-116 | 320 | 100 |
| VII-117 | 320 | 100 |
| VII-118 | 320 | 100 |
| VII-124 | 320 | 100 |
| VII-128 | 320 | 100 |
| VII-130 | 320 | 100 |
| VII-132 | 320 | 100 |
| VII-135 | 320 | 100 |
| VII-136 | 320 | 90 |
| VII-137 | 320 | 100 |
| VII-147 | 320 | 100 |
| VIII-003 | 320 | 90 |
| VIII-004 | 320 | 90 |
| VIII-006 | 320 | 100 |
| VIII-011 | 320 | 90 |
| X-001 | 320 | 100 |
| X-002 | 320 | 100 |
| X-004 | 320 | 100 |
| X-005 | 320 | 100 |
| X-007 | 320 | 100 |
| X-014 | 320 | 90 |
| X-016 | 320 | 90 |
| X-019 | 320 | 100 |
| X-021-a | 320 | 100 |
| X-031 | 320 | 80 |
| X-041 | 320 | 90 |

TABLE 18

Pre-emergence action at 320 g/ha against SETVI in %

| Example number | Dosage [g/ha] | SETVI |
|---|---|---|
| VI-004 | 320 | 90 |
| VI-007 | 320 | 100 |
| VI-011 | 320 | 100 |
| VI-012 | 320 | 100 |
| VI-013 | 320 | 100 |
| VI-016 | 320 | 100 |
| VI-018 | 320 | 100 |
| VII-001 | 320 | 100 |
| VII-002 | 320 | 90 |
| VII-003 | 320 | 100 |
| VII-004 | 320 | 100 |
| VII-005 | 320 | 100 |
| VII-008 | 320 | 100 |
| VII-010 | 320 | 100 |
| VII-012 | 320 | 100 |
| VII-012 | 320 | 90 |
| VII-014 | 320 | 100 |
| VII-015 | 320 | 100 |
| VII-016 | 320 | 100 |
| VII-018 | 320 | 100 |
| VII-019 | 320 | 100 |
| VII-023 | 320 | 100 |
| VII-025 | 320 | 100 |
| VII-026 | 320 | 80 |
| VII-028 | 320 | 100 |
| VII-029 | 320 | 90 |
| VII-031 | 320 | 100 |
| VII-032 | 320 | 90 |
| VII-034 | 320 | 100 |
| VII-035 | 320 | 100 |
| VII-036 | 320 | 100 |
| VII-037 | 320 | 100 |
| VII-040 | 320 | 100 |
| VII-052 | 320 | 100 |
| VII-057 | 320 | 90 |
| VII-057-a | 320 | 100 |
| VII-060 | 320 | 90 |
| VII-062 | 320 | 100 |
| VII-064 | 320 | 100 |
| VII-064 | 320 | 100 |
| VII-066 | 320 | 80 |
| VII-089 | 320 | 100 |
| VII-091 | 320 | 100 |
| VII-103 | 320 | 100 |
| VII-104 | 320 | 100 |
| VII-105 | 320 | 80 |
| VII-107 | 320 | 100 |
| VII-108 | 320 | 100 |
| VII-110 | 320 | 100 |
| VII-111 | 320 | 100 |
| VII-113 | 320 | 90 |
| VII-115 | 320 | 100 |
| VII-116 | 320 | 100 |
| VII-117 | 320 | 100 |
| VII-118 | 320 | 90 |
| VII-124 | 320 | 100 |
| VII-128 | 320 | 100 |
| VII-130 | 320 | 100 |
| VII-132 | 320 | 100 |
| VII-135 | 320 | 100 |
| VII-136 | 320 | 100 |
| VII-137 | 320 | 100 |
| VII-147 | 320 | 100 |
| VIII-001 | 320 | 100 |
| VIII-002 | 320 | 100 |
| VIII-003 | 320 | 100 |
| VIII-004 | 320 | 90 |
| VIII-006 | 320 | 100 |
| VIII-011 | 320 | 90 |
| X-001 | 320 | 100 |
| X-002 | 320 | 100 |
| X-004 | 320 | 100 |
| X-005 | 320 | 100 |
| X-007 | 320 | 100 |
| X-012 | 320 | 90 |
| X-014 | 320 | 90 |
| X-016 | 320 | 100 |
| X-019 | 320 | 100 |
| X-021-a | 320 | 100 |
| X-030 | 320 | 80 |
| X-031 | 320 | 100 |
| X-041 | 320 | 90 |

TABLE 11

Pre-emergence action at 320 g/ha against ABUTH in %

| Example number | Dosage [g/ha] | ABUTH |
|---|---|---|
| VI-004 | 320 | 80 |
| VI-011 | 320 | 80 |
| VI-012 | 320 | 80 |
| VI-013 | 320 | 80 |
| VI-018 | 320 | 80 |
| VII-008 | 320 | 80 |
| VII-015 | 320 | 80 |
| VII-028 | 320 | 90 |
| VII-035 | 320 | 90 |
| VII-104 | 320 | 80 |
| VII-130 | 320 | 90 |
| VII-132 | 320 | 90 |
| VII-135 | 320 | 80 |
| VII-136 | 320 | 80 |
| VII-137 | 320 | 90 |
| X-019 | 320 | 80 |
| X-031 | 320 | 80 |

TABLE 19

Pre-emergence action at 320 g/ha against AMARE in %

| Example number | Dosage [g/ha] | AMARE |
|---|---|---|
| VI-001 | 320 | 100 |
| VI-004 | 320 | 100 |
| VI-007 | 320 | 100 |
| VI-011 | 320 | 100 |
| VI-012 | 320 | 100 |
| VI-013 | 320 | 90 |
| VI-016 | 320 | 100 |
| VI-018 | 320 | 100 |
| VII-001 | 320 | 100 |
| VII-002 | 320 | 100 |
| VII-003 | 320 | 100 |
| VII-004 | 320 | 90 |
| VII-005 | 320 | 100 |
| VII-008 | 320 | 100 |
| VII-010 | 320 | 100 |
| VII-012 | 320 | 100 |
| VII-012 | 320 | 100 |
| VII-014 | 320 | 90 |
| VII-015 | 320 | 100 |
| VII-016 | 320 | 100 |
| VII-018 | 320 | 100 |
| VII-019 | 320 | 100 |
| VII-023 | 320 | 100 |
| VII-025 | 320 | 100 |
| VII-026 | 320 | 100 |
| VII-028 | 320 | 90 |
| VII-029 | 320 | 100 |
| VII-031 | 320 | 100 |
| VII-032 | 320 | 100 |
| VII-034 | 320 | 100 |
| VII-035 | 320 | 100 |
| VII-036 | 320 | 100 |
| VII-037 | 320 | 100 |
| VII-040 | 320 | 100 |
| VII-041 | 320 | 100 |
| VII-042 | 320 | 100 |
| VII-044 | 320 | 90 |
| VII-047 | 320 | 90 |
| VII-048 | 320 | 80 |
| VII-052 | 320 | 100 |
| VII-056-a | 320 | 100 |
| VII-057 | 320 | 100 |
| VII-057-a | 320 | 100 |
| VII-060 | 320 | 100 |
| VII-062 | 320 | 100 |
| VII-064 | 320 | 100 |
| VII-064 | 320 | 100 |
| VII-066 | 320 | 100 |
| VII-071-a | 320 | 100 |

TABLE 19-continued

Pre-emergence action at 320 g/ha against AMARE in %

| Example number | Dosage [g/ha] | AMARE |
|---|---|---|
| VII-078 | 320 | 100 |
| VII-089 | 320 | 100 |
| VII-091 | 320 | 100 |
| VII-103 | 320 | 100 |
| VII-104 | 320 | 100 |
| VII-105 | 320 | 90 |
| VII-107 | 320 | 100 |
| VII-108 | 320 | 100 |
| VII-110 | 320 | 100 |
| VII-111 | 320 | 100 |
| VII-113 | 320 | 100 |
| VII-115 | 320 | 100 |
| VII-116 | 320 | 100 |
| VII-117 | 320 | 100 |
| VII-118 | 320 | 100 |
| VII-124 | 320 | 100 |
| VII-128 | 320 | 100 |
| VII-130 | 320 | 100 |
| VII-132 | 320 | 100 |
| VII-135 | 320 | 100 |
| VII-136 | 320 | 100 |
| VII-137 | 320 | 100 |
| VII-147 | 320 | 100 |
| VIII-001 | 320 | 90 |
| VIII-002 | 320 | 100 |
| VIII-003 | 320 | 90 |
| VIII-004 | 320 | 100 |
| VIII-006 | 320 | 100 |
| VIII-011 | 320 | 100 |
| X-001 | 320 | 90 |
| X-002 | 320 | 100 |
| X-004 | 320 | 90 |
| X-005 | 320 | 100 |
| X-007 | 320 | 100 |
| X-012 | 320 | 100 |
| X-014 | 320 | 100 |
| X-016 | 320 | 100 |
| X-019 | 320 | 100 |
| X-021-a | 320 | 100 |
| X-030 | 320 | 90 |
| X-031 | 320 | 90 |
| X-037 | 320 | 100 |
| X-041 | 320 | 90 |

TABLE 20

Pre-emergence action at 320 g/ha against MATIN in %

| Example number | Dosage [g/ha] | MATIN |
|---|---|---|
| VI-001 | 320 | 90 |
| VI-004 | 320 | 100 |
| VI-007 | 320 | 100 |
| VI-011 | 320 | 90 |
| VI-012 | 320 | 90 |
| VI-013 | 320 | 90 |
| VI-016 | 320 | 100 |
| VI-018 | 320 | 90 |
| VII-001 | 320 | 90 |
| VII-002 | 320 | 100 |
| VII-003 | 320 | 90 |
| VII-004 | 320 | 80 |
| VII-005 | 320 | 100 |
| VII-008 | 320 | 100 |
| VII-010 | 320 | 100 |
| VII-012 | 320 | 90 |
| VII-012 | 320 | 90 |
| VII-015 | 320 | 100 |
| VII-016 | 320 | 80 |
| VII-018 | 320 | 90 |
| VII-019 | 320 | 100 |
| VII-023 | 320 | 90 |
| VII-025 | 320 | 100 |

TABLE 20-continued

Pre-emergence action at 320 g/ha against MATIN in %

| Example number | Dosage [g/ha] | MATIN |
|---|---|---|
| VII-026 | 320 | 90 |
| VII-028 | 320 | 80 |
| VII-029 | 320 | 90 |
| VII-031 | 320 | 100 |
| VII-032 | 320 | 90 |
| VII-035 | 320 | 100 |
| VII-036 | 320 | 90 |
| VII-037 | 320 | 80 |
| VII-040 | 320 | 100 |
| VII-041 | 320 | 100 |
| VII-042 | 320 | 90 |
| VII-052 | 320 | 90 |
| VII-056-a | 320 | 80 |
| VII-057 | 320 | 90 |
| VII-057-a | 320 | 90 |
| VII-060 | 320 | 90 |
| VII-062 | 320 | 100 |
| VII-064 | 320 | 100 |
| VII-064 | 320 | 100 |
| VII-066 | 320 | 100 |
| VII-071-a | 320 | 90 |
| VII-089 | 320 | 90 |
| VII-091 | 320 | 90 |
| VII-103 | 320 | 90 |
| VII-104 | 320 | 100 |
| VII-105 | 320 | 100 |
| VII-107 | 320 | 90 |
| VII-108 | 320 | 100 |
| VII-110 | 320 | 100 |
| VII-111 | 320 | 90 |
| VII-113 | 320 | 90 |
| VII-116 | 320 | 90 |
| VII-117 | 320 | 90 |
| VII-118 | 320 | 90 |
| VII-124 | 320 | 100 |
| VII-128 | 320 | 90 |
| VII-130 | 320 | 100 |
| VII-132 | 320 | 90 |
| VII-135 | 320 | 90 |
| VII-136 | 320 | 90 |
| VII-137 | 320 | 90 |
| VII-147 | 320 | 90 |
| VIII-003 | 320 | 90 |
| VIII-004 | 320 | 90 |
| VIII-006 | 320 | 90 |
| VIII-011 | 320 | 90 |
| X-001 | 320 | 90 |
| X-002 | 320 | 100 |
| X-004 | 320 | 90 |
| X-005 | 320 | 100 |
| X-007 | 320 | 100 |
| X-012 | 320 | 90 |
| X-014 | 320 | 90 |
| X-016 | 320 | 90 |
| X-019 | 320 | 100 |
| X-021-a | 320 | 90 |
| X-031 | 320 | 80 |
| X-041 | 320 | 90 |

TABLE 21

Pre-emergence action at 320 g/ha against PHBPU in %

| Example number | Dosage [g/ha] | PHBPU |
|---|---|---|
| VI-007 | 320 | 90 |
| VI-011 | 320 | 90 |
| VI-012 | 320 | 90 |
| VI-018 | 320 | 90 |
| VII-001 | 320 | 100 |
| VII-003 | 320 | 90 |
| VII-005 | 320 | 80 |
| VII-008 | 320 | 80 |
| VII-010 | 320 | 90 |
| VII-012 | 320 | 90 |
| VII-012 | 320 | 80 |
| VII-015 | 320 | 90 |
| VII-016 | 320 | 90 |
| VII-019 | 320 | 90 |
| VII-025 | 320 | 90 |
| VII-028 | 320 | 100 |
| VII-031 | 320 | 80 |
| VII-032 | 320 | 100 |
| VII-035 | 320 | 90 |
| VII-064 | 320 | 90 |
| VII-089 | 320 | 80 |
| VII-104 | 320 | 100 |
| VII-110 | 320 | 90 |
| VII-115 | 320 | 90 |
| VII-124 | 320 | 90 |
| VII-128 | 320 | 90 |
| VII-135 | 320 | 90 |
| VII-136 | 320 | 90 |
| VIII-006 | 320 | 90 |
| X-002 | 320 | 80 |
| X-005 | 320 | 90 |
| X-031 | 320 | 90 |
| X-041 | 320 | 90 |

TABLE 22

Pre-emergence action at 320 g/ha against POLCO in %

| Example number | Dosage [g/ha] | POLCO |
|---|---|---|
| VI-001 | 320 | 100 |
| VI-004 | 320 | 90 |
| VI-007 | 320 | 100 |
| VI-011 | 320 | 80 |
| VI-012 | 320 | 80 |
| VI-013 | 320 | 90 |
| VI-016 | 320 | 90 |
| VI-018 | 320 | 90 |
| VII-001 | 320 | 90 |
| VII-002 | 320 | 100 |
| VII-003 | 320 | 90 |
| VII-004 | 320 | 90 |
| VII-005 | 320 | 100 |
| VII-008 | 320 | 100 |
| VII-010 | 320 | 90 |
| VII-012 | 320 | 90 |
| VII-012 | 320 | 80 |
| VII-014 | 320 | 90 |
| VII-015 | 320 | 100 |
| VII-016 | 320 | 90 |
| VII-018 | 320 | 100 |
| VII-019 | 320 | 100 |
| VII-023 | 320 | 100 |
| VII-025 | 320 | 100 |
| VII-026 | 320 | 100 |
| VII-028 | 320 | 90 |
| VII-029 | 320 | 100 |
| VII-031 | 320 | 100 |
| VII-032 | 320 | 90 |
| VII-034 | 320 | 90 |
| VII-035 | 320 | 90 |
| VII-036 | 320 | 100 |
| VII-037 | 320 | 100 |
| VII-040 | 320 | 90 |
| VII-042 | 320 | 100 |
| VII-044 | 320 | 100 |
| VII-052 | 320 | 100 |
| VII-056-a | 320 | 90 |
| VII-057 | 320 | 90 |
| VII-057-a | 320 | 80 |
| VII-060 | 320 | 90 |

TABLE 22-continued

Pre-emergence action at 320 g/ha against POLCO in %

| Example number | Dosage [g/ha] | POLCO |
|---|---|---|
| VII-062 | 320 | 100 |
| VII-064 | 320 | 90 |
| VII-064 | 320 | 90 |
| VII-066 | 320 | 90 |
| VII-071-a | 320 | 90 |
| VII-089 | 320 | 100 |
| VII-091 | 320 | 100 |
| VII-103 | 320 | 100 |
| VII-104 | 320 | 90 |
| VII-105 | 320 | 90 |
| VII-107 | 320 | 100 |
| VII-108 | 320 | 100 |
| VII-110 | 320 | 100 |
| VII-111 | 320 | 90 |
| VII-113 | 320 | 90 |
| VII-115 | 320 | 80 |
| VII-116 | 320 | 90 |
| VII-117 | 320 | 100 |
| VII-118 | 320 | 100 |
| VII-124 | 320 | 100 |
| VII-128 | 320 | 90 |
| VII-130 | 320 | 100 |
| VII-132 | 320 | 100 |
| VII-135 | 320 | 100 |
| VII-136 | 320 | 100 |
| VII-137 | 320 | 90 |
| VII-147 | 320 | 100 |
| VIII-001 | 320 | 90 |
| VIII-002 | 320 | 90 |
| VIII-003 | 320 | 100 |
| VIII-004 | 320 | 90 |
| VIII-006 | 320 | 90 |
| X-001 | 320 | 90 |
| X-002 | 320 | 100 |
| X-004 | 320 | 90 |
| X-005 | 320 | 90 |
| X-007 | 320 | 90 |
| X-012 | 320 | 90 |
| X-016 | 320 | 80 |
| X-019 | 320 | 90 |
| X-021-a | 320 | 100 |
| X-031 | 320 | 80 |
| X-037 | 320 | 90 |
| X-041 | 320 | 90 |

TABLE 23

Pre-emeraence action at 320 g/ha against STEME in %

| Example number | Dosage [g/ha] | STEME |
|---|---|---|
| VI-004 | 320 | 90 |
| VI-007 | 320 | 100 |
| VII-002 | 320 | 90 |
| VII-003 | 320 | 90 |
| VII-005 | 320 | 90 |
| VII-012 | 320 | 100 |
| VII-016 | 320 | 90 |
| VII-019 | 320 | 90 |
| VII-023 | 320 | 90 |
| VII-028 | 320 | 90 |
| VII-029 | 320 | 90 |
| VII-032 | 320 | 90 |
| VIII-001 | 320 | 90 |
| VIII-003 | 320 | 80 |
| VIII-004 | 320 | 90 |

TABLE 24

Pre-emergence action at 320 g/ha against VERPE in %

| Example number | Dosage [g/ha] | VERPE |
|---|---|---|
| VI-001 | 320 | 100 |
| VI-004 | 320 | 100 |
| VI-007 | 320 | 100 |
| VI-011 | 320 | 90 |
| VI-012 | 320 | 100 |
| VI-016 | 320 | 100 |
| VI-018 | 320 | 80 |
| VII-001 | 320 | 100 |
| VII-002 | 320 | 100 |
| VII-003 | 320 | 100 |
| VII-005 | 320 | 100 |
| VII-008 | 320 | 100 |
| VII-010 | 320 | 100 |
| VII-012 | 320 | 100 |
| VII-012 | 320 | 100 |
| VII-014 | 320 | 100 |
| VII-015 | 320 | 100 |
| VII-016 | 320 | 90 |
| VII-018 | 320 | 100 |
| VII-019 | 320 | 100 |
| VII-023 | 320 | 80 |
| VII-025 | 320 | 100 |
| VII-026 | 320 | 80 |
| VII-028 | 320 | 100 |
| VII-029 | 320 | 100 |
| VII-031 | 320 | 100 |
| VII-032 | 320 | 100 |
| VII-034 | 320 | 80 |
| VII-035 | 320 | 100 |
| VII-036 | 320 | 100 |
| VII-037 | 320 | 100 |
| VII-040 | 320 | 100 |
| VII-041 | 320 | 100 |
| VII-042 | 320 | 90 |
| VII-052 | 320 | 90 |
| VII-056-a | 320 | 100 |
| VII-060 | 320 | 100 |
| VII-062 | 320 | 100 |
| VII-064 | 320 | 100 |
| VII-064 | 320 | 100 |
| VII-066 | 320 | 100 |
| VII-071-a | 320 | 80 |
| VII-078 | 320 | 80 |
| VII-089 | 320 | 100 |
| VII-091 | 320 | 100 |
| VII-103 | 320 | 100 |
| VII-104 | 320 | 100 |
| VII-105 | 320 | 90 |
| VII-107 | 320 | 80 |
| VII-108 | 320 | 100 |
| VII-110 | 320 | 100 |
| VII-111 | 320 | 100 |
| VII-113 | 320 | 90 |
| VII-115 | 320 | 90 |
| VII-116 | 320 | 100 |
| VII-117 | 320 | 90 |
| VII-118 | 320 | 90 |
| VII-124 | 320 | 100 |
| VII-128 | 320 | 100 |
| VII-130 | 320 | 100 |
| VII-132 | 320 | 100 |
| VII-135 | 320 | 100 |
| VII-136 | 320 | 100 |
| VII-137 | 320 | 100 |
| VII-147 | 320 | 100 |
| VIII-002 | 320 | 80 |
| VIII-003 | 320 | 90 |
| VIII-004 | 320 | 100 |
| X-001 | 320 | 80 |
| X-002 | 320 | 100 |
| X-004 | 320 | 100 |
| X-005 | 320 | 100 |
| X-007 | 320 | 100 |
| X-016 | 320 | 100 |
| X-019 | 320 | 100 |
| X-021-a | 320 | 100 |

TABLE 24-continued

Pre-emergence action at 320 g/ha against VERPE in %

| Example number | Dosage [g/ha] | VERPE |
|---|---|---|
| X-031 | 320 | 90 |
| X-034 | 320 | 90 |
| X-037 | 320 | 100 |
| X-041 | 320 | 100 |

TABLE 25

Pre-emergence action at 320 g/ha against VIOTR in %

| Example number | Dosage [g/ha] | VIOTR |
|---|---|---|
| VI-001 | 320 | 100 |
| VI-004 | 320 | 100 |
| VI-007 | 320 | 100 |
| VI-011 | 320 | 100 |
| VI-012 | 320 | 100 |
| VI-013 | 320 | 100 |
| VI-016 | 320 | 100 |
| VI-018 | 320 | 90 |
| VII-001 | 320 | 100 |
| VII-003 | 320 | 100 |
| VII-004 | 320 | 100 |
| VII-005 | 320 | 100 |
| VII-008 | 320 | 100 |
| VII-010 | 320 | 100 |
| VII-012 | 320 | 100 |
| VII-012 | 320 | 100 |
| VII-014 | 320 | 100 |
| VII-015 | 320 | 100 |
| VII-016 | 320 | 90 |
| VII-018 | 320 | 90 |
| VII-019 | 320 | 100 |
| VII-023 | 320 | 100 |
| VII-025 | 320 | 100 |
| VII-026 | 320 | 100 |
| VII-028 | 320 | 100 |
| VII-029 | 320 | 100 |
| VII-031 | 320 | 100 |
| VII-032 | 320 | 100 |
| VII-034 | 320 | 100 |
| VII-035 | 320 | 100 |
| VII-036 | 320 | 100 |
| VII-037 | 320 | 100 |
| VII-040 | 320 | 100 |
| VII-041 | 320 | 80 |
| VII-042 | 320 | 100 |
| VII-044 | 320 | 100 |
| VII-052 | 320 | 100 |
| VII-056-a | 320 | 100 |
| VII-057 | 320 | 100 |
| VII-057-a | 320 | 100 |
| VII-060 | 320 | 100 |
| VII-062 | 320 | 100 |
| VII-064 | 320 | 100 |
| VII-064 | 320 | 100 |
| VII-066 | 320 | 100 |
| VII-071-a | 320 | 100 |
| VII-078 | 320 | 90 |
| VII-089 | 320 | 100 |
| VII-091 | 320 | 100 |
| VII-103 | 320 | 100 |
| VII-104 | 320 | 100 |
| VII-105 | 320 | 90 |
| VII-107 | 320 | 100 |
| VII-108 | 320 | 100 |
| VII-110 | 320 | 100 |
| VII-111 | 320 | 100 |
| VII-113 | 320 | 100 |
| VII-115 | 320 | 100 |
| VII-116 | 320 | 90 |
| VII-117 | 320 | 100 |
| VII-118 | 320 | 100 |
| VII-124 | 320 | 100 |
| VII-128 | 320 | 100 |
| VII-130 | 320 | 100 |
| VII-132 | 320 | 100 |
| VII-135 | 320 | 100 |
| VII-136 | 320 | 100 |
| VII-137 | 320 | 100 |
| VII-147 | 320 | 100 |
| VIII-001 | 320 | 90 |
| VIII-002 | 320 | 100 |
| VIII-003 | 320 | 100 |
| VIII-004 | 320 | 90 |
| VIII-006 | 320 | 100 |
| VIII-011 | 320 | 100 |
| X-001 | 320 | 100 |
| X-002 | 320 | 100 |
| X-004 | 320 | 100 |
| X-005 | 320 | 100 |
| X-007 | 320 | 100 |
| X-012 | 320 | 100 |
| X-014 | 320 | 100 |
| X-016 | 320 | 100 |
| X-018 | 320 | 90 |
| X-019 | 320 | 100 |
| X-021-a | 320 | 100 |
| X-030 | 320 | 90 |
| X-031 | 320 | 90 |
| X-034 | 320 | 90 |
| X-041 | 320 | 100 |

TABLE 26

Pre-emergence action at 320 g/ha against HORMU in %

| Example number | Dosage [g/ha] | HORMU |
|---|---|---|
| VI-004 | 320 | 100 |
| VI-007 | 320 | 100 |
| VII-002 | 320 | 80 |
| VII-003 | 320 | 90 |
| VII-005 | 320 | 100 |
| VII-012 | 320 | 80 |
| VII-016 | 320 | 90 |
| VII-019 | 320 | 100 |
| VII-023 | 320 | 100 |
| VII-029 | 320 | 90 |
| VII-032 | 320 | 80 |
| VIII-003 | 320 | 90 |

As shown by the results, compounds of the general formula (I) of the invention, in post-emergence treatment, have very good herbicidal efficacy (90% to 100% herbicidal action) against harmful plants such as *Abutilon theophrasti, Digitaria sanguinalis, Echinochloa crus-galli, Matricaria inodora, Poa annua, Stellaria media*, at an application rate of 320 g of active substance per hectare.

Accordingly, the compounds of the invention have good herbicidal action against a broad spectrum of weed grasses and broad-leaved weeds and are therefore suitable for controlling unwanted vegetation by the pre-emergence method.

2. Post-Emergence Herbicidal Effect and Crop Plant Compatibility a) Seeds of mono- and dicotyledonous weed plants are placed in plastic pots in sandy loam soil (twin sowing with one species each of mono- or dicotyledonous weed plants per pot), covered with soil and cultivated in a greenhouse under controlled growth conditions. 2 to 3 weeks after sowing, the test plants are treated at the one-leaf stage. The compounds of the invention, formulated in the form of wettable powders (WP) or as emulsion concentrates (EC), are applied to the green parts of the plants as aqueous suspension or emulsion with addition of 0.5% additive at a water application rate equivalent to 600 litres per hectare. After the test plants have been kept in the greenhouse under optimum growth conditions for about 3 weeks, the activity of the preparations is rated visually in comparison to untreated controls. For example, 100% activity=the plants have died, 0% activity=like control plants.

As shown by the results from Tables 27 to 38, compounds of the invention have good herbicidal post-emergence efficacy against a broad spectrum of weed grasses and broad-leaved weeds.

TABLE 27

Post-emergence action against ALOMY

| Example number | Dosage [g/ha] | ALOMY |
|---|---|---|
| I-004 | 1280 | 100 |
| II-003 | 1280 | 100 |
| II-004 | 1280 | 100 |
| II-012 | 1280 | 100 |
| II-013 | 1280 | 90 |
| II-017 | 1280 | 100 |
| IV-001 | 1280 | 100 |
| IV-003 | 1280 | 100 |
| VI-005 | 1280 | 90 |
| VI-007 | 1280 | 90 |
| VI-011 | 1280 | 100 |
| VI-012 | 1280 | 100 |
| VI-013 | 1280 | 100 |
| VI-018 | 1280 | 100 |
| VII-003 | 1280 | 90 |
| VII-008 | 1280 | 100 |
| VII-010 | 1280 | 100 |
| VII-012 | 1280 | 100 |
| VII-012 | 1280 | 100 |
| VII-014 | 1280 | 100 |
| VII-015 | 1280 | 100 |
| VII-018 | 1280 | 100 |
| VII-019 | 1280 | 100 |
| VII-025 | 1280 | 100 |
| VII-026 | 1280 | 100 |
| VII-027 | 1280 | 100 |
| VII-029 | 1280 | 100 |
| VII-030 | 1280 | 100 |
| VII-031 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-068 | 1280 | 100 |
| VII-069 | 1280 | 100 |
| VII-089 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 100 |

TABLE 27-continued

Post-emergence action against ALOMY

| Example number | Dosage [g/ha] | ALOMY |
|---|---|---|
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-119 | 1280 | 100 |
| VII-123 | 1280 | 90 |
| VII-123-a | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 100 |
| VII-149 | 1280 | 100 |
| VIII-006 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-002 | 1280 | 90 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-011 | 1280 | 90 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-028 | 1280 | 100 |
| X-032 | 1280 | 100 |
| X-033 | 1280 | 100 |
| X-038 | 1280 | 90 |
| X-039 | 1280 | 90 |
| X-040 | 1280 | 100 |

TABLE 28

Post-emergence action against DIGSA

| Example number | Dosage [g/ha] | DIGSA |
|---|---|---|
| II-004 | 1280 | 100 |
| II-012 | 1280 | 90 |
| II-014 | 1280 | 90 |
| IV-002 | 1280 | 100 |
| IX-001 | 1280 | 100 |
| VI-001 | 1280 | 100 |
| VI-003 | 1280 | 100 |
| VI-006 | 1280 | 90 |
| VI-007 | 1280 | 100 |
| VI-008 | 1280 | 100 |
| VI-011 | 1280 | 100 |
| VI-012 | 1280 | 90 |
| VI-013 | 1280 | 90 |
| VI-018 | 1280 | 100 |
| VII-003 | 1280 | 100 |
| VII-010 | 1280 | 100 |
| VII-012 | 1280 | 100 |
| VII-012 | 1280 | 100 |
| VII-013 | 1280 | 90 |
| VII-015 | 1280 | 100 |
| VII-017 | 1280 | 90 |

TABLE 28-continued

Post-emergence action against DIGSA

| Example number | Dosage [g/ha] | DIGSA |
|---|---|---|
| VII-018 | 1280 | 100 |
| VII-019 | 1280 | 100 |
| VII-023 | 1280 | 90 |
| VII-025 | 1280 | 100 |
| VII-026 | 1280 | 100 |
| VII-027 | 1280 | 100 |
| VII-029 | 1280 | 100 |
| VII-031 | 1280 | 100 |
| VII-032 | 1280 | 90 |
| VII-035 | 1280 | 100 |
| VII-036 | 1280 | 100 |
| VII-037 | 1280 | 90 |
| VII-040 | 1280 | 100 |
| VII-052 | 1280 | 100 |
| VII-056 | 1280 | 90 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-069 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 90 |
| VII-101 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 100 |
| VII-149 | 1280 | 100 |
| VIII-001 | 1280 | 90 |
| VIII-006 | 1280 | 90 |
| VIII-007 | 1280 | 90 |
| VIII-008 | 1280 | 90 |
| VIII-009 | 1280 | 100 |
| VIII-010 | 1280 | 100 |
| VIII-011 | 1280 | 100 |
| VIII-012 | 1280 | 100 |
| X-002 | 1280 | 100 |
| X-003 | 1280 | 100 |
| X-004 | 1280 | 100 |
| X-006 | 1280 | 90 |
| X-007 | 1280 | 100 |
| X-009 | 1280 | 90 |
| X-019 | 1280 | 90 |
| X-021-a | 1280 | 100 |
| X-023 | 1280 | 100 |
| X-024 | 1280 | 100 |
| X-025 | 1280 | 100 |
| X-026 | 1280 | 100 |
| X-033 | 1280 | 90 |
| X-038 | 1280 | 90 |
| X-039 | 1280 | 90 |
| X-040 | 1280 | 90 |

TABLE 29

Post-emergence action against ECHCG

| Example number | Dosage [g/ha] | ECHCG |
|---|---|---|
| I-003 | 1280 | 90 |
| I-004 | 1280 | 90 |
| II-012 | 1280 | 100 |
| IV-001 | 1280 | 90 |
| IX-001 | 1280 | 90 |
| VI-001 | 1280 | 100 |
| VI-002 | 1280 | 100 |
| VI-003 | 1280 | 100 |
| VI-004 | 1280 | 90 |
| VI-005 | 1280 | 90 |
| VI-007 | 1280 | 100 |
| VI-011 | 1280 | 100 |
| VI-012 | 1280 | 100 |
| VI-013 | 1280 | 100 |
| VI-018 | 1280 | 100 |
| VII-002 | 1280 | 90 |
| VII-003 | 1280 | 90 |
| VII-008 | 1280 | 100 |
| VII-009 | 1280 | 100 |
| VII-010 | 1280 | 100 |
| VII-012 | 1280 | 100 |
| VII-012 | 1280 | 100 |
| VII-014 | 1280 | 90 |
| VII-015 | 1280 | 100 |
| VII-016 | 1280 | 90 |
| VII-018 | 1280 | 90 |
| VII-019 | 1280 | 100 |
| VII-023 | 1280 | 90 |
| VII-025 | 1280 | 100 |
| VII-026 | 1280 | 90 |
| VII-028 | 1280 | 90 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 90 |
| VII-037 | 1280 | 90 |
| VII-040 | 1280 | 100 |
| VII-052 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-088 | 1280 | 100 |
| VII-089 | 1280 | 90 |
| VII-090 | 1280 | 100 |
| VII-091 | 1280 | 100 |
| VII-095 | 1280 | 100 |
| VII-096 | 1280 | 90 |
| VII-097 | 1280 | 100 |
| VII-098 | 1280 | 90 |
| VII-100 | 1280 | 90 |

TABLE 29-continued

Post-emergence action against ECHCG

| Example number | Dosage [g/ha] | ECHCG |
| --- | --- | --- |
| VII-101 | 1280 | 100 |
| VII-103 | 1280 | 100 |
| VII-104 | 1280 | 100 |
| VII-105 | 1280 | 100 |
| VII-106 | 1280 | 90 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 100 |
| VII-123-a | 1280 | 100 |
| VII-124 | 1280 | 100 |
| VII-125 | 1280 | 90 |
| VII-132 | 1280 | 100 |
| VII-147 | 1280 | 100 |
| VIII-002 | 1280 | 100 |
| VIII-003 | 1280 | 100 |
| VIII-004 | 1280 | 90 |
| VIII-006 | 1280 | 90 |
| VIII-007 | 1280 | 90 |
| VIII-009 | 1280 | 100 |
| VIII-010 | 1280 | 100 |
| VIII-011 | 1280 | 100 |
| VIII-012 | 1280 | 100 |
| X-002 | 1280 | 90 |
| X-003 | 1280 | 90 |
| X-004 | 1280 | 100 |
| X-005 | 1280 | 100 |
| X-006 | 1280 | 100 |
| X-007 | 1280 | 100 |
| X-009 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-027 | 1280 | 90 |
| X-028 | 1280 | 100 |
| X-038 | 1280 | 90 |
| X-039 | 1280 | 90 |

TABLE 30

Post-emergence action against LOLRI

| Example number | Dosage [g/ha] | LOLRI |
| --- | --- | --- |
| VI-002 | 1280 | 100 |
| VI-004 | 1280 | 100 |
| VI-006 | 1280 | 100 |
| VI-011 | 1280 | 100 |
| VI-012 | 1280 | 90 |
| VI-013 | 1280 | 90 |
| VI-018 | 1280 | 90 |
| VII-003 | 1280 | 100 |
| VII-008 | 1280 | 100 |
| VII-012 | 1280 | 100 |
| VII-012 | 1280 | 100 |
| VII-014 | 1280 | 90 |
| VII-015 | 1280 | 100 |
| VII-016 | 1280 | 90 |
| VII-018 | 1280 | 90 |
| VII-019 | 1280 | 100 |
| VII-023 | 1280 | 100 |
| VII-028 | 1280 | 90 |
| VII-029 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 90 |
| VII-056-a | 1280 | 100 |
| VII-058 | 1280 | 100 |
| VII-059 | 1280 | 100 |
| VII-061 | 1280 | 100 |
| VII-062 | 1280 | 100 |
| VII-064 | 1280 | 100 |
| VII-064 | 1280 | 90 |
| VII-065 | 1280 | 90 |
| VII-066 | 1280 | 100 |
| VII-067 | 1280 | 100 |
| VII-068 | 1280 | 100 |
| VII-089 | 1280 | 100 |
| VII-090 | 1280 | 90 |
| VII-091 | 1280 | 100 |
| VII-095 | 1280 | 100 |
| VII-097 | 1280 | 90 |
| VII-099 | 1280 | 100 |
| VII-100 | 1280 | 100 |
| VII-101 | 1280 | 100 |
| VII-103 | 1280 | 100 |
| VII-104 | 1280 | 100 |
| VII-108 | 1280 | 100 |
| VII-109 | 1280 | 100 |
| VII-110 | 1280 | 100 |
| VII-111 | 1280 | 90 |
| VII-117 | 1280 | 100 |
| VII-118 | 1280 | 100 |
| VII-119 | 1280 | 100 |
| VII-123-a | 1280 | 100 |
| VII-124 | 1280 | 100 |
| VII-147 | 1280 | 100 |
| VII-149 | 1280 | 100 |
| VIII-001 | 1280 | 90 |
| VIII-002 | 1280 | 100 |
| VIII-003 | 1280 | 100 |
| VIII-004 | 1280 | 100 |
| VIII-006 | 1280 | 100 |
| VIII-007 | 1280 | 100 |
| VIII-010 | 1280 | 100 |
| X-005 | 1280 | 100 |
| X-006 | 1280 | 90 |
| X-007 | 1280 | 100 |
| X-019 | 1280 | 90 |
| X-021-a | 1280 | 100 |
| X-023 | 1280 | 100 |
| X-024 | 1280 | 100 |
| X-026 | 1280 | 90 |

TABLE 31

Post-emereence action aeainst POAAN

| Example number | Dosage [g/ha] | POAAN |
| --- | --- | --- |
| I-003 | 1280 | 100 |
| II-003 | 1280 | 100 |
| II-012 | 1280 | 100 |
| II-013 | 1280 | 90 |
| II-014 | 1280 | 90 |
| II-017 | 1280 | 100 |
| IV-001 | 1280 | 100 |
| IV-002 | 1280 | 100 |
| VI-001 | 1280 | 100 |
| VI-002 | 1280 | 100 |
| VI-003 | 1280 | 100 |
| VI-004 | 1280 | 100 |
| VI-005 | 1280 | 100 |
| VI-006 | 1280 | 100 |
| VI-007 | 1280 | 100 |
| VI-008 | 1280 | 100 |

TABLE 31-continued

Post-emergence action against POAAN

| Example number | Dosage [g/ha] | POAAN |
|---|---|---|
| VI-011 | 1280 | 100 |
| VI-012 | 1280 | 100 |
| VI-013 | 1280 | 100 |
| VI-016 | 1280 | 100 |
| VI-018 | 1280 | 100 |
| VII-002 | 1280 | 100 |
| VII-003 | 1280 | 100 |
| VII-008 | 1280 | 100 |
| VII-009 | 1280 | 100 |
| VII-010 | 1280 | 100 |
| VII-012 | 1280 | 100 |
| VII-012 | 1280 | 100 |
| VII-014 | 1280 | 100 |
| VII-015 | 1280 | 100 |
| VII-016 | 1280 | 100 |
| VII-018 | 1280 | 100 |
| VII-019 | 1280 | 100 |
| VII-023 | 1280 | 100 |
| VII-025 | 1280 | 100 |
| VII-026 | 1280 | 100 |
| VII-028 | 1280 | 90 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-056 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-067 | 1280 | 100 |
| VII-068 | 1280 | 100 |
| VII-088 | 1280 | 100 |
| VII-089 | 1280 | 100 |
| VII-090 | 1280 | 100 |
| VII-091 | 1280 | 100 |
| VII-095 | 1280 | 100 |
| VII-096 | 1280 | 100 |
| VII-097 | 1280 | 100 |
| VII-098 | 1280 | 100 |
| VII-099 | 1280 | 100 |
| VII-100 | 1280 | 100 |
| VII-101 | 1280 | 100 |
| VII-102 | 1280 | 100 |
| VII-103 | 1280 | 100 |
| VII-104 | 1280 | 100 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 100 |
| VII-118 | 1280 | 100 |
| VII-119 | 1280 | 100 |
| VII-123 | 1280 | 100 |
| VII-123-a | 1280 | 100 |
| VII-124 | 1280 | 100 |
| VII-125 | 1280 | 100 |
| VII-132 | 1280 | 100 |
| VII-147 | 1280 | 100 |
| VII-148 | 1280 | 100 |
| VII-149 | 1280 | 100 |
| VIII-001 | 1280 | 100 |
| VIII-002 | 1280 | 100 |
| VIII-003 | 1280 | 100 |
| VIII-004 | 1280 | 100 |
| VIII-006 | 1280 | 100 |
| VIII-007 | 1280 | 100 |
| VIII-008 | 1280 | 100 |
| VIII-009 | 1280 | 100 |
| VIII-010 | 1280 | 100 |
| VIII-011 | 1280 | 100 |
| VIII-012 | 1280 | 100 |
| X-001 | 1280 | 100 |
| X-002 | 1280 | 100 |
| X-003 | 1280 | 100 |
| X-004 | 1280 | 100 |
| X-005 | 1280 | 100 |
| X-006 | 1280 | 100 |
| X-007 | 1280 | 100 |
| X-009 | 1280 | 100 |
| X-011 | 1280 | 100 |
| X-019 | 1280 | 100 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 100 |
| X-027 | 1280 | 100 |
| X-028 | 1280 | 100 |
| X-032 | 1280 | 100 |
| X-033 | 1280 | 100 |
| X-038 | 1280 | 100 |
| X-039 | 1280 | 100 |
| X-040 | 1280 | 100 |

TABLE 32

Post-emergence action against SETVI

| Example number | Dosage [g/ha] | SETVI |
|---|---|---|
| II-012 | 1280 | 90 |
| IV-001 | 1280 | 100 |
| VI-001 | 1280 | 100 |
| VI-002 | 1280 | 90 |
| VI-003 | 1280 | 100 |
| VI-004 | 1280 | 90 |
| VI-007 | 1280 | 90 |
| VI-011 | 1280 | 100 |
| VI-012 | 1280 | 90 |
| VI-013 | 1280 | 90 |
| VII-002 | 1280 | 90 |
| VII-003 | 1280 | 90 |
| VII-008 | 1280 | 90 |
| VII-009 | 1280 | 90 |
| VII-010 | 1280 | 90 |
| VII-012 | 1280 | 100 |
| VII-012 | 1280 | 90 |
| VII-015 | 1280 | 90 |
| VII-016 | 1280 | 90 |
| VII-018 | 1280 | 100 |
| VII-019 | 1280 | 90 |
| VII-025 | 1280 | 90 |
| VII-027 | 1280 | 90 |
| VII-028 | 1280 | 90 |
| VII-031 | 1280 | 90 |
| VII-032 | 1280 | 90 |
| VII-035 | 1280 | 90 |
| VII-036 | 1280 | 90 |
| VII-037 | 1280 | 90 |
| VII-040 | 1280 | 90 |
| VII-052 | 1280 | 90 |
| VII-056-a | 1280 | 100 |

TABLE 32-continued

Post-emergence action against SETVI

| Example number | Dosage [g/ha] | SETVI |
|---|---|---|
| VII-057 | 1280 | 100 |
| VII-061 | 1280 | 90 |
| VII-064 | 1280 | 100 |
| VII-064 | 1280 | 90 |
| VII-065 | 1280 | 90 |
| VII-066 | 1280 | 90 |
| VII-068 | 1280 | 90 |
| VII-088 | 1280 | 90 |
| VII-091 | 1280 | 90 |
| VII-095 | 1280 | 100 |
| VII-096 | 1280 | 90 |
| VII-097 | 1280 | 90 |
| VII-100 | 1280 | 100 |
| VII-101 | 1280 | 100 |
| VII-103 | 1280 | 90 |
| VII-104 | 1280 | 90 |
| VII-106 | 1280 | 90 |
| VII-107 | 1280 | 90 |
| VII-108 | 1280 | 90 |
| VII-109 | 1280 | 100 |
| VII-110 | 1280 | 90 |
| VII-111 | 1280 | 100 |
| VII-119 | 1280 | 100 |
| VII-123-a | 1280 | 100 |
| VII-124 | 1280 | 90 |
| VII-132 | 1280 | 90 |
| VII-147 | 1280 | 90 |
| VIII-001 | 1280 | 90 |
| VIII-002 | 1280 | 90 |
| VIII-003 | 1280 | 100 |
| VIII-004 | 1280 | 100 |
| VIII-006 | 1280 | 90 |
| VIII-009 | 1280 | 90 |
| VIII-010 | 1280 | 100 |
| VIII-011 | 1280 | 100 |
| X-002 | 1280 | 100 |
| X-004 | 1280 | 90 |
| X-005 | 1280 | 90 |
| X-007 | 1280 | 100 |
| X-009 | 1280 | 100 |
| X-021-a | 1280 | 100 |
| X-023 | 1280 | 90 |
| X-024 | 1280 | 90 |
| X-026 | 1280 | 100 |
| X-028 | 1280 | 90 |
| X-038 | 1280 | 90 |
| X-039 | 1280 | 100 |

TABLE 33

Post-emergence action against ABUTH

| Example number | Dosage [g/ha] | ABUTH |
|---|---|---|
| I-003 | 1280 | 90 |
| I-004 | 1280 | 90 |
| II-003 | 1280 | 90 |
| II-012 | 1280 | 90 |
| II-014 | 1280 | 90 |
| IV-002 | 1280 | 90 |
| IX-001 | 1280 | 90 |
| VI-002 | 1280 | 90 |
| VI-003 | 1280 | 90 |
| VI-004 | 1280 | 90 |
| VI-005 | 1280 | 90 |
| VI-008 | 1280 | 90 |
| VI-013 | 1280 | 90 |
| VI-018 | 1280 | 90 |
| VII-002 | 1280 | 90 |
| VII-008 | 1280 | 90 |
| VII-009 | 1280 | 90 |
| VII-010 | 1280 | 90 |
| VII-012 | 1280 | 100 |

TABLE 33-continued

Post-emergence action against ABUTH

| Example number | Dosage [g/ha] | ABUTH |
|---|---|---|
| VII-015 | 1280 | 90 |
| VII-016 | 1280 | 90 |
| VII-018 | 1280 | 90 |
| VII-025 | 1280 | 90 |
| VII-026 | 1280 | 90 |
| VII-028 | 1280 | 90 |
| VII-030 | 1280 | 90 |
| VII-031 | 1280 | 90 |
| VII-032 | 1280 | 90 |
| VII-035 | 1280 | 90 |
| VII-036 | 1280 | 90 |
| VII-037 | 1280 | 90 |
| VII-040 | 1280 | 90 |
| VII-052 | 1280 | 90 |
| VII-056-a | 1280 | 90 |
| VII-058 | 1280 | 90 |
| VII-061 | 1280 | 90 |
| VII-064 | 1280 | 90 |
| VII-064 | 1280 | 90 |
| VII-065 | 1280 | 90 |
| VII-066 | 1280 | 90 |
| VII-068 | 1280 | 100 |
| VII-069 | 1280 | 90 |
| VII-088 | 1280 | 90 |
| VII-089 | 1280 | 90 |
| VII-091 | 1280 | 90 |
| VII-098 | 1280 | 90 |
| VII-099 | 1280 | 90 |
| VII-100 | 1280 | 90 |
| VII-101 | 1280 | 90 |
| VII-104 | 1280 | 90 |
| VII-107 | 1280 | 90 |
| VII-108 | 1280 | 90 |
| VII-109 | 1280 | 100 |
| VII-110 | 1280 | 90 |
| VII-111 | 1280 | 90 |
| VII-119 | 1280 | 90 |
| VII-123 | 1280 | 90 |
| VII-123-a | 1280 | 90 |
| VII-124 | 1280 | 90 |
| VII-132 | 1280 | 90 |
| VII-147 | 1280 | 90 |
| VIII-001 | 1280 | 90 |
| VIII-003 | 1280 | 90 |
| VIII-007 | 1280 | 90 |
| VIII-011 | 1280 | 90 |
| X-002 | 1280 | 90 |
| X-003 | 1280 | 90 |
| X-005 | 1280 | 90 |
| X-006 | 1280 | 90 |
| X-007 | 1280 | 90 |
| X-009 | 1280 | 100 |
| X-019 | 1280 | 90 |
| X-020 | 1280 | 90 |
| X-021-a | 1280 | 100 |
| X-023 | 1280 | 90 |
| X-024 | 1280 | 100 |
| X-026 | 1280 | 90 |
| X-029 | 1280 | 90 |
| X-038 | 1280 | 90 |
| X-039 | 1280 | 100 |
| X-040 | 1280 | 90 |

TABLE 34

Post-emergence action against AMARE

| Example number | Dosage [g/ha] | AMARE |
|---|---|---|
| I-001 | 1280 | 90 |
| I-003 | 1280 | 100 |
| I-004 | 1280 | 90 |
| II-012 | 1280 | 100 |

TABLE 34-continued

Post-emergence action against AMARE

| Example number | Dosage [g/ha] | AMARE |
|---|---|---|
| II-014 | 1280 | 90 |
| II-018 | 1280 | 100 |
| IV-002 | 1280 | 100 |
| IV-003 | 1280 | 90 |
| VI-001 | 1280 | 90 |
| VI-002 | 1280 | 90 |
| VI-003 | 1280 | 90 |
| VI-004 | 1280 | 100 |
| VI-005 | 1280 | 90 |
| VI-012 | 1280 | 90 |
| VI-013 | 1280 | 90 |
| VI-016 | 1280 | 100 |
| VI-017 | 1280 | 90 |
| VI-018 | 1280 | 90 |
| VII-003 | 1280 | 100 |
| VII-008 | 1280 | 90 |
| VII-009 | 1280 | 100 |
| VII-012 | 1280 | 100 |
| VII-012 | 1280 | 90 |
| VII-014 | 1280 | 90 |
| VII-015 | 1280 | 90 |
| VII-016 | 1280 | 90 |
| VII-019 | 1280 | 90 |
| VII-025 | 1280 | 90 |
| VII-026 | 1280 | 90 |
| VII-027 | 1280 | 90 |
| VII-028 | 1280 | 100 |
| VII-029 | 1280 | 90 |
| VII-030 | 1280 | 90 |
| VII-031 | 1280 | 90 |
| VII-032 | 1280 | 100 |
| VII-035 | 1280 | 90 |
| VII-036 | 1280 | 100 |
| VII-037 | 1280 | 90 |
| VII-040 | 1280 | 90 |
| VII-052 | 1280 | 90 |
| VII-056 | 1280 | 100 |
| VII-056-a | 1280 | 100 |
| VII-057 | 1280 | 100 |
| VII-058 | 1280 | 100 |
| VII-059 | 1280 | 100 |
| VII-061 | 1280 | 90 |
| VII-063 | 1280 | 100 |
| VII-064 | 1280 | 90 |
| VII-064 | 1280 | 100 |
| VII-065 | 1280 | 90 |
| VII-066 | 1280 | 90 |
| VII-067 | 1280 | 100 |
| VII-068 | 1280 | 100 |
| VII-088 | 1280 | 100 |
| VII-089 | 1280 | 90 |
| VII-091 | 1280 | 90 |
| VII-095 | 1280 | 90 |
| VII-096 | 1280 | 100 |
| VII-099 | 1280 | 100 |
| VII-100 | 1280 | 100 |
| VII-101 | 1280 | 90 |
| VII-102 | 1280 | 100 |
| VII-103 | 1280 | 90 |
| VII-104 | 1280 | 90 |
| VII-107 | 1280 | 100 |
| VII-108 | 1280 | 100 |
| VII-109 | 1280 | 100 |
| VII-110 | 1280 | 90 |
| VII-111 | 1280 | 90 |
| VII-117 | 1280 | 100 |
| VII-119 | 1280 | 100 |
| VII-123 | 1280 | 90 |
| VII-123-a | 1280 | 90 |
| VII-124 | 1280 | 90 |
| VII-125 | 1280 | 90 |
| VII-132 | 1280 | 100 |
| VII-147 | 1280 | 100 |
| VII-148 | 1280 | 100 |
| VII-149 | 1280 | 100 |
| VIII-001 | 1280 | 90 |
| VIII-002 | 1280 | 100 |
| VIII-003 | 1280 | 90 |
| VIII-004 | 1280 | 90 |
| VIII-006 | 1280 | 100 |
| VIII-007 | 1280 | 100 |
| VIII-008 | 1280 | 90 |
| VIII-009 | 1280 | 90 |
| VIII-010 | 1280 | 100 |
| VIII-011 | 1280 | 100 |
| VIII-012 | 1280 | 100 |
| X-001 | 1280 | 90 |
| X-002 | 1280 | 90 |
| X-003 | 1280 | 90 |
| X-004 | 1280 | 100 |
| X-005 | 1280 | 100 |
| X-006 | 1280 | 100 |
| X-007 | 1280 | 90 |
| X-009 | 1280 | 100 |
| X-011 | 1280 | 90 |
| X-019 | 1280 | 90 |
| X-020 | 1280 | 100 |
| X-021-a | 1280 | 100 |
| X-023 | 1280 | 100 |
| X-024 | 1280 | 100 |
| X-026 | 1280 | 90 |
| X-029 | 1280 | 90 |
| X-033 | 1280 | 100 |
| X-039 | 1280 | 90 |

TABLE 35

Post-emergence action against KCHSC

| Example number | Dosage [g/ha] | KCHSC |
|---|---|---|
| II-004 | 1280 | 90 |
| II-012 | 1280 | 100 |
| IV-001 | 1280 | 90 |
| IV-002 | 1280 | 90 |
| IX-001 | 1280 | 90 |
| VI-003 | 1280 | 90 |
| VI-005 | 1280 | 90 |
| VI-006 | 1280 | 90 |
| VI-008 | 1280 | 90 |
| VI-011 | 1280 | 90 |
| VI-012 | 1280 | 90 |
| VI-013 | 1280 | 100 |
| VI-018 | 1280 | 90 |
| VII-008 | 1280 | 90 |
| VII-012 | 1280 | 90 |
| VII-018 | 1280 | 90 |
| VII-019 | 1280 | 90 |
| VII-026 | 1280 | 90 |
| VII-029 | 1280 | 90 |
| VII-030 | 1280 | 90 |
| VII-040 | 1280 | 90 |
| VII-057 | 1280 | 90 |
| VII-059 | 1280 | 100 |
| VII-061 | 1280 | 90 |
| VII-062 | 1280 | 90 |
| VII-064 | 1280 | 90 |
| VII-064 | 1280 | 90 |
| VII-065 | 1280 | 100 |
| VII-066 | 1280 | 90 |
| VII-068 | 1280 | 90 |
| VII-069 | 1280 | 90 |
| VII-095 | 1280 | 100 |
| VII-096 | 1280 | 90 |
| VII-099 | 1280 | 100 |
| VII-100 | 1280 | 90 |
| VII-101 | 1280 | 90 |
| VII-102 | 1280 | 90 |
| VII-106 | 1280 | 100 |

TABLE 35-continued

Post-emergence action against KCHSC

| Example number | Dosage [g/ha] | KCHSC |
|---|---|---|
| VII-108 | 1280 | 90 |
| VII-109 | 1280 | 90 |
| VII-118 | 1280 | 90 |
| VII-123-a | 1280 | 90 |
| VII-124 | 1280 | 90 |
| VII-125 | 1280 | 90 |
| VII-132 | 1280 | 100 |
| VII-147 | 1280 | 90 |
| VIII-006 | 1280 | 90 |
| VIII-009 | 1280 | 90 |
| VIII-010 | 1280 | 90 |
| X-009 | 1280 | 90 |
| X-020 | 1280 | 100 |
| X-021-a | 1280 | 100 |
| X-024 | 1280 | 90 |
| X-025 | 1280 | 90 |
| X-028 | 1280 | 90 |
| X-029 | 1280 | 90 |
| X-032 | 1280 | 90 |
| X-039 | 1280 | 90 |

TABLE 36

Post-emergence action against MATIN

| Example number | Dosage [g/ha] | MATIN |
|---|---|---|
| I-003 | 1280 | 90 |
| II-003 | 1280 | 90 |
| II-012 | 1280 | 90 |
| II-013 | 1280 | 90 |
| II-014 | 1280 | 90 |
| II-017 | 1280 | 90 |
| II-018 | 1280 | 90 |
| IV-002 | 1280 | 90 |
| IX-001 | 1280 | 90 |
| VI-001 | 1280 | 90 |
| VI-002 | 1280 | 100 |
| VI-003 | 1280 | 100 |
| VI-004 | 1280 | 100 |
| VI-005 | 1280 | 90 |
| VI-006 | 1280 | 100 |
| VI-007 | 1280 | 90 |
| VI-008 | 1280 | 90 |
| VI-013 | 1280 | 100 |
| VI-016 | 1280 | 90 |
| VI-018 | 1280 | 100 |
| VII-002 | 1280 | 90 |
| VII-003 | 1280 | 100 |
| VII-008 | 1280 | 90 |
| VII-009 | 1280 | 100 |
| VII-010 | 1280 | 90 |
| VII-012 | 1280 | 100 |
| VII-012 | 1280 | 90 |
| VII-015 | 1280 | 100 |
| VII-016 | 1280 | 100 |
| VII-018 | 1280 | 90 |
| VII-023 | 1280 | 90 |
| VII-025 | 1280 | 90 |
| VII-026 | 1280 | 90 |
| VII-028 | 1280 | 90 |
| VII-031 | 1280 | 100 |
| VII-032 | 1280 | 90 |
| VII-035 | 1280 | 90 |
| VII-036 | 1280 | 100 |
| VII-037 | 1280 | 90 |
| VII-040 | 1280 | 90 |
| VII-052 | 1280 | 100 |
| VII-056 | 1280 | 100 |
| VII-056-a | 1280 | 100 |
| VII-057 | 1280 | 100 |
| VII-058 | 1280 | 90 |
| VII-059 | 1280 | 100 |
| VII-061 | 1280 | 100 |
| VII-063 | 1280 | 90 |
| VII-064 | 1280 | 100 |
| VII-064 | 1280 | 90 |
| VII-065 | 1280 | 100 |
| VII-066 | 1280 | 90 |
| VII-067 | 1280 | 90 |
| VII-068 | 1280 | 90 |
| VII-069 | 1280 | 90 |
| VII-088 | 1280 | 100 |
| VII-089 | 1280 | 90 |
| VII-090 | 1280 | 90 |
| VII-091 | 1280 | 90 |
| VII-095 | 1280 | 100 |
| VII-096 | 1280 | 90 |
| VII-097 | 1280 | 90 |
| VII-098 | 1280 | 100 |
| VII-099 | 1280 | 100 |
| VII-100 | 1280 | 90 |
| VII-101 | 1280 | 100 |
| VII-102 | 1280 | 100 |
| VII-103 | 1280 | 90 |
| VII-104 | 1280 | 100 |
| VII-105 | 1280 | 100 |
| VII-106 | 1280 | 90 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-117 | 1280 | 90 |
| VII-118 | 1280 | 90 |
| VII-119 | 1280 | 100 |
| VII-123 | 1280 | 90 |
| VII-123-a | 1280 | 90 |
| VII-124 | 1280 | 100 |
| VII-125 | 1280 | 90 |
| VII-132 | 1280 | 90 |
| VII-147 | 1280 | 100 |
| VII-148 | 1280 | 100 |
| VII-149 | 1280 | 100 |
| VIII-001 | 1280 | 90 |
| VIII-002 | 1280 | 90 |
| VIII-004 | 1280 | 90 |
| VIII-006 | 1280 | 100 |
| VIII-007 | 1280 | 90 |
| VIII-008 | 1280 | 90 |
| VIII-009 | 1280 | 90 |
| VIII-010 | 1280 | 100 |
| VIII-011 | 1280 | 90 |
| VIII-012 | 1280 | 100 |
| X-003 | 1280 | 100 |
| X-004 | 1280 | 90 |
| X-005 | 1280 | 100 |
| X-006 | 1280 | 100 |
| X-007 | 1280 | 90 |
| X-009 | 1280 | 90 |
| X-011 | 1280 | 100 |
| X-020 | 1280 | 90 |
| X-021-a | 1280 | 90 |
| X-023 | 1280 | 100 |
| X-024 | 1280 | 90 |
| X-025 | 1280 | 90 |
| X-026 | 1280 | 100 |
| X-028 | 1280 | 100 |
| X-032 | 1280 | 90 |
| X-033 | 1280 | 100 |
| X-038 | 1280 | 100 |
| X-039 | 1280 | 100 |
| X-040 | 1280 | 100 |

TABLE 37

Post-emergence action against STEME

| Example number | Dosage [g/ha] | STEME |
|---|---|---|
| IV-002 | 1280 | 100 |
| IX-001 | 1280 | 100 |
| VI-001 | 1280 | 100 |
| VI-002 | 1280 | 90 |
| VI-004 | 1280 | 90 |
| VI-005 | 1280 | 100 |
| VI-006 | 1280 | 100 |
| VI-007 | 1280 | 100 |
| VI-008 | 1280 | 90 |
| VI-011 | 1280 | 100 |
| VI-012 | 1280 | 90 |
| VI-013 | 1280 | 100 |
| VI-018 | 1280 | 90 |
| VII-002 | 1280 | 90 |
| VII-003 | 1280 | 100 |
| VII-008 | 1280 | 100 |
| VII-009 | 1280 | 100 |
| VII-010 | 1280 | 100 |
| VII-012 | 1280 | 100 |
| VII-012 | 1280 | 100 |
| VII-014 | 1280 | 90 |
| VII-015 | 1280 | 100 |
| VII-016 | 1280 | 100 |
| VII-018 | 1280 | 100 |
| VII-019 | 1280 | 100 |
| VII-023 | 1280 | 100 |
| VII-025 | 1280 | 100 |
| VII-026 | 1280 | 100 |
| VII-028 | 1280 | 100 |
| VII-029 | 1280 | 100 |
| VII-030 | 1280 | 100 |
| VII-031 | 1280 | 100 |
| VII-032 | 1280 | 100 |
| VII-035 | 1280 | 100 |
| VII-036 | 1280 | 100 |
| VII-037 | 1280 | 100 |
| VII-040 | 1280 | 100 |
| VII-052 | 1280 | 100 |
| VII-058 | 1280 | 90 |
| VII-059 | 1280 | 100 |
| VII-061 | 1280 | 100 |
| VII-062 | 1280 | 100 |
| VII-063 | 1280 | 100 |
| VII-064 | 1280 | 100 |
| VII-064 | 1280 | 100 |
| VII-065 | 1280 | 100 |
| VII-066 | 1280 | 100 |
| VII-069 | 1280 | 90 |
| VII-088 | 1280 | 90 |
| VII-089 | 1280 | 100 |
| VII-091 | 1280 | 90 |
| VII-095 | 1280 | 90 |
| VII-096 | 1280 | 100 |
| VII-097 | 1280 | 90 |
| VII-099 | 1280 | 100 |
| VII-100 | 1280 | 100 |
| VII-101 | 1280 | 100 |
| VII-104 | 1280 | 90 |
| VII-105 | 1280 | 100 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 100 |
| VII-118 | 1280 | 100 |
| VII-119 | 1280 | 100 |
| VII-123-a | 1280 | 100 |
| VII-124 | 1280 | 100 |
| VII-125 | 1280 | 90 |
| VII-147 | 1280 | 100 |
| VIII-001 | 1280 | 100 |
| VIII-002 | 1280 | 100 |
| VIII-003 | 1280 | 100 |
| VIII-004 | 1280 | 100 |
| VIII-006 | 1280 | 100 |
| VIII-007 | 1280 | 100 |
| VIII-008 | 1280 | 90 |
| VIII-010 | 1280 | 100 |
| VIII-012 | 1280 | 90 |
| X-002 | 1280 | 90 |
| X-003 | 1280 | 90 |
| X-004 | 1280 | 100 |
| X-005 | 1280 | 90 |
| X-006 | 1280 | 100 |
| X-007 | 1280 | 100 |
| X-009 | 1280 | 100 |
| X-020 | 1280 | 100 |
| X-023 | 1280 | 100 |
| X-024 | 1280 | 100 |
| X-026 | 1280 | 100 |
| X-028 | 1280 | 90 |
| X-039 | 1280 | 100 |

TABLE 38

Post-emergence action against VERPE

| Example number | Dosage [g/ha] | VERPE |
|---|---|---|
| I-002 | 1280 | 90 |
| I-003 | 1280 | 90 |
| I-004 | 1280 | 100 |
| II-003 | 1280 | 100 |
| II-004 | 1280 | 100 |
| II-012 | 1280 | 100 |
| II-013 | 1280 | 90 |
| II-014 | 1280 | 90 |
| II-017 | 1280 | 90 |
| IV-001 | 1280 | 90 |
| IV-002 | 1280 | 90 |
| IV-003 | 1280 | 90 |
| IX-001 | 1280 | 100 |
| VI-001 | 1280 | 100 |
| VI-002 | 1280 | 90 |
| VI-003 | 1280 | 90 |
| VI-004 | 1280 | 90 |
| VI-005 | 1280 | 90 |
| VI-006 | 1280 | 90 |
| VI-007 | 1280 | 90 |
| VI-012 | 1280 | 90 |
| VI-013 | 1280 | 100 |
| VI-016 | 1280 | 90 |
| VI-018 | 1280 | 100 |
| VII-003 | 1280 | 90 |
| VII-008 | 1280 | 100 |
| VII-009 | 1280 | 90 |
| VII-010 | 1280 | 90 |
| VII-012 | 1280 | 90 |
| VII-012 | 1280 | 90 |
| VII-013 | 1280 | 100 |
| VII-014 | 1280 | 90 |
| VII-015 | 1280 | 100 |
| VII-016 | 1280 | 90 |
| VII-017 | 1280 | 100 |
| VII-018 | 1280 | 90 |
| VII-019 | 1280 | 90 |
| VII-022 | 1280 | 90 |
| VII-023 | 1280 | 100 |
| VII-025 | 1280 | 100 |
| VII-026 | 1280 | 100 |
| VII-027 | 1280 | 90 |
| VII-028 | 1280 | 90 |
| VII-029 | 1280 | 90 |
| VII-030 | 1280 | 90 |
| VII-031 | 1280 | 100 |
| VII-032 | 1280 | 100 |
| VII-035 | 1280 | 100 |
| VII-036 | 1280 | 100 |

TABLE 38-continued

Post-emergence action against VERPE

| Example number | Dosage [g/ha] | VERPE |
|---|---|---|
| VII-037 | 1280 | 100 |
| VII-040 | 1280 | 100 |
| VII-052 | 1280 | 100 |
| VII-056 | 1280 | 90 |
| VII-056-a | 1280 | 100 |
| VII-057 | 1280 | 90 |
| VII-058 | 1280 | 90 |
| VII-059 | 1280 | 90 |
| VII-061 | 1280 | 100 |
| VII-062 | 1280 | 100 |
| VII-063 | 1280 | 90 |
| VII-064 | 1280 | 100 |
| VII-064 | 1280 | 100 |
| VII-065 | 1280 | 90 |
| VII-066 | 1280 | 90 |
| VII-068 | 1280 | 100 |
| VII-069 | 1280 | 100 |
| VII-089 | 1280 | 90 |
| VII-090 | 1280 | 100 |
| VII-091 | 1280 | 100 |
| VII-095 | 1280 | 90 |
| VII-096 | 1280 | 90 |
| VII-097 | 1280 | 100 |
| VII-098 | 1280 | 90 |
| VII-099 | 1280 | 100 |
| VII-100 | 1280 | 100 |
| VII-101 | 1280 | 100 |
| VII-102 | 1280 | 100 |
| VII-103 | 1280 | 100 |
| VII-104 | 1280 | 90 |
| VII-105 | 1280 | 90 |
| VII-106 | 1280 | 100 |
| VII-107 | 1280 | 100 |
| VII-108 | 1280 | 100 |
| VII-109 | 1280 | 100 |
| VII-110 | 1280 | 100 |
| VII-111 | 1280 | 90 |
| VII-117 | 1280 | 100 |
| VII-119 | 1280 | 100 |
| VII-123 | 1280 | 90 |
| VII-123-a | 1280 | 90 |
| VII-124 | 1280 | 100 |
| VII-125 | 1280 | 100 |
| VII-132 | 1280 | 90 |
| VII-147 | 1280 | 100 |
| VII-149 | 1280 | 90 |
| VIII-001 | 1280 | 100 |
| VIII-002 | 1280 | 90 |
| VIII-003 | 1280 | 90 |
| VIII-004 | 1280 | 90 |
| VIII-006 | 1280 | 90 |
| VIII-007 | 1280 | 100 |
| VIII-008 | 1280 | 90 |
| VIII-009 | 1280 | 100 |
| VIII-010 | 1280 | 90 |
| VIII-011 | 1280 | 100 |
| VIII-012 | 1280 | 90 |
| X-001 | 1280 | 100 |
| X-002 | 1280 | 90 |
| X-003 | 1280 | 90 |
| X-004 | 1280 | 100 |
| X-005 | 1280 | 100 |
| X-006 | 1280 | 90 |
| X-007 | 1280 | 90 |
| X-009 | 1280 | 100 |
| X-011 | 1280 | 90 |
| X-019 | 1280 | 90 |
| X-020 | 1280 | 100 |
| X-021-a | 1280 | 100 |
| X-023 | 1280 | 100 |
| X-024 | 1280 | 100 |
| X-025 | 1280 | 100 |
| X-026 | 1280 | 90 |
| X-027 | 1280 | 100 |
| X-028 | 1280 | 100 |
| X-029 | 1280 | 100 |
| X-032 | 1280 | 100 |
| X-033 | 1280 | 100 |
| X-038 | 1280 | 100 |
| X-039 | 1280 | 100 |
| X-040 | 1280 | 100 |

As shown by the results, compounds of the general formula (I) of the invention, in post-emergence treatment, have very good herbicidal efficacy (90% to 100% herbicidal action) against harmful plants such as *Abutilon theophrasti, Digitaria sanguinalis, Echinochloa crus-galli, Matricaria inodora, Poa annua*, at an application rate of 1.28 kg of active substance per hectare.

Accordingly, the compounds of the invention have good herbicidal action against a broad spectrum of weed grasses and broad-leaved weeds and are therefore suitable for controlling unwanted vegetation by the post-emergence method.

b) Seeds of monocotyledonous and dicotyledonous weeds and crop plants are placed in sandy loam in plastic or organic planting pots, covered with soil and cultivated in a greenhouse under controlled growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion with addition of 0.5% additive at a water application rate of 600 l/ha (converted). After the test plants have been kept in the greenhouse under optimum growth conditions for about 3 weeks, the activity of the preparations is rated visually in comparison to untreated controls. For example, 100% activity=the plants have died, 0% activity=like control plants.

Tables 39 to 49 below show the effects of selected compounds of the general formula (I) according to Tables 1 and 2 on various harmful plants and at an application rate corresponding to 320 g/ha, which were obtained by the experimental procedure mentioned above.

TABLE 39

Post-emergence action against ALOMY

| Example number | Dosage [g/ha] | ALOMY |
|---|---|---|
| VI-001 | 320 | 90 |
| VI-011 | 320 | 90 |
| VI-013 | 320 | 80 |
| VII-001 | 320 | 90 |
| VII-002 | 320 | 100 |
| VII-003 | 320 | 80 |
| VII-004 | 320 | 90 |
| VII-005 | 320 | 100 |
| VII-008 | 320 | 100 |
| VII-010 | 320 | 90 |
| VII-012 | 320 | 90 |
| VII-012 | 320 | 90 |
| VII-014 | 320 | 90 |
| VII-015 | 320 | 90 |
| VII-016 | 320 | 90 |
| VII-018 | 320 | 90 |
| VII-019 | 320 | 100 |
| VII-023 | 320 | 90 |
| VII-025 | 320 | 100 |
| VII-026 | 320 | 100 |
| VII-028 | 320 | 80 |

TABLE 39-continued

Post-emergence action against ALOMY

| Example number | Dosage [g/ha] | ALOMY |
|---|---|---|
| VII-029 | 320 | 100 |
| VII-031 | 320 | 100 |
| VII-032 | 320 | 90 |
| VII-034 | 320 | 90 |
| VII-035 | 320 | 90 |
| VII-036 | 320 | 90 |
| VII-037 | 320 | 100 |
| VII-040 | 320 | 100 |
| VII-052 | 320 | 90 |
| VII-056-a | 320 | 90 |
| VII-057 | 320 | 80 |
| VII-062 | 320 | 90 |
| VII-066 | 320 | 90 |
| VII-089 | 320 | 90 |
| VII-091 | 320 | 90 |
| VII-103 | 320 | 100 |
| VII-105 | 320 | 90 |
| VII-107 | 320 | 90 |
| VII-111 | 320 | 100 |
| VII-117 | 320 | 90 |
| VII-118 | 320 | 90 |
| VII-132 | 320 | 90 |
| VII-147 | 320 | 90 |
| VIII-001 | 320 | 90 |
| VIII-002 | 320 | 90 |
| VIII-003 | 320 | 90 |
| VIII-004 | 320 | 90 |
| VIII-006 | 320 | 100 |
| X-001 | 320 | 90 |
| X-002 | 320 | 100 |
| X-004 | 320 | 100 |
| X-005 | 320 | 90 |
| X-007 | 320 | 100 |

TABLE 40

Post-emergence action at 320 g/ha against DIGSA in %

| Example number | Dosage [g/ha] | DIGSA |
|---|---|---|
| VI-001 | 320 | 90 |
| VI-004 | 320 | 90 |
| VI-007 | 320 | 80 |
| VI-011 | 320 | 90 |
| VI-013 | 320 | 90 |
| VII-001 | 320 | 90 |
| VII-003 | 320 | 90 |
| VII-004 | 320 | 90 |
| VII-005 | 320 | 90 |
| VII-008 | 320 | 80 |
| VII-010 | 320 | 90 |
| VII-012 | 320 | 80 |
| VII-012 | 320 | 90 |
| VII-014 | 320 | 80 |
| VII-015 | 320 | 100 |
| VII-019 | 320 | 90 |
| VII-023 | 320 | 90 |
| VII-025 | 320 | 100 |
| VII-026 | 320 | 90 |
| VII-031 | 320 | 100 |
| VII-032 | 320 | 90 |
| VII-034 | 320 | 90 |
| VII-035 | 320 | 100 |
| VII-036 | 320 | 90 |
| VII-037 | 320 | 90 |
| VII-052 | 320 | 90 |
| VII-057 | 320 | 90 |
| VII-062 | 320 | 90 |
| VII-066 | 320 | 90 |
| VII-089 | 320 | 90 |
| VII-091 | 320 | 90 |
| VII-103 | 320 | 90 |
| VII-107 | 320 | 90 |

TABLE 40-continued

Post-emergence action at 320 g/ha against DIGSA in %

| Example number | Dosage [g/ha] | DIGSA |
|---|---|---|
| VII-111 | 320 | 90 |
| VII-117 | 320 | 90 |
| VII-118 | 320 | 90 |
| VII-132 | 320 | 90 |
| VIII-003 | 320 | 80 |
| VIII-004 | 320 | 90 |
| X-001 | 320 | 80 |
| X-002 | 320 | 100 |
| X-004 | 320 | 90 |
| X-005 | 320 | 90 |

TABLE 41

Post-emergence action at 320 g/ha against ECHCG in %

| Example number | Dosage [g/ha] | ECHCG |
|---|---|---|
| VI-007 | 320 | 80 |
| VII-001 | 320 | 100 |
| VII-002 | 320 | 90 |
| VII-003 | 320 | 90 |
| VII-004 | 320 | 90 |
| VII-005 | 320 | 90 |
| VII-008 | 320 | 90 |
| VII-010 | 320 | 90 |
| VII-012 | 320 | 90 |
| VII-012 | 320 | 90 |
| VII-014 | 320 | 80 |
| VII-015 | 320 | 90 |
| VII-016 | 320 | 80 |
| VII-019 | 320 | 90 |
| VII-023 | 320 | 80 |
| VII-025 | 320 | 90 |
| VII-028 | 320 | 80 |
| VII-029 | 320 | 80 |
| VII-031 | 320 | 90 |
| VII-032 | 320 | 90 |
| VII-034 | 320 | 90 |
| VII-035 | 320 | 90 |
| VII-036 | 320 | 80 |
| VII-037 | 320 | 80 |
| VII-040 | 320 | 80 |
| VII-056-a | 320 | 80 |
| VII-062 | 320 | 80 |
| VII-066 | 320 | 80 |
| VII-103 | 320 | 80 |
| VII-107 | 320 | 80 |
| VII-111 | 320 | 90 |
| VII-132 | 320 | 80 |
| VII-147 | 320 | 80 |
| VIII-003 | 320 | 80 |
| VIII-004 | 320 | 90 |
| VIII-006 | 320 | 90 |
| X-001 | 320 | 80 |
| X-002 | 320 | 100 |
| X-004 | 320 | 90 |
| X-005 | 320 | 80 |
| X-007 | 320 | 80 |

TABLE 42

Post-emergence action at 320 g/ha against ABUTH in %

| Example number | Dosage [g/ha] | ABUTH |
|---|---|---|
| VI-001 | 320 | 80 |
| VI-004 | 320 | 80 |
| VI-007 | 320 | 90 |
| VI-011 | 320 | 90 |
| VI-012 | 320 | 80 |
| VI-013 | 320 | 80 |

TABLE 42-continued

Post-emergence action at 320 g/ha against ABUTH in %

| Example number | Dosage [g/ha] | ABUTH |
| --- | --- | --- |
| VII-001 | 320 | 80 |
| VII-002 | 320 | 80 |
| VII-003 | 320 | 80 |
| VII-005 | 320 | 80 |
| VII-008 | 320 | 90 |
| VII-010 | 320 | 80 |
| VII-012 | 320 | 80 |
| VII-015 | 320 | 90 |
| VII-016 | 320 | 90 |
| VII-018 | 320 | 80 |
| VII-019 | 320 | 80 |
| VII-023 | 320 | 90 |
| VII-025 | 320 | 90 |
| VII-026 | 320 | 80 |
| VII-028 | 320 | 80 |
| VII-029 | 320 | 80 |
| VII-031 | 320 | 90 |
| VII-032 | 320 | 80 |
| VII-034 | 320 | 80 |
| VII-035 | 320 | 90 |
| VII-040 | 320 | 90 |
| VII-111 | 320 | 80 |
| X-001 | 320 | 80 |
| X-002 | 320 | 90 |
| X-004 | 320 | 80 |

TABLE 43

Post-emergence action at 320 g/ha against AMARE in %

| Example number | Dosage [g/ha] | AMARE |
| --- | --- | --- |
| VI-004 | 320 | 90 |
| VI-007 | 320 | 80 |
| VI-011 | 320 | 80 |
| VI-012 | 320 | 80 |
| VI-013 | 320 | 90 |
| VII-001 | 320 | 90 |
| VII-003 | 320 | 90 |
| VII-004 | 320 | 90 |
| VII-008 | 320 | 90 |
| VII-010 | 320 | 90 |
| VII-012 | 320 | 90 |
| VII-012 | 320 | 80 |
| VII-014 | 320 | 90 |
| VII-015 | 320 | 90 |
| VII-016 | 320 | 90 |
| VII-018 | 320 | 90 |
| VII-019 | 320 | 80 |
| VII-023 | 320 | 90 |
| VII-025 | 320 | 90 |
| VII-026 | 320 | 90 |
| VII-028 | 320 | 80 |
| VII-031 | 320 | 90 |
| VII-032 | 320 | 90 |
| VII-034 | 320 | 80 |
| VII-035 | 320 | 90 |
| VII-040 | 320 | 90 |
| VII-089 | 320 | 80 |
| VII-111 | 320 | 90 |
| VII-132 | 320 | 90 |
| VIII-002 | 320 | 80 |
| VIII-004 | 320 | 90 |
| VIII-006 | 320 | 80 |
| X-001 | 320 | 80 |
| X-002 | 320 | 100 |
| X-004 | 320 | 90 |
| X-005 | 320 | 80 |

TABLE 44

Post-emergence action at 320 g/ha against SETVI in %

| Example number | Dosage [g/ha] | SETVI |
| --- | --- | --- |
| VI-001 | 320 | 80 |
| VI-004 | 320 | 80 |
| VI-011 | 320 | 90 |
| VI-012 | 320 | 90 |
| VI-013 | 320 | 90 |
| VII-001 | 320 | 90 |
| VII-002 | 320 | 80 |
| VII-004 | 320 | 90 |
| VII-005 | 320 | 80 |
| VII-008 | 320 | 100 |
| VII-010 | 320 | 90 |
| VII-012 | 320 | 100 |
| VII-012 | 320 | 80 |
| VII-014 | 320 | 100 |
| VII-015 | 320 | 100 |
| VII-016 | 320 | 80 |
| VII-018 | 320 | 80 |
| VII-019 | 320 | 80 |
| VII-025 | 320 | 100 |
| VII-026 | 320 | 90 |
| VII-028 | 320 | 80 |
| VII-031 | 320 | 90 |
| VII-032 | 320 | 80 |
| VII-034 | 320 | 90 |
| VII-035 | 320 | 90 |
| VII-036 | 320 | 90 |
| VII-037 | 320 | 80 |
| VII-040 | 320 | 100 |
| VII-056-a | 320 | 80 |
| VII-057 | 320 | 80 |
| VII-091 | 320 | 80 |
| VII-103 | 320 | 80 |
| VII-107 | 320 | 80 |
| VII-111 | 320 | 90 |
| VII-117 | 320 | 80 |
| VII-118 | 320 | 80 |
| VII-147 | 320 | 80 |
| VIII-001 | 320 | 80 |
| VIII-004 | 320 | 80 |
| VIII-006 | 320 | 90 |
| X-001 | 320 | 90 |
| X-002 | 320 | 90 |
| X-004 | 320 | 90 |
| X-005 | 320 | 90 |
| X-007 | 320 | 80 |

TABLE 45

Post-emergence action at 320 g/ha against PHBPU in %

| Example number | Dosage [g/ha] | PHBPU |
| --- | --- | --- |
| VI-004 | 320 | 80 |
| VI-007 | 320 | 90 |
| VI-012 | 320 | 80 |
| VI-013 | 320 | 80 |
| VII-001 | 320 | 90 |
| VII-002 | 320 | 90 |
| VII-003 | 320 | 90 |
| VII-005 | 320 | 90 |
| VII-008 | 320 | 80 |
| VII-010 | 320 | 90 |
| VII-012 | 320 | 90 |
| VII-012 | 320 | 80 |
| VII-015 | 320 | 90 |
| VII-016 | 320 | 90 |
| VII-018 | 320 | 90 |
| VII-019 | 320 | 90 |
| VII-023 | 320 | 90 |
| VII-025 | 320 | 90 |
| VII-028 | 320 | 90 |
| VII-031 | 320 | 90 |
| VII-032 | 320 | 90 |

TABLE 45-continued

Post-emergence action at 320 g/ha against PHBPU in %

| Example number | Dosage [g/ha] | PHBPU |
|---|---|---|
| VII-034 | 320 | 90 |
| VII-035 | 320 | 100 |
| VII-036 | 320 | 80 |
| VII-037 | 320 | 80 |
| VII-040 | 320 | 90 |
| VII-052 | 320 | 80 |
| VII-062 | 320 | 80 |
| VII-089 | 320 | 80 |
| VII-103 | 320 | 80 |
| VII-111 | 320 | 80 |
| VII-132 | 320 | 90 |
| VII-147 | 320 | 90 |
| VIII-003 | 320 | 80 |
| VIII-004 | 320 | 90 |
| X-001 | 320 | 80 |
| X-002 | 320 | 90 |
| X-004 | 320 | 90 |
| X-005 | 320 | 80 |

TABLE 46

Post-emergence action at 320 g/ha against POLCO in %

| Example number | Dosage [g/ha] | POLCO |
|---|---|---|
| VI-001 | 320 | 90 |
| VI-004 | 320 | 80 |
| VI-007 | 320 | 80 |
| VI-011 | 320 | 80 |
| VII-001 | 320 | 80 |
| VII-002 | 320 | 80 |
| VII-003 | 320 | 90 |
| VII-004 | 320 | 80 |
| VII-005 | 320 | 80 |
| VII-010 | 320 | 80 |
| VII-012 | 320 | 90 |
| VII-012 | 320 | 80 |
| VII-014 | 320 | 80 |
| VII-015 | 320 | 100 |
| VII-016 | 320 | 90 |
| VII-018 | 320 | 90 |
| VII-019 | 320 | 90 |
| VII-023 | 320 | 90 |
| VII-025 | 320 | 90 |
| VII-026 | 320 | 90 |
| VII-029 | 320 | 80 |
| VII-031 | 320 | 90 |
| VII-032 | 320 | 80 |
| VII-034 | 320 | 80 |
| VII-035 | 320 | 90 |
| VII-040 | 320 | 90 |
| VII-111 | 320 | 90 |
| VIII-001 | 320 | 90 |
| VIII-002 | 320 | 80 |
| VIII-003 | 320 | 80 |
| VIII-004 | 320 | 80 |
| X-001 | 320 | 80 |
| X-002 | 320 | 90 |
| X-004 | 320 | 80 |
| X-005 | 320 | 80 |

TABLE 47

Post-emergence action at 320 g/ha against VIOTR in %

| Example number | Dosage [g/ha] | VIOTR |
|---|---|---|
| VI-004 | 320 | 80 |
| VI-007 | 320 | 90 |
| VI-011 | 320 | 90 |
| VI-012 | 320 | 100 |

TABLE 47-continued

Post-emergence action at 320 g/ha against VIOTR in %

| Example number | Dosage [g/ha] | VIOTR |
|---|---|---|
| VI-013 | 320 | 90 |
| VII-001 | 320 | 80 |
| VII-002 | 320 | 90 |
| VII-003 | 320 | 90 |
| VII-004 | 320 | 90 |
| VII-005 | 320 | 100 |
| VII-008 | 320 | 90 |
| VII-010 | 320 | 80 |
| VII-012 | 320 | 90 |
| VII-012 | 320 | 90 |
| VII-014 | 320 | 90 |
| VII-015 | 320 | 90 |
| VII-016 | 320 | 80 |
| VII-018 | 320 | 90 |
| VII-019 | 320 | 90 |
| VII-023 | 320 | 80 |
| VII-025 | 320 | 90 |
| VII-026 | 320 | 90 |
| VII-028 | 320 | 80 |
| VII-029 | 320 | 100 |
| VII-031 | 320 | 90 |
| VII-032 | 320 | 90 |
| VII-034 | 320 | 80 |
| VII-035 | 320 | 90 |
| VII-036 | 320 | 80 |
| VII-037 | 320 | 80 |
| VII-040 | 320 | 90 |
| VII-052 | 320 | 80 |
| VII-057 | 320 | 80 |
| VII-062 | 320 | 80 |
| VII-066 | 320 | 80 |
| VII-107 | 320 | 80 |
| VII-111 | 320 | 90 |
| VII-117 | 320 | 80 |
| VII-132 | 320 | 80 |
| VIII-001 | 320 | 80 |
| VIII-002 | 320 | 80 |
| VIII-003 | 320 | 80 |
| VIII-004 | 320 | 90 |
| X-002 | 320 | 90 |
| X-004 | 320 | 80 |
| X-005 | 320 | 80 |
| X-007 | 320 | 80 |

TABLE 48

Post-emergence action at 320 g/ha against AVEFA in %

| Example number | Dosage [g/ha] | AVEFA |
|---|---|---|
| VI-001 | 320 | 80 |
| VI-004 | 320 | 100 |
| VI-007 | 320 | 100 |
| VI-011 | 320 | 90 |
| VI-012 | 320 | 90 |
| VI-013 | 320 | 80 |
| VI-016 | 320 | 90 |
| VII-001 | 320 | 90 |
| VII-002 | 320 | 100 |
| VII-003 | 320 | 80 |
| VII-004 | 320 | 90 |
| VII-005 | 320 | 100 |
| VII-008 | 320 | 90 |
| VII-010 | 320 | 100 |
| VII-012 | 320 | 90 |
| VII-012 | 320 | 90 |
| VII-014 | 320 | 90 |
| VII-015 | 320 | 90 |
| VII-016 | 320 | 80 |
| VII-018 | 320 | 80 |
| VII-019 | 320 | 100 |
| VII-023 | 320 | 80 |
| VII-025 | 320 | 90 |

TABLE 48-continued

Post-emergence action at 320 g/ha against AVEFA in %

| Example number | Dosage [g/ha] | AVEFA |
|---|---|---|
| VII-026 | 320 | 80 |
| VII-028 | 320 | 80 |
| VII-029 | 320 | 90 |
| VII-031 | 320 | 90 |
| VII-032 | 320 | 100 |
| VII-034 | 320 | 90 |
| VII-035 | 320 | 90 |
| VII-036 | 320 | 80 |
| VII-037 | 320 | 80 |
| VII-040 | 320 | 90 |
| VII-052 | 320 | 90 |
| VII-062 | 320 | 90 |
| VII-089 | 320 | 80 |
| VII-091 | 320 | 80 |
| VII-103 | 320 | 80 |
| VII-111 | 320 | 90 |
| VII-117 | 320 | 90 |
| VII-132 | 320 | 80 |
| VII-147 | 320 | 80 |
| VIII-001 | 320 | 80 |
| VIII-002 | 320 | 90 |
| VIII-003 | 320 | 90 |
| VIII-004 | 320 | 100 |
| VIII-006 | 320 | 80 |
| X-001 | 320 | 90 |
| X-002 | 320 | 100 |
| X-004 | 320 | 90 |
| X-005 | 320 | 90 |
| X-007 | 320 | 80 |

TABLE 49

Post-emergence action at 320 g/ha against HORMU in %

| Example number | Dosage [g/ha] | HORMU |
|---|---|---|
| VI-004 | 320 | 90 |
| VI-007 | 320 | 90 |
| VII-002 | 320 | 90 |
| VII-003 | 320 | 90 |
| VII-005 | 320 | 90 |
| VII-012 | 320 | 90 |
| VII-016 | 320 | 80 |
| VII-019 | 320 | 100 |
| VII-023 | 320 | 90 |
| VII-028 | 320 | 80 |
| VII-029 | 320 | 90 |
| VII-032 | 320 | 90 |
| VIII-001 | 320 | 80 |
| VIII-004 | 320 | 90 |

As shown by the results, compounds of the general formula (I) of the invention, in post-emergence treatment, have very good herbicidal efficacy (90% to 100% herbicidal action) against harmful plants such as *Abutilon theophrasti, Digitaria sanguinalis, Echinochloa crus-galli, Matricaria inodora, Poa annua*, at an application rate of 320 g of active substance per hectare.

Accordingly, the compounds of the invention have good herbicidal action against a broad spectrum of weed grasses and broad-leaved weeds and are therefore suitable for controlling unwanted vegetation by the post-emergence method.

The invention claimed is:

1. A Compound of formula (I)

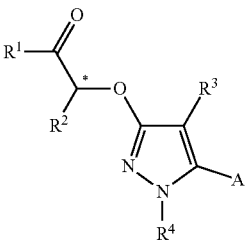

And/or an agrochemically acceptable salt thereof, where A is selected from the group consisting of A1-A15,

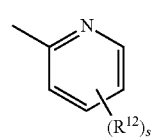
A1

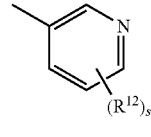
A2

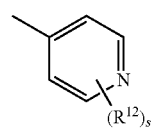
A3

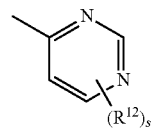
A4

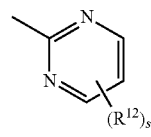
A5

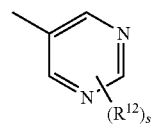
A6

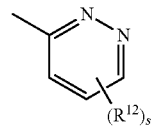
A7

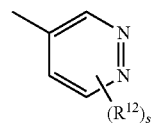
A8

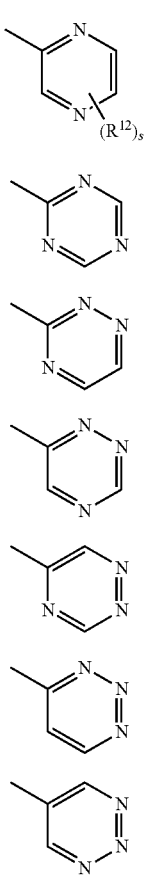

A9
A10
A11
A12
A13
A14
A15

R¹ is selected from the group consisting of
OR¹ᵃ and
NR⁹R¹⁰; where
R¹ᵃ is selected from the group consisting of
hydrogen;
($C_1$-$C_6$)-alkyl, ($C_3$-$C_6$)-cycloalkyl, which is unsubstituted or substituted by one or more substituents selected from the group consisting of halogen, ($C_1$-$C_6$)-alkyl, ($C_1$-$C_6$)-haloalkyl, ($C_3$-$C_6$)-cycloalkyl, ($C_1$-$C_6$)-alkoxy, cyano and nitro;
($C_2$-$C_4$)-alkenyl, ($C_2$-$C_4$)-alkynyl;
($C_1$-$C_4$)-alkyl-SO—($C_1$-$C_4$)—, ($C_1$-$C_4$)-alkyl-SO₂—($C_1$-$C_4$)—;
heterocyclyl-($C_1$-$C_4$)-alkyl, heteroaryl-($C_1$-$C_4$)-alkyl and aryl-($C_1$-$C_4$)-alkyl, where the aryl, heterocyclyl and heteroaryl are unsubstituted or substituted by halogen, ($C_1$-$C_6$)-alkyl and/or ($C_1$-$C_6$)-haloalkyl;
R⁹ is selected from the group consisting of hydrogen, and ($C_1$-$C_{12}$)-alkyl;
R¹⁰ is selected from the group consisting of
hydrogen;
aryl, heteroaryl, heterocyclyl;
($C_1$-$C_{12}$)-alkyl;
($C_3$-$C_8$)-cycloalkyl, ($C_3$-$C_7$)-cycloalkyl-($C_1$-$C_7$)-alkyl;
($C_2$-$C_{12}$)-alkenyl, ($C_5$-$C_7$)-cycloalkenyl, ($C_2$-$C_{12}$)-alkynyl;
$S(O)_n$NR⁵, cyano, nitro, OR⁵, SO₂NR⁶R⁷, CO₂R⁸, COR⁸, NR⁶R⁸, NR⁶COR⁸, NR⁶CO₂R⁸, and NR⁶SO₂R⁸;
which are unsubstituted or in each case independently of one another substituted by m radicals selected from the group consisting of hydrogen, halogen, cyano, nitro, OR⁵, $S(O)_n$NR⁵, SO₂NR⁶R⁷, CO₂R⁸, CONR⁶R⁸, COR⁶, NR⁶R⁸, NR⁶COR⁸, NR⁶CONR⁸R⁸, NR⁶CO₂R⁸, NR⁶SO₂R⁸, NR⁶SO₂NR⁶R⁸, and C(R⁶)=NOR⁸;
or
R⁹ and R¹⁰ together with the nitrogen atom to which they are attached form a saturated, partially or fully unsaturated five-, six- or seven-membered ring which is optionally mono- to hexasubstituted by radicals from the group consisting of halogen, ($C_1$-$C_6$)-alkyl, halo-($C_1$-$C_6$)-alkyl, OR⁵, $S(O)_n$R⁵, CO₂R⁸, CONR⁶R⁸, COR⁶ and C(R⁶)=NOR⁸ and which, in addition to this nitrogen atom, contains r carbon atoms, o oxygen atoms, p sulfur atoms and q elements from the group consisting of NR⁷, CO and NCOR⁷ as ring atoms;
R⁵ represents ($C_1$-$C_8$)-alkyl, ($C_3$-$C_6$)-cycloalkyl, ($C_1$-$C_6$)-haloalkyl or aryl;
R⁶ represents hydrogen or R⁵;
R⁷ represents hydrogen, ($C_1$-$C_6$)-alkyl, ($C_3$-$C_6$)-cycloalkyl, ($C_3$-$C_4$)-alkenyl or ($C_3$-$C_4$)-alkynyl;
R⁸ represents hydrogen, ($C_1$-$C_6$)-alkyl, ($C_3$-$C_6$)-cycloalkyl, ($C_3$-$C_4$)-alkenyl or ($C_3$-$C_4$)-alkynyl;
R² is selected from the group consisting of
hydrogen and cyano;
($C_1$-$C_6$)-alkyl, ($C_1$-$C_4$)-alkoxy-($C_1$-$C_4$)-alkyl, ($C_1$-$C_6$)-haloalkyl, ($C_1$-$C_6$)-alkoxy;
($C_2$-$C_6$)-alkenyl, ($C_2$-$C_6$)-haloalkenyl;
($C_2$-$C_6$)-alkynyl, ($C_2$-$C_6$)-haloalkynyl; and
($C_3$-$C_6$)-cycloalkyl;
R³ is selected from the group consisting of
hydrogen, halogen, cyano, isocyanato, NO₂;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_4$)-alkyloxycarbonyl;
($C_2$-$C_3$)-alkenyl, ($C_2$-$C_3$)-haloalkenyl;
($C_2$-$C_3$)-alkynyl, ($C_2$-$C_3$)-haloalkynyl;
($C_1$-$C_2$)-alkyl-$S(O)_n$ and ($C_1$-$C_2$)-haloalkyl-$S(O)_n$;
CHO; and
NH₂;
R⁴ represents phenyl, where the phenyl radical is unsubstituted or mono- or polysubstituted by a radical selected from the group consisting of
hydrogen, halogen, cyano, isocyanato, nitro;
($C_1$-$C_6$)-alkyl, halo-($C_1$-$C_6$)-alkyl, ($C_1$-$C_3$)-haloalkoxy;
($C_2$-$C_3$)-alkenyl, halo-($C_2$-$C_3$)-alkenyl, ($C_1$-$C_6$)-alkoxy;
($C_2$-$C_3$)-alkynyl, halo-($C_2$-$C_3$)-alkynyl, ($C_1$-$C_4$)-alkyl-$S(O)_n$;
CHO, ($C_1$-$C_4$)-alkyloxycarbonyl and NH₂;
R¹² is selected from the group consisting of
hydrogen, halogen, cyano, isocyanato, NO₂;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_4$)-alkyloxycarbonyl, ($C_1$-$C_6$)-alkoxy, ($C_1$-$C_3$)-haloalkoxy, ($C_1$-$C_4$)-alkyl-$S(O)_n$;
($C_2$-$C_3$)-alkenyl, ($C_2$-$C_3$)-haloalkenyl;
($C_2$-$C_3$)-alkynyl, ($C_2$-$C_3$)-haloalkynyl; and
NH₂;
and where the running number
m is 0, 1 or 2;
n is 0, 1 or 2;
o is 0, 1 or 2;

p is 0 or 1;
q is 0 or 1;
r is 3, 4, 5 or 6; and
s is 0, 1 or 2.

2. The Compound according to claim 1, wherein A is selected from the group consisting of

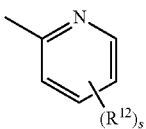
A1

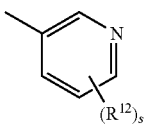
A2

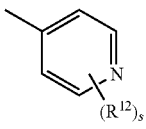
A3

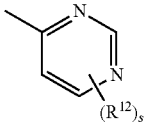
A4

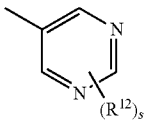
A6

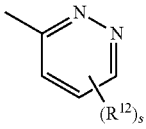
A7

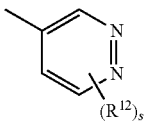
A8

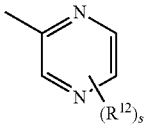
A9

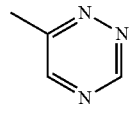
A12

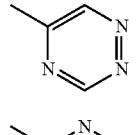
A13

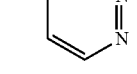
A14 and

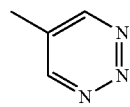
A15

$R^1$ is selected from the group consisting of
  $OR^{1a}$ and
  $NR^9R^{10}$; where
$R^{1a}$ is selected from the group consisting of
  hydrogen;
  $(C_1-C_6)$-alkyl, which is unsubstituted or substituted by one or more substituents selected from the group consisting of halogen, $(C_1-C_6)$-alkyl, $(C_1-C_6)$-haloalkyl, $(C_1-C_6)$-alkoxy, cyano and nitro;
  $(C_1-C_4)$-alkyl-SO—$(C_1-C_4)$—, $(C_1-C_4)$-alkyl-SO$_2$—$(C_1-C_4)$—; and
  aryl-$(C_1-C_4)$-alkyl, where the aryl is unsubstituted or substituted by halogen, $(C_1-C_6)$-alkyl and/or $(C_1-C_6)$-haloalkyl;
$R^9$ represents hydrogen, or $(C_1-C_4)$-alkyl;
$R^{10}$ is selected from the group consisting of
  hydrogen, aryl, $(C_1-C_4)$-alkyl, $(C_3-C_6)$-cycloalkyl, $(C_3-C_6)$-cycloalkyl-$(C_1-C_4)$-alkyl, $(C_2-C_4)$-alkenyl, $S(O)_nR^5$, cyano, nitro, $OR^5$, $SO_2NR^6R^7$, $CO_2R^8$, $COR^8$, $NR^6R^8$, and $NR^6COR^8$;
  which are unsubstituted or in each case independently of one another substituted by m radicals selected from the group consisting of
  $S(O)_nR^5$, $SO_2NR^6R^7$, $CO_2R^8$, and $NR^6CO_2R^8$;
  or
$R^9$ and $R^{10}$ together with the nitrogen atom to which they are attached form a saturated, partially or fully unsaturated five-, six- or seven-membered ring which is optionally mono-to hexasubstituted by radicals from the group consisting of halogen, $(C_1-C_4)$-alkyl, and $OR^5$, and which, in addition to this nitrogen atom, contains r carbon atoms, o oxygen atoms, p sulfur atoms and q elements from the group consisting of $NR^7$, CO and $NCOR^7$ as ring atoms;
$R^5$ represents $(C_1-C_4)$-alkyl, $(C_3-C_6)$-cycloalkyl or $(C_1-C_4)$-haloalkyl;
$R^6$ represents hydrogen or $R^5$;
$R^7$ represents hydrogen or $(C_1-C_4)$-alkyl;
$R^8$ represents hydrogen or $(C_1-C_4)$-alkyl;
$R^2$ is selected from the group consisting of
  hydrogen, cyano;
  $(C_1-C_4)$-alkyl, $(C_1-C_4)$-haloalkyl, $(C_1-C_6)$-alkoxy;
  $(C_3-C_6)$-cycloalkyl, and $(C_1-C_6)$-alkyl-$(C_1-C_3)$-alkoxy;
$R^3$ is selected from the group consisting of
  hydrogen, halogen, cyano, isocyanato, $NO_2$;
  $(C_1-C_6)$-alkyl, $(C_1-C_6)$-haloalkyl, $(C_1-C_6)$-alkylcarbonyl, $(C_1-C_6)$-haloalkylcarbonyl, $(C_1-C_2)$-alkyloxycarbonyl, $(C_1-C_3)$-alkoxy, $(C_1-C_6)$-haloalkoxy;
  $(C_1-C_6)$-alkylthio, $(C_1-C_6)$-haloalkylthio;
  $(C_2-C_3)$-alkenyl, $(C_2-C_3)$-haloalkenyl;
  $(C_2-C_3)$-alkynyl, $(C_2-C_3)$-haloalkynyl; and
  $S(O)_n$—$(C_1-C_2)$-alkyl where n=1 or 2;
$R^4$ represents phenyl, where the phenyl radical is unsubstituted or mono- or polysubstituted by a radical selected from the group consisting of hydrogen, fluorine, chlorine, bromine;
$(C_1-C_6)$-alkyl, halo-$(C_1-C_6)$-alkyl, $(C_1-C_3)$-haloalkoxy; and
$(C_1-C_6)$-alkoxy;

$R^{12}$ is selected from the group consisting of
hydrogen, halogen, cyano;
$(C_1-C_6)$-alkyl, $(C_1-C_6)$-haloalkyl;
$(C_1-C_6)$-alkoxy, and $(C_1-C_3)$-haloalkoxy;

and where the running number
m is 0 or 1;
n is 0, 1 or 2;
o is 0 or 1;
p is 0;
r is 6; and
s is 0 or 1.

3. The Compound according to claim 1, wherein
A is selected from the group consisting of

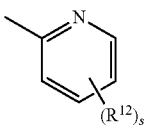
A1

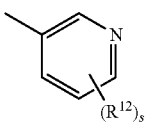
A2

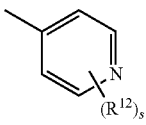
A3

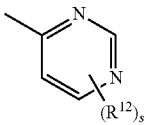
A4

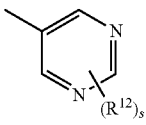
A6 and

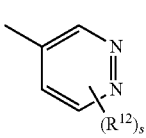
A8

$R^1$ is selected from the group consisting of
$OR^{1a}$ and
$NR^9R^{10}$; where
$R^{1a}$ is selected from the group consisting of
hydrogen;
$(C_1-C_6)$-alkyl, which is unsubstituted or substituted by one or more substituents selected from the group consisting of halogen, $(C_1-C_6)$-alkyl, $(C_1-C_6)$-haloalkyl, $(C_3-C_6)$-alkoxy; and
aryl-$(C_1-C_4)$-alkyl, where the aryl is substituted by $(C_1-C_6)$-alkyl;
$R^9$ represents hydrogen;

$R^{10}$ is selected from the group consisting of
aryl, $(C_1-C_{12})$-alkyl, $(C_3-C_8)$-cycloalkyl, $(C_3-C_7)$-cycloalkyl-$(C_1-C_7)$-alkyl, $(C_2-C_{12})$-alkenyl, $S(O)_nR^5$, $SO_2NR^6R^7$, $CO_2R^8$, and $NR^6R^8$,
which are unsubstituted or where the alkyl, cycloalkyl, alkenyl, cycloalkenyl and alkynyl radicals mentioned above are in each case independently of one another substituted by m radicals selected from the group consisting of $S(O)nR^5$, $SO_2NR^6R^7$, $CO_2R^8$, and $NR^6CO_2R^8$;
or
$R^9$ and $R^{10}$ together with the nitrogen atom to which they are attached form an unsubstituted saturated, partially or fully unsaturated five-, six- or seven-membered ring which, in addition to this nitrogen atom, contains r carbon atoms, o oxygen atoms, p sulfur atoms and q elements from the group consisting of $NR^7$, CO and $NCOR^7$ as ring atoms;
$R^5$ represents $(C_1-C_8)$-alkyl or $(C_1-C_6)$-haloalkyl;
$R^6$ represents hydrogen;
$R^7$ represents hydrogen or $(C_1-C_6)$-alkyl;
$R^8$ represents $(C_1-C_6)$-alkyl;
$R^2$ is selected from the group consisting of
hydrogen;
$(C_1-C_6)$-alkyl, $(C_1-C_6)$-haloalkyl, and $(C_1-C_4)$-alkoxy;
$R^3$ is selected from the group consisting of
hydrogen, halogen, cyano, $NO_2$;
$(C_1-C_6)$-alkyl, $(C_1-C_6)$-haloalkyl, $(C_1-C_6)$-haloalkoxy; and
$(C_1-C_6)$-alkylthio;
$R^4$ represents phenyl, where the phenyl radical is unsubstituted or mono- or polysubstituted by a radical selected from the group consisting of
hydrogen, fluorine, chlorine, bromine;
methyl, ethyl, $CF_3$, and $OCF_3$;
$R^{12}$ is selected from the group consisting of
hydrogen, fluorine, chlorine, cyano;
methyl, ethyl, $CF_3$, and $OCF_3$;
and where the running number
m is 0 or 1;
n is 0, 1 or 2;
o is 1;
p is 0;
r is 6; and
s is 0 or 1.

4. The Compound according to claim 1, wherein
$R^1$ is selected from the group consisting of
$OR^{1a}$ and
$NR^9R^{10}$; where
$R^{1a}$ is selected from the group consisting of
hydrogen;
methyl and ethyl;
allyl and propargyl; and
$PhCH_2$;
$R^9$ represents hydrogen and
$R^{10}$ is selected from the group consisting of $(C_1-C_{12})$-alkyl, $S(O)_nR^5$, $SO_2NR^6R^7$, and $CO_2R^8$, which are unsubstituted or in each case independently of one another substituted by m radicals selected from the group consisting of $S(O)_nR^5$, $SO_2NR^6R^7$, $CO_2R^8$, and $NR^6CO_2R^8$;
$R^5$ represents ethyl, methyl, $CF_3$, or $CH_2CF_3$;
$R^6$ represents hydrogen or $R^5$;
$R^7$ represents hydrogen, methyl or ethyl;
$R^8$ represents methyl or ethyl;

$R^2$ is selected from the group consisting of
hydrogen;
methyl, and ethyl;
$R^3$ is selected from the group consisting of
hydrogen, fluorine, bromine, chlorine, cyano, $NO_2$;
methyl, $CF_3$, and $OCF_3$;
$R^4$ represents phenyl, where the phenyl radical is unsubstituted or mono- or polysubstituted by a radical selected from the group consisting of hydrogen, fluorine and chlorine;
$R^{12}$ is selected from the group consisting of
hydrogen, fluorine, chlorine, cyano;
methyl, $CF_3$, and $OCF_3$.

5. The compound according to claim 1, wherein
$R^3$ is selected from the group consisting of
fluorine, chlorine, bromine, iodine, cyano, $NO_2$; and $CF_3$.

6. The compound according to claim 1, wherein $R^4$ represents phenyl which is mono- or polysubstituted by fluorine and/or chlorine.

7. The compound of the general formula (I) according to claim 1, wherein
$R^{12}$ is selected from the group consisting of
fluorine, chlorine, bromine, cyano, $NO_2$;
$CF_3$.

8. The compound

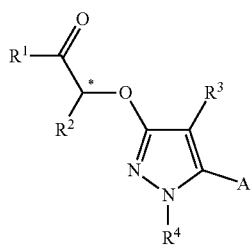

according to claim 1, wherein the chiral carbon atom marked by (*) has an (R) configuration.

9. The compound

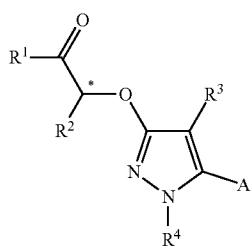

according to claim 1, wherein the chiral carbon atom marked by (*) has an (S) configuration.

10. A process for preparing the compound of formula (I) and/or an agrochemically acceptable salt thereof and/or agrochemically acceptable quaternized nitrogen derivative thereof

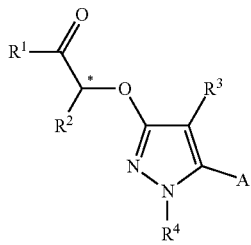

comprising
alkylation of the compound of formula (II)

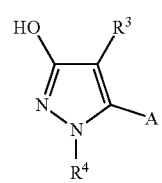

with a halide of formula (III)

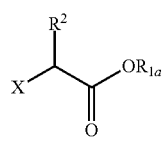

in the presence of a base.

11. An herbicidal composition and/or plant growth-regulating composition, comprising one or more compounds according to claim 1.

12. A method of controlling harmful plants and/or regulating the growth of plants, comprising applying an effective amount of one or more compounds according to claim 1 to one or more plants, plant parts, plant seeds and/or an area under cultivation.

13. A product comprising the compound of according to claim 1 as an herbicide and/or as plant growth regulator.

14. A product according to claim 13, wherein the compound is used to control one or more harmful plants and/or to regulate growth of one or more plants in one or more crops of useful plants or ornamental plants.

15. The product according to claim 13, wherein the crop plants are transgenic crop plants.

16. A compound of formula (II) and/or salt thereof

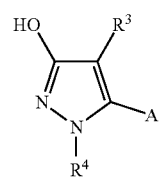

where,

A is selected from the group consisting of A1-A15,

A1 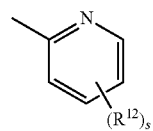

A2 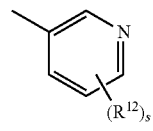

A3 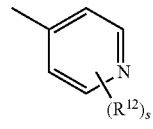

A4 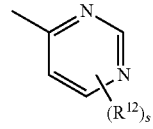

A5 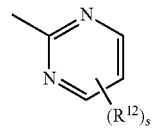

A6 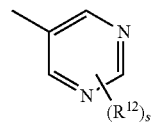

A7 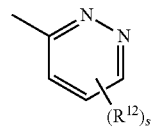

A8 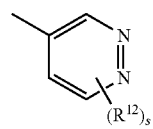

A9 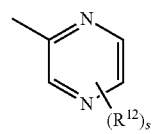

A10 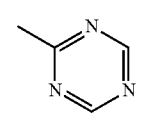

A11 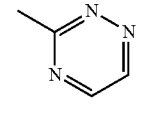

-continued

A12 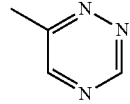

A13 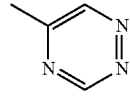

A14 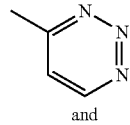

and

A15 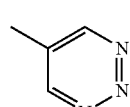

$R^1$ is selected from the group consisting of
  $OR^{1a}$ and
  $NR^9R^{10}$; where
$R^{1a}$ is selected from the group consisting of
  hydrogen;
  $(C_1\text{-}C_6)$-alkyl, $(C_3\text{-}C_6)$-cycloalkyl, which is unsubstituted or substituted by one or more substituents selected from the group consisting of halogen, $(C_1\text{-}C_6)$-alkyl, $(C_1\text{-}C_6)$-haloalkyl, $(C_3\text{-}C_6)$-cycloalkyl, $(C_1\text{-}C_6)$-alkoxy, cyano and nitro;
  $(C_2\text{-}C_4)$-alkenyl, $(C_2\text{-}C_4)$-alkynyl;
  $(C_1\text{-}C_4)$-alkyl-SO—$(C_1\text{-}C_4)$—, $(C_1\text{-}C_4)$-alkyl-SO$_2$—$(C_1\text{-}C_4)$—;
  heterocyclyl-$(C_1\text{-}C_4)$-alkyl, heteroaryl-$(C_1\text{-}C_4)$-alkyl and aryl-$(C_1\text{-}C_4)$-alkyl, where the aryl, heterocyclyl and heteroaryl are unsubstituted or substituted by halogen, $(C_1\text{-}C_6)$-alkyl and/or $(C_1\text{-}C_6)$-haloalkyl;
$R^9$ is selected from the group consisting of hydrogen, and $(C_1\text{-}C_{12})$-alkyl;
$R^{10}$ is selected from the group consisting of
  hydrogen;
  aryl, heteroaryl, heterocyclyl;
  $(C_1\text{-}C_{12})$-alkyl;
  $(C_3\text{-}C_8)$-cycloalkyl, $(C_3\text{-}C_7)$-cycloalkyl-$(C_1\text{-}C_7)$-alkyl;
  $(C_2\text{-}C_{12})$-alkenyl, $(C_5\text{-}C_7)$-cycloalkenyl, $(C_2\text{-}C_{12})$-alkynyl;
  $S(O)_nR^5$, cyano, nitro, $OR^5$, $SO_2NR^6R^7$, $CO_2R^8$, $COR^8$, $NR^6R^8$, $NR^6COR^8$, $NR^6CO_2R^8$, and $NR^6SO_2R^8$;
    which are unsubstituted or in each case independently of one another substituted by m radicals selected from the group consisting of
    hydrogen, halogen, cyano, nitro, $OR^5$, $S(O)_nR^5$, $SO_2NR^6R^7$, $CO_2R^8$, $CONR^6R^8$, $COR^6$, $NR^6R^8$, $NR^6COR^8$, $NR^6CONR^8R^8$, $NR^6CO_2R^8$, $NR^6SO_2R^8$, $NR^6SO_2NR^6R^8$, and $C(R^6)=NOR^8$;
    or
$R^9$ and $R^{10}$ together with the nitrogen atom to which they are attached form a saturated, partially or fully unsaturated five-, six- or seven-membered ring which is optionally mono-to hexasubstituted by radicals from the group consisting of halogen, $(C_1\text{-}C_6)$-alkyl, halo-$(C_1\text{-}C_6)$-alkyl, $OR^5$, $S(O)_nR^5$, $CO_2R^8$, $CONR^6R^8$, $COR^6$ and $C(R^6)=NOR^8$ and which, in addition to this nitrogen atom, contains r carbon atoms, o oxygen atoms, p sulfur atoms and q elements from the group consisting of NR$^7$, CO and NCOR$^7$ as ring atoms;

R$^5$ represents (C$_1$-C$_8$)-alkyl, (C$_3$-C$_6$)-cycloalkyl, (C$_1$-C$_6$)-haloalkyl or aryl;

R$^6$ represents hydrogen or R$^5$;

R$^7$ represents hydrogen, (C$_1$-C$_6$)-alkyl, (C$_3$-C$_6$)-cycloalkyl, (C$_3$-C$_4$)-alkenyl or (C$_3$-C$_4$)-alkynyl;

R$^8$ represents hydrogen, (C$_1$-C$_6$)-alkyl, (C$_3$-C$_6$)-cycloalkyl, (C$_3$-C$_4$)-alkenyl or (C$_3$-C$_4$)-alkynyl;

R$^2$ is selected from the group consisting of
hydrogen and cyano;
(C$_1$-C$_6$)-alkyl, (C$_1$-C$_4$)-alkoxy-(C$_1$-C$_4$)-alkyl, (C$_1$-C$_6$)-haloalkyl, (C$_1$-C$_6$)-alkoxy;
(C$_2$-C$_6$)-alkenyl, (C$_2$-C$_6$)-haloalkenyl;
(C$_2$-C$_6$)-alkynyl, (C$_2$-C$_6$)-haloalkynyl; and
(C$_3$-C$_6$)-cycloalkyl;

R$^3$ is selected from the group consisting of
hydrogen, halogen, cyano, isocyanato, NO$_2$;
(C$_1$-C$_6$)-alkyl, (C$_1$-C$_6$)-haloalkyl, (C$_1$-C$_6$)-alkylcarbonyl, (C$_1$-C$_6$)-haloalkylcarbonyl, (C$_1$-C$_4$)-alkyloxycarbonyl;
(C$_2$-C$_3$)-alkenyl, (C$_2$-C$_3$)-haloalkenyl;
(C$_2$-C$_3$)-alkynyl, (C$_2$-C$_3$)-haloalkynyl;
(C$_1$-C$_2$)-alkyl-S(O)$_n$ and (C$_1$-C$_2$)-haloalkyl-S(O)$_n$;
CHO; and
NH$_2$;

R$^4$ represents phenyl, where the phenyl radical is unsubstituted or mono- or polysubstituted by a radical selected from the group consisting of
hydrogen, halogen, cyano, isocyanato, nitro;
(C$_1$-C$_6$)-alkyl, halo-(C$_1$-C$_6$)-alkyl, (C$_1$-C$_3$)-haloalkoxy;
(C$_2$-C$_3$)-alkenyl, halo-(C$_2$-C$_3$)-alkenyl, (C$_1$-C$_6$)-alkoxy;
(C$_2$-C$_3$)-alkynyl, halo-(C$_2$-C$_3$)-alkynyl, (C$_1$-C$_4$)-alkyl-S(O)$_n$;
CHO, (C$_1$-C$_4$)-alkyloxycarbonyl and NH$_2$;

R$^{12}$ is selected from the group consisting of
hydrogen, halogen, cyano, isocyanato, NO$_2$;
(C$_1$-C$_6$)-alkyl, (C$_1$-C$_6$)-haloalkyl, (C$_1$-C$_6$)-alkylcarbonyl, (C$_1$-C$_6$)-haloalkylcarbonyl, (C$_1$-C$_4$)-alkyloxycarbonyl, (C$_1$-C$_6$)-alkoxy, (C$_1$-C$_3$)-haloalkoxy, (C$_1$-C$_4$)-alkyl-S(O)$_n$;
(C$_2$-C$_3$)-alkenyl, (C$_2$-C$_3$)-haloalkenyl;
(C$_2$-C$_3$)-alkynyl, (C$_2$-C$_3$)-haloalkynyl; and
NH$_2$;

and where the running number
m is 0, 1 or 2;
n is 0, 1 or 2;
o is 0, 1 or 2;
p is 0 or 1;
q is 0 or 1;
r is 3, 4, 5 or 6; and
s is 0, 1 or 2.

17. A process for preparing the compound of claim 16

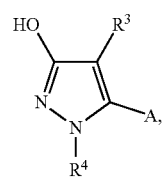
(II)

comprising a reaction of an electrophile with a 3-hydroxy-pyrazole of the formula (IIa)

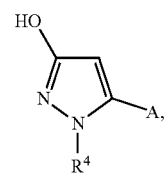
(IIa)

and comprising reacting a compound of formula (VIII)

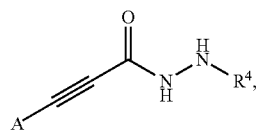
(VIII)

in a solvent
in the presence of a metal halide.

18. A process for preparing a compound of formula (VIII) where A is

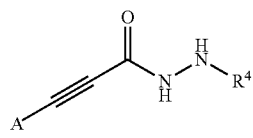
(VIII)

selected from the group consisting of A1-A15,

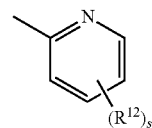
A1

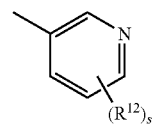
A2

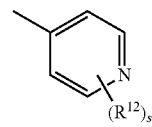
A3

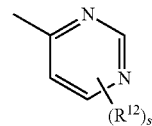
A4

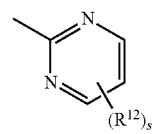
A5

-continued

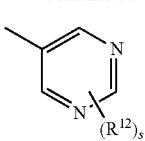
A6

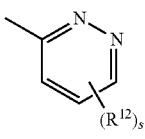
A7

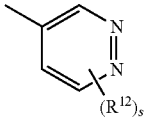
A8

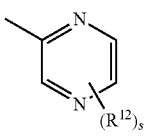
A9

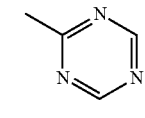
A10

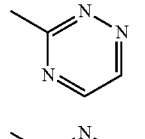
A11

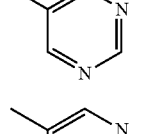
A12

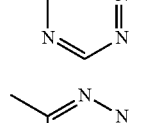
A13

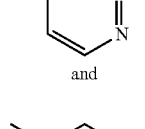
A14 and

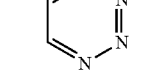
A15

$R^1$ is selected from the group consisting of
OR$^{1a}$ and
NR$^9$R$^{10}$; where
$R^{1a}$ is selected from the group consisting of
hydrogen;
$(C_1-C_6)$-alkyl, $(C_3-C_6)$-cycloalkyl, which is unsubstituted or substituted by one or more substituents selected from the group consisting of halogen, $(C_1-C_6)$-alkyl, $(C_1-C_6)$-haloalkyl, $(C_3-C_6)$-cycloalkyl, $(C_1-C_6)$-alkoxy, cyano and nitro;
$(C_2-C_4)$-alkenyl, $(C_2-C_4)$-alkynyl;
$(C_1-C_4)$-alkyl-SO—$(C_1-C_4)$—, $(C_1-C_4)$-alkyl-SO$_2$—$(C_1-C_4)$—;

heterocyclyl-$(C_1-C_4)$-alkyl, heteroaryl-$(C_1-C_4)$-alkyl and aryl-$(C_1-C_4)$-alkyl, where the aryl, heterocyclyl and heteroaryl are unsubstituted or substituted by halogen, $(C_1-C_6)$-alkyl and/or $(C_1-C_6)$-haloalkyl;
$R^9$ is selected from the group consisting of hydrogen, and $(C_1-C_{12})$-alkyl;
$R^{10}$ is selected from the group consisting of
hydrogen;
aryl, heteroaryl, heterocyclyl;
$(C_1-C_{12})$-alkyl;
$(C_3-C_8)$-cycloalkyl, $(C_3-C_7)$-cycloalkyl-$(C_1-C_7)$-alkyl;
$(C_2-C_{12})$-alkenyl, $(C_5-C_7)$-cycloalkenyl, $(C_2-C_{12})$-alkynyl;
S(O)$_n$R$^5$, cyano, nitro, OR$^5$, SO$_2$NR$^6$R$^7$, CO$_2$R$^8$, COR$^8$, NR$^6$R$^8$, NR$^6$COR$^8$, NR$^6$CO$_2$R$^8$, and NR$^6$SO$_2$R$^8$;
which are unsubstituted or in each case independently of one another substituted by m radicals selected from the group consisting of
hydrogen, halogen, cyano, nitro, OR$^5$, S(O)$_n$R$^5$, SO$_2$NR$^6$R$^7$, CO$_2$R$^8$, CONR$^6$R$^8$, COR$^6$, NR$^6$R$^8$, NR$^6$COR$^8$, NR$^6$CONR$^8$R$^8$, NR$^6$CO$_2$R$^8$, NR$^6$SO$_2$R$^8$, NR$^6$SO$_2$NR$^6$R$^8$, and C(R$^6$)=NOR$^8$;
or
$R^9$ and $R^{10}$ together with the nitrogen atom to which they are attached form a saturated, partially or fully unsaturated five-, six- or seven-membered ring which is optionally mono-to hexasubstituted by radicals from the group consisting of halogen, $(C_1-C_6)$-alkyl, halo-$(C_1-C_6)$-alkyl, OR$^5$, S(O)$_n$R$^5$, CO$_2$R$^8$, CONR$^6$R$^8$, COR$^6$ and C(R$^6$)=NOR$^8$ and which, in addition to this nitrogen atom, contains r carbon atoms, o oxygen atoms, p sulfur atoms and q elements from the group consisting of NR$^7$, CO and NCOR$^7$ as ring atoms;
$R^5$ represents $(C_1-C_8)$-alkyl, $(C_3-C_6)$-cycloalkyl, $(C_1-C_6)$-haloalkyl or aryl;
$R^6$ represents hydrogen or R$^5$;
$R^7$ represents hydrogen, $(C_1-C_6)$-alkyl, $(C_3-C_6)$-cycloalkyl, $(C_3-C_4)$-alkenyl or $(C_3-C_4)$-alkynyl;
$R^8$ represents hydrogen, $(C_1-C_6)$-alkyl, $(C_3-C_6)$-cycloalkyl, $(C_3-C_4)$-alkenyl or $(C_3-C_4)$-alkynyl;
$R^2$ is selected from the group consisting of
hydrogen and cyano;
$(C_1-C_6)$-alkyl, $(C_1-C_4)$-alkoxy-$(C_1-C_4)$-alkyl, $(C_1-C_6)$-haloalkyl, $(C_1-C_6)$-alkoxy;
$(C_2-C_6)$-alkenyl, $(C_2-C_6)$-haloalkenyl;
$(C_2-C_6)$-alkynyl, $(C_2-C_6)$-haloalkynyl; and
$(C_3-C_6)$-cycloalkyl;
$R^3$ is selected from the group consisting of
hydrogen, halogen, cyano, isocyanato, NO$_2$;
$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_4)$-alkyloxycarbonyl;
$(C_2-C_3)$-alkenyl, $(C_2-C_3)$-haloalkenyl;
$(C_2-C_3)$-alkynyl, $(C_2-C_3)$-haloalkynyl;
$(C_1-C_2)$-alkyl-S(O)$_n$ and $(C_1-C_2)$-haloalkyl-S(O)$_n$;
CHO; and
NH$_2$;
$R^4$ represents phenyl, where the phenyl radical is unsubstituted or mono- or polysubstituted by a radical selected from the group consisting of
hydrogen, halogen, cyano, isocyanato, nitro;
$(C_1-C_6)$-alkyl, halo-$(C_1-C_6)$-alkyl, $(C_1-C_3)$-haloalkoxy;
$(C_2-C_3)$-alkenyl, halo-$(C_2-C_3)$-alkenyl, $(C_1-C_6)$-alkoxy;

($C_2$-$C_3$)-alkynyl, halo-($C_2$-$C_3$)-alkynyl, ($C_1$-$C_4$)-alkyl-S(O)$_n$;

CHO, ($C_1$-$C_4$)-alkyloxycarbonyl and NH$_2$;

$R^{12}$ is selected from the group consisting of
hydrogen, halogen, cyano, isocyanato, NO$_2$;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_4$)-alkyloxycarbonyl, ($C_1$-$C_6$)-alkoxy, ($C_1$-$C_3$)-haloalkoxy, ($C_1$-$C_4$)-alkyl-S(O)$_n$;
($C_2$-$C_3$)-alkenyl, ($C_2$-$C_3$)-haloalkenyl;
($C_2$-$C_3$)-alkynyl, ($C_2$-$C_3$)-haloalkynyl; and
NH$_2$:

and where the running number m is 0, 1 or 2;
n is 0, 1 or 2;
o is 0, 1 or 2;
p is 0 or 1;
q is 0 or 1;
r is 3, 4, 5 or 6; and
s is 0, 1 or 2, comprising a reaction of an azine-A-substituted propynoic acid of formula (VI)

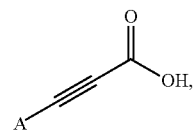

with a compound of formula (VII)

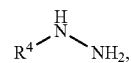

in a solvent
in the presence of an amide coupling reagent.

19. A product comprising a compound of formula (II) and/or a salt thereof according to claim 16 for preparing an agrochemically active compound.

20. A product comprising a compound of according to claim 16, as intermediate for preparation of one or more fine chemicals and/or active compounds for agriculture.

* * * * *